US011030531B2

(12) United States Patent
Wong et al.

(10) Patent No.: US 11,030,531 B2
(45) Date of Patent: Jun. 8, 2021

(54) DNA RECOMBINASE CIRCUITS FOR LOGICAL CONTROL OF GENE EXPRESSION

(71) Applicant: TRUSTEES OF BOSTON UNIVERSITY, Boston, MA (US)

(72) Inventors: Wilson W. Wong, Brookine, MA (US); Benjamin Harris Weinberg, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 276 days.

(21) Appl. No.: 15/316,353

(22) PCT Filed: Jun. 8, 2015

(86) PCT No.: PCT/US2015/034721
§ 371 (c)(1),
(2) Date: Dec. 5, 2016

(87) PCT Pub. No.: WO2015/188191
PCT Pub. Date: Dec. 10, 2015

(65) Prior Publication Data

US 2017/0183654 A1 Jun. 29, 2017

Related U.S. Application Data

(60) Provisional application No. 62/008,952, filed on Jun. 6, 2014, provisional application No. 62/144,678, filed on Apr. 8, 2015.

(51) Int. Cl.
*G06N 3/12* (2006.01)
*C12N 15/10* (2006.01)
(Continued)

(52) U.S. Cl.
CPC .......... *G06N 3/123* (2013.01); *C12N 5/0635* (2013.01); *C12N 5/0636* (2013.01);
(Continued)

(58) Field of Classification Search
None
See application file for complete search history.

(56) References Cited

U.S. PATENT DOCUMENTS

2012/0135524 A1 5/2012 Gilmore et al.
2012/0315670 A1 12/2012 Jacobson et al.
(Continued)

FOREIGN PATENT DOCUMENTS

WO WO-2008134593 A1 * 11/2008 ............ C12N 15/10

OTHER PUBLICATIONS

Bacchus, W., Aubel, D. & Fussenegger, M. Biomedically relevant circuit-design strategies in mammalian synthetic biology. Molecular Systems Biology 9, 691:1-12 (2013).*
(Continued)

*Primary Examiner* — Soren Harward
(74) *Attorney, Agent, or Firm* — Nixon Peabody LLP; Ronald I. Eisenstein; Susanna C. Benn

(57) ABSTRACT

The invention provides, inter alia, recombinase-based systems that provide for integrated logic and memory in living cells such as mammalian cells. The nucleic acid cassettes, switches, and systems described herein allow for control of gene expression or gene regulation. The invention also provides nucleic acid-based switches for adopted T-cell therapy.

7 Claims, 61 Drawing Sheets

Specification includes a Sequence Listing.

(51) Int. Cl.
*C12N 5/0783* (2010.01)
*C12N 5/0781* (2010.01)
*G16B 5/00* (2019.01)
*C12N 15/11* (2006.01)
*C12N 15/113* (2010.01)

(52) U.S. Cl.
CPC .......... *C12N 15/1082* (2013.01); *C12N 15/11* (2013.01); *C12N 15/113* (2013.01); *G16B 5/00* (2019.02); *C12N 2840/002* (2013.01)

(56) References Cited

U.S. PATENT DOCUMENTS

| | | | | |
|---|---|---|---|---|
| 2013/0280220 | A1 | 10/2013 | Ahmed et al. | |
| 2013/0287752 | A1 | 10/2013 | Davila et al. | |
| 2014/0315310 | A1* | 10/2014 | Lu et al. ................ | G06N 3/002 435/455 |

OTHER PUBLICATIONS

Benenson, Y. Biomolecular computing systems: Principles, progress and potential. Nature Reviews Genetics 13, 455-468 (2012).*
Kolb, A. F. Genome Engineering Using Site-Specific Recombinases. Cloning and Stem Cells 4, 65-80 (2002).*
Lienert, F., Lohmueller, J. J., Garg, A. & Silver, P. A. Synthetic biology in mammalian cells: Next generation research tools and therapeutics. Nature Reviews Molecular Cell Biology 15, 95-107 (2014).*
Nern, A., Pfeiffer, B. D., Svoboda, K. & Rubin, G. M. Multiple new site-specific recombinases for use in manipulating animal genomes. Proceedings of the National Academy of Sciences USA 108, 14198-14203 (2011).*
Wang, B. & Buck, M. Customizing cell signaling using engineered genetic logic circuits. Trends in Microbiology 20, 376-384 (2012).*
Daniel, R., Rubens, J. R., Sarpeshkar, R. & Lu, T. K. Synthetic analog computation in living cells. Nature 497, 619-623 (2013).*
Zabet, N. R., Hone, A. N. W. & Chu, D. F. Design principles of transcriptional logic circuits. In Synthesis and Simulation of Living Systems, ALIFE 186-193 (2010).*
Bonnet et al., "Amplifying genetic logic gates", Science, 340(6132):599-603 (2013).
Siuti et al., "Synthetic circuits integrating logic and memory in living cells", Nat Biotechnol, 31(5):448-52 (2013).
Auslander et al., "Programmable single-cell mammalian biocomputers", Nature 487(7405) 123-127 (2012).
Awatramani et al., "Cryptic boundaries in roof plate and choroid plexus identified by intersectional gene activation" Nat Genet 35(1) 70-75 (2003).
Bogorad et al., "Synthetic non-oxidative glycolysis enables complete carbon conservation", Nature 502(7473) 693-697 (2013).
Brophy et al., "Principles of Genetic Circuit Design", Nat Methods 11(5) 508-520 (2014).
Canton et al., "Refinement and standardization of synthetic biological parts and devices", Nat Biotechnol 26(7) 787-793 (2008).
Chen et al., "Characterization of 582 natural and synthetic terminators and quantification of their design constraints", Nat Methods 10(7) 659-664 (2013).
Daniel et al., "Synthetic analog computation in living cells", Nature 497(7451) 619-623 (2013).
Dueber et al., "Synthetic protein scaffolds provide modular control over metabolic flux", Nat Biotechnol 27(8) 753-759 (2009).
Elowitz et al., "A synthetic oscillatory network of transcriptional regulators", Nature 403(6767) 335-338 (2000).
Fenno et al., "INTRSECT: single-component targeting of cells using multiple-feature Boolean logic", Nat Methods 11 (7) 763-772 (2014).
Saber et al., "Designable DNA-binding domains enable construction of logic circuits in mammalian cells", Nat Chem Biol 10(3) 203-208 (2014).
Gardner et al., "Construction of a genetic toggle switch in *Escherichia coli*", Nature 403(6767) 339-342 (2000).
Guinn et al., "Biological 2-input Decoder Circuit in Human Cells", ACS Synth Biol 3(8) 627-633 (2014).
Heffner et al., "Supporting conditional mouse mutagenesis with a comprehensive cre characterization resource", Nat Commun 3(1218) 1-9 (2012).
Karimova et al., "Vika/vox, a novel efficient and specific Cre/loxP-like site-specific recombination system" Nucleic Acids Res 41(2) e37 (2012).
Keung et al., "Using targeted chromatin regulators to engineer combinatorial and spatial transcriptional regulation", Cell 158(1) 110-120 (2014).
Khalil et al., "A Synthetic Biology Framework for Programming Eukaryotic Transcription Functions", Cell 150(3) 647-658 (2012).
Lapique et al., "Digital switching in a biosensor circuit via programmable timing of gene availability", Nat Chem Biol 10(12) 1020-1027 (2014).
Lee et al., "Role of nucleotide sequences of loxP spacer region in Cre-mediated recombination" Gene 216(1) 55-56 (1998).
Leisner et al., "Rationally-designed logic integration of regulatory signals in mammalian cells", Nat Nanotechnol 5(9) 666-670 (2010).
Madisen et al., "A toolbox of Cre-dependent optogenetic transgenic mice for light-induced activation and silencing", Nat Neurosci 15(5) 793-802 (2012).
Moon et al., "Genetic programs constructed from layered logic gates in single cells", Nature 491(7423) 249-253 (2012).
Mutalik et al., "Precise and reliable gene expression via standard transcription and translation initiation elements", Nat Methods 10(4) 354-360 (2013).
Mutalik et al., "Quantitative estimation of activity and quality for collections of functional genetic elements", Nat Methods 10(4) 347-353 (2013).
Olive et al., "Mutant p53 Gain of Function in Two Mouse Models of Li-Fraumeni Syndrome" Cell 119(6) 847-860 (2004).
Ro et al., "Production of the antimalarial drug precursor artemisinic acid in engineered yeast", Nature 440(7086) 940-943 (2006).
Sajgo et al., "Dre—Cre Sequential Recombination Provides New Tools for Retinal Ganglion Cell Labeling and Manipulation in Mice", PLoS One 9(3) e91435 (2014).
Sauer et al., "DNA recombination with a heterospecific Cre homolog identified from comparison of the pac-c1 regions of P1-related phages", Nucleic Acids Res 32(20) 6086-6095 (2004).
Sauer, "Inducible Gene Targeting in Mice Using the Cre/lox System", Methods 14(4) 381-392 (1998).
Stanton et al., "Systematic Transfer of Prokaryotic Sensors and Circuits to Mammalian Cells", ACS Synth Biol 3(12) 880-891 (2014).
Stricker et al., "A fast, robust and tunable synthetic gene oscillator", Nature 456(7221) 516-519 (2008).
Suzuki et al., "VCre/VloxP and SCre/SloxP: new site-specific recombination systems for genome engineering", Nucleic Acids Res 39(8) e49 (2011).
Torella et al., "Rapid construction of insulated genetic circuits via synthetic sequence-guided isothermal assembly", Nucleic Acids Res 42(1) 681-689 (2014).
Torella et al., "Unique nucleotide sequence (UNS)-guided assembly of repetitive DNA parts for synthetic biology applications" Nat Protoc 9(9) 2075-2089 (2014).
Ventura et al., "Restoration of p53 function leads to tumon regression in vivo", Nature 445(7128) 661-665 (2007).
Wei et al., "Bacterial Virulence Proteins as Tools to Rewire Kinase Pathways in Yeast and Immune Cells", Nature 488 (7411) 384-388 (2012).
Xie et al., "Multi-Input RNAi-Based Logic Circuit for Identification of Specific Cancer Cells", Science 333(6047) 1307-1311 (2011).
Yang et al., "Permanent genetic memory with >1 byte capacity", Nat Methods 11(12) 1261-1266 (2014).
Zhang et al., "Design of a dynamic sensor-regulator system for production of chemicals and fuels derived from fatty acids", Nat Biotechnol 30(4) 354-359 (2012).

(56) References Cited

OTHER PUBLICATIONS

Zhu et al., “Prominin1 marks intestinal stem cells that are susceptible to neoplastic transformation”, Nature 457(7229) 603-607 (2009).

* cited by examiner

| TRUTH TABLE | | | | | | | |
|---|---|---|---|---|---|---|---|
| IN | | | | | | OUT | |
| A Cre | B Flp | S1 ΦC31 | S2 Vika | S3 B3 | S4 bxb1 | LOGIC | GFP |
| 0 | 0 | 0 | 1 | 1 | 1 | OR | 0 |
| 1 | 0 | | | | | | 1 |
| 0 | 1 | | | | | | 1 |
| 1 | 1 | | | | | | 1 |
| 0 | 0 | 1 | 0 | 0 | 0 | NOR | 1 |
| 1 | 0 | | | | | | 0 |
| 0 | 1 | | | | | | 0 |
| 1 | 1 | | | | | | 0 |
| 0 | 0 | 0 | 0 | 0 | 1 | AND | 0 |
| 1 | 0 | | | | | | 0 |
| 0 | 1 | | | | | | 0 |
| 1 | 1 | | | | | | 1 |
| 0 | 0 | 1 | 1 | 1 | 0 | NAND | 1 |
| 1 | 0 | | | | | | 1 |
| 0 | 1 | | | | | | 1 |
| 1 | 1 | | | | | | 0 |
| 0 | 0 | 0 | 1 | 0 | 1 | A | 0 |
| 1 | 0 | | | | | | 1 |
| 0 | 1 | | | | | | 0 |
| 1 | 1 | | | | | | 1 |
| 0 | 0 | 0 | 0 | 1 | 1 | B | 0 |
| 1 | 0 | | | | | | 0 |
| 0 | 1 | | | | | | 1 |
| 1 | 1 | | | | | | 1 |
| 0 | 0 | 1 | 0 | 1 | 0 | NOT A | 1 |
| 1 | 0 | | | | | | 0 |
| 0 | 1 | | | | | | 1 |
| 1 | 1 | | | | | | 0 |
| 0 | 0 | 1 | 1 | 0 | 0 | NOT B | 1 |
| 1 | 0 | | | | | | 1 |
| 0 | 1 | | | | | | 0 |
| 1 | 1 | | | | | | 0 |

| TRUTH TABLE | | | | | |
|---|---|---|---|---|---|
| IN | | | OUT | | |
| A Cre | B Flp | C VCre | DEC | P mCh | Q GFP |
| 0 | 0 | 0 | 0 | 0 | 0 |
| 1 | 0 | 0 | 1 | 0 | 1 |
| 0 | 1 | 0 | 1 | 0 | 1 |
| 0 | 0 | 1 | 1 | 0 | 1 |
| 1 | 1 | 0 | 2 | 1 | 0 |
| 1 | 0 | 1 | 2 | 1 | 0 |
| 0 | 1 | 1 | 2 | 1 | 0 |
| 1 | 1 | 1 | 3 | 1 | 1 |
| 0 | 0 | 0 | 0 | 0 | 0 |
| 1 | 0 | 0 | 1 | 0 | 1 |
| 0 | 1 | 0 | -1 | 1 | 1 |
| 0 | 0 | 1 | -1 | 1 | 1 |
| 1 | 1 | 0 | 0 | 0 | 0 |
| 1 | 0 | 1 | 0 | 0 | 0 |
| 0 | 1 | 1 | -2 | 1 | 0 |
| 1 | 1 | 1 | -1 | 1 | 1 |
| 0 | 0 | 0 | 0 | 0 | 0 |
| 1 | 0 | 0 | 1 | 0 | 1 |
| 0 | 1 | 0 | 1 | 0 | 1 |
| 1 | 1 | 0 | 2 | 1 | 0 |
| 0 | 0 | 1 | 0 | 0 | 0 |
| 1 | 0 | 1 | 1 | 0 | 1 |
| 0 | 1 | 1 | -1 | 1 | 1 |
| 1 | 1 | 1 | 0 | 0 | 0 |

| LOGIC GATE | | | TRUTH TABLE | | | SINGLE-CELL RESULTS |
|---|---|---|---|---|---|---|
| | | | IN | | OUT | MEAN F.I. (a.u., $10^3$) |
| NAME | SYMBOL | ARCHITECTURE | A Cre | B Flp | GFP | GFP 0 40 80 120 160 |
| NOR | | | 0 0 0 1 | 0 1 0 1 | 1 0 0 0 | |
| OR | | | 0 1 0 1 | 0 0 1 1 | 0 1 1 1 | |
| AND | | | 0 1 0 1 | 0 0 1 1 | 0 0 0 1 | |
| NAND | | | 0 1 0 1 | 0 0 1 1 | 1 1 1 0 | |
| A | | | 0 1 0 1 | 0 0 1 1 | 0 1 0 1 | |
| B | | | 0 1 0 1 | 0 0 1 1 | 0 0 1 1 | |
| NOT A | | | 0 1 0 1 | 0 0 1 1 | 1 0 1 0 | |
| NOT B | | | 0 1 0 1 | 0 0 1 1 | 1 1 0 0 | |

| LOGIC GATE | | | TRUTH TABLE | | SINGLE-CELL RESULTS |
|---|---|---|---|---|---|
| | | | IN | OUT | MEAN F.I. (a.u., $10^3$) |
| NAME | SYMBOL | ARCHITECTURE | A Cre | B Flp | GFP | GFP 0 40 80 120 160 |
| A IMPLY B | | | 0 1 0 1 | 0 0 1 1 | 1 0 1 1 | |
| B IMPLY A | | | 0 1 0 1 | 0 0 1 1 | 1 1 0 1 | |
| A NIMPLY B | | | 0 1 0 1 | 0 0 1 1 | 0 1 0 0 | |
| B NIMPLY A | | | 0 1 0 1 | 0 0 1 1 | 0 0 1 0 | |
| XOR | | | 0 1 0 1 | 0 0 1 1 | 0 1 1 0 | |
| XNOR | | | 0 1 0 1 | 0 0 1 1 | 1 0 0 1 | |
| TRUE | | | 0 1 0 1 | 0 0 1 1 | 1 1 1 1 | |
| FALSE | | | 0 1 0 1 | 0 0 1 1 | 0 0 0 0 | |

| TRUTH TABLE | | | | | | | | SINGLE CELL RESULTS |
|---|---|---|---|---|---|---|---|---|
| IN | | | | | | OUT | | MEAN F.I. (a.u., $10^3$) |
| A Cre | B Flp | S1 Dre | S2 Vika | S3 B3 | S4 VCre | LOGIC | GFP | GFP |
| 0 | 0 | | | | | OR | 0 |  |
| 1 | 0 | 0 | 1 | 1 | 1 |  | 1 | |
| 0 | 1 | | | | | | 1 | |
| 1 | 1 | | | | | | 1 | |
| 0 | 0 | | | | | NOR | 1 | |
| 1 | 0 | 1 | 0 | 0 | 0 |  | 0 | |
| 0 | 1 | | | | | | 0 | |
| 1 | 1 | | | | | | 0 | |
| 0 | 0 | | | | | AND | 0 | |
| 1 | 0 | 0 | 0 | 0 | 1 |  | 0 | |
| 0 | 1 | | | | | | 0 | |
| 1 | 1 | | | | | | 1 | |
| 0 | 0 | | | | | NAND | 1 | |
| 1 | 0 | 1 | 1 | 1 | 0 |  | 1 | |
| 0 | 1 | | | | | | 1 | |
| 1 | 1 | | | | | | 0 | |
| 0 | 0 | | | | | A | 0 | |
| 1 | 0 | 0 | 1 | 0 | 1 |  | 1 | |
| 0 | 1 | | | | | | 0 | |
| 1 | 1 | | | | | | 1 | |
| 0 | 0 | | | | | B | 0 | |
| 1 | 0 | 0 | 0 | 1 | 1 |  | 0 | |
| 0 | 1 | | | | | | 1 | |
| 1 | 1 | | | | | | 1 | |
| 0 | 0 | | | | | NOT A | 1 | |
| 1 | 0 | 1 | 0 | 1 | 0 |  | 0 | |
| 0 | 1 | | | | | | 1 | |
| 1 | 1 | | | | | | 0 | |
| 0 | 0 | | | | | NOT B | 1 | |
| 1 | 0 | 1 | 1 | 0 | 0 |  | 1 | |
| 0 | 1 | | | | | | 0 | |
| 1 | 1 | | | | | | 0 | |

| TRUTH TABLE | | | | | | | | SINGLE CELL RESULTS |
|---|---|---|---|---|---|---|---|---|
| IN | | | | | | OUT | | MEAN F.I. (a.u., $10^3$) |
| A Cre | B Flp | S1 Dre | S2 Vika | S3 B3 | S4 VCre | LOGIC | GFP | GFP 0 10 20 30 |
| 0 | 0 | 1 | 0 | 1 | 1 | A IMPLY B  | 1 |  |
| 1 | 0 | | | | | | 0 | |
| 0 | 1 | | | | | | 1 | |
| 1 | 1 | | | | | | 1 | |
| 0 | 0 | 1 | 1 | 0 | 1 | B IMPLY A  | 1 | |
| 1 | 0 | | | | | | 1 | |
| 0 | 1 | | | | | | 0 | |
| 1 | 1 | | | | | | 1 | |
| 0 | 0 | 0 | 1 | 0 | 0 | A NIMPLY B  | 0 | |
| 1 | 0 | | | | | | 1 | |
| 0 | 1 | | | | | | 0 | |
| 1 | 1 | | | | | | 0 | |
| 0 | 0 | 0 | 0 | 1 | 0 | B NIMPLY A  | 0 | |
| 1 | 0 | | | | | | 0 | |
| 0 | 1 | | | | | | 1 | |
| 1 | 1 | | | | | | 0 | |
| 0 | 0 | 0 | 1 | 1 | 0 | XOR  | 0 | |
| 1 | 0 | | | | | | 1 | |
| 0 | 1 | | | | | | 1 | |
| 1 | 1 | | | | | | 0 | |
| 0 | 0 | 1 | 0 | 0 | 1 | XNOR  | 1 | |
| 1 | 0 | | | | | | 0 | |
| 0 | 1 | | | | | | 0 | |
| 1 | 1 | | | | | | 1 | |
| 0 | 0 | 1 | 1 | 1 | 1 | TRUE  | 1 | |
| 1 | 0 | | | | | | 1 | |
| 0 | 1 | | | | | | 1 | |
| 1 | 1 | | | | | | 0 | |
| 0 | 0 | 0 | 0 | 0 | 0 | FALSE  | 0 | |
| 1 | 0 | | | | | | 0 | |
| 0 | 1 | | | | | | 0 | |
| 1 | 1 | | | | | | 0 | |

| TRUTH TABLE | | | | | | | |
|---|---|---|---|---|---|---|---|
| IN | | | | | | OUT | |
| A Cre | B Flp | S1 Dre | S2 Vika | S3 B3 | S4 VCre | LOGIC | GFP |
| 0 | 0 | 0 | 1 | 1 | 1 | OR | 0 |
| 1 | 0 | | | | |  | 1 |
| 0 | 1 | | | | | | 1 |
| 1 | 1 | | | | | | 1 |
| 0 | 0 | 1 | 0 | 0 | 0 | NOR | 1 |
| 1 | 0 | | | | |  | 0 |
| 0 | 1 | | | | | | 0 |
| 1 | 1 | | | | | | 0 |
| 0 | 0 | 0 | 0 | 0 | 1 | AND | 0 |
| 1 | 0 | | | | |  | 0 |
| 0 | 1 | | | | | | 0 |
| 1 | 1 | | | | | | 1 |
| 0 | 0 | 1 | 1 | 1 | 0 | NAND | 1 |
| 1 | 0 | | | | |  | 1 |
| 0 | 1 | | | | | | 1 |
| 1 | 1 | | | | | | 0 |
| 0 | 0 | 0 | 1 | 0 | 1 | A | 0 |
| 1 | 0 | | | | |  | 1 |
| 0 | 1 | | | | | | 0 |
| 1 | 1 | | | | | | 1 |
| 0 | 0 | 0 | 0 | 1 | 1 | B | 0 |
| 1 | 0 | | | | |  | 0 |
| 0 | 1 | | | | | | 1 |
| 1 | 1 | | | | | | 1 |
| 0 | 0 | 1 | 0 | 1 | 0 | NOT A | 1 |
| 1 | 0 | | | | |  | 0 |
| 0 | 1 | | | | | | 1 |
| 1 | 1 | | | | | | 0 |
| 0 | 0 | 1 | 1 | 0 | 0 | NOT B | 1 |
| 1 | 0 | | | | |  | 1 |
| 0 | 1 | | | | | | 0 |
| 1 | 1 | | | | | | 0 |

SINGLE CELL RESULTS

MEAN F.I. (a.u., $10^3$)

| TRUTH TABLE | | | | | | | | SINGLE CELL RESULTS |
|---|---|---|---|---|---|---|---|---|
| IN | | | | | | OUT | | MEAN F.I. (a.u., $10^3$) |
| A Cre | B Flp | S1 Dre | S2 Vika | S3 B3 | S4 VCre | LOGIC | GFP | GFP |
| 0 | 0 | 1 | 0 | 1 | 1 | A IMPLY B | 1 |  |
| 1 | 0 | | | | |  | 0 | |
| 0 | 1 | | | | | | 1 | |
| 1 | 1 | | | | | | 1 | |
| 0 | 0 | 1 | 1 | 0 | 1 | B IMPLY A | 1 | |
| 1 | 0 | | | | |  | 1 | |
| 0 | 1 | | | | | | 0 | |
| 1 | 1 | | | | | | 1 | |
| 0 | 0 | 0 | 1 | 0 | 0 | A NIMPLY B | 0 | |
| 1 | 0 | | | | |  | 1 | |
| 0 | 1 | | | | | | 0 | |
| 1 | 1 | | | | | | 0 | |
| 0 | 0 | 0 | 0 | 1 | 0 | B NIMPLY A | 0 | |
| 1 | 0 | | | | |  | 0 | |
| 0 | 1 | | | | | | 1 | |
| 1 | 1 | | | | | | 0 | |
| 0 | 0 | 0 | 1 | 1 | 0 | XOR | 0 | |
| 1 | 0 | | | | |  | 1 | |
| 0 | 1 | | | | | | 1 | |
| 1 | 1 | | | | | | 0 | |
| 0 | 0 | 1 | 0 | 0 | 1 | XNOR | 1 | |
| 1 | 0 | | | | |  | 0 | |
| 0 | 1 | | | | | | 0 | |
| 1 | 1 | | | | | | 1 | |
| 0 | 0 | 1 | 1 | 1 | 1 | TRUE | 1 | |
| 1 | 0 | | | | |  | 1 | |
| 0 | 1 | | | | | | 1 | |
| 1 | 1 | | | | | | 1 | |
| 0 | 0 | 0 | 0 | 0 | 0 | FALSE | 0 | |
| 1 | 0 | | | | |  | 0 | |
| 0 | 1 | | | | | | 0 | |
| 1 | 1 | | | | | | 0 | |

A=bxb1, B=PhiC31, C=Cre, D=Flp, E=SCre, F=VCre, G=Vika, H=Dre, I=B3, J=KD

| LOGIC GATE | | TRUTH TABLE | | SINGLE-CELL RESULTS |
|---|---|---|---|---|
| NAME | SYMBOL | INPUT | OUT | MEAN GFP FLUORESCENCE (A.U., $10^3$) |

| TRUTH TABLE | | | | |
|---|---|---|---|---|
| INPUT | | OUT | | |
| A | B | mRuby2 | iRFP | GFP |
| 0 | 0 | 0 | 0 | 0 |
| 1 | 0 | 0 | 0 | 1 |
| 0 | 1 | 0 | 1 | 0 |
| 1 | 1 | 1 | 0 | 0 |

| NAME | A Cre | B Flp | BOUT mCh | D GFP |
|---|---|---|---|---|
| HALF SUBTRACTOR (3-plasmids) | 0 | 0 | 0 | 0 |
| | 1 | 0 | 0 | 1 |
| | 0 | 1 | 1 | 1 |
| | 1 | 1 | 0 | 0 |
| HALF SUBTRACTOR (2-plasmids) | 0 | 0 | 0 | 0 |
| | 1 | 0 | 0 | 1 |
| | 0 | 1 | 1 | 1 |
| | 1 | 1 | 0 | 0 |
| HALF SUBTRACTOR (1-plasmid) | 0 | 0 | 0 | 0 |
| | 1 | 0 | 0 | 1 |
| | 0 | 1 | 1 | 1 |
| | 1 | 1 | 0 | 0 |

| FINITE STATE MACHINE | | STATE TABLE | | | | | | | | | | | | |
|---|---|---|---|---|---|---|---|---|---|---|---|---|---|---|
| NAME | STATE DIAGRAM | CURRENT STATE | | | INPUT | | NEXT STATE | | | OUT | | | | |
| | | X | Y | Z | A Cre | B Flp | X | Y | Z | BFP | GFP | iRFP | mRb | OFP |
| FIVE-STATE, FIVE-COLOR FSM |  | 0 | 0 | 0 | 0 | 0 | 0 | 0 | 0 | 1 | 0 | 0 | 0 | 0 |
| | | 0 | 0 | 0 | 1 | 0 | 0 | 0 | 1 | 0 | 1 | 0 | 0 | 0 |
| | | 0 | 0 | 0 | 0 | 1 | 0 | 1 | 0 | 0 | 0 | 1 | 0 | 0 |
| | GENETIC ARCHITECTURE | 0 | 0 | 1 | 0 | 1 | 0 | 1 | 1 | 0 | 0 | 0 | 1 | 0 |
| |  | 0 | 1 | 0 | 1 | 0 | 1 | 0 | 0 | 0 | 0 | 0 | 0 | 1 |

LOGIC GATE

NAME: RIPPLE CARRY ADDER

SYMBOL

ARCHITECTURE

TRUTH TABLE

| IN | | | | OUT | | | |
|---|---|---|---|---|---|---|---|
| A1 Cre | A0 VCre | B1 Flp | B0 KD | DEC | COUT mCh | S1 GFP | S0 BFP |
| 0 | 0 | 0 | 0 | 0 | 0 | 0 | 0 |
| 0 | 1 | 0 | 0 | 1 | 0 | 0 | 1 |
| 1 | 0 | 0 | 0 | 2 | 0 | 1 | 0 |
| 1 | 1 | 0 | 0 | 3 | 0 | 1 | 1 |
| 0 | 0 | 0 | 1 | 1 | 0 | 0 | 1 |
| 0 | 1 | 0 | 1 | 2 | 0 | 1 | 0 |
| 1 | 0 | 0 | 1 | 3 | 0 | 1 | 1 |
| 1 | 1 | 0 | 1 | 4 | 1 | 0 | 0 |
| 0 | 0 | 1 | 0 | 2 | 0 | 1 | 0 |
| 0 | 1 | 1 | 0 | 3 | 0 | 1 | 1 |
| 1 | 0 | 1 | 0 | 4 | 1 | 0 | 0 |
| 1 | 1 | 1 | 0 | 5 | 1 | 0 | 1 |
| 0 | 0 | 1 | 1 | 3 | 0 | 1 | 1 |
| 0 | 1 | 1 | 1 | 4 | 1 | 0 | 0 |
| 1 | 0 | 1 | 1 | 5 | 1 | 0 | 1 |
| 1 | 1 | 1 | 1 | 6 | 1 | 1 | 0 |

| A1 VCre | A0 KD | B1 bxb1 | B0 ΦC31 | DEC | P3 mRb | P2 GFP | P1 BFP | P0 iRFP |
|---|---|---|---|---|---|---|---|---|
| 0 | 0 | 0 | 0 | 0 | 0 | 0 | 0 | 0 |
| 0 | 1 | 0 | 0 | 0 | 0 | 0 | 0 | 0 |
| 1 | 0 | 0 | 0 | 0 | 0 | 0 | 0 | 0 |
| 1 | 1 | 0 | 0 | 0 | 0 | 0 | 0 | 0 |
| 0 | 0 | 0 | 1 | 0 | 0 | 0 | 0 | 0 |
| 0 | 1 | 0 | 1 | 1 | 0 | 0 | 0 | 1 |
| 1 | 0 | 0 | 1 | 2 | 0 | 0 | 1 | 0 |
| 1 | 1 | 0 | 1 | 3 | 0 | 0 | 1 | 1 |
| 0 | 0 | 1 | 0 | 0 | 0 | 0 | 0 | 0 |
| 0 | 1 | 1 | 0 | 2 | 0 | 0 | 1 | 0 |
| 1 | 0 | 1 | 0 | 4 | 0 | 1 | 0 | 0 |
| 1 | 1 | 1 | 0 | 6 | 0 | 1 | 1 | 0 |
| 0 | 0 | 1 | 1 | 0 | 0 | 0 | 0 | 0 |
| 0 | 1 | 1 | 1 | 3 | 0 | 0 | 1 | 1 |
| 1 | 0 | 1 | 1 | 6 | 0 | 1 | 1 | 0 |
| 1 | 1 | 1 | 1 | 9 | 1 | 0 | 0 | 1 |

LOOKUP TABLE

| IN | | | | | OUT |
|---|---|---|---|---|---|
| S1 ΦC31 | S2 Vika | S3 B3 | S4 bxb1 | M VCre | LOGIC |
| 0 | 0 | 0 | 0 | 0 | FALSE |
| 0 | 0 | 0 | 1 | 0 | AND |
| 0 | 0 | 1 | 0 | 0 | BNIMPLYA |
| 0 | 0 | 1 | 1 | 0 | B |
| 0 | 1 | 0 | 0 | 0 | ANIMPLYB |
| 0 | 1 | 0 | 1 | 0 | A |
| 0 | 1 | 1 | 0 | 0 | XOR |
| 0 | 1 | 1 | 1 | 0 | OR |
| 1 | 0 | 0 | 0 | 0 | NOR |
| 1 | 0 | 0 | 1 | 0 | XNOR |
| 1 | 0 | 1 | 0 | 0 | NOTA |
| 1 | 0 | 1 | 1 | 0 | AIMPLYB |
| 1 | 1 | 0 | 0 | 0 | NOTB |
| 1 | 1 | 0 | 1 | 0 | BIMPLYA |
| 1 | 1 | 1 | 0 | 0 | NAND |

| LOOKUP TABLE | | | | | | |
|---|---|---|---|---|---|---|
| IN | | | | | | OUT |
| S1 ΦC31 | S2 Vika | S3 B3 | S4 bxb1 | M1 KD | M2 VCre | LOGIC |
| 0 | 0 | 0 | 0 | 0 | 0 | FALSE |
| 0 | 0 | 0 | 1 | 0 | 0 | AND |
| 0 | 0 | 1 | 0 | 0 | 0 | BNIMPLYA |
| 0 | 0 | 1 | 1 | 0 | 0 | B |
| 0 | 1 | 0 | 0 | 0 | 0 | ANIMPLYB |
| 0 | 1 | 0 | 1 | 0 | 0 | A |
| 0 | 1 | 1 | 0 | 0 | 0 | XOR |
| 0 | 1 | 1 | 1 | 0 | 0 | OR |
| 1 | 0 | 0 | 0 | 0 | 0 | NOR |
| 1 | 0 | 0 | 1 | 0 | 0 | XNOR |
| 1 | 0 | 1 | 0 | 0 | 0 | NOTA |
| 1 | 0 | 1 | 1 | 0 | 0 | AIMPLYB |
| 1 | 1 | 0 | 0 | 0 | 0 | NOTB |
| 1 | 1 | 0 | 1 | 0 | 0 | BIMPLYA |
| 1 | 1 | 1 | 0 | 0 | 0 | NAND |
| 1 | 1 | 1 | 1 | 0 | 0 | TRUE |
| X | X | X | X | 1 | 0 | HALF ADDER |
| X | X | X | X | 1 | 1 | HALF SUBTRACTOR |

*FIG. 26F (cont.)*

SEQUENCE LISTING

```
<160> NUMBER OF SEQ ID NOS: 851

<210> SEQ ID NO 1
<211> LENGTH: 511
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

ggggttgggg ttgcgccttt tccaaggcag ccctgggttt gcgcagggac gcggctgctc      60

tgggcgtggt tccgggaaac gcagcggcgc cgaccctggg tctcgcacat tcttcacgtc     120

cgttcgcagc gtcacccgga tcttcgccgc tacccttgtg ggccccccgg cgacgcttcc     180

tgctccgccc ctaagtcggg aaggttcctt gcggttcgcg gcgtgccgga cgtgacaaac     240

ggaagccgca cgtctcacta gtaccctcgc agacggacag cgccagggag caatggcagc     300

gcgccgaccg cgatgggctg tggccaatag cggctgctca gcagggcgcg ccgagagcag     360

cggccgggaa ggggcggtgc gggaggcggg gtgtggggcg gtagtgtggg ccctgttcct     420

gcccgcgcgg tgttccgcat tctgcaagcc tccggagcgc acgtcggcag tcggctccct     480

cgttgaccga atcaccgacc tctctcccca g                                    511


<210> SEQ ID NO 2
<211> LENGTH: 1184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

cgtgaggctc cggtgcccgt cagtgggcag agcgcacatc gcccacagtc cccgagaagt      60

tggggggagg ggtcggcaat tgaaccggtg cctagagaag gtggcgcggg gtaaactggg     120

aaagtgatgt cgtgtactgg ctccgccttt ttcccgaggg tgggggagaa ccgtatataa     180
```

gtgcagtagt cgccgtgaac gttctttttc gcaacgggtt tgccgccaga acacaggtaa 240
gtgccgtgtg tggttcccgc gggcctggcc tctttacggg ttatggccct tgcgtgcctt 300
gaattacttc cacctggctg cagtacgtga ttcttgatcc cgagcttcgg gttggaagtg 360
ggtgggagag ttcgaggcct tgcgcttaag gagccccttc gcctcgtgct tgagttgagg 420
cctggcctgg gcgctggggc cgccgcgtgc gaatctggtg gcaccttcgc gcctgtctcg 480
ctgctttcga taagtctcta gccatttaaa atttttgatg acctgctgcg acgctttttt 540
tctggcaaga tagtcttgta aatgcgggcc aagatctgca cactggtatt tcggtttttg 600
gggccgcggg cggcgacggg gcccgtgcgt cccagcgcac atgttcggcg aggcggggcc 660
tgcgagcgcg gccaccgaga atcggacggg ggtagtctca agctggccgg cctgctctgg 720
tgcctggcct cgcgccgccg tgtatcgccc cgccctgggc ggcaaggctg gcccggtcgg 780
caccagttgc gtgagcggaa agatggccgc ttcccggccc tgctgcaggg agctcaaaat 840
ggaggacgcg gcgctcggga gagcgggcgg gtgagtcacc cacacaaagg aaaagggcct 900
ttccgtcctc agccgtcgct tcatgtgact ccacggagta ccgggcgccg tccaggcacc 960
tcgattagtt ctcgagcttt tggagtacgt cgtctttagg ttggggggag gggttttatg 1020
cgatggagtt tccccacact gagtgggtgg agactgaagt taggccagct tggcacttga 1080
tgtaattctc cttggaattt gccctttttg agtttggatc ttggttcatt ctcaagcctc 1140
agacagtggt tcaaagtttt tttcttccat ttcaggtgtc gtga 1184

<210> SEQ ID NO 3
<211> LENGTH: 492
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
ccgataaaat aaaagatttt atttagtctc cagaaaaagg ggggaatgaa agaccccacc 60
tgtaggtttg gcaagctagc tgcagtaacg ccattttgca aggcatggaa aaataccaaa 120
ccaagaatag agaagttcag atcaagggcg ggtacatgaa aatagctaac gttgggccaa 180
acaggatatc tgcggtgagc agtttcggcc ccggcccggg gccaagaaca gatggtcacc 240
gcagtttcgg ccccggcccg aggccaagaa cagatggtcc ccagatatgg cccaaccctc 300
agcagtttct taagacccat cagatgtttc caggctcccc caaggacctg aaatgaccct 360
gcgccttatt tgaattaacc aatcagcctg cttctcgctt ctgttcgcgc gcttctgctt 420
cccgagctct ataaaagagc tcacaacccc tcactcggcg cgccagtcct ccgacagact 480
gagtcgcccg gg 492

<210> SEQ ID NO 4
<211> LENGTH: 1701
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
actagttatt aatagtaatc aattacgggg tcattagttc atagcccata tatggagttc 60
cgcgttacat aacttacggt aaatggcccg cctggctgac cgcccaacga cccccgccca 120

-continued

```
ttgacgtcaa taatgacgta tgttcccata gtaacgccaa tagggacttt ccattgacgt    180

caatgggtgg actatttacg gtaaactgcc cacttggcag tacatcaagt gtatcatatg    240

ccaagtacgc cccctattga cgtcaatgac ggtaaatggc ccgcctggca ttatgcccag    300

tacatgacct tatgggactt tcctacttgg cagtacatct acgtattagt catcgctatt    360

accatgggtc gaggtgagcc ccacgttctg cttcactctc cccatctccc ccccctcccc    420

acccccaatt ttgtatttat ttatttttta attattttgt gcagcgatgg gggcgggggg    480

gggggggcg cgcgccaggc ggggcggggc ggggcgaggg gcggggcggg gcgaggcgga    540

gaggtgcggc ggcagccaat cagagcggcg cgctccgaaa gtttcctttt atggcgaggc    600

ggcggcggcg gcggccctat aaaaagcgaa gcgcgcggcg ggcgggagtc gctgcgttgc    660

cttcgccccg tgccccgctc cgcgccgcct cgcgccgccc gccccggctc tgactgaccg    720

cgttactccc acaggtgagc gggcgggacg gcccttctcc tccgggctgt aattagcgct    780

tggtttaatg acggctcgtt tcttttctgt ggctgcgtga aagccttaaa gggctccggg    840

agggcccttt gtgcgggggg gagcggctcg gggggtgcgt gcgtgtgtgt gtgcgtgggg    900

agcgccgcgt gcggcccgcg ctgcccggcg gctgtgagcg ctgcgggcgc ggcgcggggc    960

tttgtgcgct ccgcgtgtgc gcgaggggag cgcggccggg ggcggtgccc cgcggtgcgg   1020

gggggctgcg aggggaacaa aggctgcgtg cggggtgtgt gcgtgggggg gtgagcaggg   1080

ggtgtgggcg cggcggtcgg gctgtaaccc ccccctgcac ccccctcccc gagttgctga   1140

gcacggcccg gcttcgggtg cggggctccg tgcggggcgt ggcgcggggc tcgccgtgcc   1200

gggcgggggg tggcggcagg tgggggtgcc gggcggggcg gggccgcctc gggccgggga   1260

gggctcgggg gaggggcgcg gcggccccgg agcgccggcg gctgtcgagg cgcggcgagc   1320

cgcagccatt gccttttatg gtaatcgtgc gagagggcgc agggacttcc tttgtcccaa   1380

atctggcgga gccgaaatct gggaggcgcc gccgcacccc ctctagcggg cgcgggcgaa   1440

gcggtgcggc gccggcagga aggaaatggg cggggagggc cttcgtgcgt cgccgcgccg   1500

ccgtcccctt ctccatctcc agcctcgggg ctgccgcagg gggacggctg ccttcggggg   1560

ggacggggca gggcggggtt cggcttctgg cgtgtgaccg gcggctctag agcctctgct   1620

aaccatgttc atgccttctt ctttttccta cagctcctgg gcaacgtgct ggttattgtg   1680

ctgtctcatc attttggcaa a                                              1701
```

```
<210> SEQ ID NO 5
<211> LENGTH: 1056
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

atggtgccca agaagaagag gaaagtctcc aacctgctga ctgtgcacca aaacctgcct     60

gccctccctg tggatgccac ctctgatgaa gtcaggaaga acctgatgga catgttcagg    120

gacaggcagg ccttctctga acacacctgg aagatgctcc tgtctgtgtg cagatcctgg    180

gctgcctggt gcaagctgaa caacaggaaa tggttccctg ctgaacctga ggatgtgagg    240

gactacctcc tgtacctgca agccagaggc ctggctgtga agaccatcca acagcacctg    300

ggccagctca acatgctgca caggagatct ggcctgcctc gcccttctga ctccaatgct    360

gtgtccctgg tgatgaggag aatcagaaag gagaatgtgg atgctgggga gagagccaag    420
```

```
caggccctgg cctttgaacg cactgacttt gaccaagtca gatccctgat ggagaactct    480
gacagatgcc aggacatcag gaacctggcc ttcctgggca ttgcctacaa caccctgctg    540
cgcattgccg aaattgccag aatcagagtg aaggacatct cccgcaccga tggtgggaga    600
atgctgatcc acattggcag gaccaagacc ctggtgtcca cagctggtgt ggagaaggcc    660
ctgtccctgg gggttaccaa gctggtggag agatggatct ctgtgtctgg tgtggctgat    720
gaccccaaca actacctgtt ctgccgggtc agaaagaatg gtgtggctgc cccttctgcc    780
acctcccaac tgtccacccg ggccctggaa gggatctttg aggccaccca ccgcctgatc    840
tatggtgcca aggatgactc tgggcagaga tacctggcct ggtctggcca ctctgccaga    900
gtgggtgctg ccagggacat ggccagggct ggtgtgtcca tccctgaaat catgcaggct    960
ggtggctgga ccaatgtgaa cattgtgatg aactacatca gaaacctgga ctctgagact   1020
ggggccatgg tgaggctgct cgaggatggg gactga                             1056
```

<210> SEQ ID NO 6
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atggctccta agaagaagag gaaggtgatg agccagttcg acatcctgtg caagaccccc     60
cccaaggtgc tggtgcggca gttcgtggag agattcgaga ggcccagcgg cgagaagatc    120
gccagctgtg ccgccgagct gacctacctg tgctggatga tcacccacaa cggcaccgcc    180
atcaagaggg ccaccttcat gagctacaac accatcatca gcaacagcct gagcttcgac    240
atcgtgaaca agagcctgca gttcaagtac aagacccaga aggccaccat cctggaggcc    300
agcctgaaga agctgatccc cgcctgggag ttcaccatca tcccttacaa cggccagaag    360
caccagagcg acatcaccga catcgtgtcc agcctgcagc tgcagttcga gagcagcgag    420
gaggccgaca agggcaacag ccacagcaag aagatgctga aggccctgct gtccgagggc    480
gagagcatct gggagatcac cgagaagatc ctgaacagct tcgagtacac cagcaggttc    540
accaagacca agaccctgta ccagttcctg ttcctggcca cattcatcaa ctgcggcagg    600
ttcagcgaca tcaagaacgt ggaccccaag agcttcaagc tggtgcagaa caagtacctg    660
ggcgtgatca ttcagtgcct ggtgaccgag accaagacaa gcgtgtccag gcacatctac    720
tttttcagcg ccagaggcag gatcgacccc ctggtgtacc tggacgagtt cctgaggaac    780
agcgagcccg tgctgaagag agtgaacagg accggcaaca gcagcagcaa caagcaggag    840
taccagctgc tgaaggacaa cctggtgcgc agctacaaca aggccctgaa gaagaacgcc    900
ccctacccca tcttcgctat caagaacggc cctaagagcc acatcggcag gcacctgatg    960
accagctttc tgagcatgaa gggcctgacc gagctgacaa acgtggtggg caactggagc   1020
gacaagaggg cctccgccgt ggccaggacc acctacaccc accagatcac cgccatcccc   1080
gaccactact tcgccctggt gtccaggtac tacgcctacg accccatcag caaggagatg   1140
atcgccctga aggacgagac caaccccatc gaggagtggc agcacatcga gcagctgaag   1200
ggcagcgccg agggcagcat cagatacccc gcctggaacg gcatcatcag ccaggaggtg   1260
ctggactacc tgagcagcta catcaacagg cggatctga                          1299
```

<210> SEQ ID NO 7

-continued

<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgcctaaga agaagaggaa ggtttctgag ctgattatta gtggttcatc tggtggattc 60
ctgcgaaaca tcggcaaaga gtatcaggag gccgctgaaa acttcatgag gtttatgaat 120
gaccaggggg cgtacgctcc taacactttg agggatttga ggttggtctt tcatagctgg 180
gccagatggt gccatgctcg gcagcttgca tggtttccaa ttagtcctga aatggcacgc 240
gaatactttc ttcagttgca cgatgcagac ctggcctcca ctaccatcga caagcactat 300
gctatgctta atatgcttct gtcccactgc ggactgccac ccttgtccga cgacaagtca 360
gtgagtcttg ccatgagaag aattagaaga gaagccgcaa ccgaaaaggg tgagaggaca 420
ggacaggcaa tccccctgcg ctgggacgac ctgaagctgc tggatgtgct gctcagcagg 480
agcgagcggc tggtcgacct gcgcaacagg gctttcctgt tcgtagccta taacaccctc 540
atgagaatgt ctgaaatatc acgcatcagg gttggggact tggatcagac aggagacaca 600
gtgaccctgc acatcagtca cactaagaca atcaccacag ctgcgggcct tgacaaagtg 660
ctctcccggc gaaccacagc agtgctcaat gactggctgg acgtcagtgg gcttagagaa 720
catccagacg ctgtgctctt cccacctata caccggtcaa acaaagcccg cattactacc 780
acgcccctga ccgcccctgc catggagaag attttcagtg atgcctgggt gctgctgaac 840
aaacgggacg ccacccccaa taaagggagg tataggacct ggaccggcca ttccgccagg 900
gtgggtgccg caatagacat ggccgagaaa caggtgtcta tggtcgagat tatgcaggaa 960
gggacatgga agaagcctga aacactgatg cggtatctca gaaggggcgg agtgtccgtg 1020
ggagccaatt ctcgactgat ggatagctaa 1050

<210> SEQ ID NO 8
<211> LENGTH: 1137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgcccaaga aaaagcggaa ggtgtccctg ctgaccacca acaaccacag cgtggccctg 60
agctacggcg agcctcctag caccctgaac gacagcctga aggacagcta ccagcggagc 120
accgatgagc tgcaggccct gctgtctaag cctctggccc agctgaccga cgccgacaag 180
ctgcggatca gagagatcac ccaggccaag ctgaagcact tcctggacaa cggccaccgg 240
accagaaggg ccaacacttg gagagccctg atgagcagat gggccaagtt cgagagctgg 300
tgcctgacca acaatctgac ccccctgcct gccacccctg aggtggtggc cacattcatc 360
gagtactacc aggccagcag ctacaccacc ctgagccagt atgcctgggc catcaacagc 420
tttcacgtgg aatgcggcct gctgagcccc gtgtctagca agaccgtgca ggacaagcag 480
aacgagatca gaatcgtgaa gctggaatct ggcggcctgg cccaggaaca ggccacccct 540
tttagactgc accatctgca gatgctgatc gagagctatg gcgagagcga gcggctgctg 600
gacaagagaa acctggctct gctgaatatc gcctacgaga gcctgctgcg cgagtccgag 660
ctgctgagaa tcaaagtggg ccacctgaag tccaccttcg agggcgacta cgtgctgagc 720
gtgccctaca ccaagaccaa cgacagcggc gaagaggaag tcgtgaacat cacccccctg 780
ggcttcaagc tgatccagcg gtacatccag ggcgctggcc tgacaaaaga ggactacctg 840
ttccagccca tcggccggtc caacaaggtg tccgtgcagg ccaaacccat gagcacccgg 900
accgtggaca gagtgttcct gtgggccttt gagagcctgg gcatcgacag acacagcgct 960
tggagcggcc acagcgccag aattggagcc gctcaggatc tgctggccgc tggctattct 1020
atcgcccaga tccaggaaaa cggccgctgg aagtccccca tgatggtgct gagatacggc 1080
aaggacatca aggccaaaga aagcgccatg gccaagatgc tggccgagcg gagatga 1137

<210> SEQ ID NO 9
<211> LENGTH: 1164
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
atgcccaaga aaaagcggaa agtgatcgag aaccagctga gcctgctggg cgacttttct 60
ggcgtgcggc ccgacgatgt gaaaaccgcc attcaggccg cccagaaaaa gggcatcaac 120
gtggccgaga acgagcagtt caaggccgcc ttcgagcatc tgctgaacga gttcaagaag 180
cgggaagaga gatacagccc caacaccctg cggcggctgg aaagcgcctg gacctgcttc 240
gtggattggt gcctggccaa ccacagacac agcctgcctg ccaccccga taccgtggaa 300 gccttcttca tcgagcgggc cgaggaactg caccggaaca ccctgagcgt gtacagatgg 360
gccatcagcc gggtgcacag agtggccgga tgccctgatc cctgcctgga catctacgtg 420
gaagatcggc tgaaggccat tgcccggaag aaagtgcggg aaggcgaggc cgtgaagcag 480
gccagccctt tcaacgagca gcatctgctg aagctgacca gcctgtggta cagaagcgac 540
aagctgctgc tgcggcggaa cctggctctg ctggctgtgg cctacgagag catgctgaga 600
gccagcgagc tggccaacat ccgggtgtcc gatatggaac tggccggcga cggaaccgcc 660
atcctgacca tccctatcac caagaccaac cactccggcg agcccgatac ctgcatcctg 720
tcccaggatg tggtgtccct gctgatggac tacaccgagg ccggcaagct ggatatgagc 780
agcgacggct tcctgttcgt gggcgtgtcc aagcacaaca cctgtatcaa gcccaagaag 840
gacaagcaga ccggcgaggt gctgcacaag cccatcacca ccaagacagt ggaaggcgtg 900
ttctacagcg cctgggagac actggacctg ggcagacagg gcgtgaagcc tttcacagcc 960
cacagcgcca gagtgggagc cgctcaggac ctgctgaaga agggctacaa taccctgcag 1020
atccagcagt ccggccggtg gtctagcgga gccatggtgg ccagatacgg cagagccatc 1080
ctggctaggg atggcgctat ggcccacagc agagtgaaaa ccagatccgc ccccatgcag 1140
tggggcaagg acgagaagga ctga 1164

<210> SEQ ID NO 10
<211> LENGTH: 1107
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10
atgcccaaga aaaagcggaa agtgaccgac ctgaccccat tccccccct ggaacacctg 60 gaacccgacg agtttgccga cctcgtgcgg aaggccatca agagggatcc tcaggctggc 120
gcccaccctg ccatccagtc tgccatcagc cacttccagg acgagttcgt gcggagacag 180
ggcgaatggc agcctgccac actgcagaga ctgagaaacg cctggaatgt gtttgtgcgg 240
tggtgcaccc accagggcat tccagctctg cctgccagac accaggacgt ggaaagatac 300
ctgatcgagc ggcggaacga gctgcaccgg aacaccctga aagtgcacct gtgggccatc 360
ggcaagaccc acgtgatcag cggcctgccc aatccctgcg cccacagata cgtgaaagcc 420
cagatggccc agatcacaca ccagaaagtg cgcgagagag agcggatcga acaggcccct 480
gccttcagag agtccgacct ggacagactg accgagctgt ggagcgccac cagaagcgtg 540
acccagcagc gggacctgat gatcgtgtcc ctggcctacg agacactgct gcggaagaac 600
aatctggaac agatgaaagt gggcgacatc gagttctgcc aggacggctc tgccctgatc 660
accatcccct tcagcaagac caaccacagc ggcagggatg acgtgcggtg gatctctccc 720
caggtggcca atcaggtgca cgcctacctg cagctgccca acatcgacgc cgacccccag 780
tgcttcctgc tgcagagagt gaagagaagc ggcaaggccc tgaaccccga gagccacaat 840
accctgaacg gccaccaccc cgtgtccgag aagctgatct cccgggtgtt cgagcgggct 900
tggagagccc tgaatcacga gacaggcccc agatacaccg gccacagcgc tagagtggga 960
gccgctcagg atctgctgca ggaaggctac agcaccctgc aagtgatgca ggcaggcggc 1020
tggtccagcg agaagatggt gctgagatac ggccggcatc tgcacgccca cacatctgcc 1080
atggctcaga aacggcggca gcggtga 1107

<210> SEQ ID NO 11
<211> LENGTH: 1728
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
atgcccaaga aaaagcggaa ggtgtccagc tacatggacc tggtggacga cgagcccgcc 60
accctgtacc acaagttcgt ggaatgcctg aaggccggcg agaacttctg cggcgataag 120
ctgagcggca tcatcaccat ggccattctg aaggccatca aggccctgac cgaagtgaag 180
aaaaccacct tcaacaagta caagaccacc atcaagcagg gcctgcagta cgacgtgggc 240
agcagcacca tcagcttcgt gtaccacctg aaggactgcg acgagctgag cagaggcctg 300
agcgacgcct tcgagcccta caagttcaag atcaagagca acaaagaggc caccagcttc 360
aagaccctgt tcaggggccc tagcttcggc agccagaaga actggcggaa gaaagaggtg 420
gaccgcgagg tggacaacct gttccacagc accgagacag acgagagcat cttcaagttc 480
atcctgaaca ccctggacag catcgaaacc cagaccaaca ccgaccggca gaaaaccgtg 540
ctgaccttta tcctgctgat gaccttcttc aactgctgcc ggaacaacga cctgatgaac 600
gtggacccca gcaccttcaa gatcgtgaag aacaagtttg tgggctacct gctgcaggct 660
gaagtgaagc agaccaagac cagaaagagc cggaatatct tcttcttccc catccgggaa 720
aaccgcttcg acctgttcct ggccctgcac gacttcttca gaacctgcca gcccaccccc 780
aagagcagac tgagcgatca ggtgtccgag cagaagtggc agctgttccg ggacagcatg 840
gtcatcgact acaaccggtt ctttcggaag ttccccgcca gccccatctt cgccattaag 900
cacggcccca agtcccacct gggccggcat ctgatgaaca gctttctgca caagaacgag 960

-continued

```
ctggacagct gggccaacag cctgggcaat tggagcagct cccagaacca gagagagagc   1020

ggcgccagac tgggctacac acacggcgga agagatctgc cccagcccct gtttggcttc   1080

ctggccggat actgcgtgcg gaacgaagag ggccacatcg tgggcctggg cctggaaaag   1140

gacatcaacg atctgttcga cggcatcatg gacccccctga acgagaaaga ggacaccgag   1200

atctgcgaga gctacggcga gtgggccaag attgtgtcca aggacgtgct gatcttcctg   1260

aagagatacc acagcaagaa cgcctgtcgg agataccaga acagcaccct gtatgcccgg   1320

accttcctga aaaccgagag cgtgaccctg agcggctcca agggcagcga ggaaccttct   1380

agccctgtgc ggatccccat cctgagcatg ggaaaggcca gcccctccga gggaagaaag   1440

ctgagagcca gcgagcacgc caacgacgac aacgagatcg agaagatcga cagcgacagc   1500

agccagagcg aagagatccc tatcgagatg agcgactccg aggacgagac aaccgccagc   1560

aacatcagcg gcatctacct ggacatgagc aaggccaact ccaacgtggt gtacagcccc   1620

cctagccaga caggcagagc tgctggcgcc ggaagaaaaa gaggcgtggg aggcagacgg   1680

accgtggaaa gcaagcggag aagagtgctg gcccccatca accggtga                1728
```

```
<210> SEQ ID NO 12
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

atgcccaaga aaaagcggaa ggtgtccacc ttcgccgagg ccgcccatct gacacctcac     60

cagtgcgcca acgagatcaa tgagatcctg gaaagcgaca ccttcaacat caacgccaaa    120

gagatccgga acaagctggc ctccctgttc agcatcctga ccatgcagag cctgagcatc    180

cgcagagaga tgaagatcaa cacctaccgg tcctacaaga gcgccatcgg caagagcctg    240

tccttcgaca aggacgacaa gatcatcaag ttcaccgtgc ggctgagaaa gaccgagagc    300

ctgcagaagg acatcgagag cgccctgccc agctacaagg tggtggtgtc ccattcaag     360

aaccaggaag tgtccctgtt cgaccgctac gaggaaaccc acaaatacga cgccagcatg    420

gtgggactgc agttcaccaa catcctgagc aaagagaagg atatctggaa gatcgtgtcc    480

cggatcgcct gcttcttcga ccagagctgc gtgaccacca ccaagcgggc cgagtacaga    540

ctgctgctgc tgggcgctgt gggcaactgc tgcagataca gcgacctgaa gaacctggac    600

ccccggacct tcgagatcta caacaacagc ttcctgggcc ccatcgtgcg ggccaccgtg    660

acagagacaa agagccggac cgagagatac gtgaacttct accccgtgaa cggcgactgc    720

gacctgctga tctccctgta cgactacctg agagtgtgca gccccatcga gaaaaccgtg    780

tccagcaacc ggcccaccaa ccagacccac cagtttctgc ctgagagcct ggccagaacc    840

ttcagccggt tcctgaccca gcacgtggac gagcccgtgt tcaagatctg gaacggcccc    900

aagagccact tcggcagaca cctgatggcc acctttctga gcagaagcga gaagggcaaa    960

tacgtgtcct ccctgggcaa ttgggctggc gaccgggaaa tccagtctgc cgtggccaga   1020

agccactaca gccacggctc tgtgaccgtg gacgaccggg tgttcgcctt catcagcggc   1080

ttctacaaag aggcccccct gggcagcgag atctatgtgc tgaaggaccc cagcaacaag   1140

cccctgagca gagaggaact gctggaagag gaaggcaaca gcctgggctc cccacctctg   1200

agccctccaa gctctcctag actggtggcc cagagcttca gcgcccaccc aagcctgcag   1260
```

ctgttcgagc agtggcacgg catcatcagc gacgaggtgc tgcagtttat cgccgagtac 1320
cggcggaagc acgagctgag aagccagaga accgtggtgg cctga 1365

<210> SEQ ID NO 13
<211> LENGTH: 1446
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
atgcccaaga aaaagcggaa ggtgtccgag ttcagcgagc tcgtgcggat cctgcccctg 60
gatcaggtgg ccgagatcaa gagaatcctg agcagaggcg accccatccc cctgcagaga 120
ctggcctctc tgctgaccat ggtcatcctg accgtgaaca tgagcaagaa gagaaagagc 180
agccccatca agctgagcac cttcaccaag taccggcgga acgtggccaa gagcctgtac 240
tacgacatga gcagcaagac cgtgttcttc gagtaccacc tgaagaacac ccaggacctg 300
caggaaggcc tggaacaggc cattgccccc tacaacttcg tcgtgaaagt gcacaagaag 360
cccatcgact ggcagaaaca gctgagcagc gtgcacgagc ggaaggccgg ccacagatcc 420
atcctgtcca acaacgtggg cgccgagatc tccaagctgg ccgagacaaa ggacagcacc 480
tggtccttca tcgagcggac catggacctg atcgaggcca gaaccagaca gcccaccacc 540
agagtggcct accggttcct gctgcagctg accttcatga actgctgccg ggccaacgat 600
ctgaagaacg ccgaccccag caccttccag atcattgccg atccccacct gggccggatc 660
ctgagagcct tcgtgcccga gactaagacc tctatcgagc ggtttatcta cttcttccca 720
tgcaagggcc gctgcgaccc tctgctggcc ctggattctt acctgctgtg ggtgggaccc 780
gtgcccaaga cccagaccac cgatgaggaa acccagtacg actaccagct gctgcaggac 840
accctgctga tctcttacga ccggtttatc gccaaagaga gcaaagagaa catcttcaag 900
atccccaacg gccccaaggc ccatctgggc agacatctga tggccagcta cctgggcaac 960
aacagcctga agtccgaggc caccctgtac ggcaattgga gcgtggaaag acaggaaggc 1020
gtgtccaaaa tggccgacag ccggtacatg cacaccgtga agaagtcccc cccctcctac 1080
ctgttcgcct ttctgagcgg ctactacaag aagtccaacc agggcgagta cgtgctggcc 1140
gaaaccctgt acaacccccct ggactacgat aagaccctgc ccatcaccac caacgagaag 1200
ctgatctgca gacgctacgg caagaacgcc aaagtgatcc ccaaggatgc cctgctgtac 1260
ctgtacacct acgcccagca gaagcggaag cagctggctg accccaacga gcagaaccgg 1320
ctgttcagca gcgagagccc tgcccaccca tttctgaccc ctcagagcac aggcagcagc 1380
acccctctga catggaccgc ccctaagaca ctgagcaccg gcctgatgac ccctggcgag 1440
gaatga 1446

<210> SEQ ID NO 14
<211> LENGTH: 1494
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14
atgcccaaga aaaagcggaa ggtgcagctg accaaggaca ccgagatcag caccatcaac 60
cggcagatga gcgacttcag cgagctgagc cagatcctgc ccctgcacca gatctccaag 120

```
atcaaggaca tcctggaaaa cgagaacccc ctgcccaaag agaagctggc ctcccacctg    180

accatgatca tcctgatggc caacctggcc agccagaaac ggaaggacgt gcccgtgaag    240

cggagcacct tcctgaagta ccagcggagc atcagcaaga ccctgcagta cgacagcagc    300

accaagaccg tgtccttcga gtaccacctg aaggacccca gcaagctgat caagggcctg    360

gaagatgtgg tgtcccccta cagattcgtc gtgggcgtgc acgagaagcc cgacgacgtg    420

atgtctcacc tgagcgccgt gcacatgcgg aaagaggccg gcagaaagcg ggacctgggc    480

aacaagatca acgacgagat cacaaagatc gccgagacac aggaaaccat ctggggcttc    540

gtgggcaaga ccatggacct gatcgaggcc agaaccaccc ggcctacaac aaaggccgcc    600

tacaacctgc tgctgcaggc caccttcatg aactgctgca gagccgacga cctgaagaac    660

accgacatca agaccttcga agtgatcccc gacaagcacc tgggccggat gctgagagcc    720

ttcgtgcccg agacaaagac cggaaccaga ttcgtgtact tcttcccatg caagggcaga    780

tgcgaccccc tgctggccct ggattcttac ctgcagtgga ccgaccccat ccccaagacc    840

agaacaaccg acgaggacgc cagatacgac taccagctgc tgcggaacag cctgctgggc    900

agctacgacg gcttcatctc caagcagagc gacgagagca tcttcaagat ccccaacggc    960

cccaaggccc acctgggcag acatgtgaca gccagctacc tgagcaacaa cgagatggac   1020

aaagaggcca ccctgtacgg caattggagc gccgctagag aagagggcgt gtccagagtg   1080

gccaaggccc ggtacatgca caccatcgag aagtcccccc cctcctacct gttcgccttc   1140

ctgagcggct tctacaacat caccgccgag agggcctgcg agctggtgga ccccaatagc   1200

aacccctgcg agcaggacaa gaacatcccc atgatcagcg acatcgagac actgatggct   1260

cgctacggca agaacgccga gatcatccct atggacgtgc tggtgttcct gagcagctac   1320

gcccggttca agaacaacga gggcaaagag tacaagctgc aggctcggag cagcagaggc   1380

gtgcccgact tccccgataa tggcagaacc gccctgtaca acgccctgac agccgcccac   1440

gtgaagaggc ggaagatcag cattgtcgtg ggccggtcca tcgacaccag ctga         1494
```

<210> SEQ ID NO 15
<211> LENGTH: 1839
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
atgcctaaga aaaagcggaa agtggatacc tacgccggag cctacgacag acagagccgg     60

gagagagaga acagcagcgc cgccagcccc gccacccaga gaagcgccaa cgaggataag    120

gccgccgatc tgcagagaga ggtggagagg gacggcggca gattcagatt tgtgggccac    180

ttcagcgagg cccctggcac cagcgccttc ggcaccgccg agagacccga gttcgagaga    240

atcctgaacg agtgtagggc cggcaggctg aacatgatca tcgtgtacga cgtgtcccgg    300

ttcagcaggc tgaaggtgat ggacgccatc cctatcgtgt ccgagctgct ggccctgggc    360

gtgaccatcg tgtccaccca ggaaggcgtc tttagacagg gcaacgtgat ggacctgatc    420

cacctgatca tgaggctgga cgccagccac aaggagagca gcctgaagag cgccaagatc    480

ctggacacca agaacctgca gagggagctg ggcggctatg tgggcggcaa ggcccccctac    540

ggcttcgagc tggtgtccga gaccaaggag atcacccgga acggcaggat ggtgaacgtg    600

gtgatcaaca agctggccca cagcaccacc cccctgaccg gccccttcga gtttgagccc    660
```

gacgtgatca ggtggtggtg gcgggagatc aagacccaca agcacctgcc tttcaagccc 720
ggcagccagg ccgccatcca ccccggcagc atcaccggcc tgtgtaagag aatggacgcc 780
gacgccgtgc ccaccagagg cgagaccatc ggcaagaaaa ccgccagcag cgcctgggac 840
cccgccaccg tgatgagaat cctgagggac cctaggatcg ccggcttcgc cgccgaggtg 900
atctacaaga agaagcccga cggcaccccc accaccaaga tcgagggcta cagaatccag 960
agagacccca tcaccctgag acctgtggag ctggactgtg gccctatcat cgagcctgcc 1020
gagtggtacg agctgcaggc ctggctggac ggcagaggca gaggcaaggg cctgagcaga 1080
ggccaggcca tcctgagcgc catggacaag ctgtactgtg agtgtggcgc cgtgatgacc 1140
agcaagagag gcgaggagag catcaaggac agctaccggt gccggagaag aaaggtggtg 1200
gaccccagcg cccctggcca gcacgagggc acctgtaatg tgagcatggc cgccctggac 1260
aagttcgtgg ccgagcggat cttcaacaag atccggcacg ccgagggcga cgaggagacc 1320
ctggccctgc tgtgggaggc cgccagaaga ttcggcaagc tgaccgaggc ccccgagaag 1380
agcggcgaga gggccaacct ggtggccgag agagccgacg ccctgaacgc cctggaggag 1440
ctgtacgagg acagagccgc cggagcctat gacggccctg tgggcaggaa gcacttcaga 1500
aagcagcagg ccgccctgac cctgagacag cagggcgccg aggaaagact ggccgagctg 1560
gaggccgccg aggcccctaa gctgcccctg gatcagtggt tccccgagga tgccgacgcc 1620
gaccccaccg gccccaagtc ctggtggggc agagccagcg tggacgacaa gagggtgttc 1680
gtgggcctgt tcgtggataa gatcgtggtg accaagagca ccaccggcag gggccagggc 1740
acccccatcg agaagagagc cagcatcacc tgggccaagc ctcccaccga cgacgacgag 1800
gatgacgccc aggacggcac cgaggacgtg gccgcctga 1839

<210> SEQ ID NO 16
<211> LENGTH: 1530
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16
atggatccta agaaaaagcg aaaagtgatg cgagccctgg tggtcattcg cctgagcaga 60
gtcacagacg ctactacaag ccctgagcgg cagctggagt cctgtcagca gctgtgcgca 120
cagcgaggat gggatgtggt cggagtggca gaggatctgg acgtgagcgg ggctgtcgat 180
ccattcgacc gaaagcggag acccaacctg gcacgatggc tggctttcga ggaacagccc 240
tttgatgtga tcgtcgccta cagagtggac aggctgacac gctcaattcg acatctgcag 300
cagctggtgc attgggccga ggatcacaag aaactggtgg tcagcgcaac tgaagcccac 360
ttcgacacca caactccttt tgccgctgtg gtcatcgcac tgatgggcac cgtggcccag 420
atggagctgg aagctatcaa ggagcgaaac cggagcgcag cccatttcaa tattcgggcc 480
gggaaataca gaggcagcct gccccccttgg ggctatctgc ctacccgggt ggatggggag 540
tggagactgg tgccagaccc cgtccagaga gagaggattc tggaagtgta ccacagagtg 600
gtggacaacc acgaaccact gcatctggtg gcccacgatc tgaataggcg cggagtcctg 660
tctccaaagg actattttgc tcagctgcag ggaagggagc cacagggacg agaatggagt 720
gctaccgcac tgaagcggtc tatgatcagt gaggctatgc tgggctatgc aactctgaat 780
gggaaaaccg tgagagacga tgacggagca ccactggtgc gggctgagcc tattctgaca 840
agagagcagc tggaagctct gagggcagaa ctggtgaaaa ccagtagggc caagcctgct 900
gtgtcaacac caagcctgct gctgcgagtg ctgttctgcg cagtctgtgg cgagccagca 960
tacaaatttg ccggcggggg aaggaagcat ccccgctatc gatgccggag catggggttc 1020
cctaagcact gtggaaacgg cactgtggct atggccgaat gggacgcctt ttgtgaggaa 1080
caggtgctgg atctgctggg ggacgcagag cgcctggaaa aagtgtgggt cgctggaagc 1140
gattccgctg tggagctggc agaagtcaat gccgagctgg tggacctgac ctccctgatc 1200
ggatctcctg catacaggc aggctcccca cagcgagaag ctctggatgc acgaattgct 1260
gcactggcag ctcgacagga ggaactggag gggctggaag ccagaccctc tggatgggag 1320
tggcgagaaa caggccagcg gtttggggat tggtggaggg agcaggacac agcagccaag 1380
aacacttggc tgagatccat gaatgtcagg ctgactttcg acgtgcgagg aggactgacc 1440
cgaacaatcg attttggcga cctgcaggag tatgaacagc atctgcgcct gggaagtgtg 1500
gtcgagcgac tgcacaccgg catgtcataa 1530

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
ataacttcgt atagcataca ttatacgaag ttat 34

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
ataacttcgt ataggatacc ttatacgaag ttat 34

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
ataacttcgt atagtatacc ttatacgaag ttat 34

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
gaagttccta ttctctagaa agtataggaa cttc 34

<210> SEQ ID NO 21

<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
gaagttccta ttcttcaaat agtataggaa cttc 34

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
gaagttccta ttctatcaga agtataggaa cttc 34

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
taactttaaa taattggcat tatttaaagt ta 32

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
tcaatttctg agaactgtca ttctcggaaa ttga 34

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
tcaatttctg agaagtgtct ttctcggaaa ttga 34

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
ctcgtgtccg ataactgtaa ttatcggaca tgat 34

<210> SEQ ID NO 27
<211> LENGTH: 34

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
ctcgtgtccg ataactgtaa ttatcggaca cgag 34

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
ctcgtgtccg ataagtgtat ttatcggaca tgat 34

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
aataggtctg agaacgccca ttctcagacg tatt 34

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
ggttgcttaa gaataagtaa ttcttaagca acc 33

<210> SEQ ID NO 31
<211> LENGTH: 61
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
aaacgatatc agacatttgt ctgataatgc ttcattatca gacaaatgtc tgatatcgtt 60
t 61

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
gagtttcatt aaggaataac taattcccta atgaaactc 39

<210> SEQ ID NO 33

<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
ttgatgaaag aataacgtat tctttcatca a 31

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
tgcgggtgcc agggcgtgcc cttgggctcc ccgggcgcgt actcc 45

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
gtgccccaac tggggtaacc tttgagttct ctcagttggg gg 42

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
tcggccggct tgtcgacgac ggcggtctcc gtcgtcagga tcatccgggc 50

<210> SEQ ID NO 37
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
tcgtggtttg tctggtcaac caccgcggtc tcagtggtgt acggtacaaa ccc 53

<210> SEQ ID NO 38
<211> LENGTH: 286
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38
aagaaaccaa ttgtccatat tgcatcagac attgccgtca ctgcgtcttt tactggctct 60
tctcgctaac caaaccggta accccgctta ttaaaagcat tctgtaacaa agcgggacca 120
aagccatgac aaaaacgcgt aacaaaagtg tctataatca cggcagaaaa gtccacattg 180
attatttgca cggcgtcaca ctttgctatg ccatagcatt tttatccata agattagcgg 240
atcctacctg acgcttttta tcgcaactct ctactgtttc tccata 286

<210> SEQ ID NO 39
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
acctgtagga tcgtacaggt ttacgcaaga aaatggtttg ttatagtcga ataaa 55

<210> SEQ ID NO 40
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
aatttgggga tcgtacaggt ttacgcaaga aaatggtttg ttatagtcga ataaa 55

<210> SEQ ID NO 41
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
ctggcgggga tcgtacaggt ttacgcaaga aaatggtttg ttatagtcga ataaa 55

<210> SEQ ID NO 42
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
tggggtagga tcgtacaggt ttacgcaaga aaatggtttg ttatagtcga ataaa 55

<210> SEQ ID NO 43
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
gcatgctccc tatcagtgat agagattgac atccctatca gtgatagaga tactgagcac 60
atcagcagga cgcactgacc agga 84

<210> SEQ ID NO 44
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
ccatcgaatg gctgaaatga gctgttgaca attaatcatc cggctcgtat aatgtgtgga 60
attgtgagcg gataacaatt tcacacagga 90

<210> SEQ ID NO 45
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
ataaatgtga gcggataaca ttgacattgt gagcggataa caagatactg agcactcagc 60
aggacgcact gacc 74

<210> SEQ ID NO 46
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
aaaatttatc aaaaagagtg ttgacttgtg agcggataac aatgatactt agattcaatt 60
gtgagcggat aacaatttca caca 84

<210> SEQ ID NO 47
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 47
catagcattt ttatccataa gattagcgga tcctaagctt tacaattgtg agcgctcaca 60
attatgatag attcaattgt gagcggataa caatttcaca ca 102

<210> SEQ ID NO 48
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48
gcatgcacag ataaccatct gcggtgataa attatctctg gcggtgttga cataaatacc 60
actggcggtt ataatgagca catcagcagg gtatgcaaag ga 102

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49

-continued gtttatacat aggcgagtac tctgttatgg 30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
agaggttcca actttcacca taatgaaaca 30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 51
taaacaacta acggacaatt ctacctaaca 30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 52
acatcaagcc aaattaaaca ggattaacac 30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 53
gaggtaaaat agtcaacacg cacggtgtta 30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 54
caggccggaa taactcccta taatgcgcca 30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
ggctagctca gtcctaggta cagtgctagc 30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 56
agctagctca gtcctaggta ttatgctagc 30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 57
agctagctca gtcctaggta ctgtgctagc 30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 58
agctagctca gtcctaggga ttatgctagc 30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
agctagctca gtcctaggta ttgtgctagc 30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 60
ggctagctca gtcctaggta ctatgctagc 30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 61
ggctagctca gtcctaggta tagtgctagc 30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 62
ggctagctca gccctaggta ttatgctagc 30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
agctagctca gtcctaggta taatgctagc 30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
agctagctca gtcctaggga ctgtgctagc 30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
ggctagctca gtcctaggta caatgctagc 30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
ggctagctca gtcctaggta tagtgctagc 30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
agctagctca gtcctaggga ttatgctagc 30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
ggctagctca gtcctaggga ttatgctagc 30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 69
ggctagctca gtcctaggta caatgctagc 30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 70
agctagctca gcccttggta caatgctagc 30

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
agctagctca gtcctaggga ctatgctagc 30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
agctagctca gtcctaggga ttgtgctagc 30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
ggctagctca gtcctaggta ttgtgctagc 30

<210> SEQ ID NO 74

<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
agctagctca gtcctaggta taatgctagc 30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
ggctagctca gtcctaggta ttatgctagc 30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
ggctagctca gtcctaggta caatgctagc 30

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
aaagtgtgac gccgtgcaaa taatcaatgt 30

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
gacgaatact taaaatcgtc atacttattt 30

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
aaacctttcg cggtatggca tgatagcgcc 30

<210> SEQ ID NO 80
<211> LENGTH: 30

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
tgatagcgcc cggaagagag tcaattcagg 30

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
ttatttaccg tgacgaacta attgctcgtg 30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
catacgccgt tatacgttgt ttacgctttg 30

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
ttatgcttcc ggctcgtatg ttgtgtggac 30

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
ttatgcttcc ggctcgtatg gtgtgtggac 30

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 85
atatatatat atatataatg gaagcgtttt 30

<210> SEQ ID NO 86
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 86
atatatatat atatataatg gaagcgtttt 30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87
ccccgaaagc ttaagaatat aattgtaagc 30

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
ccccgaaagc ttaagaatat aattgtaagc 30

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
tgacaatata tatatatata taatgctagc 30

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
acaatatata tatatatata taatgctagc 30

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
aatatatata tatatatata taatgctagc 30

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
tatatatata tatatatata taatgctagc 30

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
tatatatata tatatatata taatgctagc 30

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
aaaaaaaaaa aaaaaaaata taatgctagc 30

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
aaaaaaaaaa aaaaaaaata taatgctagc 30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
caccttcggg tgggcctttc tgcgtttata 30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 97
caccttcggg tgggcctttc tgcgtttata 30

<210> SEQ ID NO 98
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 98
caccttcggg tgggcctttc tgcgtttata 30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
caccttcggg tgggcctttc tgcgtttata 30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ggctagctca gtcctaggta cagtgctagc 30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgctagctac tagagattaa agaggagaaa 30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
cctgttttta tgttattctc tctgtaaagg 30

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaatatttgc ttatacaatc ttcctgtttt 30

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
gctgataaac cgatacaatt aaaggctcct 30

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 105
ctcttctcag cgtcttaatc taagctatcg 30

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 106
atgagccagt tcttaaaatc gcataaggta 30

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
ctattgattg tgacaaaata aacttattcc 30

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 108
gtttcgcgct tggtataatc gctgggggtc 30

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
ctttgcttct gactataata gtcagggtaa 30

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
aaaccgatac aattaaaggc tcctgctagc 30

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
gccggaataa ctccctataa tgcgccacca 30

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
gccggaataa ctccctataa tgcgccacca 30

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
ttgacaagct tttcctcagc tccgtaaact 30

<210> SEQ ID NO 114
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
ttgacagcta gctcagtcct aggtataatg ctagc 35

<210> SEQ ID NO 115
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
ttgacggcta gctcagtcct aggtacagtg ctagc 35

<210> SEQ ID NO 116
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
tttacagcta gctcagtcct aggtattatg ctagc 35

<210> SEQ ID NO 117
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
ttgacagcta gctcagtcct aggtactgtg ctagc 35

<210> SEQ ID NO 118
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 118
ctgatagcta gctcagtcct agggattatg ctagc 35

<210> SEQ ID NO 119
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119
ttgacagcta gctcagtcct aggtattgtg ctagc 35

<210> SEQ ID NO 120
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
tttacggcta gctcagtcct aggtactatg ctagc 35

<210> SEQ ID NO 121
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
tttacggcta gctcagtcct aggtatagtg ctagc 35

<210> SEQ ID NO 122
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
tttacggcta gctcagccct aggtattatg ctagc 35

<210> SEQ ID NO 123
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
ctgacagcta gctcagtcct aggtataatg ctagc 35

<210> SEQ ID NO 124
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
tttacagcta gctcagtcct agggactgtg ctagc 35

<210> SEQ ID NO 125
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
tttacggcta gctcagtcct aggtacaatg ctagc 35

<210> SEQ ID NO 126
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
ttgacggcta gctcagtcct aggtatagtg ctagc 35

<210> SEQ ID NO 127
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127
ctgatagcta gctcagtcct agggattatg ctagc 35

<210> SEQ ID NO 128
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
ctgatggcta gctcagtcct agggattatg ctagc 35

<210> SEQ ID NO 129
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 129
tttatggcta gctcagtcct aggtacaatg ctagc 35

<210> SEQ ID NO 130
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 130
tttatagcta gctcagccct tggtacaatg ctagc 35

<210> SEQ ID NO 131
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 131
ttgacagcta gctcagtcct agggactatg ctagc 35

<210> SEQ ID NO 132
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 132
ttgacagcta gctcagtcct agggattgtg ctagc 35

<210> SEQ ID NO 133
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 133
ttgacggcta gctcagtcct aggtattgtg ctagc 35

<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 134
ggtttcaaaa ttgtgatcta tatttaacaa 30

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 135
ggtttcaaaa ttgtgatcta tatttaacaa 30

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
tctattccaa taaagaaatc ttcctgcgtg 30

<210> SEQ ID NO 137
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
aaaaatgggc tcgtgttgta caataaatgt 30

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 138
aaaaaaagcg cgcgattatg taaaatataa 30

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
atccttatcg ttatgggtat tgtttgtaat 30

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
taaaagaatt gtgagcggga atacaacaac 30

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 141
aaaaaaagcg cgcgattatg taaaatataa 30

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 142
tacaaaataa ttcccctgca aacattatca 30

<210> SEQ ID NO 143
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 143
tacaaaataa ttcccctgca aacattatcg 30

<210> SEQ ID NO 144
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
agggaataca agctacttgt tctttttgca 30

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 145
taatacgact cactataggg aga 23

<210> SEQ ID NO 146
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
gaatttaata cgactcacta tagggaga 28

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 147
taatacgact cactatagg 19

<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
gagtcgtatt aatacgactc actatagggg 30

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
agtgagtcgt actacgactc actatagggg 30

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
gagtcgtatt aatacgactc tctatagggg 30

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
taatacgact cactataggg aga 23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
ttatacgact cactataggg aga 23

<210> SEQ ID NO 153

<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 153
gaatacgact cactataggg aga 23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 154
taatacgtct cactataggg aga 23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 155
tcatacgact cactataggg aga 23

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 156
taatacgact cactataggg agaccacaac 30

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 157
taattgaact cactaaaggg agaccacagc 30

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 158
cgaagtaata cgactcacta ttagggaaga 30

<210> SEQ ID NO 159
<211> LENGTH: 22

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 159
attaaccctc actaaaggga ga 22

<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 160
atttaggtga cactataga 19

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 161
acaaacacaa atacacacac taaattaata 30

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 162
ccaagcatac aatcaactat ctcatataca 30

<210> SEQ ID NO 163
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 163
gatacaggat acagcggaaa caacttttaa 30

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 164
tttcaagcta taccaagcat acaatcaact 30

<210> SEQ ID NO 165
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 165
cctttgcagc ataaattact atacttctat 30

<210> SEQ ID NO 166
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 166
cctttgcagc ataaattact atacttctat 30

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 167
cctttgcagc ataaattact atacttctat 30

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 168
cctttgcagc ataaattact atacttctat 30

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 169
cctttgcagc ataaattact atacttctat 30

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 170
ttatctactt tttacaacaa atataaaaca 30

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
acaaacacaa atacacacac taaattaata                                    30

<210> SEQ ID NO 172
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gtttcgaata aacacacata aacaaacaaa                                    30

<210> SEQ ID NO 173
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
accatcaaag gaagctttaa tcttctcata                                    30

<210> SEQ ID NO 174
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
agaacccact gcttactggc ttatcgaaat                                    30

<210> SEQ ID NO 175
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ggccgttttt ggcttttttg ttagacgaag                                    30

<210> SEQ ID NO 176
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tgttatagtc gaatacctct ggcggtgata                                    30

<210> SEQ ID NO 177
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 177
ttttggtaca ctccctatca gtgatagaga 30

<210> SEQ ID NO 178
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ctttttggta cactacctct ggcggtgata 30

<210> SEQ ID NO 179
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tacgcaagaa aatggtttgt tatagtcgaa 30

<210> SEQ ID NO 180
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cgtgcgtgtt gataacaccg tgcgtgttga 30

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
agattgtact aaatcgtata atgacagtga 30

<210> SEQ ID NO 182
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
gtgttgatgc ttttatcacc gccagtggta 30

<210> SEQ ID NO 183
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 183
agtgtgtgga attgtgagcg gataacaatt 30

<210> SEQ ID NO 184
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 184
acatcttaaa agttttagta tcatattcgt 30

<210> SEQ ID NO 185
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 185
tacgcaagaa aatggtttgt tatagtcgaa 30

<210> SEQ ID NO 186
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 186
atcctccttt agtcttcccc ctcatgtgtg 30

<210> SEQ ID NO 187
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 187
taaaattatg aaatttgcat aaattcttca 30

<210> SEQ ID NO 188
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 188
gtgttgacta ttttacctct ggcggtgata 30

<210> SEQ ID NO 189
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 189
gaaatctggc agtttttggt acacgaaagc 30

<210> SEQ ID NO 190
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 190
acaccgtgcg tgttgatata gtcgaataaa 30

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 191
aaaattatga aatttgtata aattcttcag 30

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 192
ggttcttttt ggtacctctg gcggtgataa 30

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 193
tgtaggatcg tacaggtata aattcttcag 30

<210> SEQ ID NO 194
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 194
caagaaaatg gtttgttata gtcgaataaa 30

<210> SEQ ID NO 195
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 195
ctatctcatt tgctagtata gtcgaataaa 30

<210> SEQ ID NO 196
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 196
tagtttataa tttaagtgtt ctttaatttc 30

<210> SEQ ID NO 197
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 197
caccttcggg tgggcctttc tgcgtttata 30

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 198
aataactctg atagtgctag tgtagatctc 30

<210> SEQ ID NO 199
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 199
caccttcggg tgggcctttc tgcgtttata 30

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 200
caccttcggg tgggcctttc tgcgtttata 30

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 201
ttgacacctg taggatcgta caggtataat 30

<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 202
caagaaaatg gtttgttata gtcgaataaa 30

<210> SEQ ID NO 203
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 203
cacgcaaaac ttgcgacaaa caataggtaa 30

<210> SEQ ID NO 204
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 204
gttagctttc gaattggcta aaaagtgttc 30

<210> SEQ ID NO 205
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 205
ccattctgct ttccacgaac ttgaaaacgc 30

<210> SEQ ID NO 206
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 206
ggccgcgggt tctttttggt acacgaaagc 30

<210> SEQ ID NO 207
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 207
aagaaaatgg tttgttgata ctcgaataaa 30

<210> SEQ ID NO 208
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 208
gaaaaccttg tcaatgaaga gcgatctatg 30

<210> SEQ ID NO 209
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 209
ttctcgttcg actcatagct gaacacaaca 30

<210> SEQ ID NO 210
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 210
atgacaaaat tgtcat 16

<210> SEQ ID NO 211
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 211
accaatgctg ggaacggcca gggcacctaa 30

<210> SEQ ID NO 212
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 212
ctgaaagcgc ataccgctat ggagggggtt 30

<210> SEQ ID NO 213
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 213
tagatatgcc tgaaagcgca taccgctatg 30

<210> SEQ ID NO 214
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 214
agggaataca agctacttgt tctttttgca 30

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215
taatacgact cactataggg aga 23

<210> SEQ ID NO 216
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 216
gaatttaata cgactcacta tagggaga 28

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 217
taatacgact cactatagg 19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 218
atttaggtga cactataga 19

<210> SEQ ID NO 219
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 219
gagtcgtatt aatacgactc actatagggg 30

<210> SEQ ID NO 220
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 220
agtgagtcgt actacgactc actatagggg 30

<210> SEQ ID NO 221
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 221
gagtcgtatt aatacgactc tctatagggg 30

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 222
taatacgact cactataggg aga 23

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 223
ttatacgact cactataggg aga 23

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 224
gaatacgact cactataggg aga 23

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 225
taatacgtct cactataggg aga 23

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 226
tcatacgact cactataggg aga 23

<210> SEQ ID NO 227
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 227
ataggggaat tgtgagcgga taacaattcc 30

<210> SEQ ID NO 228
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 228
ataggggaat tgtgagcgga taacaattcc 30

<210> SEQ ID NO 229
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 229
ataggggaat tgtgagcgga taacaattcc 30

<210> SEQ ID NO 230
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 230
ataggggaat tgtgagcgga taacaattcc 30

<210> SEQ ID NO 231
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 231
taatacgact cactataggg agaccacaac 30

<210> SEQ ID NO 232

<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 232
taattgaact cactaaaggg agaccacagc 30

<210> SEQ ID NO 233
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 233
cgaagtaata cgactcacta ttagggaaga 30

<210> SEQ ID NO 234
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 234
ttgtgagcgg ataacaagat actgagcaca 30

<210> SEQ ID NO 235
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 235
ttgtgagcgg ataacaattc tgaagaacaa 30

<210> SEQ ID NO 236
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 236
ttgtgagcgg ataacaattc tgataaaaca 30

<210> SEQ ID NO 237
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 237
ttgtgagcgg ataacatcta accctttaga 30

<210> SEQ ID NO 238
<211> LENGTH: 30

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 238
ttgtgagcgg ataacatagc agataagaaa 30

<210> SEQ ID NO 239
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 239
gtttgagcga gtaacgccga aaatcttgca 30

<210> SEQ ID NO 240
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 240
gtgtgagcga gtaacgacga aaatcttgca 30

<210> SEQ ID NO 241
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 241
tttgagcgag taacagccga aaatcttgca 30

<210> SEQ ID NO 242
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 242
tgtgagcgag taacagccga aaatcttgca 30

<210> SEQ ID NO 243
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 243
ttgtgagcga gtggcaccat taagtacgta 30

<210> SEQ ID NO 244
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 244
ttgtgagcga gtgacaccat taagtacgta 30

<210> SEQ ID NO 245
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 245
ttgtgagcga gtaacaccat taagtacgta 30

<210> SEQ ID NO 246
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 246
ttgtgagcga gtaacaccat taagtacgta 30

<210> SEQ ID NO 247
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 247
cagtgagcga gtaacaacta cgctgtttta 30

<210> SEQ ID NO 248
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 248
cagtgagcga gtaacaacta cgctgtttta 30

<210> SEQ ID NO 249
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 249
atgtgagcgg ataacactat aattaataga 30

<210> SEQ ID NO 250
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 250
atgtgagcgg ataacactat aattaataga 30

<210> SEQ ID NO 251
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 251
gaattgtgag cggataacaa ttggatccgg 30

<210> SEQ ID NO 252
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 252
ggaattgtga gcgctcacaa ttggatccgg 30

<210> SEQ ID NO 253
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 253
ggaattgtaa gcgcttacaa ttggatccgg 30

<210> SEQ ID NO 254
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 254
ggaattgtaa acgtttacaa ttggatccgg 30

<210> SEQ ID NO 255
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 255
ggaattgtga acgttcacaa ttggatccgg 30

<210> SEQ ID NO 256
<211> LENGTH: 30
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 256
ggaattttga gcgctcaaaa ttggatccgg 30

<210> SEQ ID NO 257
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 257
ggaattatga gcgctcataa ttggatccgg 30

<210> SEQ ID NO 258
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 258
gggacgactg tatacagtcg tcggatccgg 30

<210> SEQ ID NO 259
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 259
ggaattgtga gcgcttacaa ttggatccgg 30

<210> SEQ ID NO 260
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 260
ggaattgtga gcgctcataa ttggatccgg 30

<210> SEQ ID NO 261
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 261
ggaattgtga gctacagtcg tcggatccgg 30

<210> SEQ ID NO 262
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 262
ggaattgtaa gcgctcacaa ttggatccgg 30

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 263
ggaattgtaa gcgttcacaa ttggatccgg 30

<210> SEQ ID NO 264
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 264
ggaattgtaa gcgctcataa ttggatccgg 30

<210> SEQ ID NO 265
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 265
ggaattgtaa gctacagtcg tcggatccgg 30

<210> SEQ ID NO 266
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 266
ggaattgtga acgctcataa ttggatccgg 30

<210> SEQ ID NO 267
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 267
ggaattgtga actacagtcg tcggatccgg 30

<210> SEQ ID NO 268
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 268
ggaattatga gcgctcacaa ttggatccgg 30

<210> SEQ ID NO 269
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 269
ggaattgtga gcgctcataa ttggatccgg 30

<210> SEQ ID NO 270
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 270
ggaattgtga gctacagtcg tcggatccgg 30

<210> SEQ ID NO 271
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 271
ggaattgtga acgctcataa ttggatccgg 30

<210> SEQ ID NO 272
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 272
ggaattgtga actacagtcg tcggatccgg 30

<210> SEQ ID NO 273
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 273
taaattgtga acgctcataa ttggatccgg 30

<210> SEQ ID NO 274
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 274
gaaattgtaa gcgcttacaa ttggatccgg 30

<210> SEQ ID NO 275
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 275
gaaattgtaa gcgcttacaa ttggatccgg 30

<210> SEQ ID NO 276
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 276
ggaattgtaa gcgcttacaa ttggatccgg 30

<210> SEQ ID NO 277
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 277
gccaaattaa acaggattaa caggatccgg 30

<210> SEQ ID NO 278
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 278
gccaaattaa acaggattaa caggatccgg 30

<210> SEQ ID NO 279
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 279
gccaaattaa acaggattaa caggatccgg 30

<210> SEQ ID NO 280
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 280
gccaaattaa acaggattaa caggatccgg 30

<210> SEQ ID NO 281
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 281
gccaaattaa acaggattaa caggatccgg 30

<210> SEQ ID NO 282
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 282
gccaaattaa acaggattaa caggatccgg 30

<210> SEQ ID NO 283
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 283
gccaaattaa acaggattaa caggatccgg 30

<210> SEQ ID NO 284
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 284
gaaattgtaa gcgcttacaa ttggatccgg 30

<210> SEQ ID NO 285
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 285
taaattgtaa gcgcttacaa ttggatccgg 30

<210> SEQ ID NO 286
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 286
gtaattgtaa gcgcttacaa ttggatccgg 30

<210> SEQ ID NO 287
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 287
tcaattgtaa gcgcttacaa ttggatccgg 30

<210> SEQ ID NO 288
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 288
aaaattgtaa gcgcttacaa ttggatccgg 30

<210> SEQ ID NO 289
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 289
caaattgtaa gcgcttacaa ttggatccgg 30

<210> SEQ ID NO 290
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 290
gaaattgtaa gcgcttacaa ttggatccgg 30

<210> SEQ ID NO 291
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 291
taaattgtaa gcgcttacaa ttggatccgg 30

<210> SEQ ID NO 292
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 292
gtaattgtaa gcgcttacaa ttggatccgg 30

<210> SEQ ID NO 293
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
tcaattgtaa gcgcttacaa ttggatccgg 30

<210> SEQ ID NO 294
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
aaaattgtaa gcgcttacaa ttggatccgg 30

<210> SEQ ID NO 295
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
caaattgtaa gcgcttacaa ttggatccgg 30

<210> SEQ ID NO 296
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
gaaattgtaa gcgcttacaa ttggatccgg 30

<210> SEQ ID NO 297
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
taaattgtaa gcgcttacaa ttggatccgg 30

<210> SEQ ID NO 298
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gtaattgtaa gcgcttacaa ttggatccgg 30

<210> SEQ ID NO 299
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 299
tcaattgtaa gcgcttacaa ttggatccgg 30

<210> SEQ ID NO 300
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 300
aaaattgtaa gcgcttacaa ttggatccgg 30

<210> SEQ ID NO 301
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 301
caaattgtaa gcgcttacaa ttggatccgg 30

<210> SEQ ID NO 302
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 302
gaaattgtaa gcgcttacaa ttggatccgg 30

<210> SEQ ID NO 303
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 303
taaattgtaa gcgcttacaa ttggatccgg 30

<210> SEQ ID NO 304
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 304
gtaattgtaa gcgcttacaa ttggatccgg 30

<210> SEQ ID NO 305
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 305
tcaattgtaa gcgcttacaa ttggatccgg 30

<210> SEQ ID NO 306
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 306
aaaattgtaa gcgcttacaa ttggatccgg 30

<210> SEQ ID NO 307
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 307
caaattgtaa gcgcttacaa ttggatccgg 30

<210> SEQ ID NO 308
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 308
gaaattgtaa gcgcttacaa ttggatccgg 30

<210> SEQ ID NO 309
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 309
taaattgtaa gcgcttacaa ttggatccgg 30

<210> SEQ ID NO 310
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 310
gtaattgtaa gcgcttacaa ttggatccgg 30

<210> SEQ ID NO 311

<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 311
tcaattgtaa gcgcttacaa ttggatccgg 30

<210> SEQ ID NO 312
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 312
aaaattgtaa gcgcttacaa ttggatccgg 30

<210> SEQ ID NO 313
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 313
caaattgtaa gcgcttacaa ttggatccgg 30

<210> SEQ ID NO 314
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 314
gaaattgtaa gcgcttacaa ttggatccgg 30

<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 315
taaattgtaa gcgcttacaa ttggatccgg 30

<210> SEQ ID NO 316
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 316
gtaattgtaa gcgcttacaa ttggatccgg 30

<210> SEQ ID NO 317
<211> LENGTH: 30

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 317
tcaattgtaa gcgcttacaa ttggatccgg 30

<210> SEQ ID NO 318
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 318
aaaattgtaa gcgcttacaa ttggatccgg 30

<210> SEQ ID NO 319
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 319
caaattgtaa gcgcttacaa ttggatccgg 30

<210> SEQ ID NO 320
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 320
gaaattgtaa gcgcttacaa ttggatccgg 30

<210> SEQ ID NO 321
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 321
taaattgtaa gcgcttacaa ttggatccgg 30

<210> SEQ ID NO 322
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 322
gtaattgtaa gcgcttacaa ttggatccgg 30

<210> SEQ ID NO 323
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 323
tcaattgtaa gcgcttacaa ttggatccgg 30

<210> SEQ ID NO 324
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 324
aaaattgtaa gcgcttacaa ttggatccgg 30

<210> SEQ ID NO 325
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 325
caaattgtaa gcgcttacaa ttggatccgg 30

<210> SEQ ID NO 326
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 326
gccaaattaa acaggattaa caggatccgg 30

<210> SEQ ID NO 327
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 327
gccaaattaa acaggattaa caggatccgg 30

<210> SEQ ID NO 328
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 328
caaattatga gcgctcacaa ttggatccgg 30

<210> SEQ ID NO 329
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 329
gtttctccat acccgttttt ttgggctagc 30

<210> SEQ ID NO 330
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 330
tgttatagtc gaatacctct ggcggtgata 30

<210> SEQ ID NO 331
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 331
attacaaact ttcttgtata gatttaacgt 30

<210> SEQ ID NO 332
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 332
atttataaat agtggtgata gatttaacgt 30

<210> SEQ ID NO 333
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 333
tttcttgtat agatttacaa tgtatcttgt 30

<210> SEQ ID NO 334
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 334
tttcttgtag atacttacaa tgtatcttgt 30

<210> SEQ ID NO 335
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 335
ctttatgctt ccggctcgta tgttgtgtgg 30

<210> SEQ ID NO 336
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
ttttttgggc tagcaagctt taccatggat 30

<210> SEQ ID NO 337
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
tgtttctcca taccgttttt ttgggctagc 30

<210> SEQ ID NO 338
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
ttttggtaca ctccctatca gtgatagaga 30

<210> SEQ ID NO 339
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
ctttttggta cactacctct ggcggtgata 30

<210> SEQ ID NO 340
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
tacgcaagaa aatggtttgt tatagtcgaa 30

<210> SEQ ID NO 341
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 341
gaaaaccttg tcaatgaaga gcgatctatg 30

<210> SEQ ID NO 342
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 342
ctcaaagcgg gccagccgta gccgttacgc 30

<210> SEQ ID NO 343
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 343
ttctcgttcg actcatagct gaacacaaca 30

<210> SEQ ID NO 344
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 344
gttctttaat tatttaagtg ttctttaatt 30

<210> SEQ ID NO 345
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 345
cgtgcgtgtt gataacaccg tgcgtgttga 30

<210> SEQ ID NO 346
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 346
gttacgttta tcgcggtgat tgttacttat 30

<210> SEQ ID NO 347
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 347
gcaaaataaa atggaatgat gaaactgggt 30

<210> SEQ ID NO 348
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 348
gttacgttta tcgcggtgat tgttacttat 30

<210> SEQ ID NO 349
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 349
atttcacact gctattgaga taattcacaa 30

<210> SEQ ID NO 350
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 350
agattgtact aaatcgtata atgacagtga 30

<210> SEQ ID NO 351
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 351
gacatctccg gcgcaactga aaataccact 30

<210> SEQ ID NO 352
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 352
gaggatgcgc atcgtcggga aactgatgcc 30

<210> SEQ ID NO 353
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 353
catccgggac tgatggcgga ggatgcgcat 30

<210> SEQ ID NO 354
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 354
aacttttata tattgtgcaa tctcacatgc 30

<210> SEQ ID NO 355
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 355
tgttgtccgg tgtacgtcac aattttctta 30

<210> SEQ ID NO 356
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 356
aatggctgtg tgttttttgt tcatctccac 30

<210> SEQ ID NO 357
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 357
gtgttgatgc ttttatcacc gccagtggta 30

<210> SEQ ID NO 358
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 358
agtgtgtgga attgtgagcg gataacaatt 30

<210> SEQ ID NO 359
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 359
atgacaaaat tgtcat 16

<210> SEQ ID NO 360
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 360
acatcttaaa agttttagta tcatattcgt 30

<210> SEQ ID NO 361
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 361
ctgaaagcgc ataccgctat ggagggggtt 30

<210> SEQ ID NO 362
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 362
ctgaaagcgc ataccgctat ggagggggtt 30

<210> SEQ ID NO 363
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 363
aacgaatata acaggtggga gatgagagga 30

<210> SEQ ID NO 364
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 364
aatatttcct cattttccac agtgaagtga 30

<210> SEQ ID NO 365
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 365
tacgcaagaa aatggtttgt tatagtcgaa 30

<210> SEQ ID NO 366
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 366
atttaattgt tttgatcaat tatttttctg 30

<210> SEQ ID NO 367
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 367
attattctgc atttttgggg agaatggact 30

<210> SEQ ID NO 368
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 368
ccttgctgga aggtttaacc tttatcacag 30

<210> SEQ ID NO 369
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 369
atgatgtgtc catggatta 19

<210> SEQ ID NO 370
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 370
atgatagacg atgtgcggac aacgtg 26

<210> SEQ ID NO 371
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 371
cattagccgc caccatgggg ttaagtagca 30

<210> SEQ ID NO 372
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 372
atttataaat agtggtgata gatttaacgt 30

<210> SEQ ID NO 373
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 373
ataaagccat cacgagtacc atagaggatc 30

<210> SEQ ID NO 374
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 374
tttgtctttt cttgcttaat aatgttgtca 30

<210> SEQ ID NO 375
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 375
tttgtctttt cttgcttaat aatgttgtca 30

<210> SEQ ID NO 376
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 376
atcctccttt agtcttcccc ctcatgtgtg 30

<210> SEQ ID NO 377
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 377
taaaattatg aaatttgcat aaattcttca 30

<210> SEQ ID NO 378
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 378
gaaatctggc agtttttggt acacgaaagc 30

<210> SEQ ID NO 379
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 379
tgccagttct ggcaggtcta aaaagtgttc 30

<210> SEQ ID NO 380
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 380
cacagaactt gcatttatat aaagggaaag 30

<210> SEQ ID NO 381
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 381
acaccgtgcg tgttgatata gtcgaataaa 30

<210> SEQ ID NO 382
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 382
aaaattatga aatttgtata aattcttcag 30

<210> SEQ ID NO 383
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 383
ggttcttttt ggtacctctg gcggtgataa 30

<210> SEQ ID NO 384
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 384
tgtaggatcg tacaggtata aattcttcag 30

<210> SEQ ID NO 385
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 385
caagaaaatg gtttgttata gtcgaataaa 30

<210> SEQ ID NO 386
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 386
ctatctcatt tgctagtata gtcgaataaa 30

<210> SEQ ID NO 387
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 387
gttacgttta tcgcggtgat tgttacttat 30

<210> SEQ ID NO 388
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 388
gttacgttta tcgcggtgat tgttacttat 30

<210> SEQ ID NO 389
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 389
gttacgttta tcgcggtgat tgttacttat 30

<210> SEQ ID NO 390

<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 390
ataaatgctt gactctgtag cgggaaggcg 30

<210> SEQ ID NO 391
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 391
aaaactggta gtaggactgg agattggtac 30

<210> SEQ ID NO 392
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 392
gggacacaaa catcaagagg atatgagatt 30

<210> SEQ ID NO 393
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 393
gtcaaaatga ccgaaacggg tggtaacttc 30

<210> SEQ ID NO 394
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 394
agtaatctta tcgccagttt ggtctggtca 30

<210> SEQ ID NO 395
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 395
agtaatctta tcgccagttt ggtctggtca 30

<210> SEQ ID NO 396
<211> LENGTH: 30

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 396
aattctgaac aacatccgta ctcttcgtgc 30

<210> SEQ ID NO 397
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 397
tcgataagat taccgatctt acctgaagct 30

<210> SEQ ID NO 398
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 398
cgatctattc acctgaaaga gaaataaaaa 30

<210> SEQ ID NO 399
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 399
atcgcaacct atttattaca acactagtgc 30

<210> SEQ ID NO 400
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 400
aaacgttagt ttgaatggaa agatgcctgc 30

<210> SEQ ID NO 401
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 401
tttgcacgaa ccatatgtaa gtatttcctt 30

<210> SEQ ID NO 402
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 402
taacacttat ttaattaaaa agaggagaaa 30

<210> SEQ ID NO 403
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 403
tagaaacaaa atgtaacatc tctatggaca 30

<210> SEQ ID NO 404
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 404
acaggaaaca gctatgacca tgattacgcc 30

<210> SEQ ID NO 405
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 405
agcgacgtct gatgacgtaa tttctgcctc 30

<210> SEQ ID NO 406
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 406
gttcactcta taccgctgaa ggtgtaatgg 30

<210> SEQ ID NO 407
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 407
tagtttataa tttaagtgtt ctttaatttc 30

<210> SEQ ID NO 408
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 408
cgagcacttc accaacaagg accatagcat 30

<210> SEQ ID NO 409
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 409
caccttcggg tgggcctttc tgcgtttata 30

<210> SEQ ID NO 410
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 410
catggcatgg atgaactata caaataataa 30

<210> SEQ ID NO 411
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 411
caccttcggg tgggcctttc tgcgtttata 30

<210> SEQ ID NO 412
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 412
caccttcggg tgggcctttc tgcgtttata 30

<210> SEQ ID NO 413
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 413
caccttcggg tgggcctttc tgcgtttata 30

<210> SEQ ID NO 414
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 414
caccttcggg tgggcctttc tgcgtttata 30

<210> SEQ ID NO 415
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
caccttcggg tgggcctttc tgcgtttata 30

<210> SEQ ID NO 416
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
caccttcggg tgggcctttc tgcgtttata 30

<210> SEQ ID NO 417
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
caccttcggg tgggcctttc tgcgtttata 30

<210> SEQ ID NO 418
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
caccttcggg tgggcctttc tgcgtttata 30

<210> SEQ ID NO 419
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
caccttcggg tgggcctttc tgcgtttata 30

<210> SEQ ID NO 420
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 420
caccttcggg tgggcctttc tgcgtttata 30

<210> SEQ ID NO 421
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 421
caccttcggg tgggcctttc tgcgtttata 30

<210> SEQ ID NO 422
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 422
caccttcggg tgggcctttc tgcgtttata 30

<210> SEQ ID NO 423
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 423
caccttcggg tgggcctttc tgcgtttata 30

<210> SEQ ID NO 424
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 424
caccttcggg tgggcctttc tgcgtttata 30

<210> SEQ ID NO 425
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 425
caccttcggg tgggcctttc tgcgtttata 30

<210> SEQ ID NO 426
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 426
tgtttctcca taccgttttt ttgggctagc 30

<210> SEQ ID NO 427
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 427
tgtttctcca taccgttttt ttgggctagc 30

<210> SEQ ID NO 428
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 428
ttttatcgca actctctact gtttctccat 30

<210> SEQ ID NO 429
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 429
gtttctccat tactagagaa agaggggaca 30

<210> SEQ ID NO 430
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 430
caccttcggg tgggcctttc tgcgtttata 30

<210> SEQ ID NO 431
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 431
aataactctg atagtgctag tgtagatctc 30

<210> SEQ ID NO 432
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 432
caccttcggg tgggcctttc tgcgtttata 30

<210> SEQ ID NO 433
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 433
caccttcggg tgggcctttc tgcgtttata 30

<210> SEQ ID NO 434
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 434
gggacacaaa catcaagagg atatgagatt 30

<210> SEQ ID NO 435
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 435
ataataagcg aagttagcga gatgaatgcg 30

<210> SEQ ID NO 436
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 436
agttggcaca gatttcgctt tatctttttt 30

<210> SEQ ID NO 437
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 437
caagaaaatg gtttgttata gtcgaataaa 30

<210> SEQ ID NO 438
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 438
gtgttgacta ttttacctct ggcggtgata 30

<210> SEQ ID NO 439
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 439
gttagctttc gaattggcta aaaagtgttc 30

<210> SEQ ID NO 440
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 440
ccattctgct ttccacgaac ttgaaaacgc 30

<210> SEQ ID NO 441
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 441
ggccgcgggt tctttttggt acacgaaagc 30

<210> SEQ ID NO 442
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 442
ttttatcgca actctctact gtttctccat 30

<210> SEQ ID NO 443
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 443
attattctgc atttttgggg agaatggact 30

<210> SEQ ID NO 444
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 444
attattctgc atttttgggg agaatggact 30

<210> SEQ ID NO 445
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 445
aacgttagtt tgaatggaaa gatgcctgca 30

<210> SEQ ID NO 446
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 446
aagaaaatgg tttgttgata ctcgaataaa 30

<210> SEQ ID NO 447
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 447
aacgcagtcg ttaagttcta caaagtcggt 30

<210> SEQ ID NO 448
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 448
gtcggtgaca gataacagga gtaagtaatg 30

<210> SEQ ID NO 449
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 449
tattggctga ctataataag cgcaaattca 30

<210> SEQ ID NO 450

<400> SEQUENCE: 450

000

<210> SEQ ID NO 451
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 451
cgaaacggga accctatatt gatctctact 30

<210> SEQ ID NO 452
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 452
aagttggcac gcatcgtgct ttatacagat 30

<210> SEQ ID NO 453
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 453
gaggaaacta gacccgccgc caccatggag 30

<210> SEQ ID NO 454
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 454
gagtaaccaa aaccaaaaca gatttcaacc 30

<210> SEQ ID NO 455
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 455
aaagtaagaa tttttgaaaa ttcaatataa 30

<210> SEQ ID NO 456
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 456
atacggtcaa cgaactataa ttaactaaac 30

<210> SEQ ID NO 457
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 457
cacaaataca cacactaaat taataactag 30

<210> SEQ ID NO 458
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
cacaaataca cacactaaat taataactag 30

<210> SEQ ID NO 459
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
cacaaataca cacactaaat taataactag 30

<210> SEQ ID NO 460
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
atactttaac gtcaaggaga aaaaactata 30

<210> SEQ ID NO 461
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
accgttaaga accatatcca agaatcaaaa 30

<210> SEQ ID NO 462
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
cttcatatat aaaccgccag aaatgaatta 30

<210> SEQ ID NO 463
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 463
atcttcatac aacaataact accaacctta 30

<210> SEQ ID NO 464
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 464
tttcatacac aatataaacg attaaaagaa 30

<210> SEQ ID NO 465
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 465
aaattccagt aaattcacat attggagaaa 30

<210> SEQ ID NO 466
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 466
gggagccaga acgcttctgg tggtgtaaat 30

<210> SEQ ID NO 467
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 467
gcacagactt agattggtat atatacgcat 30

<210> SEQ ID NO 468
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 468
aagtgcaaga aagaccagaa acgcaactca 30

<210> SEQ ID NO 469
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 469
taaaaaaaaa aaaaaaaaaa aaaaaaaaaa 30

<210> SEQ ID NO 470
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 470
ggggcgaggg ccccgcctcc ggaggcgggg 30

<210> SEQ ID NO 471
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 471
gaggggacgg ctccggcccc ggggccggag 30

<210> SEQ ID NO 472
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 472
ggggcgaggg ctccggcccc ggggccggag 30

<210> SEQ ID NO 473
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 473
gaggggacgg ccccgcctcc ggaggcgggg 30

<210> SEQ ID NO 474
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 474
tgttatagtc gaatacctct ggcggtgata 30

<210> SEQ ID NO 475
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 475
gatttaacgt atcagcacaa aaaagaaacc 30

<210> SEQ ID NO 476
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 476
attacaaact ttcttgtata gatttaacgt 30

<210> SEQ ID NO 477
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 477
tttcttgtat agatttacaa tgtatcttgt 30

<210> SEQ ID NO 478
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 478
tttcttgtag atacttacaa tgtatcttgt 30

<210> SEQ ID NO 479
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 479
actctgtcaa tgatagagtg gattcaaaaa 30

<210> SEQ ID NO 480
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 480
ttttggtaca ctccctatca gtgatagaga 30

<210> SEQ ID NO 481
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 481
ctttttggta cactacctct ggcggtgata 30

<210> SEQ ID NO 482
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 482
aaacctttcg cggtatggca tgatagcgcc 30

<210> SEQ ID NO 483
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 483
tattttacct ctggcggtga taatggttgc 30

<210> SEQ ID NO 484
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 484
actctcggca tggacgagct gtacaagtaa 30

<210> SEQ ID NO 485
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 485
ttgtgagcgg ataacaatat gttgagcaca 30

<210> SEQ ID NO 486
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 486
cattgagaca cttgtttgca cagaggatgg 30

<210> SEQ ID NO 487
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 487
ttctcgttcg actcatagct gaacacaaca 30

<210> SEQ ID NO 488
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 488
gaattgtgag cggataacaa ttggatccgg 30

<210> SEQ ID NO 489
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 489
ggaattgtga gcgctcacaa ttggatccgg 30

<210> SEQ ID NO 490
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 490
ggaattgtaa gcgcttacaa ttggatccgg 30

<210> SEQ ID NO 491
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 491
ggaattgtaa acgtttacaa ttggatccgg 30

<210> SEQ ID NO 492
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 492
ggaattgtga acgttcacaa ttggatccgg 30

<210> SEQ ID NO 493
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 493
ggaattttga gcgctcaaaa ttggatccgg 30

<210> SEQ ID NO 494
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 494
ggaattatga gcgctcataa ttggatccgg 30

<210> SEQ ID NO 495
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 495
gggacgactg tatacagtcg tcggatccgg 30

<210> SEQ ID NO 496
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 496
ggaattgtga gcgcttacaa ttggatccgg 30

<210> SEQ ID NO 497
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 497
ggaattgtga gcgctcataa ttggatccgg 30

<210> SEQ ID NO 498
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 498
ggaattgtga gctacagtcg tcggatccgg 30

<210> SEQ ID NO 499
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 499
ggaattgtaa gcgctcacaa ttggatccgg 30

<210> SEQ ID NO 500
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 500
ggaattgtaa gcgttcacaa ttggatccgg 30

<210> SEQ ID NO 501
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 501
ggaattgtaa gcgctcataa ttggatccgg 30

<210> SEQ ID NO 502
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 502
ggaattgtaa gctacagtcg tcggatccgg 30

<210> SEQ ID NO 503
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 503
ggaattgtga acgctcataa ttggatccgg 30

<210> SEQ ID NO 504
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 504
ggaattgtga actacagtcg tcggatccgg 30

<210> SEQ ID NO 505
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 505
ggaattatga gcgctcacaa ttggatccgg 30

<210> SEQ ID NO 506
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 506
ggaattgtga gcgctcataa ttggatccgg 30

<210> SEQ ID NO 507
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 507
ggaattgtga gctacagtcg tcggatccgg 30

<210> SEQ ID NO 508
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 508
ggaattgtga acgctcataa ttggatccgg 30

<210> SEQ ID NO 509
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 509
ggaattgtga actacagtcg tcggatccgg 30

<210> SEQ ID NO 510
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 510
taaattgtga acgctcataa ttggatccgg 30

<210> SEQ ID NO 511
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 511
gaaattgtaa gcgcttacaa ttggatccgg 30

<210> SEQ ID NO 512

-continued

<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
gaaattgtaa gcgcttacaa ttggatccgg 30

<210> SEQ ID NO 513
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
ggaattgtaa gcgcttacaa ttggatccgg 30

<210> SEQ ID NO 514
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
gccaaattaa acaggattaa caggatccgg 30

<210> SEQ ID NO 515
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
gccaaattaa acaggattaa caggatccgg 30

<210> SEQ ID NO 516
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
gccaaattaa acaggattaa caggatccgg 30

<210> SEQ ID NO 517
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
gccaaattaa acaggattaa caggatccgg 30

<210> SEQ ID NO 518
<211> LENGTH: 30

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
gccaaattaa acaggattaa caggatccgg 30

<210> SEQ ID NO 519
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
gccaaattaa acaggattaa caggatccgg 30

<210> SEQ ID NO 520
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
gccaaattaa acaggattaa caggatccgg 30

<210> SEQ ID NO 521
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
gaaattgtaa gcgcttacaa ttggatccgg 30

<210> SEQ ID NO 522
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
taaattgtaa gcgcttacaa ttggatccgg 30

<210> SEQ ID NO 523
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
gtaattgtaa gcgcttacaa ttggatccgg 30

<210> SEQ ID NO 524
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 524
tcaattgtaa gcgcttacaa ttggatccgg 30

<210> SEQ ID NO 525
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 525
aaaattgtaa gcgcttacaa ttggatccgg 30

<210> SEQ ID NO 526
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 526
caaattgtaa gcgcttacaa ttggatccgg 30

<210> SEQ ID NO 527
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 527
gaaattgtaa gcgcttacaa ttggatccgg 30

<210> SEQ ID NO 528
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 528
taaattgtaa gcgcttacaa ttggatccgg 30

<210> SEQ ID NO 529
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 529
gtaattgtaa gcgcttacaa ttggatccgg 30

<210> SEQ ID NO 530
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 530
tcaattgtaa gcgcttacaa ttggatccgg 30

<210> SEQ ID NO 531
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 531
aaaattgtaa gcgcttacaa ttggatccgg 30

<210> SEQ ID NO 532
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 532
caaattgtaa gcgcttacaa ttggatccgg 30

<210> SEQ ID NO 533
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 533
gaaattgtaa gcgcttacaa ttggatccgg 30

<210> SEQ ID NO 534
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 534
taaattgtaa gcgcttacaa ttggatccgg 30

<210> SEQ ID NO 535
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 535
gtaattgtaa gcgcttacaa ttggatccgg 30

<210> SEQ ID NO 536
<211> LENGTH: 30
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 536
tcaattgtaa gcgcttacaa ttggatccgg 30

<210> SEQ ID NO 537
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 537
aaaattgtaa gcgcttacaa ttggatccgg 30

<210> SEQ ID NO 538
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 538
caaattgtaa gcgcttacaa ttggatccgg 30

<210> SEQ ID NO 539
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 539
gaaattgtaa gcgcttacaa ttggatccgg 30

<210> SEQ ID NO 540
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 540
taaattgtaa gcgcttacaa ttggatccgg 30

<210> SEQ ID NO 541
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 541
gtaattgtaa gcgcttacaa ttggatccgg 30

<210> SEQ ID NO 542
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 542
tcaattgtaa gcgcttacaa ttggatccgg 30

<210> SEQ ID NO 543
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 543
aaaattgtaa gcgcttacaa ttggatccgg 30

<210> SEQ ID NO 544
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 544
caaattgtaa gcgcttacaa ttggatccgg 30

<210> SEQ ID NO 545
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 545
gaaattgtaa gcgcttacaa ttggatccgg 30

<210> SEQ ID NO 546
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 546
taaattgtaa gcgcttacaa ttggatccgg 30

<210> SEQ ID NO 547
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 547
gtaattgtaa gcgcttacaa ttggatccgg 30

<210> SEQ ID NO 548
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 548
tcaattgtaa gcgcttacaa ttggatccgg 30

<210> SEQ ID NO 549
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 549
aaaattgtaa gcgcttacaa ttggatccgg 30

<210> SEQ ID NO 550
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 550
caaattgtaa gcgcttacaa ttggatccgg 30

<210> SEQ ID NO 551
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 551
gaaattgtaa gcgcttacaa ttggatccgg 30

<210> SEQ ID NO 552
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 552
taaattgtaa gcgcttacaa ttggatccgg 30

<210> SEQ ID NO 553
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 553
gtaattgtaa gcgcttacaa ttggatccgg 30

<210> SEQ ID NO 554
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 554
tcaattgtaa gcgcttacaa ttggatccgg 30

<210> SEQ ID NO 555
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 555
aaaattgtaa gcgcttacaa ttggatccgg 30

<210> SEQ ID NO 556
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 556
caaattgtaa gcgcttacaa ttggatccgg 30

<210> SEQ ID NO 557
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 557
gaaattgtaa gcgcttacaa ttggatccgg 30

<210> SEQ ID NO 558
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 558
taaattgtaa gcgcttacaa ttggatccgg 30

<210> SEQ ID NO 559
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 559
gtaattgtaa gcgcttacaa ttggatccgg 30

<210> SEQ ID NO 560
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 560
tcaattgtaa gcgcttacaa ttggatccgg 30

<210> SEQ ID NO 561
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 561
aaaattgtaa gcgcttacaa ttggatccgg 30

<210> SEQ ID NO 562
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 562
caaattgtaa gcgcttacaa ttggatccgg 30

<210> SEQ ID NO 563
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 563
gccaaattaa acaggattaa caggatccgg 30

<210> SEQ ID NO 564
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 564
gccaaattaa acaggattaa caggatccgg 30

<210> SEQ ID NO 565
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 565
caaattatga gcgctcacaa ttggatccgg 30

<210> SEQ ID NO 566
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 566
tgatagagat tccctatcag tgatagagat 30

<210> SEQ ID NO 567
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 567
tgatagagat tccctatcag tgatagagat 30

<210> SEQ ID NO 568
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 568
gttctttaat tatttaagtg ttctttaatt 30

<210> SEQ ID NO 569
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 569
gttctttaat tatttaagtg ttctttaatt 30

<210> SEQ ID NO 570
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 570
cgtgcgtgtt gataacaccg tgcgtgttga 30

<210> SEQ ID NO 571
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 571
gtgttcttta atatttaagt gttctttaat 30

<210> SEQ ID NO 572
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 572
ggaattgtga gcggataaca atttcacaca 30

<210> SEQ ID NO 573
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 573
tgtgtgtaat tgtgagcgga taacaattaa 30

<210> SEQ ID NO 574
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 574
ttttacctct ggcggtgata atggttgcag 30

<210> SEQ ID NO 575
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 575
gtgttgatgc ttttatcacc gccagtggta 30

<210> SEQ ID NO 576
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 576
agtgtgtgga attgtgagcg gataacaatt 30

<210> SEQ ID NO 577
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 577
agggggtggg ggcgcgttgg cgcgccacac 30

<210> SEQ ID NO 578
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 578
acatcttaaa agttttagta tcatattcgt 30

<210> SEQ ID NO 579
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 579
tattttacct ctggcggtga taatggttgc 30

<210> SEQ ID NO 580
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 580
atttataaat agtggtgata gatttaacgt 30

<210> SEQ ID NO 581
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 581
acccttctcg ttcgactcat agctgaacac 30

<210> SEQ ID NO 582
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 582
tgacttatcc gcttcgaaga gagacactac 30

<210> SEQ ID NO 583
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 583
aggtgttaaa ttgatcacgt tttagaccat 30

<210> SEQ ID NO 584
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 584
caatttggta aaggctccat catgtaataa 30

<210> SEQ ID NO 585
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 585
gagaaacaat ttggtaaagg ctccatcatg 30

<210> SEQ ID NO 586
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 586
aacgcgcggg gagaggcggt ttgcgtattg 30

<210> SEQ ID NO 587
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 587
cagtgataga gatactgagc acatcagcac 30

<210> SEQ ID NO 588
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 588
ttatgcttcc ggctcgtata atgtttcaaa 30

<210> SEQ ID NO 589
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 589
ggctcgtatg ttgtgtcgac cgagctgcgc 30

<210> SEQ ID NO 590
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 590
aaacctttcg cggtatggca tgatagcgcc 30

<210> SEQ ID NO 591

<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 591
atttgtcact gtcgttacta tatcggctgc 30

<210> SEQ ID NO 592
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 592
gtccaatcaa taaccgcttt aatagataaa 30

<210> SEQ ID NO 593
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 593
actttattat caataagtta aatcggtacc 30

<210> SEQ ID NO 594
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 594
gtgttgacta ttttacctct ggcggtgata 30

<210> SEQ ID NO 595
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 595
gtgttgacta ttttacctct ggcggtgata 30

<210> SEQ ID NO 596
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 596
atacctctgg cggtgatata taatggttgc 30

<210> SEQ ID NO 597
<211> LENGTH: 30

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
gtgttgacta ttttacctct ggcggtgata 30

<210> SEQ ID NO 598
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
gaaatctggc agtttttggt acacgaaagc 30

<210> SEQ ID NO 599
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
tgccagttct ggcaggtcta aaaagtgttc 30

<210> SEQ ID NO 600
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
agcgctcaca atttaatacg actcactata 30

<210> SEQ ID NO 601
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
taataattgt gagcgctcac aattttgaca 30

<210> SEQ ID NO 602
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
atccctatca gtgatagaga tactgagcac 30

<210> SEQ ID NO 603
<211> LENGTH: 30
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 603
ttgtgagcgg ataacaagat actgagcaca 30

<210> SEQ ID NO 604
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
ggaattgtga gcggataaca atttcacaca 30

<210> SEQ ID NO 605
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
ggaattgtga gcggataaca atttcacaca 30

<210> SEQ ID NO 606
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
ggaattgtga gcggataaca atttcacaca 30

<210> SEQ ID NO 607
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
agaactgtaa tccctatcag tgatagagat 30

<210> SEQ ID NO 608
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
tgttgattta tctaacaccg tgcgtgttga 30

<210> SEQ ID NO 609
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 609
acaccgtgcg tgttgatata gtcgaataaa 30

<210> SEQ ID NO 610
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 610
cctttcgcgg tatggcatga tagcgcccgg 30

<210> SEQ ID NO 611
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 611
cctttcgcgg tatggcatga tagcgcccgg 30

<210> SEQ ID NO 612
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 612
cctttcgcgg tatggcatga tagcgcccgg 30

<210> SEQ ID NO 613
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 613
ggttcttttt ggtacctctg gcggtgataa 30

<210> SEQ ID NO 614
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 614
tgtaggatcg tacaggtata aattcttcag 30

<210> SEQ ID NO 615
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 615
ctatctcatt tgctagtata gtcgaataaa 30

<210> SEQ ID NO 616
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
gtatatatat acagtataat tgcttcaaca 30

<210> SEQ ID NO 617
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
cacaatgtca attgttatcc gctcacaatt 30

<210> SEQ ID NO 618
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
aattgtgagc ggataacaat ttcacacaga 30

<210> SEQ ID NO 619
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
ccggaagaga gtcaattcag ggtggtgaat 30

<210> SEQ ID NO 620
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
acggtgacct agatctccga tactgagcac 30

<210> SEQ ID NO 621
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 621
tggaattgtg agcggataaa atttcacaca 30

<210> SEQ ID NO 622
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 622
tagtagataa tttaagtgtt ctttaatttc 30

<210> SEQ ID NO 623
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 623
ccaacgcgtt cacagcgtac aattactagt 30

<210> SEQ ID NO 624
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 624
aacaaaaaaa cggatcctct agttgcggcc 30

<210> SEQ ID NO 625
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 625
ataaatgctt gactctgtag cgggaaggcg 30

<210> SEQ ID NO 626
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 626
atttcatgat gatacgtgag cggatagaag 30

<210> SEQ ID NO 627
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 627
caaacagaaa gcgttggcgg cagcactggg 30

<210> SEQ ID NO 628
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 628
gtcaaaatga ccgaaacggg tggtaacttc 30

<210> SEQ ID NO 629
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 629
agtaatctta tcgccagttt ggtctggtca 30

<210> SEQ ID NO 630
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 630
agtaatctta tcgccagttt ggtctggtca 30

<210> SEQ ID NO 631
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 631
aattctgaac aacatccgta ctcttcgtgc 30

<210> SEQ ID NO 632
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 632
tttacgttat cattcacttt acatcagagt 30

<210> SEQ ID NO 633
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 633
gtttctccat acccgttttt ttgggctagc 30

<210> SEQ ID NO 634
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 634
cgatctattc acctgaaaga gaaataaaaa 30

<210> SEQ ID NO 635
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 635
aaacgttagt ttgaatggaa agatgcctgc 30

<210> SEQ ID NO 636
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 636
attgccgaat taatactaag aattattatc 30

<210> SEQ ID NO 637
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 637
acaggaaaca gctatgacca tgattacgcc 30

<210> SEQ ID NO 638
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 638
actggcggtt ataatgagca catcagcagg 30

<210> SEQ ID NO 639
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 639
caccgacaaa caacagataa aacgaaaggc 30

<210> SEQ ID NO 640
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 640
agtgttatta agctactaaa gcgtagtttt 30

<210> SEQ ID NO 641
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 641
gaataagaag gctggctctg caccttggtg 30

<210> SEQ ID NO 642
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 642
ttagcgactt gatgctcttg atcttccaat 30

<210> SEQ ID NO 643
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 643
acatctaaaa cttttagcgt tattacgtaa 30

<210> SEQ ID NO 644
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 644
ttccgacctc attaagcagc tctaatgcgc 30

<210> SEQ ID NO 645
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 645
caatttttaa acctgtagga tcgtacaggt 30

<210> SEQ ID NO 646
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 646
caatttttaa aattaaaggc gttacccaac 30

<210> SEQ ID NO 647
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 647
tagtttataa tttaagtgtt ctttaatttc 30

<210> SEQ ID NO 648
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 648
gaaaatgtga gcgagtaaca acctcacaca 30

<210> SEQ ID NO 649
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 649
caccttcggg tgggcctttc tgcgtttata 30

<210> SEQ ID NO 650
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 650
ttttatcgca actctctact gtttctccat 30

<210> SEQ ID NO 651
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 651
gtttctccat tactagagaa agaggggaca 30

<210> SEQ ID NO 652
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 652
caccttcggg tgggcctttc tgcgtttata 30

<210> SEQ ID NO 653
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 653
caccttcggg tgggcctttc tgcgtttata 30

<210> SEQ ID NO 654
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 654
caccttcggg tgggcctttc tgcgtttata 30

<210> SEQ ID NO 655
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 655
aataactctg atagtgctag tgtagatctc 30

<210> SEQ ID NO 656
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 656
caccttcggg tgggcctttc tgcgtttata 30

<210> SEQ ID NO 657
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 657
caccttcggg tgggcctttc tgcgtttata 30

<210> SEQ ID NO 658
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 658
ttgtgagcgg ataacaagat actgagcaca 30

<210> SEQ ID NO 659
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 659
actgagcaca tactagagaa agaggagaaa 30

<210> SEQ ID NO 660
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 660
actgagcaca tactagagaa agaggagaaa 30

<210> SEQ ID NO 661
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 661
tcacacatac tagagattaa agaggagaaa 30

<210> SEQ ID NO 662
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 662
ggaattgtga gcggataaca atttcacaca 30

<210> SEQ ID NO 663
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 663
ggaattgtga gcggataaca atttcacaca 30

<210> SEQ ID NO 664
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 664
ttgtgagcgg ataacaagat actgagcaca 30

<210> SEQ ID NO 665
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 665
atccctatca gtgatagaga tactgagcac 30

<210> SEQ ID NO 666
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 666
ccgtcataat atgaaccata agttcaccac 30

<210> SEQ ID NO 667
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 667
tattttacct ctggcggtga taatggttgc 30

<210> SEQ ID NO 668
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 668
attgtatgaa aatacaagaa agtttgttga 30

<210> SEQ ID NO 669
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 669
tagtagataa tttaagtgtt ctttaatttc 30

<210> SEQ ID NO 670

<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 670
ttgacacctg taggatcgta caggtataat 30

<210> SEQ ID NO 671
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 671
cacgcaaaac ttgcgacaaa caataggtaa 30

<210> SEQ ID NO 672
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 672
gtgttgacta ttttacctct ggcggtgata 30

<210> SEQ ID NO 673
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 673
tagatctcct atagtgagtc gtattaattt 30

<210> SEQ ID NO 674
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 674
tactttcaaa gactacattt gtaagatttg 30

<210> SEQ ID NO 675
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 675
cataaagttc atgaaacgtg aactgaaatt 30

<210> SEQ ID NO 676
<211> LENGTH: 30

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 676
ccgtgatact atgaaccata agttcaccac 30

<210> SEQ ID NO 677
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 677
aattttacct ctggcggtga tactggttgc 30

<210> SEQ ID NO 678
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 678
attgtatgat actacaagaa agtttgttga 30

<210> SEQ ID NO 679
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 679
tagtagatac tttaagtgtt ctttaatttc 30

<210> SEQ ID NO 680
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 680
tggtcccacg cgcgtgggat actacgtcag 30

<210> SEQ ID NO 681
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 681
attacggtga gatactccca cgcgcgtggg 30

<210> SEQ ID NO 682
<211> LENGTH: 30
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 682
acgcgcgtgg gatactccca cgcgcgtggg 30

<210> SEQ ID NO 683
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
gattagattc ataaatttga gagaggagtt 30

<210> SEQ ID NO 684
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
acttagattc ataaatttga gagaggagtt 30

<210> SEQ ID NO 685
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
ggttagattc ataaatttga gagaggagtt 30

<210> SEQ ID NO 686
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
acttagattc ataaatttga gagaggagtt 30

<210> SEQ ID NO 687
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
aattagattc ataaatttga gagaggagtt 30

<210> SEQ ID NO 688
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 688
acttagattc ataaatttga gagaggagtt 30

<210> SEQ ID NO 689
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 689
atttagattc ataaatttga gagaggagtt 30

<210> SEQ ID NO 690
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 690
cacgcgcgtg ggaatgttat aatacgtcag 30

<210> SEQ ID NO 691
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 691
actgagcaca tactagagaa agaggagaaa 30

<210> SEQ ID NO 692
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 692
cagtgagcga gtaacaacta cgctgtttta 30

<210> SEQ ID NO 693
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 693
cagtgagcga gtaacaacta cgctgtttta 30

<210> SEQ ID NO 694
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 694
atgtgagcgg ataacactat aattaataga 30

<210> SEQ ID NO 695
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
atgtgagcgg ataacactat aattaataga 30

<210> SEQ ID NO 696
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
atttcatgat gatacgtgag cggatagaag 30

<210> SEQ ID NO 697
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
ttgtgagcga gtggcaccat taagtacgta 30

<210> SEQ ID NO 698
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
ttgtgagcga gtgacaccat taagtacgta 30

<210> SEQ ID NO 699
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
ttgtgagcga gtaacaccat taagtacgta 30

<210> SEQ ID NO 700
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 700
ttgtgagcga gtaacaccat taagtacgta 30

<210> SEQ ID NO 701
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 701
agttggcaca gatttcgctt tatctttttt 30

<210> SEQ ID NO 702
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 702
tggaattgtg agcggataac aattaagctt 30

<210> SEQ ID NO 703
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 703
agtttgttta aacaacaaac taataggtga 30

<210> SEQ ID NO 704
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 704
aatgtgtgta attgtgagcg gataacaatt 30

<210> SEQ ID NO 705
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 705
ataggggaat tgtgagcgga taacaattcc 30

<210> SEQ ID NO 706
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 706 atagggggaat tgtgagcgga taacaattcc 30

<210> SEQ ID NO 707
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 707
ataggggaat tgtgagcgga taacaattcc 30

<210> SEQ ID NO 708
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 708
ataggggaat tgtgagcgga taacaattcc 30

<210> SEQ ID NO 709
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 709
aaacaaacaa acaaaaaaaa aaaaaaaaaa 30

<210> SEQ ID NO 710
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 710
atactttaac gtcaaggaga aaaaactata 30

<210> SEQ ID NO 711
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 711
tagatacaat tctattaccc ccatccatac 30

<210> SEQ ID NO 712
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 712
ttagtgaacc gtcagatcac tagtctgcag 30

<210> SEQ ID NO 713
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 713
ttagtgaacc gtcagatcac tagtctgcag 30

<210> SEQ ID NO 714
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 714
ggaaaggacg aaacaccgac tagtctgcag 30

<210> SEQ ID NO 715
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 715
attgtttgtg tattttagac tagtctgcag 30

<210> SEQ ID NO 716
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 716
attgtttgtg tattttagac tagtctgcag 30

<210> SEQ ID NO 717
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 717
attgtttgtg tattttagac tagtctgcag 30

<210> SEQ ID NO 718
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 718
ttagtgaacc gtcagatcac tagtctgcag 30

<210> SEQ ID NO 719
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 719
tgttatagtc gaatacctct ggcggtgata 30

<210> SEQ ID NO 720
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 720
attacaaact ttcttgtata gatttaacgt 30

<210> SEQ ID NO 721
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 721
tttcttgtat agatttacaa tgtatcttgt 30

<210> SEQ ID NO 722
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 722
tttcttgtag atacttacaa tgtatcttgt 30

<210> SEQ ID NO 723
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 723
ttttggtaca ctccctatca gtgatagaga 30

<210> SEQ ID NO 724
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 724 cttttggta cactacctct ggcggtgata 30

<210> SEQ ID NO 725
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 725
actctcggca tggacgagct gtacaagtaa 30

<210> SEQ ID NO 726
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 726
ttctcgttcg actcatagct gaacacaaca 30

<210> SEQ ID NO 727
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 727
ggaattgtga gcgctcataa ttggatccgg 30

<210> SEQ ID NO 728
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 728
ggaattgtga gctacagtcg tcggatccgg 30

<210> SEQ ID NO 729
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 729
ggaattgtga acgctcataa ttggatccgg 30

<210> SEQ ID NO 730
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 730
ggaattgtga actacagtcg tcggatccgg 30

<210> SEQ ID NO 731
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 731
taaattgtga acgctcataa ttggatccgg 30

<210> SEQ ID NO 732
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 732
gaaattgtaa gcgcttacaa ttggatccgg 30

<210> SEQ ID NO 733
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 733
gaaattgtaa gcgcttacaa ttggatccgg 30

<210> SEQ ID NO 734
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 734
ggaattgtaa gcgcttacaa ttggatccgg 30

<210> SEQ ID NO 735
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 735
gccaaattaa acaggattaa caggatccgg 30

<210> SEQ ID NO 736
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 736
gccaaattaa acaggattaa caggatccgg 30

<210> SEQ ID NO 737
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
gccaaattaa acaggattaa caggatccgg 30

<210> SEQ ID NO 738
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
gccaaattaa acaggattaa caggatccgg 30

<210> SEQ ID NO 739
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
gccaaattaa acaggattaa caggatccgg 30

<210> SEQ ID NO 740
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
gccaaattaa acaggattaa caggatccgg 30

<210> SEQ ID NO 741
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
gccaaattaa acaggattaa caggatccgg 30

<210> SEQ ID NO 742
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
gaaattgtaa gcgcttacaa ttggatccgg 30

<210> SEQ ID NO 743
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 743
taaattgtaa gcgcttacaa ttggatccgg 30

<210> SEQ ID NO 744
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 744
gtaattgtaa gcgcttacaa ttggatccgg 30

<210> SEQ ID NO 745
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 745
tcaattgtaa gcgcttacaa ttggatccgg 30

<210> SEQ ID NO 746
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 746
aaaattgtaa gcgcttacaa ttggatccgg 30

<210> SEQ ID NO 747
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 747
caaattgtaa gcgcttacaa ttggatccgg 30

<210> SEQ ID NO 748
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 748
gaaattgtaa gcgcttacaa ttggatccgg 30

<210> SEQ ID NO 749

<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 749
taaattgtaa gcgcttacaa ttggatccgg 30

<210> SEQ ID NO 750
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 750
gtaattgtaa gcgcttacaa ttggatccgg 30

<210> SEQ ID NO 751
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 751
tcaattgtaa gcgcttacaa ttggatccgg 30

<210> SEQ ID NO 752
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 752
aaaattgtaa gcgcttacaa ttggatccgg 30

<210> SEQ ID NO 753
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 753
caaattgtaa gcgcttacaa ttggatccgg 30

<210> SEQ ID NO 754
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 754
gaaattgtaa gcgcttacaa ttggatccgg 30

<210> SEQ ID NO 755
<211> LENGTH: 30

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 755
taaattgtaa gcgcttacaa ttggatccgg 30

<210> SEQ ID NO 756
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 756
gtaattgtaa gcgcttacaa ttggatccgg 30

<210> SEQ ID NO 757
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 757
tcaattgtaa gcgcttacaa ttggatccgg 30

<210> SEQ ID NO 758
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 758
aaaattgtaa gcgcttacaa ttggatccgg 30

<210> SEQ ID NO 759
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 759
caaattgtaa gcgcttacaa ttggatccgg 30

<210> SEQ ID NO 760
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 760
gaaattgtaa gcgcttacaa ttggatccgg 30

<210> SEQ ID NO 761
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 761
taaattgtaa gcgcttacaa ttggatccgg 30

<210> SEQ ID NO 762
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 762
gtaattgtaa gcgcttacaa ttggatccgg 30

<210> SEQ ID NO 763
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 763
tcaattgtaa gcgcttacaa ttggatccgg 30

<210> SEQ ID NO 764
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 764
aaaattgtaa gcgcttacaa ttggatccgg 30

<210> SEQ ID NO 765
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 765
caaattgtaa gcgcttacaa ttggatccgg 30

<210> SEQ ID NO 766
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 766
gaaattgtaa gcgcttacaa ttggatccgg 30

<210> SEQ ID NO 767
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 767
taaattgtaa gcgcttacaa ttggatccgg 30

<210> SEQ ID NO 768
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 768
gtaattgtaa gcgcttacaa ttggatccgg 30

<210> SEQ ID NO 769
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 769
tcaattgtaa gcgcttacaa ttggatccgg 30

<210> SEQ ID NO 770
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 770
aaaattgtaa gcgcttacaa ttggatccgg 30

<210> SEQ ID NO 771
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 771
caaattgtaa gcgcttacaa ttggatccgg 30

<210> SEQ ID NO 772
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 772
gaaattgtaa gcgcttacaa ttggatccgg 30

<210> SEQ ID NO 773
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 773
taaattgtaa gcgcttacaa ttggatccgg 30

<210> SEQ ID NO 774
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
gtaattgtaa gcgcttacaa ttggatccgg 30

<210> SEQ ID NO 775
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
tcaattgtaa gcgcttacaa ttggatccgg 30

<210> SEQ ID NO 776
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
aaaattgtaa gcgcttacaa ttggatccgg 30

<210> SEQ ID NO 777
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 777
caaattgtaa gcgcttacaa ttggatccgg 30

<210> SEQ ID NO 778
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
gaaattgtaa gcgcttacaa ttggatccgg 30

<210> SEQ ID NO 779
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 779
taaattgtaa gcgcttacaa ttggatccgg 30

<210> SEQ ID NO 780
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 780
gtaattgtaa gcgcttacaa ttggatccgg 30

<210> SEQ ID NO 781
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 781
tcaattgtaa gcgcttacaa ttggatccgg 30

<210> SEQ ID NO 782
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 782
aaaattgtaa gcgcttacaa ttggatccgg 30

<210> SEQ ID NO 783
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 783
caaattgtaa gcgcttacaa ttggatccgg 30

<210> SEQ ID NO 784
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 784
gccaaattaa acaggattaa caggatccgg 30

<210> SEQ ID NO 785
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 785
gccaaattaa acaggattaa caggatccgg 30

<210> SEQ ID NO 786
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 786
caaattatga gcgctcacaa ttggatccgg 30

<210> SEQ ID NO 787
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 787
tgatagagat tccctatcag tgatagagat 30

<210> SEQ ID NO 788
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 788
gttctttaat tatttaagtg ttctttaatt 30

<210> SEQ ID NO 789
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 789
gttctttaat tatttaagtg ttctttaatt 30

<210> SEQ ID NO 790
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 790
cgtgcgtgtt gataacaccg tgcgtgttga 30

<210> SEQ ID NO 791
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 791
gtgttcttta atatttaagt gttctttaat 30

<210> SEQ ID NO 792
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 792
ggaattgtga gcggataaca atttcacaca 30

<210> SEQ ID NO 793
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 793
gttacgttta tcgcggtgat tgttacttat 30

<210> SEQ ID NO 794
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 794
gcaaaataaa atggaatgat gaaactgggt 30

<210> SEQ ID NO 795
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 795
aacgcgcggg gagaggcggt ttgcgtattg 30

<210> SEQ ID NO 796
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 796
gtgttgatgc ttttatcacc gccagtggta 30

<210> SEQ ID NO 797
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 797
agtgtgtgga attgtgagcg gataacaatt 30

<210> SEQ ID NO 798
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 798
acatcttaaa agttttagta tcatattcgt 30

<210> SEQ ID NO 799
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 799
ctgaaagcgc ataccgctat ggagggggtt 30

<210> SEQ ID NO 800
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 800
tattttacct ctggcggtga taatggttgc 30

<210> SEQ ID NO 801
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 801
atttataaat agtggtgata gatttaacgt 30

<210> SEQ ID NO 802
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 802
atttataaat agtggtgata gatttaacgt 30

<210> SEQ ID NO 803
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 803
gaaatctggc agtttttggt acacgaaagc 30

<210> SEQ ID NO 804
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 804
tgccagttct ggcaggtcta aaaagtgttc 30

<210> SEQ ID NO 805
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 805
cacagaactt gcatttatat aaagggaaag 30

<210> SEQ ID NO 806
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 806
agttggcaca gatttcgctt tatctttttt 30

<210> SEQ ID NO 807
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 807
agcgctcaca atttaatacg actcactata 30

<210> SEQ ID NO 808
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 808
ggaattgtga gcggataaca atttcacaca 30

<210> SEQ ID NO 809
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 809
ggaattgtga gcggataaca atttcacaca 30

<210> SEQ ID NO 810
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 810
ggaattgtga gcggataaca atttcacaca 30

<210> SEQ ID NO 811
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 811
agaactgtaa tccctatcag tgatagagat 30

<210> SEQ ID NO 812
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 812
tgttgattta tctaacaccg tgcgtgttga 30

<210> SEQ ID NO 813
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 813
acaccgtgcg tgttgatata gtcgaataaa 30

<210> SEQ ID NO 814
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 814
ggttcttttt ggtacctctg gcggtgataa 30

<210> SEQ ID NO 815
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 815
tgtaggatcg tacaggtata aattcttcag 30

<210> SEQ ID NO 816
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 816
ctatctcatt tgctagtata gtcgaataaa 30

<210> SEQ ID NO 817
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 817
aattgtgagc ggataacaat ttcacacaga 30

<210> SEQ ID NO 818
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 818
gttacgttta tcgcggtgat tgttacttat 30

<210> SEQ ID NO 819
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 819
acggtgacct agatctccga tactgagcac 30

<210> SEQ ID NO 820
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 820
tggaattgtg agcggataaa atttcacaca 30

<210> SEQ ID NO 821
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 821
tagtagataa tttaagtgtt ctttaatttc 30

<210> SEQ ID NO 822
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 822
aacaaaaaaa cggatcctct agttgcggcc 30

<210> SEQ ID NO 823
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 823
ataaatgctt gactctgtag cgggaaggcg 30

<210> SEQ ID NO 824
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 824
atttcatgat gatacgtgag cggatagaag 30

<210> SEQ ID NO 825
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 825
gggacacaaa catcaagagg atatgagatt 30

<210> SEQ ID NO 826
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 826
gtcaaaatga ccgaaacggg tggtaacttc 30

<210> SEQ ID NO 827
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 827
agtaatctta tcgccagttt ggtctggtca 30

<210> SEQ ID NO 828

<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 828
agtaatctta tcgccagttt ggtctggtca 30

<210> SEQ ID NO 829
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 829
aattctgaac aacatccgta ctcttcgtgc 30

<210> SEQ ID NO 830
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 830
cgatctattc acctgaaaga gaaataaaaa 30

<210> SEQ ID NO 831
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 831
aaacgttagt ttgaatggaa agatgcctgc 30

<210> SEQ ID NO 832
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
acaggaaaca gctatgacca tgattacgcc 30

<210> SEQ ID NO 833
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 833
gttcactcta taccgctgaa ggtgtaatgg 30

<210> SEQ ID NO 834
<211> LENGTH: 30

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 834
tagtttataa tttaagtgtt ctttaatttc 30

<210> SEQ ID NO 835
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 835
gaaaatgtga gcgagtaaca acctcacaca 30

<210> SEQ ID NO 836
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 836
ttttatcgca actctctact gtttctccat 30

<210> SEQ ID NO 837
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 837
gtttctccat tactagagaa agaggggaca 30

<210> SEQ ID NO 838
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 838
aataactctg atagtgctag tgtagatctc 30

<210> SEQ ID NO 839
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 839
caccttcggg tgggcctttc tgcgtttata 30

<210> SEQ ID NO 840
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 840
caccttcggg tgggcctttc tgcgtttata 30

<210> SEQ ID NO 841
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 841
gtgttgacta ttttacctct ggcggtgata 30

<210> SEQ ID NO 842
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 842
cgaaacggga accctatatt gatctctact 30

<210> SEQ ID NO 843
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 843
accgttaaga accatatcca agaatcaaaa 30

<210> SEQ ID NO 844
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 844
accgttaaga accatatcca agaatcaaaa 30

<210> SEQ ID NO 845
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 845
cacaaataca cacactaaat taataactag 30

<210> SEQ ID NO 846
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 846
atacggtcaa cgaactataa ttaactaaac 30

<210> SEQ ID NO 847
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 847
tagatacaat tctattaccc ccatccatac 30

<210> SEQ ID NO 848
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 848
ggggcgaggg ccccgcctcc ggaggcgggg 30

<210> SEQ ID NO 849
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 849
gaggggacgg ctccggcccc ggggccggag 30

<210> SEQ ID NO 850
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 850
ggggcgaggg ctccggcccc ggggccggag 30

<210> SEQ ID NO 851
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 851
gaggggacgg ccccgcctcc ggaggcgggg 30

DNA RECOMBINASE CIRCUITS FOR LOGICAL CONTROL OF GENE EXPRESSION

CROSS REFERENCE TO RELATED APPLICATIONS

This application is a 371 National Phase Entry of International Application PCT/US15/34721 filed on Jun. 8, 2015 which claims benefit under 35 U.S.C. § 119(e) of U.S. Provisional Application Nos. 62/008,952 filed Jun. 6, 2014, and 62/144,678 filed Apr. 8, 2015, the contents of each of which are incorporated herein by reference in their entirety.

GOVERNMENT SUPPORT

This invention was made with Government Support under Contract Nos. CA186574 and GM008764 awarded by the National Institutes of Health and Contract No. DGE1247312 awarded by the National Science Foundation. The Government has certain rights in the invention.

SEQUENCE LISTING

The sequence listing of the present application has been submitted electronically via EFS-Web as an ASCII formatted sequence listing with a file name "701586-081803-PCT_SL" creation date of Dec. 5, 2016 and a size of 227,944 bytes. The sequence listing submitted via EFS-Web is part of the specification and is herein incorporated by reference in its entirety.

TECHNICAL FIELD

The present invention relates generally to controlled gene expression, engineered gene circuits, and adoptive T cell therapies.

BACKGROUND OF THE INVENTION

Synthetic genetic circuits hold vast potential at revolutionizing therapeutics, animal models[2], and biotechnological processes[3-6]. Despite rapid advances in recent years, engineering complex genetic circuits remains a challenge due to difficult circuit performance predictability stemming from unintended interactions between cascading biological components[7], such as transcription factors[8-12], chaperonins[13], or miRNAs[14-17].

A major goal in synthetic biology is to predictably design and construct genetic circuits to control cellular functions. Numerous success, such as logic gates, toggle switches, feedback loops and oscillators, has been demonstrated. Due to the complexity of mammalian systems, sophisticated genetic circuits that can integrate multiple input signals and deliver multiple outputs are highly desirable. For instance, the specificity of tissue-restricted gene expression can be greatly enhanced with the logical integration of several tissue-specific promoters. However, synthetic biology remains mostly a microbial centric discipline and high performance genetic circuits are lacking in mammalian cells. Furthermore, complex multi-input/multi-output genetic circuits are challenging to engineer, regardless of the host.

A common strategy for restricting gene expression in a specific cell type is to identify a single cell type specific promoter and use it to control recombinase expression. Although some cell type specific promoters have been identified, they do not cover the diversity represented by all the different cell types in complex organs, such as the mammalian brain. It is, however, much more likely to identify a set of promoters that collectively define a specific subset of cells rather than relying on one promoter. Extensive gene expression profiling in different brain regions and cells had allowed researchers to identify promoters that can define different type of brain cells.

A central goal of synthetic biology is to create cellular networks that integrate input signals for decision making and actuation. In recent years, artificial logic gates and memory devices have been independently constructed. In previous implementations of cellular logic, complex gates required the layering of multiple genetic circuits, thus necessitating significant efforts for circuit construction and tuning. These complex logic gates can achieve only combinatorial logic.

SUMMARY OF THE INVENTION

Synthetic genetic circuits that can integrate multiple input signals and deliver multiple outputs are increasingly important in cell-based therapy and animal model development. However, synthetic biology remains mostly a microbial centric discipline and complex genetic circuits remain challenging to engineer, regardless of the host.

Provided herein are strategies and genetic tools to incorporate input to regulate gene expression—genetic logic gates that can integrate different recombinase inputs in a single layered platform (e.g., a nucleic acid construct). The invention provides, inter alia, synthetic recombinase-based systems for integrating combinatorial logic and memory in living cells. Integrated logic and memory are crucial for performing complex and persistent state-dependent computation such as sequential logic. Using a defined set of programming rules, the logic and memory systems of the invention enable efficient, one-step assembly of any Boolean logic function with stable, DNA-based memory of events. These systems utilize chemical inducer as inputs to drive the expression of orthogonal recombinases from promoters. These recombinases target genetic elements for DNA inversion (e.g., reversible), or excision (e.g., irreversible), resulting in conditional nucleic acid expression. Such logic and memory systems are useful for a variety of applications, including programming cellular state machines, behaviors and pathways for therapeutic, diagnostic and basic science applications.

Some of the most powerful tools in genome engineering are site-specific DNA recombinases (SSR), which can be used to activate or inhibit expression of genes. One of the main functions of recombinases in genome engineering is to regulate gene expression, both for exogenous and endogenous genes.

The methodology of constructing complex nucleic acid logic cassettes described herein takes advantage of the simple operation principles of site-specific recombinases. As shown in FIG. 11A, when a nucleic acid sequence (e.g., a target gene) is flanked by a pair of recombinase recognition sequences (RRS) in the same orientation, the nucleic acid sequence can be excised upon the recognition of the RRS by the proper recombinase; when a nucleic acid sequence is flanked by a pair of recombinase recognition sequences (RRS) in an inverse orientation, the nucleic acid sequence can be inverted upon the recognition of the RRS by the proper recombinase. The inversion and/or excision reactions will place the nucleic acid sequence (e.g., a target gene) in a new location and/or orientation to make it operatively linked to a promoter, thereby driving expression of the nucleic acid sequence. Based on these operation principles, depending on the combination of excision and inversion of 1, 2, or more nucleic acid sequence(s), one can select from the growing number of recombinases and their corresponding RRS to construct nucleic acid logic cassettes for a specific logic function.

Depending on the location of the recombinase recognition sequences, the excision reaction by a recombinase can lead to activation or inhibition of gene expression. For example, to activate gene expression, one can put a transcription termination sequence, flanked on both sides by recombination sites, upstream of a target gene of interest. In the presence of the recombinase, the transcription termination sequence is removed, thus allowing gene expression to occur. In contrast, to inhibit gene expression, the recombination sites can be engineered to flank the gene of interest. The gene expresses without the recombinase. Once the recombinase is induced, the gene will be excised and thus the gene expression is completely and irreversibly inhibited. The determinant factor that governs the on/off state of the gene resides in the presence of the recombinase. The expression of the recombinase can be regulated by a signal inducible promoter, thus restricting the expression of the recombinase in a certain subset of cells that are undergoing that particular signal. For instance, by controlling the expression of Cre recombinase with neuron specific promoters, one can turn genes on or off in neurons only while leaving the same gene unperturbed in other tissues. These enzymes have been engineered to be very active in a wide range of organisms, including bacteria, mammals, insects, plants and fish. Due to their ability to modify DNA in almost any tissues and conditions, recombinases have proven to be invaluable in regulating gene expression for many studies.

However, most existing recombinase-based expression platform utilizes one, or at most two recombinase. Therefore, these systems have limited capacity to perform complex and high level signal integration and computation.

Recently, orthogonal site-specific DNA recombinases (SSR) have been identified. It is therefore possible to use such orthogonal recombinases to perform complex logic computation. By coupling the expression of the recombinase with cell-type or condition specific promoters, the inventors have demonstrated robust spatiotemporal control of gene expression in living animals (e.g., mammals) in vivo.

Using these newly discovered recombinases, the inventors demonstrate herein sophisticated genetic logic gates, such as a Full Adder, Multi-Input (e.g., 3, 4, 6 and 8 inputs) AND gate, and Decoder. Furthermore, the inventors have developed a highly robust and modular genetic circuit platform in living human cells wherein the majority of computation is achieved by a single transcriptional unit, which can be rapidly and intuitively designed and constructed. Using the platform, the inventors have developed a large number of complex multi-input, multi-output circuits, including, but not limited to, (i) a 6-input AND gate, (ii) 2-input decoder, (iii) half adder, (iv) half subtractor, (v) Feynman gate, (vi) full adder, (vii) full subtractor, as well as (viii) two field-programmable genetic devices: a half adder-subtractor and Boolean Logic Look-Up Table. Accordingly, the inventors have created all sixteen two-input Boolean logic gates to regulate expression of a gene of interest. Gene circuits that can perform more complex logic functions can be created from a combination of these logic gates. Additionally, the inventors have created biological computers that utilize these recombinases to permit very fined-tuned and logic control of exogenous and endogenous genes.

To demonstrate the robustness of this platform, the inventors demonstrate the successful engineering of a variety of functionally distinct logic gates, and developed a quantitative metric to objectively assess the performance of the circuits. Given the importance of DNA recombinases in animal genetics[2,18,19] and the simplicity of the single transcriptional unit design disclosed herein, this platform can greatly improve tissue-specific gene expression and thus, the complexity of animal models available for studying diseases and drug development.

Furthermore, the inventors demonstrate that in contrast to prior genetic circuits, all of the circuits described herein are created in single layer and single transcription unit (e.g., in a single nucleic acid cassette or construct). Importantly, multiple plasmids are not necessary, and no linkages are needed between different transcriptional units in order to achieve the desired function. Thus the inventors have developed a modular genetic circuit platform that overcomes one of the most difficult challenges in synthetic circuit design—connecting various transcription units, and greatly accelerated the circuit development.

In one aspect, the invention relates to a nucleic acid logic cassette comprising: (i) a nucleic acid sequence encoding a promoter; (ii) a first recombination unit (U1) comprising a first pair of recombinase recognition sequences (RRS1) for a first site-specific recombinase (R1), wherein each of the RRS1 flanks each side of a first nucleic acid sequence, and wherein the RRS1 are in the same orientation or in an inverse orientation with respect to each other, and wherein at least one of the RRS1 is positioned downstream of the promoter, whereby when the R1 recognizes the RRS1, the first nucleic acid sequence is excised when the RRS1 are in the same orientation or is inverted when the RRS1 are in the inverse orientation; (iii) a second recombination unit (U2) comprising a second pair of recombinase recognition sequences (RRS2) for a second recombinase (R2), wherein each of the RRS2 flanks each side of a second nucleic acid sequence, and wherein the RRS2 are in the same orientation or in an inverse orientation with respect to each other, and wherein at least one of the RRS2 is positioned downstream of at least one of the RRS1, whereby when the R2 recognizes the RRS2, the second nucleic acid sequence is excised when the RRS2 are in the same orientation or is inverted when the RRS2 are in the inverse orientation; (iv) a third recombination unit (U3) comprising a third pair of recombinase recognition sequences (RRS3) adapted to be recognized by the R1, R2, or a third recombinase (R3), wherein each of the RRS3 flanks each side of a third nucleic acid sequence, wherein the RRS3 are in the same orientation or in an inverse orientation with respect to each other, and wherein at least one of the RRS3 is positioned downstream of at least one of the RRS2, whereby when the R1, R2, or R3 recognizes the RRS3, the third nucleic acid sequence is excised when the RRS3 are in the same orientation, or is inverted when the RRS3 are in the inverse orientation; wherein the first, second or third nucleic acid sequence comprises a target gene, and wherein presence or absence of at least one of the R1, R2, and R3 operatively links the promoter to at least one of the first, second or third nucleic acid sequence, thereby driving expression of the first, second or third nucleic acid sequence.

In some embodiments of the nucleic acid logic cassette, the R2 does not recognize the RRS1 or RRS3. Stated another way, the R2 is orthogonal to the R1 and R3. In some embodiments, the R3 does not recognize the RRS1 or RRS2. Stated another way, the R3 is orthogonal to the R1 or R2.

In some embodiments of the nucleic acid logic cassette, the cassette is adapted to function as a decoder (e.g., 2-input 4-output decoder, 3-input 8-output decoder), multi-input AND gate, full adder, full subtractor, or half adder-subtractor.

In another aspect, the invention relates to a switch operable in a mammalian immune cell. The switch can be used to control the expression of a gene or a set of genes of interest. For examples, the genes of interest include, but are not limited to, chimeric antigen receptor, T cell receptor, cytokines (e.g., IL-2, IL-12, IL-15), and suicide genes (e.g., HSV-TK, iCasp9). The switch comprises: (i) a nucleic acid sequence encoding a mammalian promoter; (ii) a first pair of recombinase recognition sequences (RRS1) for a first recombinase (R1), wherein each of the RRS1 flanks each side of a first nucleic acid sequence, and wherein the RRS1 are in an inverse orientation with respect to each other, and wherein at least one of the RRS1 is positioned downstream of the promoter; (iii) a second pair of recombinase recognition sequences (RRS2) for a second recombinase (R2), wherein each of the RRS2 flanks each side of a second nucleic acid sequence, and wherein the RRS2 are in an inverse orientation with respect to each other, and wherein at least one of the RRS2 is positioned downstream of at least one of the RRS1; and (iv) a target gene positioned downstream of at least one of the RRS1, whereby expression of the target gene is controlled by the presence or absence of at least one of the R1 and R2. The switch can be used in a variety of applications such as cell-based immunotherapy.

In some embodiments of any one of the above aspects, the mammalian cell is a human cell.

In some embodiments of any one of the above aspects, the human cell is a B cell.

In some embodiments of any one of the above aspects, the human cell is a T cell.

DETAILED DESCRIPTION OF THE FIGURES

FIGS. 1A-1D shows orthogonal site-specific tyrosine recombinases and serine integrases enable implementation of multi-input AND gates in mammalian cells. FIG. 1A shows that recombinases can perform simple buffer (BUF) logic operations, either by tyrosine recombinase-mediated excision (left) or serine integrase-mediated inversion (right). FIG. 1B shows recombinases are tested for their recombination efficiency and orthogonality on all BUF logic reporters. FIG. 1C shows recombinases are tested for heterospecific recombination sites. FIG. 1D shows an exemplary 6-input AND-gate that produces GFP when all inputs are present. M.F.I.=mean fluorescence intensity; a.u.=arbitrary units.

FIGS. 2A-2B shows exemplary 2-input BLADE platform can produce four distinct output functions based on two inputs. FIG. 2A shows an embodiment of a 2-input BLADE template on one plasmid with a single transcriptional unit. This template contains four distinct regions of DNA (addresses) downstream of a promoter. Each address corresponds to an output function and is accessed or deleted via site-specific DNA recombination. Each address can be programmed from different configurations ranging from zero-inputs to Boolean functions. The first address ($Z_{00}$), which is the closest to the promoter, corresponds to a state where no recombinase is expressed (A=0, B=0). If the $Z_{00}$ address contains a protein coding sequence, then that gene will be expressed. Gene expression from the other addresses downstream of $Z_{00}$ will be blocked by the presence of $Z_{00}$ protein coding region. In the presence of recombinase A, which corresponds to state (A=1, B=0), addresses $Z_{00}$ and $Z_{01}$ will be removed, thus moving address $Z_{10}$ directly downstream of the promoter and allowing gene expression of address $Z_{10}$ only to occur. Similarly, when only recombinase B is present (A=0, B=1), addresses $Z_{00}$ and $Z_{10}$ are excised, allowing $Z_{01}$ to be moved directly downstream of the promoter. Finally, when both recombinases are expressed (A=1, B=1), addresses $Z_{00}$, $Z_{01}$, $Z_{10}$ are all excised, thus placing $Z_{11}$ downstream of the promoter unobstructed by the other addresses. FIG. 2B shows an exemplary 2-input BLADE template with tagBFP, EGFP, iRFP720, and mRuby2 as addresses $Z_{00}$, $Z_{10}$, $Z_{01}$, and $Z_{11}$ respectively. a.u.=arbitrary units.

FIGS. 3A-3B show that over one hundred robust gene circuits with up to two inputs and two outputs implemented using the 2-input BLADE template. FIG. 3A shows that to generate 2-input, 2-output circuits, a 2-input BLADE template can be configured with different combinations of output functions: zero-output (transcription termination sequence), one-output (GFP or mCherry) or two-output (GFP-T2A-mCherry). FIG. 3B shows a diverse library of >100 gene circuits, each shown as an individual column with predicted truth table GFP/mCherry ON/OFF behavior (black=no output, green=GFP ON, red=mCherry ON) and corresponding experimental averaged single-cell results obtained from flow cytometry. Shown above is an expanded view of one of the logic gates made using this platform. M.F.I.=mean fluorescence intensity.

FIG. 4 shows a field-programmable storage and retrieval of logic and memory using a Boolean Logic Look-Up Table (LUT). The Boolean Logic LUT is a six-input-one-output genetic device that receives two data inputs, A and B, and is controlled by four select inputs, $S_1$, $S_2$, $S_3$, and $S_4$, producing an output of GFP. The select inputs are used to change data input-output behavior; each combination configures the device to any of the sixteen Boolean logic gates. F.I.=fluorescence intensity.

FIGS. 5A-5B show that a 3-input BLADE template can be applied to create 3-input arithmetic computational circuits. FIG. 5A shows that an exemplary 3-input BLADE template can receive up to three inputs and has eight distinct outputs. FIG. 5B shows an exemplary three 3-input-2-output binary arithmetic computational circuits made using the 3-input BLADE template. The full adder can add A+B+C while the full subtractor calculates A−B−C. For addition, input C, output P, and output Q represent Carry In, Carry Out and Sum, respectively. For subtraction, input C, output P, and output Q signify Borrow In, Borrow Out and Difference, respectively. The half adder-subtractor performs either binary addition of A+B or binary subtraction of A−B depending on the presence of select input C. F.I.=fluorescence intensity.

FIGS. 6A-6C shop recombinase cross-reactivity dose-response profile of Cre, Dre, VCre and Vika. FIG. 6A is a summary of intended and unintended recombination of Cre, Dre, VCre and Vika site-specific recombinases. Cre and Dre are mutually cross-reactive, whereas VCre can recombine Vika's recombination sites, but not the other way around. FIG. 6B shows a dose-response profile of Cre (left) and Dre (right) on both Cre and Dre reporter constructs. FIG. 6C shows a dose-response profile of VCre (left) and Vika (right) on both VCre and Vika reporter constructs.

FIG. 7 shows a recombinase-based 2-input, 1-output Boolean logic gates using Cre and Flp recombinases. Recombination sites for Cre and Flp are placed around termination sequences or GFP to enable or disable GFP expression. In this fashion all sixteen Boolean logic functions were created in mammalian cells.

FIGS. 8A-8B show alternative versions of the Boolean Logic Look-up Table (LUT). (FIG. 8A) A Boolean Logic LUT using Dre, Vika, B3 and VCre as select inputs. (FIG. 8B) The same Boolean LUT using low amounts of select inputs to reduce cross-reactivity effects of Cre/Dre and VCre/Vika, as noticeably illustrated in the AND and A gates.

FIG. 9 shows that a unique Nucleotide Sequence guided assembly provides a fast and modular approach for creating DNA constructs. A library of 2-Input 2-Output circuit can be used by using a combinatorial Gibson assembly strategy using the 2-4 decoder framework as the basis, and 4 parts can be constructed for each slot—stop cassette, GFP, mCherry, and GFP-2A-mCherry. Since the 2-4 decoder has 4 slots, a total of 16 components can be used. Then a combinatorial assembly strategy can be employed to create all 256 possible 2-Input 2-Output circuits. Genes are first cloned into part entry vectors that contain 40 bp unique nucleotide sequences (UNSes). These part vectors are then digested with either Asc1+Not1 or Asc1+Nhe1 restriction endonucleases to expose UNSes. The part fragments are then gel purified and assembled into a linearized destination vector using Gibson isothermal assembly.

FIGS. 10A-10B show the construction of BLADE constructs using Unique Nucleotide Sequence Guided Assembly. FIG. 10A shows that to create a 3:8 BLADE construct, part vectors are created that contain output states for each address. The part vectors, along with a destination (DEST) vector, are digested and gel purified to expose unique nucleotide sequences (UNSes). FIG. 10B shows the part fragments and linearized destination vector are then assembled together in order of UNS via Gibson isothermal assembly.

FIGS. 11A-11B shows an exemplary buffer gate construct. FIG. 11A is a schematic of the construct that, when recombinase is expressed, it will bind to the two recombination sites and excise the stop cassette between the recombination sites. For serine recombinases, the recombination sites are placed between a GFP that is in antisense direction, so that the expression of the corresponding serine recombinase inverts the DNA fragment between the recombination sites, inverting the GFP into the sense direction and allowing GFP to be expressed. FIG. 11B shows that transient transfection of the recombinase and the reporter plasmid, most of the enzymes tested are highly active and sufficiently orthogonal for the circuit design.

FIGS. 12A-12C show embodiments of the multi-Input AND gates which are a single layer and can be used in the mammalian genetic systems of the 16 2-Input Boolean logic gates shown in FIG. 7. FIG. 12A shows embodiments of different 2-input AND gates and resulting GFP expression with different input SSRs; bxb1, PhiC31, Cre, Flp, SCre, VCre, Vika, Dre, B3 and KD. Note that the AND is created by placing two stop cassettes in tandem. Because of the othoganoality of the recombinases, it becomes possible to generate multi-Input AND gates simply by placing more stop cassettes in tandem between a GFP and the promoter. FIG. 12B shows embodiments of the genetic construct circuits of exemplary 4-input, 6-input and 8-input AND gates with different input SSRs (othogonal recombinases); bxb1, PhiC31, Cre, Flp, SCre, VCre, Vika, Dre, B3 and KD. FIG. 12C shows GFP expression from the genetic construct circuits of shown in FIG. 12B with exemplary 4-input, 6-input and 8-input AND gates with different input SSRs; bxb1, PhiC31, Cre, Flp, SCre, VCre, Vika, Dre, B3 and KD.

FIGS. 13A-13D shows exemplary logic gates, including a 2-to-4 decoder, a 3-input-2-output, a half adder, a half subtractor and a full adder gate. FIG. 13A shows an exemplary 2-to-4 decoder and a 3-input-2-output logic gate, demonstrating a signal to noise ratio of over 100 for each state for the 2-to-4 decoder. FIG. 13B shows exemplary half adder logic gates, using 1, 2 or 3 plasmids, with a stop cassette in the Z00 slot, a GFP in Z10 and Z01, and a GFP-2A-mCherry cassette in Z11. FIG. 13C shows an exemplary half substractor logic gate using 1, 2 or 3 plasmids where a stop cassette is placed in the Z00 slot, a GFP in Z01, and a GFP-P2A-mCherry in Z10. FIG. 13D shows an exemplary full adder logic gate, a 3-input 2-output logic gate, using Cre, Flp and Vcre as input, where the slots are filled with either a stop cassette, GFP, mCherry or GFP-2A-mCherry, depending on the output of the full adder truth table, and resulting mCherry and GFP expression depending on the input shown in the truth table.

FIGS. 14A-14B shows exemplary 2-to-4 decoders and 3-to-8 decoders using serine recombinases, which has a complementary directionality factor that when expressed together with the recombinase, will revert the inversion generated by the recombinase back to the original configuration. FIG. 14A shows an exemplary 2-to-4 decoder, using the inversion property of serine recombinases, and depending on the presence of directionality factor or not, which can revert the system back to the original state. FIG. 14B shows an exemplary 3-to-8 decoder, using the inversion property of serine recombinases, and depending on the presence of directionality factor or not, which can revert the system back to the original state.

FIG. 15A shows a 2-input BP Advanced Excision and Integration Synthetic (AXIS) template on one plasmid with a single transcriptional unit. This template contains four distinct regions of DNA (addresses) downstream of a promoter. Each address corresponds to an output function and is accessed via site-specific DNA recombination. The first address ($Z_{00}$), which is the closest to the promoter, corresponds to a state where no recombinase is expressed (A=0, B=0). If the $Z_{00}$ address contains a protein coding sequence, then that gene will be expressed. Gene expression from the other addresses downstream of $Z_{00}$ will be blocked by the presence of $Z_{00}$ protein coding region. In the presence of recombinase A, which corresponds to state (A=1, B=0), each DNA cassette between recombinase A's two orthogonal pairs of attB/P recombination sites, will each be inverted, thus moving address $Z_{10}$ directly downstream of the promoter and allowing gene expression of address $Z_{10}$ only to occur. Similarly, when only recombinase B is present (A=0, B=1), the entire DNA cassette between the recombinase B's attB/P recombination sites will be inverted, allowing $Z_{01}$ to be moved directly downstream of the promoter. Finally, when both recombinases are expressed (A=1, B=1), DNA cassettes between both recombinase A and B's pairs of attB/P recombination sites will be inverted, thus placing $Z_{11}$ downstream of the promoter unobstructed by the other addresses.

FIG. 15B shows a schematic of the 2-input BP AXIS template with iRFP720, tagBFP, mRuby2, and EGFP as addresses $Z_{00}$, $Z_{10}$, $Z_{01}$, and $Z_{11}$ respectively. Also shown is averaged single-cell results of the 2-Input BP AXIS decoder using PhiC31 and TP901-1 integrases. Mean fluorescence intensity from n=3 independent transfections. a.u.=arbitrary units.

FIG. 16A is a schematic illustrating the architecture of a full adder in accordance with some embodiments of the invention. "$RRS_{for}$" refers to the RRS in the forward orientation. "$RRS_{rev}$" refers to the RRS in the reverse orientation. "$TG_{for}$" refers to the TG in the forward orientation. "$TG_{rev}$" refers to the TG in the reverse orientation. "$TT_{for}$" refers to the transcriptional terminator in the forward orientation. R1 recognizes RRS1. R2 recognizes RRS2, RRS6, and RRS7. R3 recognizes RRS3, RRS4, and RRS5.

FIG. 16B is a schematic illustrating the architecture of a full subtractor in accordance with some embodiments of the invention. R1 recognizes RRS1. R2 recognizes RRS2, RRS6, and RRS7. R3 recognizes RRS3, RRS4, and RRS5.

FIG. 16C is a schematic illustrating the architecture of a half adder-subtractor in accordance with some embodiments of the invention. R1 recognizes RRS1. R2 recognizes RRS2, RRS6, and RRS7. R3 recognizes RRS3, RRS4, and RRS5.

FIGS. 21A-21C show tamoxifen induction in Jurkat T-cells of Cre activity on (FIG. 21A) a fluorescent reporter stable inversion switch. Seven days after induction, (FIG. 21B) mCherry expression decreases as the gene is excised and (FIG. 21C) GFP expression is turned on.

(FIG. 22B) Expression of CAR increases upon induction and (FIG. 22C) Activation of the T-cell occurs in response to the antigen.

(FIG. 23A) Structure of the switch. Switching was observed for both the (FIG. 23B) Cre/lox and (FIG. 23C) Flp/frt system.

Figure 24A:
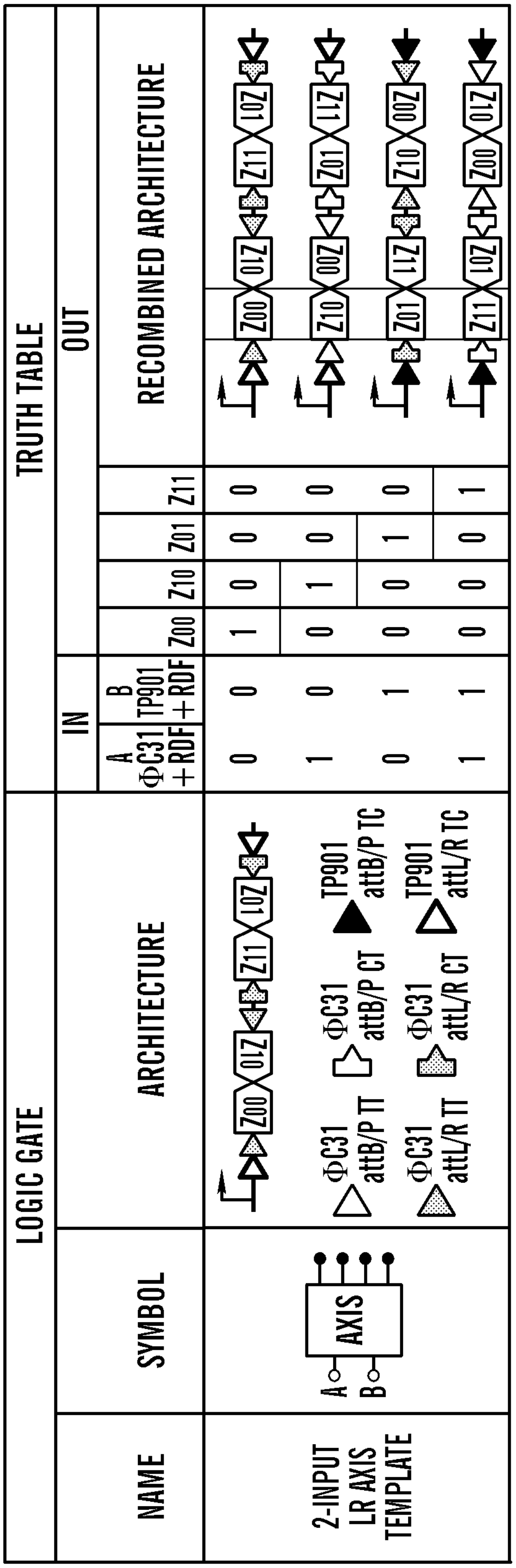
Figure 24B:
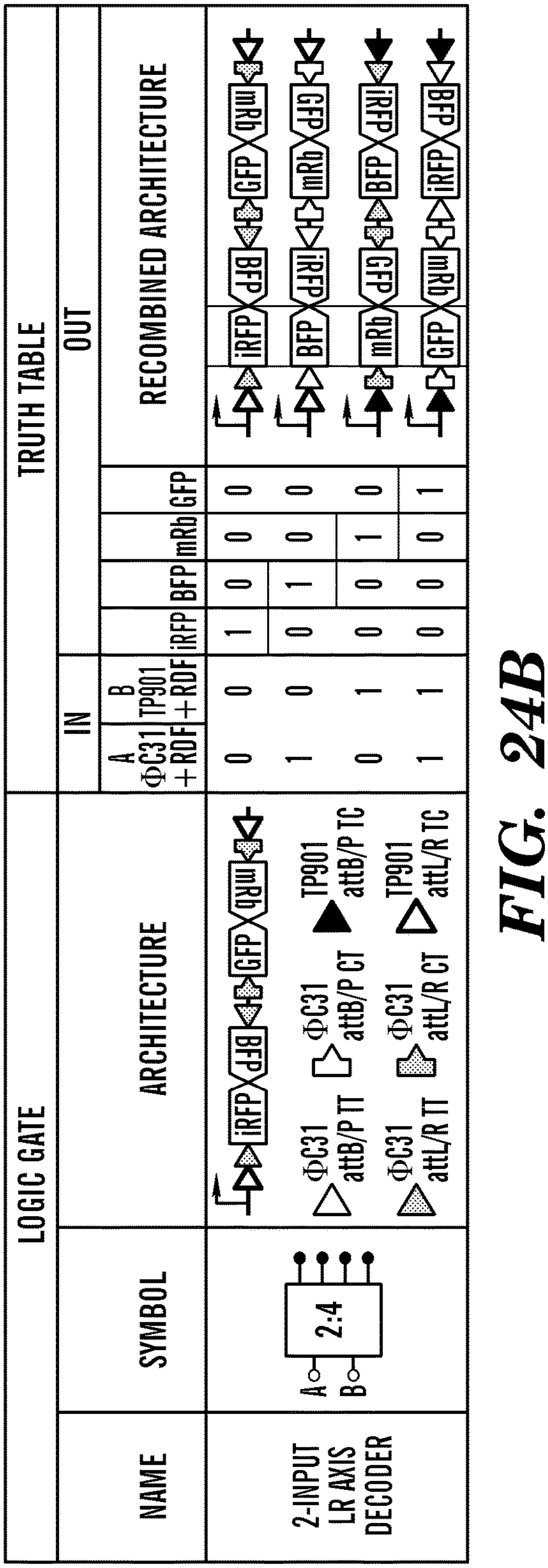
Figure 24C:
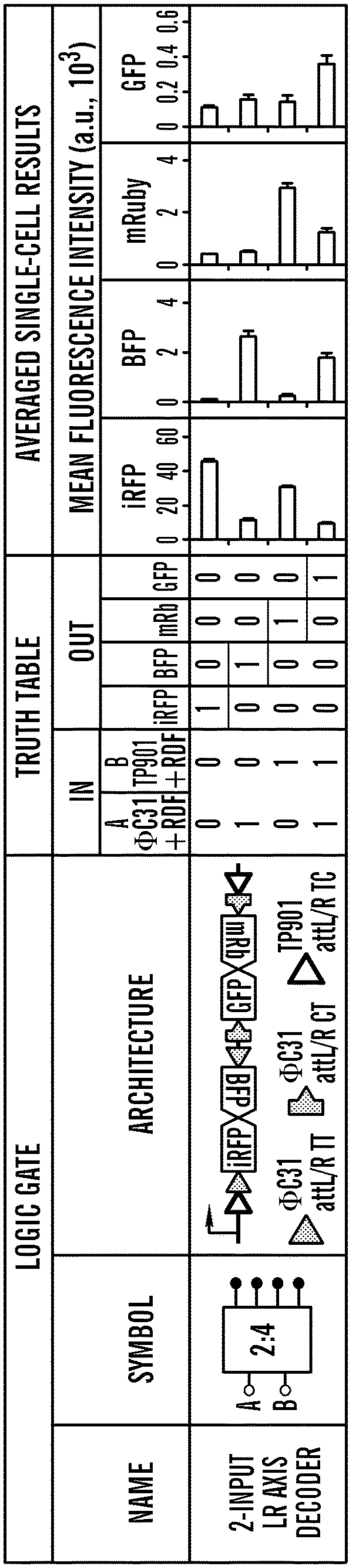

FIGS. 24A-24C show that 2-input LR AXIS platform can produce four distinct outputs based on two integrase and RDF inputs. (FIG. 24A) 2-input LR AXIS template on one plasmid with a single transcriptional unit. This template contains four distinct regions of DNA (addresses) downstream of a promoter. Each address corresponds to an output function and is accessed via site-specific DNA recombination. The first address ($Z_{00}$), which is the closest to the promoter, corresponds to a state where no recombinase is expressed (A=0, B=0). If the $Z_{00}$ address contains a protein coding sequence, then that gene will be expressed. Gene expression from the other addresses downstream of $Z_{00}$ will be blocked by the presence of $Z_{00}$ protein coding region. In the presence of recombinase A and its associated RDF, which corresponds to state (A=1, B=0), each DNA cassette between recombinase A's two orthogonal pairs of attL/R recombination sites, will each be inverted, thus moving address $Z_{10}$ directly downstream of the promoter and allowing gene expression of address $Z_{10}$ only to occur. Similarly, when only recombinase B and its associated RDF are present (A=0, B=1), the entire DNA cassette between the recombinase B's attL/R recombination sites will be inverted, allowing $Z_{01}$ to be moved directly downstream of the promoter. Finally, when both recombinases and RDFs are expressed (A=1, B=1), DNA cassettes between both recombinase A and B's pairs of recombination attL/R sites will be inverted, thus placing $Z_{11}$ downstream of the promoter unobstructed by the other addresses. (FIG. 24B) A schematic of the 2-input LR AXIS template with iRFP720, tagBFP, mRuby2, and EGFP as addresses $Z_{00}$, $Z_{10}$, $Z_{01}$, and $Z_{11}$ respectively (FIG. 24C) Averaged single-cell results of the 2-Input LR AXIS decoder using PhiC31 integrase and gp3, and TP901-1 integrase and orf7. Mean fluorescence intensity from n=3 independent transfections. a.u.=arbitrary units.

Figure 25:
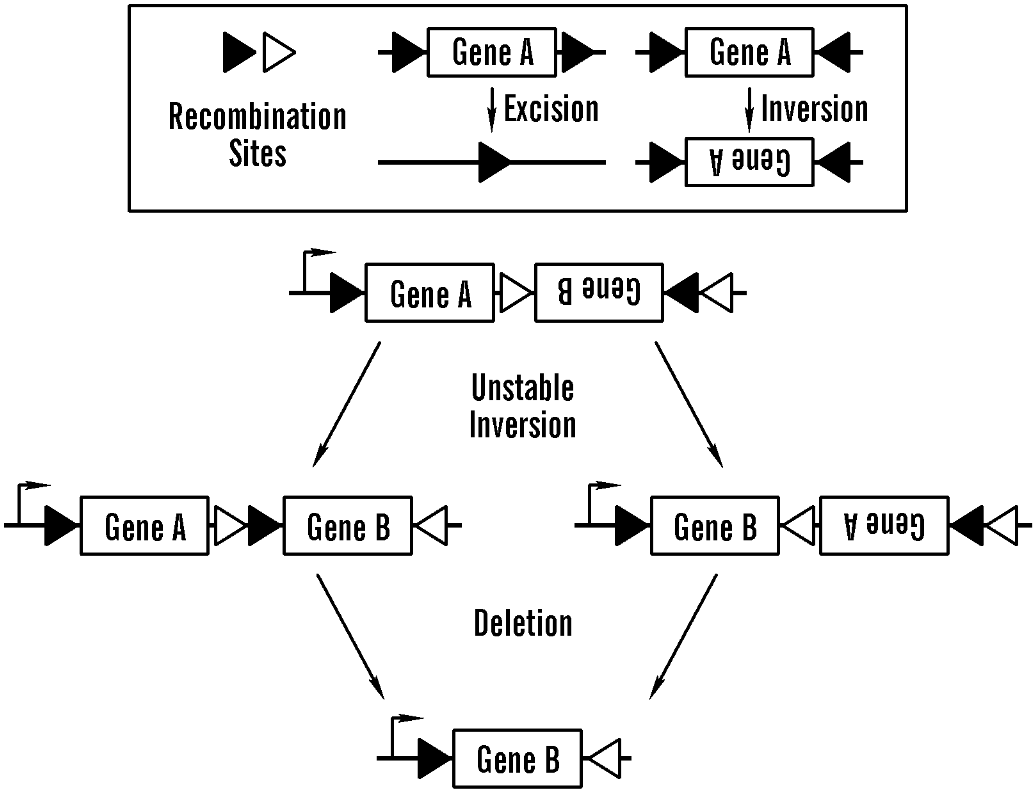

FIG. 25 shows the mechanism of recombinase-based stable inversion switch. The stable inversion switch is a two-step process that takes the cell from expressing one gene to another upon recombination. Using pairs of recombination sites, this switch allows for stable memory of the change in genetic expression. In addition, this switch can be used to control the promoter driving gene expression.

Figure 26A:
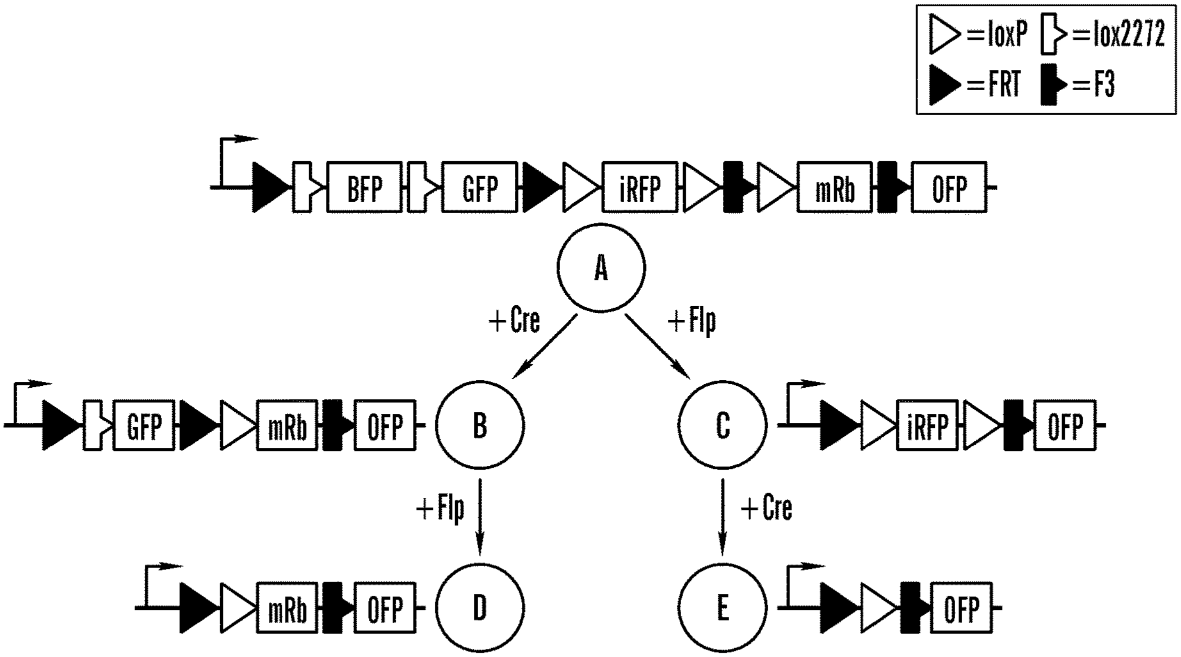

FIG. 26A shows an order-dependent, five-color and five-state finite state machine. With no recombinase input, the circuit produces BFP. Upon addition of input A, Cre recombinase, acts on the circuit to yield GFP expression; if input B, Flp recombinase, is added next, the circuit yields mRuby2 expression. If input B is introduced first to the circuit, the output is iRFP rather than GFP and if input A is added next, expression of OFP is produced.

Figure 26B:
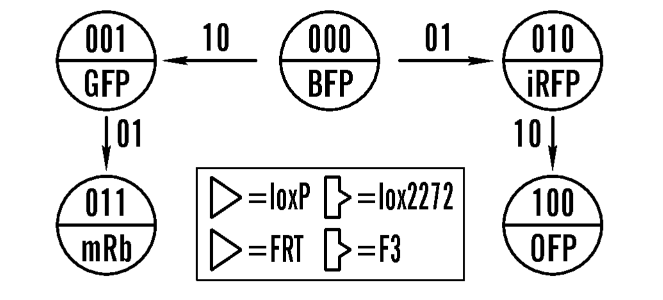
Figure 26B:

FIG. 26B shows state table and state diagram representations of the five-color, five-state finite state machine.

Figure 26C:
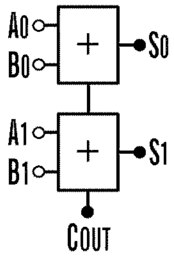
Figure 26C:
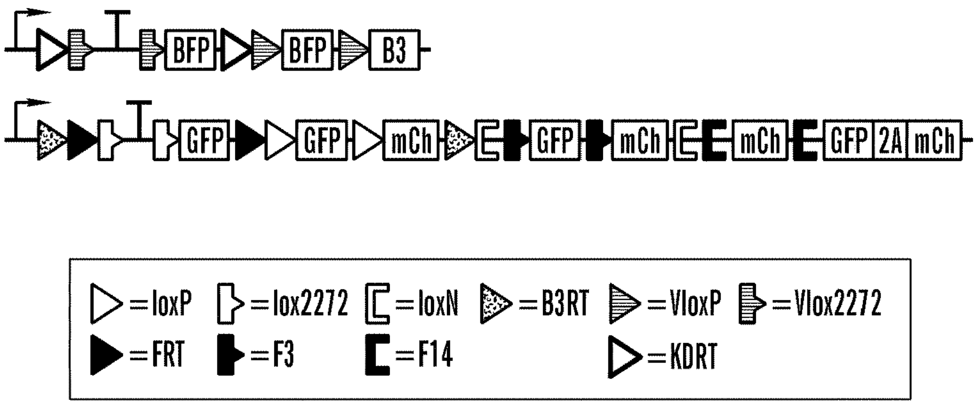

FIG. 26C shows a ripple carry adder circuit is created through connection of a half adder and full adder. The circuit can add two 2-bit inputs, thereby allowing summation up to 3+3=6.

Figure 26D:
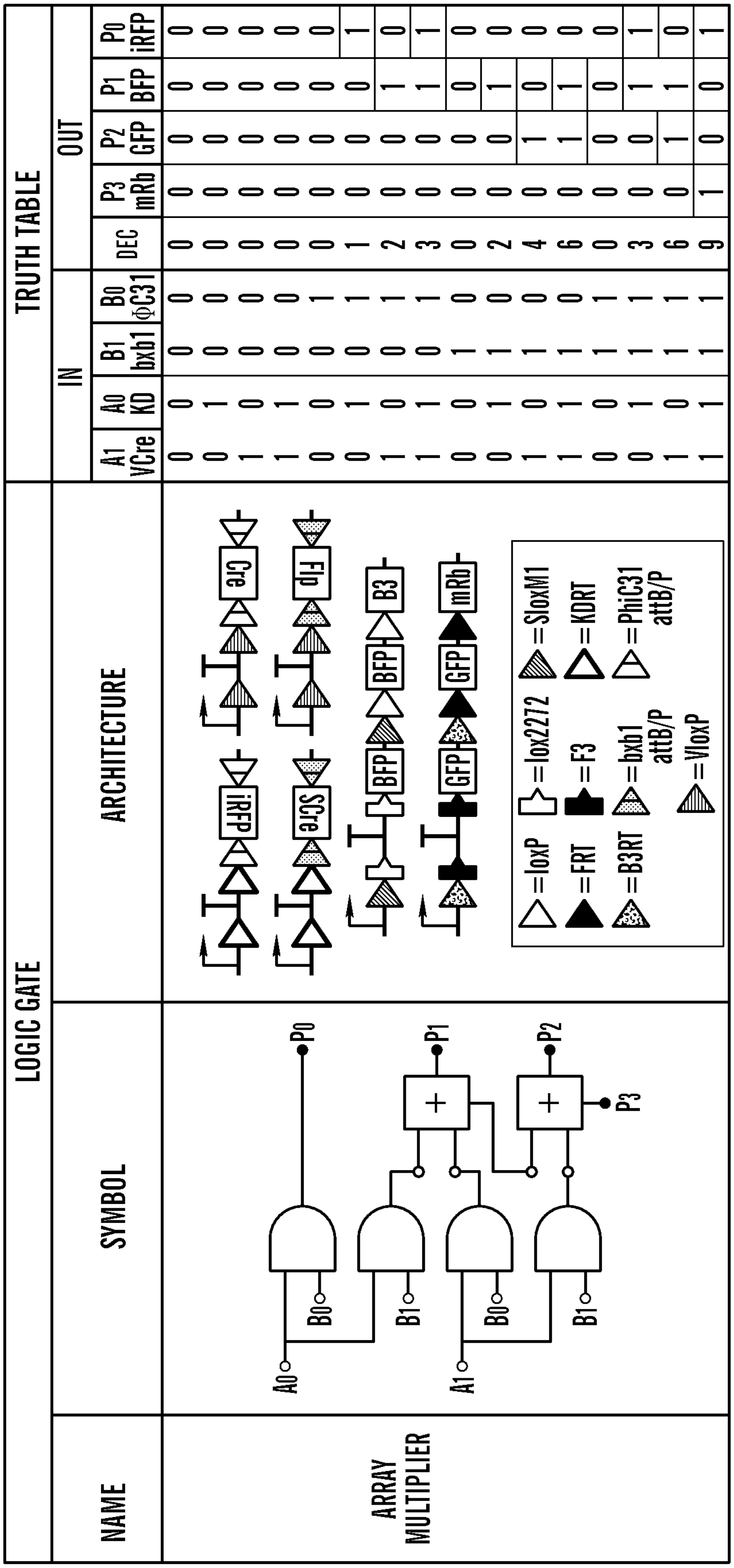

FIG. 26D shows a multiplier circuit is created through connection of four AND gates and two half adders. The circuit can multiply two 2-bit inputs, thereby allowing multiplication up to 3*3=9.

Figure 26E:
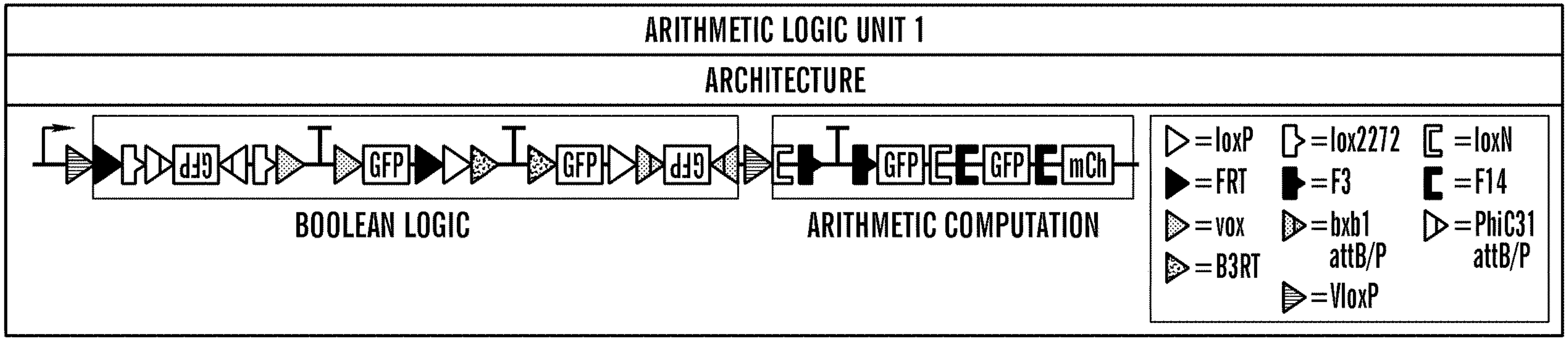
Figure 26E:
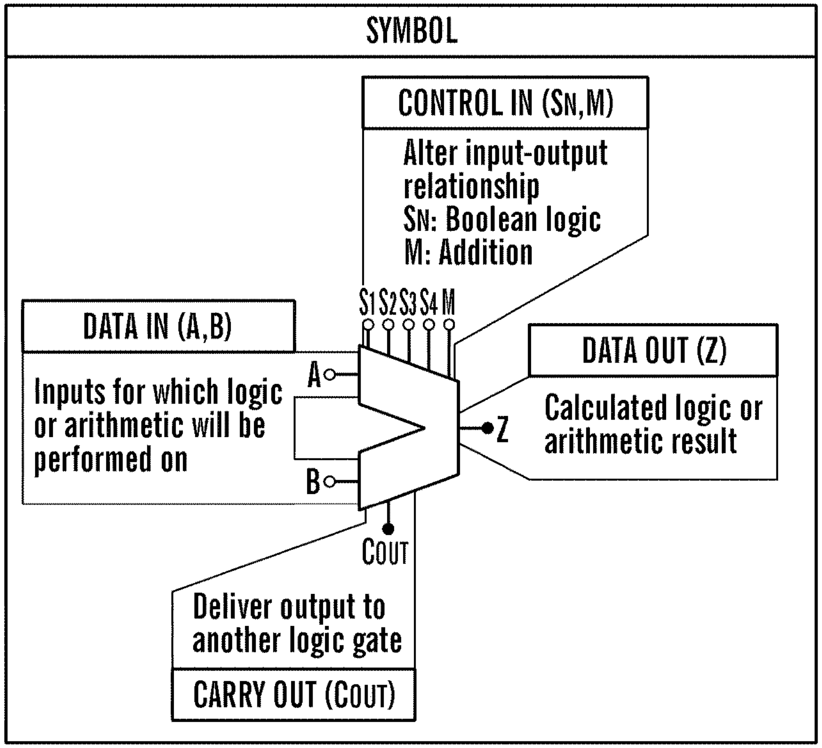

FIG. 26E shows an arithmetic logic unit that permits all sixteen basic boolean logic functions as well as performing as a half adder.

Figure 26F:
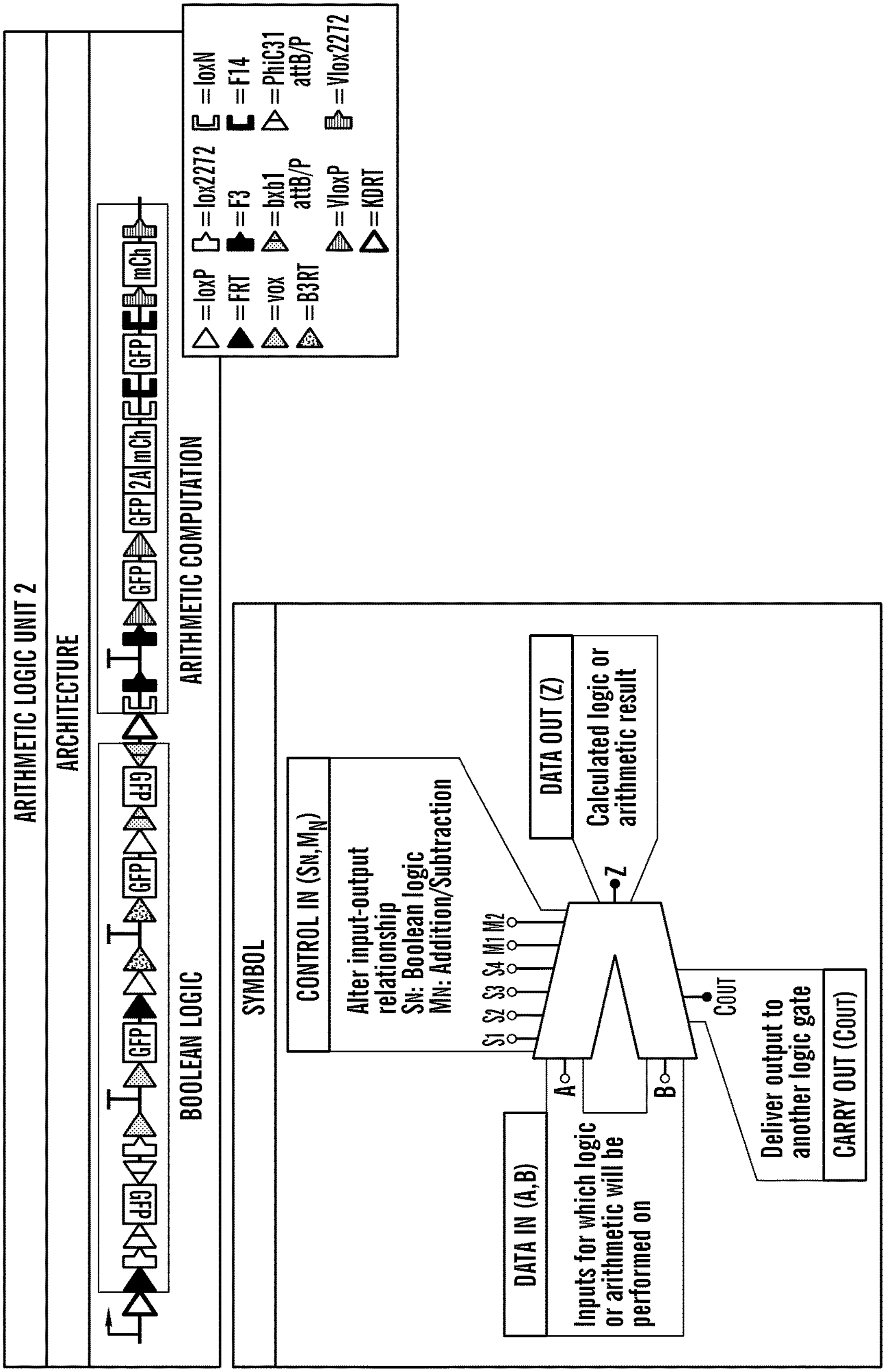

FIG. 26F shows an arithmetic logic unit that permits all sixteen basic boolean logic functions as well as performing as a half adder or a half subtractor.

DETAILED DESCRIPTION OF THE INVENTION

The present invention provides a platform to construct complex nucleic acid logic cassettes on single transcriptional units. The nucleic acid logic cassettes can perform simple or complex logic functions, e.g., in mammalian cells, including, but not limited to, A, N, NOT A, NOT B, NOR, OR, AND, NAND, A IMPLY B, B IMPLY A, A NIMPLY B, B NIMPLY A, XOR, XNOR, decoder, half adder, half subtractor, half adder-subtractor, full adder, full subtractor, Feynman gate, logic selector, memory, Ripple carry adder, array multiplier, arithmetic logic unit, and any combinations thereof. To perform a logic function, a nucleic acid logic cassette can receive at least one input, preferably at least two inputs (e.g., 2, 3, 4, 5, 6, 7, or more), and produce at least one output (e.g., 1, 2, 3, 4, 5, 6, or more) as a function of the input(s).

To perform complex logic functions, existing genetic logic circuits assemble a complex circuitry from a plurality of simple cassettes; signal relay is required as an output from one cassette serves as an input for another cassette. Given the complexity of the assembly, such multi-layered approach makes these logic circuits difficult to reproduce and insert into cells. In addition, at least due to the requirement for signal relay, the fidelity of these logic circuits is low. And thus using these logic circuits in higher organisms such as mammals has been challenging. In contrast, because the logic cassettes of the present invention are constructed on single transcriptional units, no signal relay is necessary, and they are easy to reproduce and insert into cells. The complexity lies in the design of the logic cassettes on the back end, which ultimately allows simple and reliable utilization of these logic cassettes on the front end. Due to these significant advantages, the logic cassettes described herein have been demonstrated by the inventors to work in mammalian cells such as human cells.

Figure 11A:
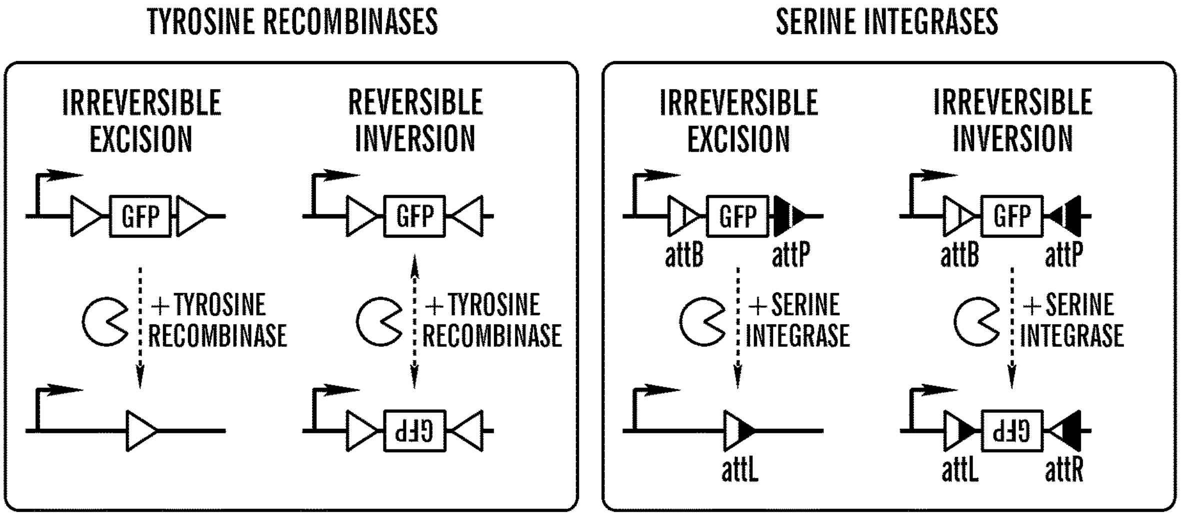

The methodology of constructing complex nucleic acid logic cassettes takes advantage of the simple operation principles of site-specific recombinases. As shown in FIG. 11A, when a nucleic acid sequence (e.g., a target gene) is flanked by a pair of recombinase recognition sequences (RRS) in the same orientation, the nucleic acid sequence can be excised upon the recognition of the RRS by the proper recombinase; when a nucleic acid sequence is flanked by a pair of recombinase recognition sequences (RRS) in an inverse orientation, the nucleic acid sequence can be inverted upon the recognition of the RRS by the proper recombinase. The inversion and/or excision reactions will place the nucleic acid sequence (e.g., a target gene) in a new location and/or orientation to make it operatively linked to a promoter, thereby driving expression of the nucleic acid sequence. Based on these operation principles, depending on the combination of excision and inversion of 1, 2, or more nucleic acid sequence(s), one can select from the growing number of recombinases and their corresponding RRS to construct nucleic acid logic cassettes for a specific logic function.

The construction of the nucleic acid logic cassettes can be modular. Each module can be a nucleic acid sequence flanked by a pair of RRS. Depending on the specific logic functions, the modules can be connected in series, or there can be overlapping nucleic acid regions between the modules. A truth table for a desired logic function can be used to guide the placement of each module. Generally, a truth table is composed of one column for each input variable (for example, A and B), and one final column for all of the possible results of the logical operation that the table is meant to represent (for example, A XOR B).

It has been reported in US2014/0315310, which is incorporated herein by reference, the creation of recombinase-based logic gates in bacterial cells only. US2014/0315310 describes simple recombinase-based logic gates, i.e., logic gates that require no more than two inputs and produce no more than one output. In contrast, the present invention relates to recombinase-based expression vectors or gene circuits in mammalian cells. For example, the inventors have used recombinases and their corresponding heterospecific DNA binding sites to create all sixteen Boolean logic gates in the human embryonic kidney cell line. Additionally, the inventors have created expression vectors that can perform complex logic functions with more than two inputs (e.g., 3, 4, 5, 6, 7, 8, or more) and/or more than one output (e.g., 2, 3, 4, or more) in a single transcription unit. This is a significant advantage, as the present invention provides methods and cassettes for complex logic functions in mammalian cells using a series arrangement of simple modules in a single cassette.

The nucleic acid logic cassettes described herein can be used in vitro or in vivo. An example of in vitro use is the study of cell culture, in which cells contain the nucleic acid logic cassettes described herein. An example of in vivo use is the use of the nucleic acid logic cassettes described herein to regulate or control gene expression in a subject such as a human.

Genetic Circuit Platforms

Through the use of site-specific DNA recombinases (SSR) and their corresponding heterospecific DNA binding sites (e.g., recombinase recognition sequences (RRS)), the inventors have constructed and demonstrated, in mammalian cells, a suite of multi-input-multi-output (MIMO) circuits, such as a Half Adder, Half Subtractor, 2-Input Decoder, Full Adder, Full Subtractor, and Half Adder-Subtractor. Moreover, the inventors also created a Programmable Read Only Memory (PROM) device that can select between 16 2-Input logic gates based on 4 inputs. More importantly, the inventors were able to create all of the computation circuits in a single transcription unit (e.g., cassette)—no linkages between different transcription units are required to achieve the desired circuits. This development bypasses one of the most difficult challenges in synthetic circuit design, and allows all of the circuits to be successfully implemented on first attempt without optimization. For example, it is not necessary to have multiple plasmids for each logic function, nor is it necessary to calibrate the ratios of each plasmid with respect to each other for the correct logic function. This platform provides a powerful tool for complex gene regulation and expression in mammalian cells and high-level mammalian cells reprogramming for development of animal models. Furthermore, the circuit design platform described herein minimizes the typical "design-test-build" cycle that plagues the progress of most synthetic biology projects, and illustrates a new paradigm in the design of synthetic genetic logic circuits.

The inventors have demonstrated the use of the platform for the generation of N-input order-independent logic gates called Boolean Logic and Arithmetic through DNA Excision (BLADE). All logic computation for BLADE circuits is done on a single transcriptional layer and circuit construction is based on a BLADE template. N-input BLADE templates feature $2^N$ distinct regions of DNA termed addresses (Z). Each address is accessible only via a specific combination of inputs. For example, the 2-input BLADE template contains four addresses, $Z=Z_{AB}=Z_{00}$, $Z_{10}$, $Z_{01}$, and $Z_{11}$, corresponding to each state of A and B inputs (see FIG. 2A). Each address contains one output function, which ranges from having zero outputs (e.g., transcription terminator), through arbitrary numbers of outputs separated by ribosomal skip sequences (2A), to Boolean functions like buffer (BUF). A 2-input 4-output decoder has been constructed using the BLADE platform (e.g., FIG. 2B).

Figure 5A:
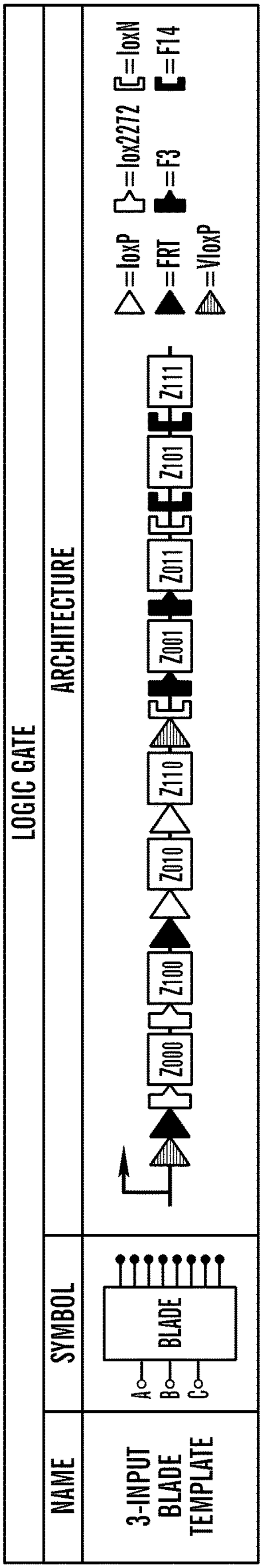
Figure 5B:
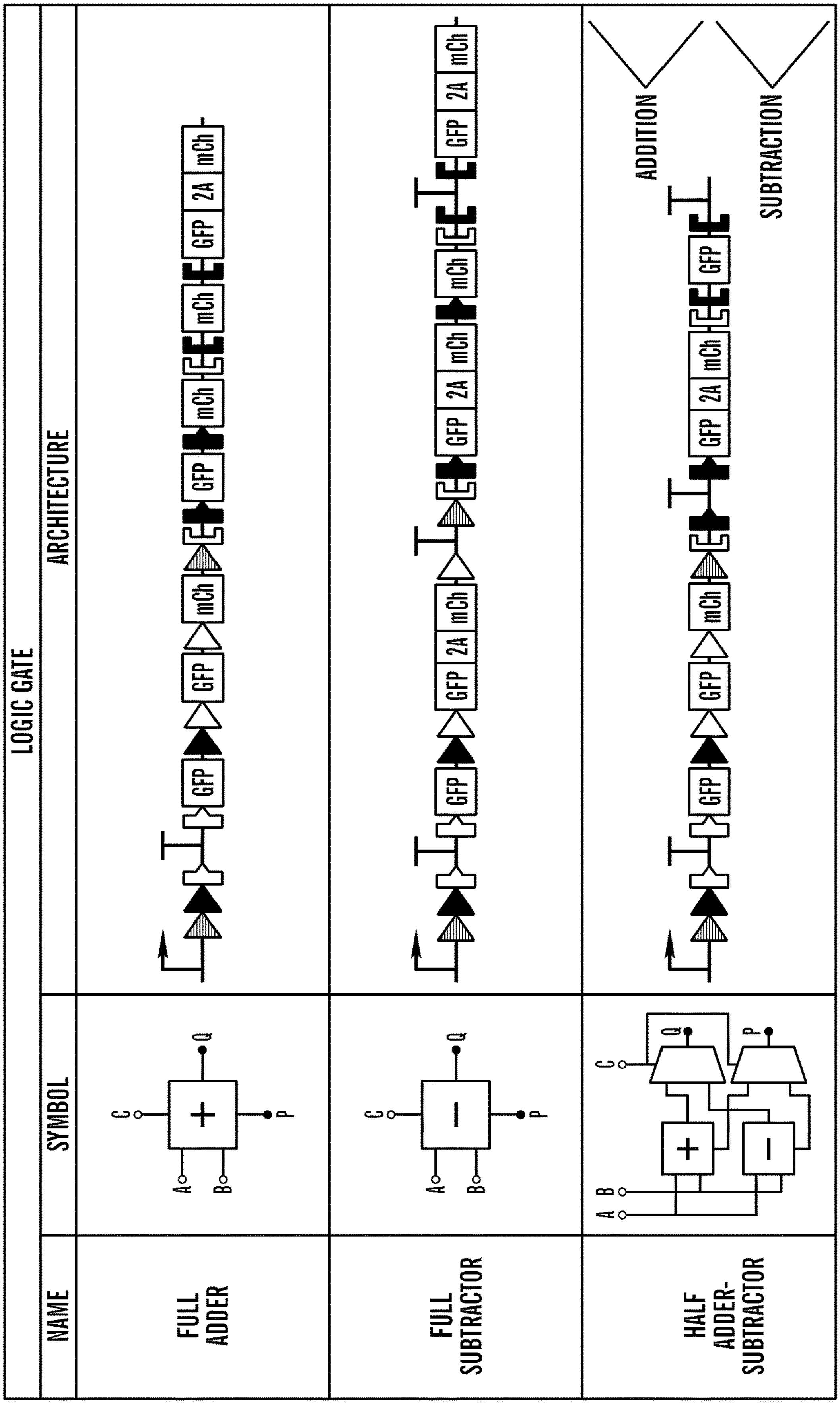
Figure 5B:
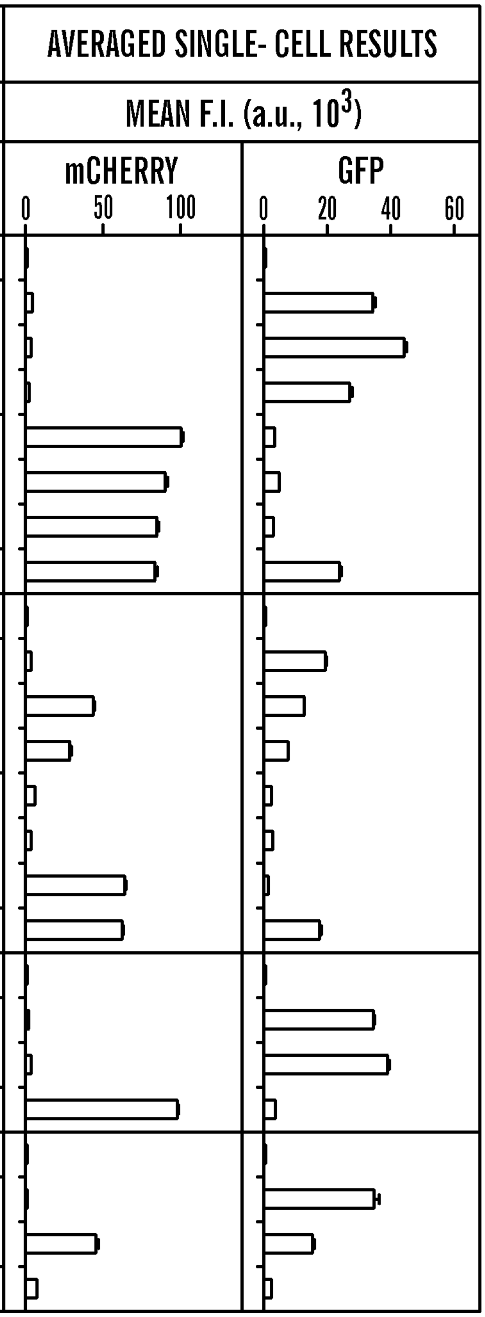

Extending the BLADE framework further, the inventors also demonstrate a 3-input BLADE template (in some embodiments as a 3-input 8-output decoder) for constructing sophisticated arithmetic functions in human cells (FIG. 5A). Such a 3-input BLADE genetic circuit responds to three inputs (Cre, Flp, and VCre) and contains eight addresses for expression of up to eight distinct output functions. This design utilizes three different heterospecific sites (e.g., RRS) for Cre and Flp, but just one site for VCre. Three 3-input-2-ouput arithmetic computational circuits were made and tested in mammalian cells from the 3-input BLADE template (FIG. 5B). The full adder and full subtractor can perform either binary addition or subtraction of three 1-bit inputs, respectively. Furthermore, the half adder-subtractor is an arithmetic FPROM circuit that can compute addition or subtraction on two data inputs, A and B, depending on the presence of one select input C.

Similarly, exploiting the principal of Field-Programmable Read-Only Memory (FPROM) in electronic circuits, the inventors configured the input-output behavior of these circuits in the field post-manufacturing, allowing them to customize their circuits and devices at a later time. In particular, the inventors built a FPROM device termed a Boolean Logic Look-Up Table (LUT) that is based on placing BUF gates into the four addresses of the 2-input BLADE template (see FIG. 4). This circuit has two data inputs, A and B, and four select inputs, $S_1$, $S_2$, $S_3$, and $S_4$. Each select input can control which buffer gates are GFP ON or OFF. Thus, each combination of select inputs configures the device to a specific Boolean logic gate with up to two inputs and one output. For instance, an OR function can be achieved using select inputs $S_2$, $S_3$, and $S_4$, keeping address $Z_{00}$ GFP OFF and setting addresses $Z_{10}$, $Z_{01}$, and $Z_{11}$ GFP ON. This circuit behaves as expected in mammalian cells.

Accordingly, the present invention provides a platform which is the foundation for generating logic gates with arbitrary number of inputs and outputs.

The following are examples of the use of the platform:

1. As powerful genetic tools for investigating and manipulating genetic functions
    - Cell-type expression of exogenous genes.
        - Expression of optogenetic proteins for optical control and study of specific cell types in the brain
        - Delivery of proteins/peptides/RNAs for therapeutic purposes
    - Cell-type overexpression, knockdown, knockout or mutation of endogenous genes (via genome modifying proteins such as TAL, Zinc finger and Cas9 effectors and nucleases)
        - Generation of animal models for study of diseases (e.g. cancer, neurological diseases, and other genetic pathologies)
        - Therapeutic correction of a pathogenic gene (e.g. repression of a cancer-causing oncogene or reactivation of a mutated tumor suppressing gene)
2. As advanced implantable cellular computers for seek-and-destroy or diagnostic purposes
    - a. Cell-based therapeutics
        - i. Cancer cell and pathogen seek-and-destroy engineered immune cells
    - b. Cell-based diagnostics
        - i. Disease biomarker sensing (e.g. detection of overexpression of an oncogene)
        - ii. Metabolite sensing and regulation (e.g. blood sugar regulation)
        - iii. Pathogen detection (e.g. HIV, pathogenic bacteria)

The biological devices and circuits as disclosed herein have wide-reaching applications and commercial interest. As a research tool, this technology can allow a scientist to genetically target specific cell-types in the body for studying and manipulating physiological functions. Moreover, cell-based gene therapies have shown tremendous clinical success and investor interest. The technology described herein can vastly enhance such strategies by integrating advanced cellular computations. For instance, one can create implantable cellular computers that could act as early-warning systems for diseases, attack cancerous cells, or monitor and regulate blood-glucose levels. Current technologies can't integrate the large numbers and logical nature of biological and environmental signals that these applications would require.

Many commercial applications would also benefit by the use of the genetic logic gates as disclosed herein. For example, adoptive T cell therapy is a type of gene therapy that has had tremendous clinical success and gained significant investor interest. The therapy involves the replacement of a cancer patient's immune cells with genetically engineered ones that are programmed with a chimeric antigen receptor (CAR) that targets proteins overexpressed on cancer cells. However, most other cancers are not as easily targeted since markers are not exclusively expressed on the surface of the cells. The use of the genetic logic gates as disclosed herein can offer a novel solution for these difficulties to target cancers by employing digital logic.

With the genetic logic gate systems disclosed herein, one is not limited to just targeting proteins that are overexpressed on the surface of cancer cells, it can be used to also induce or repress activation of the genetically engineered T cells with the abundance or absence of cellular and environmental signals. For instance, it can be used to limit off-target effects by limiting activation of the engineered T cells to the location of the cancer. This can be done via logical integration of multiple signals, such as the presence/absence of metabolites and cytokines found in the cancer, oxygen levels (i.e. tumor hypoxia) and spatial release of a chemical inducer.

Others have utilized other strategies for programming digital logic in living organisms. Most utilize transcription-factor based methods in both bacteria and in mammalian cells. DNA-binding proteins are expressed that either promote or repress gene expression on the transcriptional level. Although this method can be highly modular, a plurality levels of cascading components is required to achieve complex logical tasks. A plurality of plasmids is often necessary, which makes implementation into organisms more difficult, as all of the elements need to be expressed in single cells and at the correct ratio for these systems to function properly.

In contrast, the genetic logic gates as disclosed herein are advantageous in that they rely on the use of SSR and their corresponding RRS. Accordingly, one can create a single nucleic acid cassette capable of performing complicated logical tasks by utilizing heterospecific recombination sites. For instance, one of the genetic circuits, the full adder, is a three-input, two-output logic circuit that can digitally add up to three. It requires only one plasmid, far fewer than transcription-factor-based strategies would necessitate, thus making incorporation of all of the components into the genome of a single cell much easier. Therefore, the platform as disclosed herein using site-specific recombinases is well suited for the wide variety of commercial applications involving the need for cell-type specification and sensing of environmental signals.

In one aspect, the invention relates to a nucleic acid logic cassette comprising: (i) a nucleic acid sequence encoding a promoter; (ii) a first recombination unit (U1) comprising a first pair of recombinase recognition sequences (RRS1) for a first site-specific recombinase (R1), wherein each of the RRS1 flanks each side of a first nucleic acid sequence, and wherein the RRS1 are in the same orientation or in an inverse orientation with respect to each other, and wherein at least one of the RRS1 is positioned downstream of the promoter, whereby when the R1 recognizes the RRS1, the first nucleic acid sequence is excised when the RRS1 are in the same orientation or is inverted when the RRS1 are in the inverse orientation; (iii) a second recombination unit (U2) comprising a second pair of recombinase recognition sequences (RRS2) for a second recombinase (R2), wherein each of the RRS2 flanks each side of a second nucleic acid sequence, and wherein the RRS2 are in the same orientation or in an inverse orientation with respect to each other, and wherein at least one of the RRS2 is positioned downstream of at least one of the RRS1, whereby when the R2 recognizes the RRS2, the second nucleic acid sequence is excised when the RRS2 are in the same orientation or is inverted when the RRS2 are in the inverse orientation; (iv) a third recombination unit (U3) comprising a third pair of recombinase recognition sequences (RRS3) adapted to be recognized by the R1, R2, or a third recombinase (R3), wherein each of the RRS3 flanks each side of a third nucleic acid sequence, wherein the RRS3 are in the same orientation or in an inverse orientation with respect to each other, and wherein at least one of the RRS3 is positioned downstream of at least one of the RRS2, whereby when the R1, R2, or R3 recognizes the RRS3, the third nucleic acid sequence is excised when the RRS3 are in the same orientation, or is inverted when the RRS3 are in the inverse orientation; wherein the first, second or third nucleic acid sequence comprises a target gene, and wherein presence or absence of at least one of the R1, R2, and R3 operatively links the promoter to at least one of the first, second or third nucleic acid sequence, thereby driving expression of the first, second or third nucleic acid sequence.

In some embodiments, the R2 does not recognize the RRS1 or RRS3. Stated another way, the R2 is orthogonal to the R1 and R3. In some embodiments, the R3 does not recognize the RRS1 or RRS2. Stated another way, the R3 is orthogonal to the R1 or R2.

In some embodiments, the nucleic acid logic cassette further comprises a pair of flanking nucleic acid sequences, wherein each of the flanking nucleic acid sequences flanks each side of the nucleic acid logic cassette, permitting the cassette to be inserted into the genome of a mammalian cell. Examples of flanking nucleic acid sequences include, but are not limited to, AAVS1 and Rosa26 left and right arms.

In some embodiments, the U1, U2, and U3 can be connected in series. In some embodiments, there can be an overlap between the U1 and U2, U1 and U3, or U2 and U3. In some embodiments, the U1 can comprise the U2. In some embodiments, the U1 can comprise the U3. In some embodiments, the U2 can comprise the U3. In some embodiments, the U1 can comprise the U2 and U3.

In some embodiments, the nucleic acid logic cassette can further comprise a fourth recombination unit (U4) comprising a fourth pair of recombinase recognition sequences (RRS4) adapted to be recognized by the R1, R2, R3, or a fourth recombinase (R4), wherein each of the RRS4 flanks each side of a fourth nucleic acid sequence, and wherein the RRS4 are in the same orientation or in an inverse orientation with respect to each other, and wherein at least one of the RRS4 is positioned downstream of at least one of the RRS3, whereby when the R1, R2, R3, or R4 recognizes the RRS4, the fourth nucleic acid sequence is excised when the RRS4 are in the same orientation or is inverted when the RRS4 are in the inverse orientation.

Factors that can be taken into consideration for designing the nucleic acid logic cassette include, but are not limited to, the number of recombination units, the position of each recombination unit, the orientation of each pair of RRS, the identity of each pair of RRS, the orientation of the genetic elements (e.g., promoters, transcriptional terminators, target genes), the number of genetic elements, and the type of genetic elements.

In some embodiments, the mammalian cell is a human cell. In some embodiments, the mammalian cell is an embryonic stem cell. In some embodiments, the mammalian cell is an immune cell such as T or B cell. It should be noted that the technology described herein can also be applied to non-mammalian cells such as bacteria.

In some embodiments, the cassettes described herein can perform logic functions with memory, where removal of the input afterwards does not make the circuit return to its original state.

In some embodiments, the cassettes described herein can perform logic functions without memory, where removal of the input afterwards returns the circuit to its original state. In some of these embodiments, serine integrases can be used. Integrases (which do not recognize the attL/R sites on their own) and the recombination directionality factors (RDFs) are the main sensing inputs that convert the L/R sites to B/P. However, upon removal of the RDFs, the circuit returns to its original state due to the constitutively expressing integrases that convert the B/P sites back to L/R.

In some embodiments, a plurality of nucleic acid logic cassettes can be assembled to carry out a desired logic function.

In one aspect, the invention relates to a logic system comprising a nucleic acid logic cassette described herein, and at least one nucleic acid sequence encoding at least one inducible promoter operatively linked to at least one recombinase, whereby expression of the at least one recombinase provides an input to the nucleic acid logic cassette adapted to perform a logic function as a function of the input.

In some embodiments, the logic system comprises two or more nucleic acid sequences, wherein each of the nucleic acid sequences can encode an inducible promoter and a recombinase operatively linked to the promoter.

In some embodiments, a single nucleic acid sequence can encode two or more recombinases operatively linked to an inducible promoter.

In some embodiments, the logic system can further comprising at least one nucleic acid sequence encoding at least one inducible promoter operatively linked to a RDF specific for the at least one recombinase.

In one aspect, the invention relates to a mammalian cell containing a nucleic acid logic cassette or logic system described herein. The logic cassette or system can be introduced into a cell using any method known to one of skill in the art. The term "transformation" as used herein refers to the introduction of genetic material into a cell, tissue or organism. Transformation of a cell can be stable or transient. The term "transient transformation" or "transiently transformed" refers to the introduction of one or more transgenes into a cell in the absence of integration of the transgene into the host cell's genome. Transient transformation can be detected by, for example, enzyme linked immunosorbent assay (ELISA), which detects the presence of a polypeptide encoded by one or more of the transgenes. For example, a molecular circuit can further comprise a promoter operatively linked to an output product, such as a reporter protein. Expression of that reporter protein indicates that a cell has been transformed or transfected with the molecular circuit, and is hence implementing the circuit. Alternatively, transient transformation can be detected by detecting the activity of the protein encoded by the transgene. The term "transient transformant" refers to a cell which has transiently incorporated one or more transgenes.

In contrast, the term "stable transformation" or "stably transformed" refers to the introduction and integration of one or more transgenes into the genome of a cell or cellular system, preferably resulting in chromosomal integration and stable heritability through meiosis. Stable transformation of a cell can be detected by Southern blot hybridization of genomic DNA of the cell with nucleic acid sequences, which are capable of binding to one or more of the transgenes. Alternatively, stable transformation of a cell can also be detected by the polymerase chain reaction of genomic DNA of the cell to amplify transgene sequences. The term "stable transformant" refers to a cell or cellular, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which can exhibit variable properties with respect to meiotic stability. Transformed cells, tissues, or plants are understood to encompass not only the end product of a transformation process, but also transgenic progeny thereof.

In one aspect, the invention relates to a mammalian cell containing a nucleic acid logic cassette, the cassette comprising: (i) a nucleic acid sequence encoding a mammalian promoter; (ii) a first recombination unit (U1) comprising a first pair of recombinase recognition sequences (RRS1) for a first recombinase (R1), wherein each of the RRS1 flanks each side of a first nucleic acid sequence, and wherein the RRS1 are in the same orientation or in an inverse orientation with respect to each other, and wherein at least one of the RRS1 is positioned downstream of the promoter, whereby when the R1 recognizes the RRS1, the first nucleic acid sequence is excised when the RRS1 are in the same orientation or is inverted when the RRS1 are in the inverse orientation; (iii) a second recombination unit (U2) comprising a second pair of recombinase recognition sequences (RRS2) for a second recombinase (R2), wherein each of the RRS2 flanks each side of a second nucleic acid sequence, and wherein the RRS2 are in the same orientation or in an inverse orientation with respect to each other, and wherein at least one of the RRS2 is positioned downstream of at least one of the RRS1, whereby when the R2 recognizes the RRS2, the second nucleic acid sequence is excised when the RRS2 are in the same orientation or is inverted when the RRS2 are in the inverse orientation, wherein the first or second nucleic acid sequence comprises a target gene, and wherein presence or absence of at least one of the R1 and R2 operatively links the promoter to at least one of the first and second nucleic acid sequence, thereby driving expression of the first or second nucleic acid sequence. In some embodiments, the mammalian cell is an immune cell. In some embodiments, the cassette can perform a logic function selected from the group consisting of NOR, OR, AND, NAND, A IMPLY B, B IMPLY A, A NIMPLY B, B NIMPLY A, XOR, XNOR, decoder, half adder, half subtractor, half adder-subtractor, full adder, full subtractor, Feynman gate, logic selector, Ripple carry adder, array multiplier, arithmetic logic unit, and any combinations thereof.

Switches for Adoptive T-Cell Therapy

One aspect of the invention relates to nucleic acid-based switches and their use in adoptive T-cell therapy. These nucleic acid-based switches are based on the DNA recombinase systems. Chimeric antigen receptors (CARs) direct T-cell activity towards cancer cells. CARs are a fusion of the single chain variable fragment (scFv) of an antibody fused to the signaling domain from the T-cell receptor (TCR).

In one aspect, the invention relates to a switch operable in a mammalian immune cell, comprising: (i) a nucleic acid sequence encoding a mammalian promoter; (ii) a first pair of recombinase recognition sequences (RRS1) for a first recombinase (R1), wherein each of the RRS1 flanks each side of a first nucleic acid sequence, and wherein the RRS1 are in an inverse orientation with respect to each other, and wherein at least one of the RRS1 is positioned downstream of the promoter; (iii) a second pair of recombinase recognition sequences (RRS2) for a second recombinase (R2), wherein each of the RRS2 flanks each side of a second nucleic acid sequence, and wherein the RRS2 are in an inverse orientation with respect to each other, and wherein at least one of the RRS2 is positioned downstream of at least one of the RRS1; and (iv) a target gene positioned downstream of at least one of the RRS1, whereby expression of the target gene is controlled by the presence or absence of at least one of the R1 and R2.

The working mechanism of the switches described herein is a two-step process. In the first step, the presence of the R2 inverts a second nucleic acid sequence. This inversion is not stable as the switch keep switching uncontrollably. In the second step, the presence of the R1 excises a portion of the switch, thus making the inversion permanent. In some embodiments, the switching mechanism is shown in FIG. 25.

In some embodiments, the R1 and R2 are each a tyrosine recombinase. Without wishing to be bound by theory, one pair of tyrosine recombinase sites would lead to bidirectional inversion, i.e. the switch would keep switching uncontrollably.

In some embodiments, the R1 and R2 are each a serine recombinase.

Figure 18:
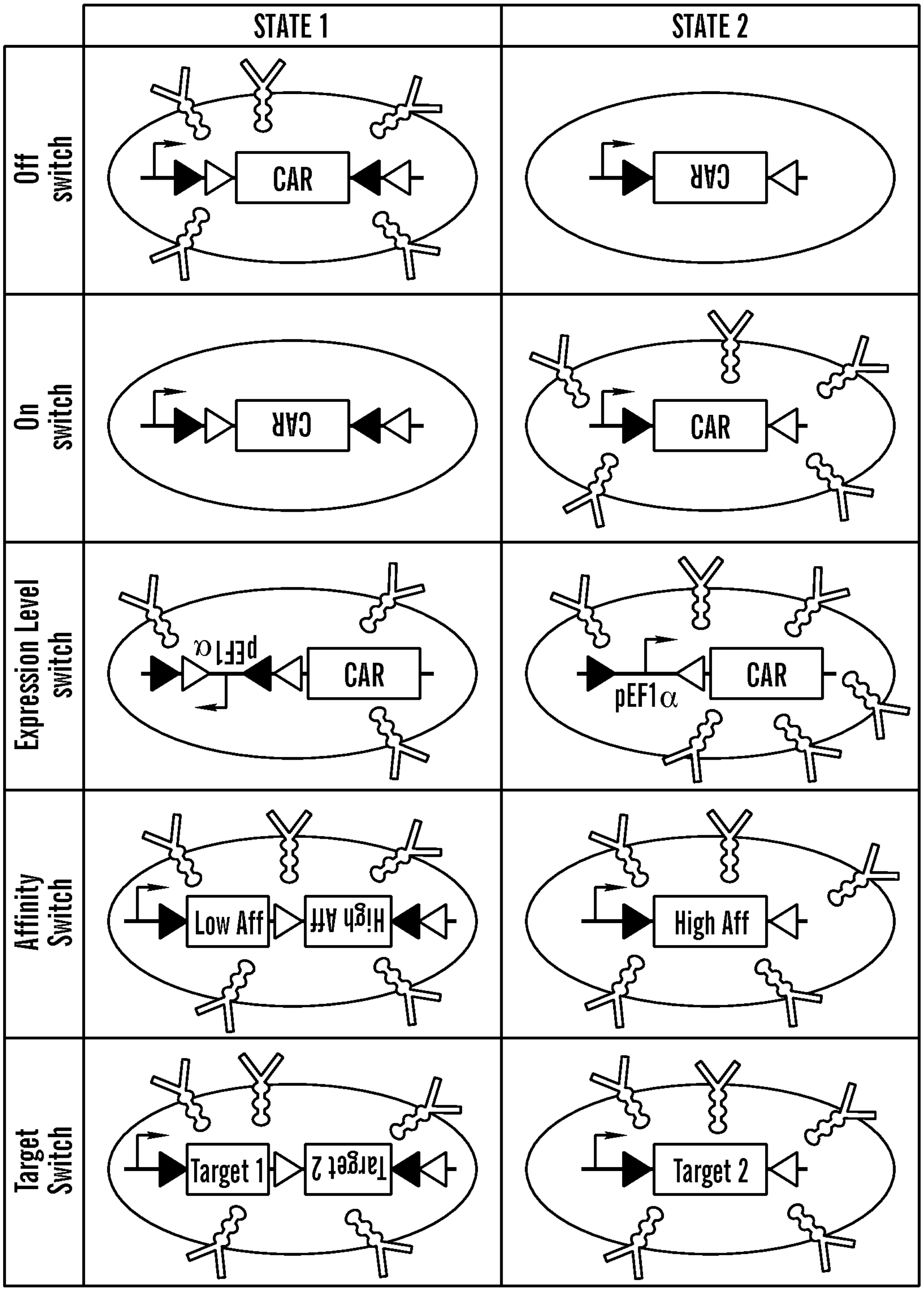
FIG. 18 shows structure of switches in State 1 and State 2. Using the stable inversion switch, the expression of CARs can be controlled to control T-cell response to an antigen.

The switches described herein can control the response of the T-cell to a target antigen. FIG. 18 illustrates some embodiments of these switches. In some embodiments, the switch is a temporal switch. The temporal switch can be an On switch, which allows the cell to stay in an "off" state where no CAR is expressed until the drug is added, at which point the CAR is expressed and the T-cell is "on." This design allows for a doctor to turn the CAR on only when they feel it is necessary. The temporal switch can also be an OFF switch, which begins with the T-cell in the "on" state, and upon drug addition, will turn the T-cell "off." This switch can be used to turn the therapy off upon remission to minimize the possibility of cytotoxic effects.

In some embodiments of the On switch, there is an overlap between the first nucleic acid sequence and the second nucleic acid sequence. Specifically, the first nucleic acid sequence comprises one of the RRS2 and the target gene in an inverted orientation with respect to the promoter, and the second nucleic acid sequence comprises the target gene and one of the RRS1. The target gene is not expressed in the absence of the correct input. In the presence of the R2 and then R1, the target gene is inverted, thereby turning on the expression of the target gene.

In some embodiments of the Off switch, there is an overlap between the first nucleic acid sequence and the second nucleic acid sequence. Specifically, the first nucleic acid sequence comprises one of the RRS2 and the target gene in the same orientation as the promoter, and the second nucleic acid sequence comprises the target gene and one of the RRS1. The target gene is expressed in the absence of the correct input. In the presence of the R2 and then R1, the target gene is inverted, thereby turning off the expression of the target gene.

In some embodiments, the switch is a target switch. Different targets for CARs can provoke different responses in the T-cell due to the variability in antigen expression level and activation levels. As cancers can have multiple targets, this switch will allow for tuning of the therapy by changing the target. This switch can be adapted for different targets.

In some embodiments of the target switch, there is an overlap between the first nucleic acid sequence and the second nucleic acid sequence. Specifically, the first nucleic acid sequence comprises a first target gene in the same orientation as the promoter, one of the RRS2, and a second target gene in an inverted orientation. The second nucleic acid sequence comprises the second target gene and one of the RRS1. The first target gene is expressed in the absence of the correct input. In the presence of the R1 and R2, the second target gene is operatively linked to the promoter, thereby turning on the expression of the second target gene and turning off the expression of the first target gene.

In some embodiments, the switch is an affinity switch. T-cell activation using CARs is dependent in part on the affinity of the scFv for the target antigen. Anti-Her2 CARs have varying affinities and can be used to construct a switch that can change the affinity of the T-cell for the antigen. Her2 is an EGFR family receptor that is overexpressed in a number of cancers, including breast, colon, and ovarian cancer. Existing versions of Her2-CAR have affinities that span four orders of magnitude. In some embodiments, this switch will start with expression of a low-affinity CAR. While using a low-affinity CAR may reduce the probability of binding to a cancer cell, it will also reduce the probability of binding to a healthy cell that expresses Her2. In the case that the patient does not respond to a low-affinity Her2-CAR, they will then be switched to a high-affinity Her2-CAR.

In some embodiments, the genetic architecture of the affinity switch is the same as that of the target switch. In these embodiments, the first target gene is a low-affinity CAR, and the second target gene is a high-affinity CAR. In some embodiments, the high-affinity CAR has an affinity to a target at least 20% (e.g., at least 50%, at least 60%, at least 70%, at least 80%, at least 90%, at least 100%, at least 2 fold, at least 3 fold) higher than that of the low affinity CAR to the same target.

In some embodiments, the switch is an expression level switch. Another method to impact T-cell activation is to alter the level of expression of CARs. One strategy to affect expression level is to change the promoter under which the CAR is expressed. In the expression level switch, the T-cell will start with the CAR transcribed under a low-expressing promoter. To increase the strength of the treatment, the circuit will then drive the expression of CAR under a different, high-expressing promoter.

In some embodiments of the expression level switch, the promoter is in an inverted orientation. There is an overlap between the first nucleic acid sequence and the second nucleic acid sequence. Specifically, the first nucleic acid sequence comprises the promoter and one of the RRS2. The second nucleic acid sequence comprises the promoter and one of the RRS1. The target gene is positioned downstream of the RRS1 and RRS2, whereby in the presence of the R1 and R2, the promoter is inverted, thereby turning on the expression of the target gene. In the absence of the correct input, the target gene is not expressed.

The switches described herein can be used in adoptive T-cell therapy. Adoptive T-cell therapy uses a patient's own immune cells to target and kill cancer cells. One of the primary challenges are potential autoimmune effects of the therapy, as many of the target antigens that are overexpressed on cancer cells can also be found at lower levels on healthy cells. While the use of CARs in some patients allows for targeted killing of cancer cells, other patients who express high amounts of the antigen on normal cells have experienced fatal autoimmune effects upon targeting of healthy tissue. By implementing the switches in the adoptive T-cell therapy, the autoimmune effects can be reduced.

Accordingly, in one aspect, a method is provided herein to treat cancer in a subject, the method comprising incorporating a switch described herein into T cells and administering the T cells to the subject. In some embodiments, the method further comprises administering a lymphodepletion procedure to the subject prior to the administration of the T cells. In a lymphodepletion procedure, drugs such as fludarabine and Cytoxan can be used to significantly reduce the number of normal lymphocytes circulating in the patient's body.

In some embodiments, the method further comprises culturing and/or expanding the T cells containing the switch prior to their administration. Methods of culturing and/or expanding cells are known in the art. For switches that comprise an inducible promoter, the method further comprises administering a compound to activate the switch. The compound can be selected from the group consisting of doxycycline, tamoxifen, rapamycin, and abscisic acid, depending on the inducible promoter.

Site Specific Recombinases (SSR) and Recombination Recognition Sequences

Provided herein are recombinases used to impart stable, DNA-base memory to the logic and memory systems of the invention. A "recombinase," as used herein, is a site-specific enzyme that recognizes short DNA sequence(s), which sequence(s) are typically between about 30 base pairs (bp) and 40 bp, and that mediates the recombination between these recombinase recognition sequences, which results in the excision, integration, inversion, or exchange of DNA fragments between the recombinase recognition sequences. A "genetic element," as used herein, refers to a sequence of DNA that has a role in gene expression. For example, a promoter, a transcriptional terminator, and a nucleic acid encoding a product (e.g., a protein product) is each considered to be a genetic element.

Exemplary recombinases include, but are not limited to, Cre, Flp, Dre, SCre, VCre, Vika, B2, B3, KD, ΦC31, Bxb1, λ, HK022, HP1, γδ, ParA, Tn3, Gin, R4, TP901-1, TG1, PhiRv1, PhiBT1, SprA, XisF, TnpX, R, A118, spoIVCA, PhiMR11, SCCmec, TndX, XerC, XerD, XisA, Hin, Cin, mrpA, beta, PhiFC1, Fre, Clp, sTre, FimE, and HbiF.

Exemplary RRS include, but are not limited to, loxP, loxN, lox511, lox5171, lox2272, M2, M3, M7, M11, lox71, lox66, FRT, rox, SloxM1, VloxP, vox, B3RT, KDRT, F3, F14, attB/P, F5, F13, Vlox2272, Slox2272, SloxP, RSRT, and B2RT.

Recombinases can be classified into two distinct families: serine recombinases (e.g., resolvases and invertases) and tyrosine recombinases (e.g., integrases), based on distinct biochemical properties. Serine recombinases and tyrosine recombinases are further divided into bidirectional recombinases and unidirectional recombinases. Examples of bidirectional serine recombinases include, without limitation, β-six, CinH, ParA and γδ; and examples of unidirectional serine recombinases include, without limitation, Bxb1, ΦC31 (phiC31), TP901, TGI, φBTI, R4, cpRV1, cpFC1, MRU, A118, U153 and gp29. Examples of bidirectional tyrosine recombinases include, without limitation, Cre, FLP, and R; and unidirectional tyrosine recombinases include, without limitation, Lambda, HK1O1, HK022 and pSAM2. The serine and tyrosine recombinase names stem from the conserved nucleophilic amino acid residue that the recombinase uses to attack the DNA and which becomes covalently linked to the DNA during strand exchange. Recombinases have been used for numerous standard biological applications, including the creation of gene knockouts and the solving of sorting problems.

In some embodiments, the recombinases for use in the present invention are orthogonal recombinases. When a first recombinase is orthogonal to the second recombinase, it means that the second recombinase does not recognize the RRS specific for the first recombinase, neither does the first recombinase recognize the RRS specific for the second recombinase.

The outcome of recombination depends, in part, on the location and orientation of two short repeated DNA sequences (e.g., RRS) that are to be recombined, typically less than 30 bp long. The site-specific recombinases bind to these repeated sequences, which are specific to each recombinase, and are herein referred to as "recombinase recognition sequences" or "recombinase recognition sites." Thus, as used herein, a recombinase is "specific for" a recombinase recognition site when the recombinase can mediate inversion or excision between the repeat DNA sequences. As used herein, a recombinase may also be said to recognize its "cognate recombinase recognition sites," which flank an intervening genetic element (e.g., promoter, terminator, or target gene). A genetic element is said to be "flanked" by recombinase recognition sites when the element is located between and immediately adjacent to two repeated DNA sequences. In some embodiments, the recombinase recognition sites do not overlap each other. However, in other embodiments, recombinase recognition sites do overlap each other, such as described herein below, which permits greatly increased combinatorial complexity.

Inversion recombination happens between two short, inverted, repeated DNA sequences. Without wishing to be bound by theory, a DNA loop formation, assisted by DNA bending proteins, brings the two repeat sequences together, at which point DNA cleavage and ligation occur. This reaction is ATP independent and requires supercoiled DNA. The end result of such an inversion recombination event is that the stretch of DNA between the repeated site inverts (i.e., the stretch of DNA reverses orientation) such that what was the coding strand is now the non-coding strand and vice versa. In such reactions, the DNA is conserved with no net gain or no loss of DNA.

Conversely, excision (integration) recombination occurs between two short, repeated DNA sequences that are oriented in the same direction. In this case, the intervening DNA is excised/removed. For example, an AND gate can be assembled by placing a terminator between each of two different sets of recombinase sites oriented for excision, flanked by a promoter and an output such as a GFP-encoding sequence. In this example, both terminators must be excised by input-dependent action of the recombinase(s) to permit readthrough from the promoter to the GFP-encoding sequence. Thus two inputs are needed to excise both terminators to generate output.

Recombinases can also be classified as irreversible or reversible. As used herein, an "irreversible recombinase" refers to a recombinase that can catalyze recombination between two complementary recombination sites, but cannot catalyze recombination between the hybrid sites that are formed by this recombination without the assistance of an additional factor. Thus, an "irreversible recognition site" refers to a recombinase recognition site that can serve as the first of two DNA recognition sequences for an irreversible recombinase and that is modified to a hybrid recognition site following recombination at that site. A "complementary irreversible recognition site" refers to a recombinase recognition site that can serve as the second of two DNA recognition sequences for an irreversible recombinase and that is modified to a hybrid recombination site following homologous recombination at that site. For example, attB and attP, described below, are the irreversible recombination sites for Bxb1 and phiC31 recombinases—attB is the complementary irreversible recombination site of attP, and vice versa. Recently, it was shown that the attB/attP sites can be mutated to create orthogonal B/P pairs that only interact with each other but not the other mutants [72]. This allows a single recombinase to control the excision or integration or inversion of multiple orthogonal B/P pairs.

The phiC31 (ϕC31) integrase, for example, catalyzes only the attB×attP reaction in the absence of an additional factor not found in eukaryotic cells. The recombinase cannot mediate recombination between the attL and attR hybrid recombination sites that are formed upon recombination between attB and attP. Because recombinases such as the phiC31 integrase cannot alone catalyze the reverse reaction, the phiC31 attB×attP recombination is stable.

Irreversible recombinases, and nucleic acids that encode the irreversible recombinases, are described in the art and can be obtained using routine methods. Examples of irreversible recombinases include, without limitation, phiC31 (ϕC31) recombinase, coliphage P4 recombinase, coliphage lambda integrase, Listeria A118 phage recombinase, and actinophage R4 Sre recombinase, HK101, HK022, pSAM2, Bxb1, TP901, TGI, ϕBTI, cpRV1, cpFC1, MRU, U153 and gp29. Conversely, a "reversible recombinase" refers to a recombinase that can catalyze recombination between two complementary recombinase recognition sites and, without the assistance of an additional factor, can catalyze recombination between the sites that are formed by the initial recombination event, thereby reversing it. The product-sites generated by recombination are themselves substrates for subsequent recombination. Examples of reversible recombinase systems include, without limitation, the Cre-lox and the Flp-frt systems, R, β-six, CinH, ParA and γδ.

The recombinases provided herein are not meant to be exclusive examples of recombinases that can be used in embodiments of the invention. The complexity of cassettes and systems of the invention can be expanded by mining databases for new orthogonal recombinases or designing synthetic recombinases with defined DNA specificities. Other examples of recombinases that are useful in the invention described herein are known to those of skill in the art, and any new recombinase that is discovered or generated is expected to be able to be used in the different embodiments of the invention.

In some embodiments, the recombinase is serine recombinase. Thus, in some embodiments, the recombinase is considered to be irreversible. For some serine recombinases, an initial recombination event can be reversed when a recombinase directionality factor (RDF) is present. RDFs are a diverse group of proteins involved in controlling the directionality of integrase-mediated site-specific recombination reactions. Typically, RDFs are small DNA-binding proteins acting as accessory factors to influence the choice of substrates that are recombined by their cognate recombinase. See Lewis and Hatfull, Nucleic Acids Res. 2001 Jun. 1; 29(11): 2205-2216. For example, when the recombination sites, attB and attP are placed in the antiparallel orientation, the presence of recombinases Till stably invert the DNA sequence between the two sites and generate an attL and attR site ("BP reaction"). This inversion remains stable unless a RDF is also expressed along with bxb1 or phiC, which will invert the sequence between attL and attR and regenerate attB and attP site ("LR reaction"). Examples of RDF include, but are not limited to, gp47 for bxb1, gp3 for phiC31, gp3 for PhiBT1, ORF7 for TP901-1, gp25 for TG1, and gp3 for PhiRv1.

In some embodiments, the recombinase is a tyrosine recombinase. Thus, in some embodiments, the recombinase is considered to be reversible.

In some embodiments, all the recombinases for a specific nucleic acid logic cassette can be of the same type (e.g., serine or tyrosine). For example, the BLADE platform described herein utilizes a plurality of tyrosine recombinases; the AXIS platform described herein utilized a plurality of serine recombinases. In some embodiments, tyrosine recombinases and serine recombinases can be used together in the same logic cassette.

In some embodiments, the recombinase comprises the sequence of Bxb1 recombinase, and the corresponding recombinase recognition sequences are Bxb1 attB and Bxb1 attP.

In some embodiments, the recombinase comprises the sequence of phiC31 (ϕC31) recombinase and the corresponding recombinase recognition sequences comprise phiC31 attB and phiC31 attP.

A recombinase can recognize multiple pairs of RRS. In some embodiments, the recombinase comprises the sequence of Cre and the corresponding recombinase recognition sequences comprise loxP. In some embodiments, the recombinase comprises the sequence of Cre and the corresponding recombinase recognition sequences comprise lox2272. In some embodiments, the recombinase comprises the sequence of Cre and the corresponding recombinase recognition sequences comprise loxN.

In some embodiments, the recombinase comprises the sequence of Dre and the corresponding recombinase recognition sequences comprise rox.

In some embodiments, the recombinase comprises the sequence of VCre and the corresponding recombinase recognition sequences comprise VloxP.

In some embodiments, the recombinase comprises the sequence of VCre and the corresponding recombinase recognition sequences comprise VloxP.

In some embodiments, the recombinase comprises the sequence of Flp and the corresponding recombinase recognition sequences comprise FRT.

In some embodiments, the recombinase comprises the sequence of SCre and the corresponding recombinase recognition sequences comprise SloxM1.

In some embodiments, the recombinase comprises the sequence of Vika and the corresponding recombinase recognition sequences comprise vox.

In some embodiments, the recombinase comprises the sequence of B3 and the corresponding recombinase recognition sequences comprise B3RT.

In some embodiments, the recombinase comprises the sequence of KD and the corresponding recombinase recognition sequences comprise KDRT.

The sequences for some recombinases are shown below:

```
hPGK (SEQ ID NO: 1):
ggggttggggttgcgccttttccaaggcagccctgggtttgcgcagggac

gcggctgctctgggcgtggttccgggaaacgcagcggcgccgaccctggg

tctcgcacattcttcacgtccgttcgcagcgtcacccggatcttcgccgc

tacccttgtgggcccccggcgacgcttcctgctccgcccctaagtcggg

aaggttccttgcggttcgcggcgtgccggacgtgacaaacggaagccgca

cgtctcactagtaccctcgcagacggacagcgccagggagcaatggcagc

gcgccgaccgcgatgggctgtggccaatagcggctgctcagcagggcgcg

ccgagagcagcggccgggaaggggcggtgcgggaggcggggtgtggggcg

gtagtgtgggccctgttcctgcccgcgcggtgttccgcattctgcaagcc

tccggagcgcacgtcggcagtcggctccctcgttgaccgaatcaccgacc

tctctccccag

EF1alpha (SEQ ID NO: 2):
cgtgaggctccggtgcccgtcagtgggcagagcgcacatcgcccacagtc

cccgagaagttggggggaggggtcggcaattgaaccggtgcctagagaag

gtggcgcggggtaaactgggaaagtgatgtcgtgtactggctccgccttt

ttcccgagggtgggggagaaccgtatataagtgcagtagtcgccgtgaac

gttctttttcgcaacgggtttgccgccagaacacaggtaagtgccgtgtg

tggttcccgcgggcctggcctctttacgggttatggcccttgcgtgcctt

gaattacttccacctggctgcagtacgtgattcttgatcccgagcttcgg

gttggaagtgggtgggagagttcgaggccttgcgcttaaggagccccttc

gcctcgtgcttgagttgaggcctggcctgggcgctggggccgccgcgtgc

gaatctggtggcaccttcgcgcctgtctcgctgctttcgataagtctcta

gccatttaaaatttttgatgacctgctgcgacgctttttttctggcaaga

tagtcttgtaaatgcgggccaagatctgcacactggtatttcggtttttg

gggccgcgggcggcgacggggcccgtgcgtcccagcgcacatgttcggcg

aggcggggcctgcgagcgcggccaccgagaatcggacgggggtagtctca

agctggccggcctgctctggtgcctggcctcgcgccgccgtgtatcgccc

cgccctgggcggcaaggctggcccggtcggcaccagttgcgtgagcggaa

agatggccgcttcccggccctgctgcagggagctcaaaatggaggacgcg

gcgctcgggagagcgggcgggtgagtcacccacacaaaggaaaagggcct

ttccgtcctcagccgtcgcttcatgtgactccacggagtaccgggcgccg

tccaggcacctcgattagttctcgagcttttggagtacgtcgtctttagg

ttgggggggaggggttttatgcgatggagtttccccacactgagtgggtgg

agactgaagttaggccagcttggcacttgatgtaattctccttggaattt

gccctttttgagtttggatcttggttcattctcaagcctcagacagtggt

tcaaagtttttttcttccatttcaggtgtcgtga

SFFV (SEQ ID NO: 3):
ccgataaaataaaagattttatttagtctccagaaaaaggggggaatgaa

agaccccacctgtaggtttggcaagctagctgcagtaacgccattttgca

aggcatggaaaaataccaaaccaagaatagagaagttcagatcaagggcg
```

ggtacatgaaaatagctaacgttgggccaaacaggatatctgcggtgagc agtttcggccccggcccggggccaagaacagatggtcaccgcagtttcgg ccccggcccgaggccaagaacagatggtccccagatatggcccaaccctc agcagtttcttaagacccatcagatgtttccaggctcccccaaggacctg aaatgaccctgcgccttatttgaattaaccaatcagcctgcttctcgctt ctgttcgcgcgcttctgcttcccgagctctataaaagagctcacaacccc tcactcggcgcgccagtcctccgacagactgagtcgcccggg

CAG (SEQ ID NO: 4):
ACTAGTTATTAATAGTAATCAATTACGGGGTCATTAGTTCATAGCCCATA

TATGGAGTTCCGCGTTACATAACTTACGGTAAATGGCCCGCCTGGCTGAC

CGCCCAACGACCCCCGCCCATTGACGTCAATAATGACGTATGTTCCCATA

GTAACGCCAATAGGGACTTTCCATTGACGTCAATGGGTGGACTATTTACG

GTAAACTGCCCACTTGGCAGTACATCAAGTGTATCATATGCCAAGTACGC

CCCCTATTGACGTCAATGACGGTAAATGGCCCGCCTGGCATTATGCCCAG

TACATGACCTTATGGGACTTTCCTACTTGGCAGTACATCTACGTATTAGT

CATCGCTATTACCATGGGTCGAGGTGAGCCCCACGTTCTGCTTCACTCTC

CCCATCTCCCCCCCCTCCCCACCCCCAATTTTGTATTTATTTATTTTTTA

ATTATTTTGTGCAGCGATGGGGGCGGGGGGGGGGGGGGCGCGCGCCAGGC

GGGGCGGGGCGGGGCGAGGGGCGGGGCGGGGCGAGGCGGAGAGGTGCGGC

GGCAGCCAATCAGAGCGGCGCGCTCCGAAAGTTTCCTTTTATGGCGAGGC

GGCGGCGGCGGCGGCCCTATAAAAAGCGAAGCGCGCGGCGGGCGGGAGTC

GCTGCGTTGCCTTCGCCCCGTGCCCCGCTCCGCGCCGCCTCGCGCCGCCC

GCCCCGGCTCTGACTGACCGCGTTACTCCCACAGGTGAGCGGGCGGGACG

GCCCTTCTCCTCCGGGCTGTAATTAGCGCTTGGTTTAATGACGGCTCGTT

TCTTTTCTGTGGCTGCGTGAAAGCCTTAAAGGGCTCCGGGAGGGCCCTTT

GTGCGGGGGGGAGCGGCTCGGGGGGTGCGTGCGTGTGTGTGTGCGTGGGG

AGCGCCGCGTGCGGCCCGCGCTGCCCGGCGGCTGTGAGCGCTGCGGGCGC

GGCGCGGGGCTTTGTGCGCTCCGCGTGTGCGCGAGGGGAGCGCGGCCGGG

GGCGGTGCCCCGCGGTGCGGGGGGGCTGCGAGGGGAACAAAGGCTGCGTG

CGGGGTGTGTGCGTGGGGGGGTGAGCAGGGGGTGTGGGCGCGGCGGTCGG

GCTGTAACCCCCCCCTGCACCCCCCTCCCCGAGTTGCTGAGCACGGCCCG

GCTTCGGGTGCGGGGCTCCGTGCGGGGCGTGGCGCGGGGCTCGCCGTGCC

GGGCGGGGGGTGGCGGCAGGTGGGGGTGCCGGGCGGGGCGGGGCCGCCTC

GGGCCGGGGAGGGCTCGGGGGAGGGGCGCGGCGGCCCCGGAGCGCCGGCG

GCTGTCGAGGCGCGGCGAGCCGCAGCCATTGCCTTTTATGGTAATCGTGC

GAGAGGGCGCAGGGACTTCCTTTGTCCCAAATCTGGCGGAGCCGAAATCT

GGGAGGCGCCGCCGCACCCCCTCTAGCGGGCGCGGGCGAAGCGGTGCGGC

GCCGGCAGGAAGGAAATGGGCGGGGAGGGCCTTCGTGCGTCGCCGCGCCG

CCGTCCCCTTCTCCATCTCCAGCCTCGGGGCTGCCGCAGGGGGACGGCTG

CCTTCGGGGGGGACGGGGCAGGGCGGGGTTCGGCTTCTGGCGTGTGACCG

GCGGCTCTAGAGCCTCTGCTAACCATGTTCATGCCTTCTTCTTTTTCCTA

CAGCTCCTGGGCAACGTGCTGGTTATTGTGCTGTCTCATCATTTTGGCAA

A

NLS-iCre (SEQ ID NO: 5):
atggtgcccaagaagaagaggaaagtctccaacctgctgactgtgcacca aaacctgcctgccctccctgtggatgccacctctgatgaagtcaggaaga acctgatggacatgttcagggacaggcaggccttctctgaacacacctgg aagatgctcctgtctgtgtgcagatcctgggctgcctggtgcaagctgaa caacaggaaatggttccctgctgaacctgaggatgtgagggactacctcc tgtacctgcaagccagaggcctggctgtgaagaccatccaacagcacctg ggccagctcaacatgctgcacaggagatctggcctgcctcgcccttctga ctccaatgctgtgtccctggtgatgaggagaatcagaaaggagaatgtgg atgctggggagagagccaagcaggccctggcctttgaacgcactgacttt gaccaagtcagatccctgatggagaactctgacagatgccaggacatcag gaacctggccttcctgggcattgcctacaacaccctgctgcgcattgccg aaattgccagaatcagagtgaaggacatctcccgcaccgatggtgggaga atgctgatccacattggcaggaccaagaccctggtgtccacagctggtgt ggagaaggccctgtccctgggggttaccaagctggtggagagatggatct ctgtgtctggtgtggctgatgaccccaacaactacctgttctgccgggtc agaaagaatggtgtggctgccccttctgccacctcccaactgtccacccg ggccctggaagggatctttgaggccacccaccgcctgatctatggtgcca aggatgactctgggcagagatacctggcctggtctggccactctgccaga gtgggtgctgccagggacatggccagggctggtgtgtccatccctgaaat catgcaggctggtggctggaccaatgtgaacattgtgatgaactacatca gaaacctggactctgagactggggccatggtgaggctgctcgaggatggg gactga NLS-FlpO (SEQ ID NO: 6):
atggctcctaagaagaagaggaaggtgatgagccagttcgacatcctgtg caagacccccccaaggtgctggtgcggcagttcgtggagagattcgaga ggcccagcggcgagaagatcgccagctgtgccgccgagctgacctacctg tgctggatgatcacccacaacggcaccgccatcaagagggccaccttcat gagctacaacaccatcatcagcaacagcctgagcttcgacatcgtgaaca agagcctgcagttcaagtacaagacccagaaggccaccatcctggaggcc agcctgaagaagctgatccccgcctgggagttcaccatcatcccttacaa cggccagaagcaccagagcgacatcaccgacatcgtgtccagcctgcagc tgcagttcgagagcagcgaggaggccgacaagggcaacagccacagcaag aagatgctgaaggccctgctgtccgagggcgagagcatctgggagatcac cgagaagatcctgaacagcttcgagtacaccagcaggttcaccaagacca agaccctgtaccagttcctgttcctggccacattcatcaactgcggcagg ttcagcgacatcaagaacgtggaccccaagagcttcaagctggtgcagaa caagtacctgggcgtgatcattcagtgcctggtgaccgagaccaagacaa -continued gcgtgtccaggcacatctactttttcagcgccagaggcaggatcgacccc
ctggtgtacctggacgagttcctgaggaacagcgagcccgtgctgaagag
agtgaacaggaccggcaacagcagcagcaacaagcaggagtaccagctgc
tgaaggacaacctggtgcgcagctacaacaaggccctgaagaagaacgcc
ccctaccccatcttcgctatcaagaacggccctaagagccacatcggcag
gcacctgatgaccagctttctgagcatgaagggcctgaccgagctgacaa
acgtggtgggcaactggagcgacaagagggcctccgccgtggccaggacc
acctacacccaccagatcaccgccatccccgaccactacttcgccctggt
gtccaggtactacgcctacgaccccatcagcaaggagatgatcgccctga
aggacgagaccaaccccatcgaggagtggcagcacatcgagcagctgaag
ggcagcgccgagggcagcatcagataccccgcctggaacggcatcatcag
ccaggaggtgctggactacctgagcagctacatcaacaggcggatctga NLS-DreO (SEQ ID NO: 7):
ATGCCTAAGAAGAAGAGGAAGGTTTCTGAGCTGATTATTAGTGGTTCATC
TGGTGGATTCCTGCGAAACATCGGCAAAGAGTATCAGGAGGCCGCTGAAA
ACTTCATGAGGTTTATGAATGACCAGGGGGCGTACGCTCCTAACACTTTG
AGGGATTTGAGGTTGGTCTTTCATAGCTGGGCCAGATGGTGCCATGCTCG
GCAGCTTGCATGGTTTCCAATTAGTCCTGAAATGGCACGCGAATACTTTC
TTCAGTTGCACGATGCAGACCTGGCCTCCACTACCATCGACAAGCACTAT
GCTATGCTTAATATGCTTCTGTCCCACTGCGGACTGCCACCCTTGTCCGA
CGACAAGTCAGTGAGTCTTGCCATGAGAAGAATTAGAAGAGAAGCCGCAA
CCGAAAAGGGTGAGAGGACAGGACAGGCAATCCCCCTGCGCTGGGACGAC
CTGAAGCTGCTGGATGTGCTGCTCAGCAGGAGCGAGCGGCTGGTCGACCT
GCGCAACAGGGCTTTCCTGTTCGTAGCCTATAACACCCTCATGAGAATGT
CTGAAATATCACGCATCAGGGTTGGGGACTTGGATCAGACAGGAGACACA
GTGACCCTGCACATCAGTCACACTAAGACAATCACCACAGCTGCGGGCCT
TGACAAAGTGCTCTCCCGGCGAACCACAGCAGTGCTCAATGACTGGCTGG
ACGTCAGTGGGCTTAGAGAACATCCAGACGCTGTGCTCTTCCCACCTATA
CACCGGTCAAACAAAGCCCGCATTACTACCACGCCCCTGACCGCCCCTGC
CATGGAGAAGATTTTCAGTGATGCCTGGGTGCTGCTGAACAAACGGGACG
CCACCCCCAATAAAGGGAGGTATAGGACCTGGACCGGCCATTCCGCCAGG
GTGGGTGCCGCAATAGACATGGCCGAGAAACAGGTGTCTATGGTCGAGAT
TATGCAGGAAGGGACATGGAAGAAGCCTGAAACACTGATGCGGTATCTCA
GAAGGGGCGGAGTGTCCGTGGGAGCCAATTCTCGACTGATGGATAGCTAA NLS-SCre (SEQ ID NO: 8):
ATGCCCAAGAAAAAGCGGAAGGTGTCCCTGCTGACCACCAACAACCACAG
CGTGGCCCTGAGCTACGGCGAGCCTCCTAGCACCCTGAACGACAGCCTGA
AGGACAGCTACCAGCGGAGCACCGATGAGCTGCAGGCCCTGCTGTCTAAG
CCTCTGGCCCAGCTGACCGACGCCGACAAGCTGCGGATCAGAGAGATCAC
CCAGGCCAAGCTGAAGCACTTCCTGGACAACGGCCACCGGACCAGAAGGG
CCAACACTTGGAGAGCCCTGATGAGCAGATGGGCCAAGTTCGAGAGCTGG
TGCCTGACCAACAATCTGACCCCCCTGCCTGCCACCCCTGAGGTGGTGGC -continued CACATTCATCGAGTACTACCAGGCCAGCAGCTACACCACCCTGAGCCAGT
ATGCCTGGGCCATCAACAGCTTTCACGTGGAATGCGGCCTGCTGAGCCCC
GTGTCTAGCAAGACCGTGCAGGACAAGCAGAACGAGATCAGAATCGTGAA
GCTGGAATCTGGCGGCCTGGCCCAGGAACAGGCCACCCCTTTTAGACTGC
ACCATCTGCAGATGCTGATCGAGAGCTATGGCGAGAGCGAGCGGCTGCTG
GACAAGAGAAACCTGGCTCTGCTGAATATCGCCTACGAGAGCCTGCTGCG
CGAGTCCGAGCTGCTGAGAATCAAAGTGGGCCACCTGAAGTCCACCTTCG
AGGGCGACTACGTGCTGAGCGTGCCCTACACCAAGACCAACGACAGCGGC
GAAGAGGAAGTCGTGAACATCACCCCCCCTGGGCTTCAAGCTGATCCAGCG
GTACATCCAGGGCGCTGGCCTGACAAAAGAGGACTACCTGTTCCAGCCCA
TCGGCCGGTCCAACAAGGTGTCCGTGCAGGCCAAACCCATGAGCACCCGG
ACCGTGGACAGAGTGTTCCTGTGGGCCTTTGAGAGCCTGGGCATCGACAG
ACACAGCGCTTGGAGCGGCCACAGCGCCAGAATTGGAGCCGCTCAGGATC
TGCTGGCCGCTGGCTATTCTATCGCCCAGATCCAGGAAAACGGCCGCTGG
AAGTCCCCCATGATGGTGCTGAGATACGGCAAGGACATCAAGGCCAAAGA
AAGCGCCATGGCCAAGATGCTGGCCGAGCGGAGATGA NLS-VCre (SEQ ID NO: 9):
ATGCCCAAGAAAAAGCGGAAAGTGATCGAGAACCAGCTGAGCCTGCTGGG
CGACTTTTCTGGCGTGCGGCCCGACGATGTGAAAACCGCCATTCAGGCCG
CCCAGAAAAAGGGCATCAACGTGGCCGAGAACGAGCAGTTCAAGGCCGCC
TTCGAGCATCTGCTGAACGAGTTCAAGAAGCGGGAAGAGAGATACAGCCC
CAACACCCTGCGGCGGCTGGAAAGCGCCTGGACCTGCTTCGTGGATTGGT
GCCTGGCCAACCACAGACACAGCCTGCCTGCCACCCCCGATACCGTGGAA
GCCTTCTTCATCGAGCGGGCCGAGGAACTGCACCGGAACACCCTGAGCGT
GTACAGATGGGCCATCAGCCGGGTGCACAGAGTGGCCGGATGCCCTGATC
CCTGCCTGGACATCTACGTGGAAGATCGGCTGAAGGCCATTGCCCGGAAG
AAAGTGCGGGAAGGCGAGGCCGTGAAGCAGGCCAGCCCTTTCAACGAGCA
GCATCTGCTGAAGCTGACCAGCCTGTGGTACAGAAGCGACAAGCTGCTGC
TGCGGCGGAACCTGGCTCTGCTGGCTGTGGCCTACGAGAGCATGCTGAGA
GCCAGCGAGCTGGCCAACATCCGGGTGTCCGATATGGAACTGGCCGGCGA
CGGAACCGCCATCCTGACCATCCCTATCACCAAGACCAACCACTCCGGCG
AGCCCGATACCTGCATCCTGTCCCAGGATGTGGTGTCCCTGCTGATGGAC
TACACCGAGGCCGGCAAGCTGGATATGAGCAGCGACGGCTTCCTGTTCGT
GGGCGTGTCCAAGCACAACACCTGTATCAAGCCCAAGAAGGACAAGCAGA
CCGGCGAGGTGCTGCACAAGCCCATCACCACCAAGACAGTGGAAGGCGTG
TTCTACAGCGCCTGGGAGACACTGGACCTGGGCAGACAGGGCGTGAAGCC
TTTCACAGCCCACAGCGCCAGAGTGGGAGCCGCTCAGGACCTGCTGAAGA
AGGGCTACAATACCCTGCAGATCCAGCAGTCCGGCCGGTGGTCTAGCGGA
GCCATGGTGGCCAGATACGGCAGAGCCATCCTGGCTAGGGATGGCGCTAT
GGCCCACAGCAGAGTGAAAACCAGATCCGCCCCCATGCAGTGGGGCAAGG
ACGAGAAGGACTGA -continued NLS-VikaO (SEQ ID NO: 10):
ATGCCCAAGAAAAAGCGGAAAGTGACCGACCTGACCCCATTCCCCCCCCT
GGAACACCTGGAACCCGACGAGTTTGCCGACCTCGTGCGGAAGGCCATCA
AGAGGGATCCTCAGGCTGGCGCCCACCCTGCCATCCAGTCTGCCATCAGC
CACTTCCAGGACGAGTTCGTGCGGAGACAGGGCGAATGGCAGCCTGCCAC
ACTGCAGAGACTGAGAAACGCCTGGAATGTGTTTGTGCGGTGGTGCACCC
ACCAGGGCATTCCAGCTCTGCCTGCCAGACACCAGGACGTGGAAAGATAC
CTGATCGAGCGGCGGAACGAGCTGCACCGGAACACCCTGAAAGTGCACCT
GTGGGCCATCGGCAAGACCCACGTGATCAGCGGCCTGCCCAATCCCTGCG
CCCACAGATACGTGAAAGCCCAGATGGCCCAGATCACACACCAGAAAGTG
CGCGAGAGAGAGCGGATCGAACAGGCCCCTGCCTTCAGAGAGTCCGACCT
GGACAGACTGACCGAGCTGTGGAGCGCCACCAGAAGCGTGACCCAGCAGC
GGGACCTGATGATCGTGTCCCTGGCCTACGAGACACTGCTGCGGAAGAAC
AATCTGGAACAGATGAAAGTGGGCGACATCGAGTTCTGCCAGGACGGCTC
TGCCCTGATCACCATCCCCTTCAGCAAGACCAACCACAGCGGCAGGGATG
ACGTGCGGTGGATCTCTCCCCAGGTGGCCAATCAGGTGCACGCCTACCTG
CAGCTGCCCAACATCGACGCCGACCCCCAGTGCTTCCTGCTGCAGAGAGT
GAAGAGAAGCGGCAAGGCCCTGAACCCCGAGAGCCACAATACCCTGAACG
GCCACCACCCCGTGTCCGAGAAGCTGATCTCCCGGGTGTTCGAGCGGGCT
TGGAGAGCCCTGAATCACGAGACAGGCCCCAGATACACCGGCCACAGCGC
TAGAGTGGGAGCCGCTCAGGATCTGCTGCAGGAAGGCTACAGCACCCTGC
AAGTGATGCAGGCAGGCGGCTGGTCCAGCGAGAAGATGGTGCTGAGATAC
GGCCGGCATCTGCACGCCCACACATCTGCCATGGCTCAGAAACGGCGGCA
GCGGTGA NLS-B3 (SEQ ID NO: 11):
ATGCCCAAGAAAAAGCGGAAGGTGTCCAGCTACATGGACCTGGTGGACGA
CGAGCCCGCCACCCTGTACCACAAGTTCGTGGAATGCCTGAAGGCCGGCG
AGAACTTCTGCGGCGATAAGCTGAGCGGCATCATCACCATGGCCATTCTG
AAGGCCATCAAGGCCCTGACCGAAGTGAAGAAAACCACCTTCAACAAGTA
CAAGACCACCATCAAGCAGGGCCTGCAGTACGACGTGGGCAGCAGCACCA
TCAGCTTCGTGTACCACCTGAAGGACTGCGACGAGCTGAGCAGAGGCCTG
AGCGACGCCTTCGAGCCCTACAAGTTCAAGATCAAGAGCAACAAAGAGGC
CACCAGCTTCAAGACCCTGTTCAGGGGCCCTAGCTTCGGCAGCCAGAAGA
ACTGGCGGAAGAAAGAGGTGGACCGCGAGGTGGACAACCTGTTCCACAGC
ACCGAGACAGACGAGAGCATCTTCAAGTTCATCCTGAACACCCTGGACAG
CATCGAAACCCAGACCAACACCGACCGGCAGAAAACCGTGCTGACCTTTA
TCCTGCTGATGACCTTCTTCAACTGCTGCCGGAACAACGACCTGATGAAC
GTGGACCCCAGCACCTTCAAGATCGTGAAGAACAAGTTTGTGGGCTACCT
GCTGCAGGCTGAAGTGAAGCAGACCAAGACCAGAAAGAGCCGGAATATCT
TCTTCTTCCCCATCCGGGAAAACCGCTTCGACCTGTTCCTGGCCCTGCAC
GACTTCTTCAGAACCTGCCAGCCCACCCCCAAGAGCAGACTGAGCGATCA -continued GGTGTCCGAGCAGAAGTGGCAGCTGTTCCGGGACAGCATGGTCATCGACT
ACAACCGGTTCTTTCGGAAGTTCCCCGCCAGCCCCATCTTCGCCATTAAG
CACGGCCCCAAGTCCCACCTGGGCCGGCATCTGATGAACAGCTTTCTGCA
CAAGAACGAGCTGGACAGCTGGGCCAACAGCCTGGGCAATTGGAGCAGCT
CCCAGAACCAGAGAGAGAGCGGCGCCAGACTGGGCTACACACACGGCGGA
AGAGATCTGCCCCAGCCCCTGTTTGGCTTCCTGGCCGGATACTGCGTGCG
GAACGAAGAGGGCCACATCGTGGGCCTGGGCCTGGAAAAGGACATCAACG
ATCTGTTCGACGGCATCATGGACCCCCTGAACGAGAAAGAGGACACCGAG
ATCTGCGAGAGCTACGGCGAGTGGGCCAAGATTGTGTCCAAGGACGTGCT
GATCTTCCTGAAGAGATACCACAGCAAGAACGCCTGTCGGAGATACCAGA
ACAGCACCCTGTATGCCCGGACCTTCCTGAAAACCGAGAGCGTGACCCTG
AGCGGCTCCAAGGGCAGCGAGGAACCTTCTAGCCCTGTGCGGATCCCCAT
CCTGAGCATGGGAAAGGCCAGCCCCTCCGAGGGAAGAAAGCTGAGAGCCA
GCGAGCACGCCAACGACGACAACGAGATCGAGAAGATCGACAGCGACAGC
AGCCAGAGCGAAGAGATCCCTATCGAGATGAGCGACTCCGAGGACGAGAC
AACCGCCAGCAACATCAGCGGCATCTACCTGGACATGAGCAAGGCCAACT
CCAACGTGGTGTACAGCCCCCCTAGCCAGACAGGCAGAGCTGCTGGCGCC
GGAAGAAAAAGAGGCGTGGGAGGCAGACGGACCGTGGAAAGCAAGCGGAG
AAGAGTGCTGGCCCCCATCAACCGGTGA NLS-KD (SEQ ID NO: 12):
ATGCCCAAGAAAAAGCGGAAGGTGTCCACCTTCGCCGAGGCCGCCCATCT
GACACCTCACCAGTGCGCCAACGAGATCAATGAGATCCTGGAAAGCGACA
CCTTCAACATCAACGCCAAAGAGATCCGGAACAAGCTGGCCTCCCTGTTC
AGCATCCTGACCATGCAGAGCCTGAGCATCCGCAGAGAGATGAAGATCAA
CACCTACCGGTCCTACAAGAGCGCCATCGGCAAGAGCCTGTCCTTCGACA
AGGACGACAAGATCATCAAGTTCACCGTGCGGCTGAGAAAGACCGAGAGC
CTGCAGAAGGACATCGAGAGCGCCCTGCCCAGCTACAAGGTGGTGGTGTC
CCCATTCAAGAACCAGGAAGTGTCCCTGTTCGACCGCTACGAGGAAACCC
ACAAATACGACGCCAGCATGGTGGGACTGCAGTTCACCAACATCCTGAGC
AAAGAGAAGGATATCTGGAAGATCGTGTCCCGGATCGCCTGCTTCTTCGA
CCAGAGCTGCGTGACCACCACCAAGCGGGCCGAGTACAGACTGCTGCTGC
TGGGCGCTGTGGGCAACTGCTGCAGATACAGCGACCTGAAGAACCTGGAC
CCCCGGACCTTCGAGATCTACAACAACAGCTTCCTGGGCCCCATCGTGCG
GGCCACCGTGACAGAGACAAAGAGCCGGACCGAGAGATACGTGAACTTCT
ACCCCGTGAACGGCGACTGCGACCTGCTGATCTCCCTGTACGACTACCTG
AGAGTGTGCAGCCCCATCGAGAAAACCGTGTCCAGCAACCGGCCCACCAA
CCAGACCCACCAGTTTCTGCCTGAGAGCCTGGCCAGAACCTTCAGCCGGT
TCCTGACCCAGCACGTGGACGAGCCCGTGTTCAAGATCTGGAACGGCCCC
AAGAGCCACTTCGGCAGACACCTGATGGCCACCTTTCTGAGCAGAAGCGA
GAAGGGCAAATACGTGTCCTCCCTGGGCAATTGGGCTGGCGACCGGGAAA
TCCAGTCTGCCGTGGCCAGAAGCCACTACAGCCACGGCTCTGTGACCGTG -continued GACGACCGGGTGTTCGCCTTCATCAGCGGCTTCTACAAAGAGGCCCCCCT
GGGCAGCGAGATCTATGTGCTGAAGGACCCCAGCAACAAGCCCCTGAGCA
GAGAGGAACTGCTGGAAGAGGAAGGCAACAGCCTGGGCTCCCCACCTCTG
AGCCCTCCAAGCTCTCCTAGACTGGTGGCCCAGAGCTTCAGCGCCCACCC
AAGCCTGCAGCTGTTCGAGCAGTGGCACGGCATCATCAGCGACGAGGTGC
TGCAGTTTATCGCCGAGTACCGGCGGAAGCACGAGCTGAGAAGCCAGAGA
ACCGTGGTGGCCTGA NLS-B2 (SEQ ID NO: 13):
ATGCCCAAGAAAAAGCGGAAGGTGTCCGAGTTCAGCGAGCTCGTGCGGAT
CCTGCCCCTGGATCAGGTGGCCGAGATCAAGAGAATCCTGAGCAGAGGCG
ACCCCATCCCCCTGCAGAGACTGGCCTCTCTGCTGACCATGGTCATCCTG
ACCGTGAACATGAGCAAGAAGAGAAAGAGCAGCCCCATCAAGCTGAGCAC
CTTCACCAAGTACCGGCGGAACGTGGCCAAGAGCCTGTACTACGACATGA
GCAGCAAGACCGTGTTCTTCGAGTACCACCTGAAGAACACCCAGGACCTG
CAGGAAGGCCTGGAACAGGCCATTGCCCCCTACAACTTCGTCGTGAAAGT
GCACAAGAAGCCCATCGACTGGCAGAAACAGCTGAGCAGCGTGCACGAGC
GGAAGGCCGGCCACAGATCCATCCTGTCCAACAACGTGGGCGCCGAGATC
TCCAAGCTGGCCGAGACAAAGGACAGCACCTGGTCCTTCATCGAGCGGAC
CATGGACCTGATCGAGGCCAGAACCAGACAGCCCACCACCAGAGTGGCCT
ACCGGTTCCTGCTGCAGCTGACCTTCATGAACTGCTGCCGGGCCAACGAT
CTGAAGAACGCCGACCCCAGCACCTTCCAGATCATTGCCGATCCCCACCT
GGGCCGGATCCTGAGAGCCTTCGTGCCCGAGACTAAGACCTCTATCGAGC
GGTTTATCTACTTCTTCCCATGCAAGGGCCGCTGCGACCCTCTGCTGGCC
CTGGATTCTTACCTGCTGTGGGTGGGACCCGTGCCCAAGACCCAGACCAC
CGATGAGGAAACCCAGTACGACTACCAGCTGCTGCAGGACACCCTGCTGA
TCTCTTACGACCGGTTTATCGCCAAAGAGAGCAAAGAGAACATCTTCAAG
ATCCCCAACGGCCCCAAGGCCCATCTGGGCAGACATCTGATGGCCAGCTA
CCTGGGCAACAACAGCCTGAAGTCCGAGGCCACCCTGTACGGCAATTGGA
GCGTGGAAAGACAGGAAGGCGTGTCCAAAATGGCCGACAGCCGGTACATG
CACACCGTGAAGAAGTCCCCCCCCTCCTACCTGTTCGCCTTTCTGAGCGG
CTACTACAAGAAGTCCAACCAGGGCGAGTACGTGCTGGCCGAAACCCTGT
ACAACCCCCTGGACTACGATAAGACCCTGCCCATCACCACCAACGAGAAG
CTGATCTGCAGACGCTACGGCAAGAACGCCAAAGTGATCCCCAAGGATGC
CCTGCTGTACCTGTACACCTACGCCCAGCAGAAGCGGAAGCAGCTGGCTG
ACCCCAACGAGCAGAACCGGCTGTTCAGCAGCGAGAGCCCTGCCCACCCA
TTTCTGACCCCTCAGAGCACAGGCAGCAGCACCCCTCTGACATGGACCGC
CCCTAAGACACTGAGCACCGGCCTGATGACCCCTGGCGAGGAATGA NLS-R (SEQ ID NO: 14):
ATGCCCAAGAAAAAGCGGAAGGTGCAGCTGACCAAGGACACCGAGATCAG
CACCATCAACCGGCAGATGAGCGACTTCAGCGAGCTGAGCCAGATCCTGC
CCCTGCACCAGATCTCCAAGATCAAGGACATCCTGGAAAACGAGAACCCC
CTGCCCAAAGAGAAGCTGGCCTCCCACCTGACCATGATCATCCTGATGGC
CAACCTGGCCAGCCAGAAACGGAAGGACGTGCCCGTGAAGCGGAGCACCT
TCCTGAAGTACCAGCGGAGCATCAGCAAGACCCTGCAGTACGACAGCAGC
ACCAAGACCGTGTCCTTCGAGTACCACCTGAAGGACCCCAGCAAGCTGAT
CAAGGGCCTGGAAGATGTGGTGTCCCCCTACAGATTCGTCGTGGGCGTGC
ACGAGAAGCCCGACGACGTGATGTCTCACCTGAGCGCCGTGCACATGCGG
AAAGAGGCCGGCAGAAAGCGGGACCTGGGCAACAAGATCAACGACGAGAT
CACAAAGATCGCCGAGACACAGGAAACCATCTGGGGCTTCGTGGGCAAGA
CCATGGACCTGATCGAGGCCAGAACCACCCGGCCTACAACAAAGGCCGCC
TACAACCTGCTGCTGCAGGCCACCTTCATGAACTGCTGCAGAGCCGACGA
CCTGAAGAACACCGACATCAAGACCTTCGAAGTGATCCCCGACAAGCACC
TGGGCCGGATGCTGAGAGCCTTCGTGCCCGAGACAAAGACCGGAACCAGA
TTCGTGTACTTCTTCCCATGCAAGGGCAGATGCGACCCCCTGCTGGCCCT
GGATTCTTACCTGCAGTGGACCGACCCCATCCCCAAGACCAGAACAACCG
ACGAGGACGCCAGATACGACTACCAGCTGCTGCGGAACAGCCTGCTGGGC
AGCTACGACGGCTTCATCTCCAAGCAGAGCGACGAGAGCATCTTCAAGAT
CCCCAACGGCCCCAAGGCCCACCTGGGCAGACATGTGACAGCCAGCTACC
TGAGCAACAACGAGATGGACAAAGAGGCCACCCTGTACGGCAATTGGAGC
GCCGCTAGAGAAGAGGGCGTGTCCAGAGTGGCCAAGGCCCGGTACATGCA
CACCATCGAGAAGTCCCCCCCCTCCTACCTGTTCGCCTTCCTGAGCGGCT
TCTACAACATCACCGCCGAGAGGGCCTGCGAGCTGGTGGACCCCAATAGC
AACCCCTGCGAGCAGGACAAGAACATCCCCATGATCAGCGACATCGAGAC
ACTGATGGCTCGCTACGGCAAGAACGCCGAGATCATCCCTATGGACGTGC
TGGTGTTCCTGAGCAGCTACGCCCGGTTCAAGAACAACGAGGGCAAAGAG
TACAAGCTGCAGGCTCGGAGCAGCAGAGGCGTGCCCGACTTCCCCGATAA
TGGCAGAACCGCCCTGTACAACGCCCTGACAGCCGCCCACGTGAAGAGGC
GGAAGATCAGCATTGTCGTGGGCCGGTCCATCGACACCAGCTGA NLS-PhiC31 (SEQ ID NO: 15):
atgcctaagaaaaagcggaaagtggatacctacgccggagcctacgacag
acagagccgggagagagagagaacagcagcgccgccagccccgccacccaga
gaagcgccaacgaggataaggccgccgatctgcagagagaggtggagagg
gacggcggcagattcagatttgtgggccacttcagcgaggcccctggcac
cagcgccttcggcaccgccgagagacccgagttcgagagaatcctgaacg
agtgtagggccggcaggctgaacatgatcatcgtgtacgacgtgtcccgg
ttcagcaggctgaaggtgatggacgccatccctatcgtgtccgagctgct
ggccctgggcgtgaccatcgtgtccacccaggaaggcgtctttagacagg
gcaacgtgatggacctgatccacctgatcatgaggctggacgccagccac
aaggagagcagcctgaagagcgccaagatcctggacaccaagaacctgca
gagggagctgggcggctatgtgggcggcaaggccccctacggcttcgagc
tggtgtccgagaccaaggagatcacccggaacggcaggatggtgaacgtg
gtgatcaacaagctggcccacagcaccacccccctgaccggccccttcga
gtttgagcccgacgtgatcaggtggtggtggcgggagatcaagacccaca -continued agcacctgcctttcaagcccggcagccaggccgccatccaccccggcagc atcaccggcctgtgtaagagaatggacgccgacgccgtgcccaccagagg cgagaccatcggcaagaaaaccgccagcagcgcctgggaccccgccaccg tgatgagaatcctgagggaccctaggatcgccggcttcgccgccgaggtg atctacaagaagaagcccgacggcacccccaccaccaagatcgagggcta cagaatccagagagaccccatcaccctgagacctgtggagctggactgtg gccctatcatcgagcctgccgagtggtacgagctgcaggcctggctggac ggcagaggcagaggcaagggcctgagcagaggccaggccatcctgagcgc catggacaagctgtactgtgagtgtggcgccgtgatgaccagcaagagag gcgaggagagcatcaaggacagctaccggtgccggagaagaaaggtggtg gaccccagcgcccctggccagcacgagggcacctgtaatgtgagcatggc cgccctggacaagttcgtggccgagcggatcttcaacaagatccggcacg ccgagggcgacgaggagaccctggccctgctgtgggaggccgccagaaga ttcggcaagctgaccgaggcccccgagaagagcggcgagagggccaacct ggtggccgagagagccgacgccctgaacgccctggaggagctgtacgagg acagagccgccggagcctatgacggccctgtgggcaggaagcacttcaga aagcagcaggccgccctgaccctgagacagcagggcgccgaggaaagact ggccgagctggaggccgccgaggcccctaagctgcccctggatcagtggt tccccgaggatgccgacgccgaccccaccggccccaagtcctggtggggc agagccagcgtggacgacaagagggtgttcgtgggcctgttcgtggataa gatcgtggtgaccaagagcaccaccggcaggggccagggcacccccatcg agaagagagccagcatcacctgggccaagcctcccaccgacgacgacgag gatgacgcccaggacggcaccgaggacgtggccgcctga NLS-bxb1 (SEQ ID NO: 16):
ATGGATCCTAAGAAAAAGCGAAAAGTGATGCGAGCCCTGGTGGTCATTCG

CCTGAGCAGAGTCACAGACGCTACTACAAGCCCTGAGCGGCAGCTGGAGT

CCTGTCAGCAGCTGTGCGCACAGCGAGGATGGGATGTGGTCGGAGTGGCA

GAGGATCTGGACGTGAGCGGGGCTGTCGATCCATTCGACCGAAAGCGGAG

ACCCAACCTGGCACGATGGCTGGCTTTCGAGGAACAGCCCTTTGATGTGA

TCGTCGCCTACAGAGTGGACAGGCTGACACGCTCAATTCGACATCTGCAG

CAGCTGGTGCATTGGGCCGAGGATCACAAGAAACTGGTGGTCAGCGCAAC

TGAAGCCCACTTCGACACCACAACTCCTTTTGCCGCTGTGGTCATCGCAC

TGATGGGCACCGTGGCCCAGATGGAGCTGGAAGCTATCAAGGAGCGAAAC

CGGAGCGCAGCCCATTTCAATATTCGGGCCGGGAAATACAGAGGCAGCCT

GCCCCCTTGGGGCTATCTGCCTACCCGGGTGGATGGGGAGTGGAGACTGG

TGCCAGACCCCGTCCAGAGAGAGAGGATTCTGGAAGTGTACCACAGAGTG

GTGGACAACCACGAACCACTGCATCTGGTGGCCCACGATCTGAATAGGCG

CGGAGTCCTGTCTCCAAAGGACTATTTTGCTCAGCTGCAGGGAAGGGAGC

CACAGGGACGAGAATGGAGTGCTACCGCACTGAAGCGGTCTATGATCAGT

GAGGCTATGCTGGGCTATGCAACTCTGAATGGGAAAACCGTGAGAGACGA

TGACGGAGCACCACTGGTGCGGGCTGAGCCTATTCTGACAAGAGAGCAGC

-continued

TGGAAGCTCTGAGGGCAGAACTGGTGAAAACCAGTAGGGCCAAGCCTGCT

GTGTCAACACCAAGCCTGCTGCTGCGAGTGCTGTTCTGCGCAGTCTGTGG

CGAGCCAGCATACAAATTTGCCGGCGGGGAAGGAAGCATCCCCGCTATC

GATGCCGGAGCATGGGGTTCCCTAAGCACTGTGGAAACGGCACTGTGGCT

ATGGCCGAATGGGACGCCTTTTGTGAGGAACAGGTGCTGGATCTGCTGGG

GGACGCAGAGCGCCTGGAAAAAGTGTGGGTCGCTGGAAGCGATTCCGCTG

TGGAGCTGGCAGAAGTCAATGCCGAGCTGGTGGACCTGACCTCCCTGATC

GGATCTCCTGCATACAGGGCAGGCTCCCCACAGCGAGAAGCTCTGGATGC

ACGAATTGCTGCACTGGCAGCTCGACAGGAGGAACTGGAGGGGCTGGAAG

CCAGACCCTCTGGATGGGAGTGGCGAGAAACAGGCCAGCGGTTTGGGGAT

TGGTGGAGGGAGCAGGACACAGCAGCCAAGAACACTTGGCTGAGATCCAT

GAATGTCAGGCTGACTTTCGACGTGCGAGGAGGACTGACCCGAACAATCG

ATTTTGGCGACCTGCAGGAGTATGAACAGCATCTGCGCCTGGGAAGTGTG

GTCGAGCGACTGCACACCGGCATGTCATAA

The sequences for some RRS are shown below:

loxP (SEQ ID NO: 17):
ATAACTTCGTATAgcatacatTATACGAAGTTAT lox2272 (SEQ ID NO: 18):
ATAACTTCGTATAggatacctTATACGAAGTTAT loxN (SEQ ID NO: 19):
ATAACTTCGTATAgtatacctTATACGAAGTTAT

FRT (SEQ ID NO: 20):
GAAGTTCCTATTCTCTAGAAAGTATAGGAACTTC

F3 (SEQ ID NO: 21):
GAAGTTCCTATTCttcaaataGTATAGGAACTTC

F14 (SEQ ID NO: 22):
GAAGTTCCTATTCtatcagaaGTATAGGAACTTC

Rox (SEQ ID NO: 23):
TAACTTTAAATAattggcatTATTTAAAGTTA

VloxP (SEQ ID NO: 24):
TCAATTTCTGAGAactgtcatTCTCGGAAATTGA

Vlox2272 (SEQ ID NO: 25):
TCAATTTCTGAGAagtgtcttTCTCGGAAATTGA

SloxP (SEQ ID NO: 26):
CTCGTGTCCGATAactgtaatTATCGGACATGAT

SloxM1 (SEQ ID NO: 27):
CTCGTGTCCGATAactgtaatTATCGGACACGAG

Slox2272 (SEQ ID NO: 28):
CTCGTGTCCGATAagtgtattTATCGGACATGAT

Vox (SEQ ID NO: 29):
AATAGGTCTGAGAacgcccatTCTCAGACGTATT

B3RT (SEQ ID NO: 30):
GGTTGCTTAAGAATAAGTAATTCTTAAGCAACC

KDRT (SEQ ID NO: 31):
AAACGATATCAGACATTTGTCTGATAATGCTTCATTATCAGACAAATGTC

TGATATCGTTT

-continued

B2RT (SEQ ID NO: 32):
GAGTTTCATTAAGGAATAACTAATTCCCTAATGAAACTC

RSRT (SEQ ID NO: 33):
TTGATGAAAGAATAACGTATTCTTTCATCAA

PhiC31 attB (SEQ ID NO: 34):
TGCGGGTGCCAGGGCGTGCCCTTGGGCTCCCCGGGCGCGTACTCC

PhiC31 attP (SEQ ID NO: 35):
GTGCCCCAACTGGGGTAACCTTTGAGTTCTCTCAGTTGGGGG

Bxb1 attB (SEQ ID NO: 36):
TCGGCCGGCTTGTCGACGACGGCGGTCTCCGTCGTCAGGATCATCCGGGC

Bxb1 attP (SEQ ID NO: 37):
TCGTGGTTTGTCTGGTCAACCACCGCGGTCTCAGTGGTGTACGGTACAAA

CCC

Logic Gates

Figure 4:
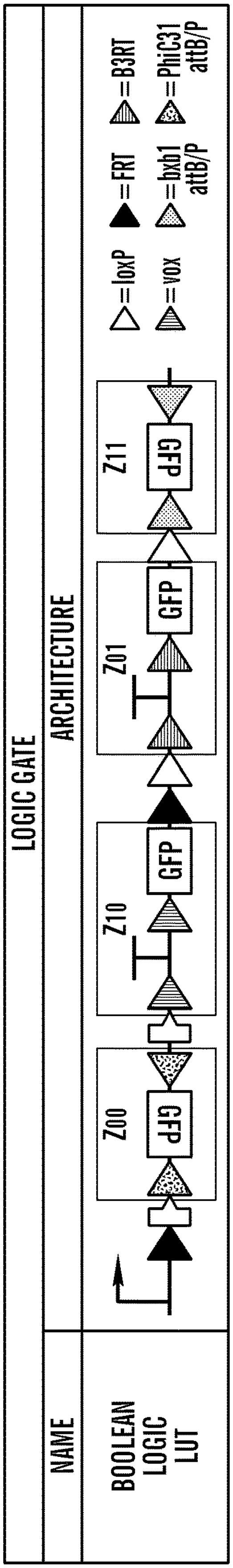
Figure 4:
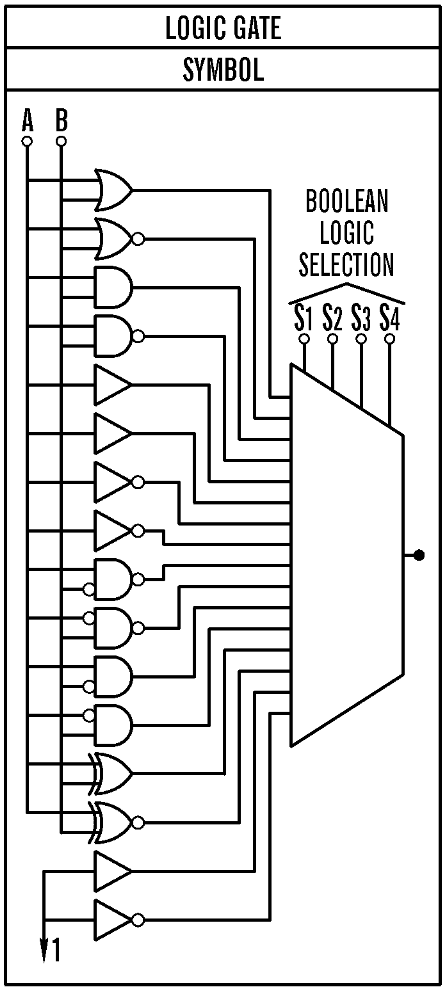
Figure 4:
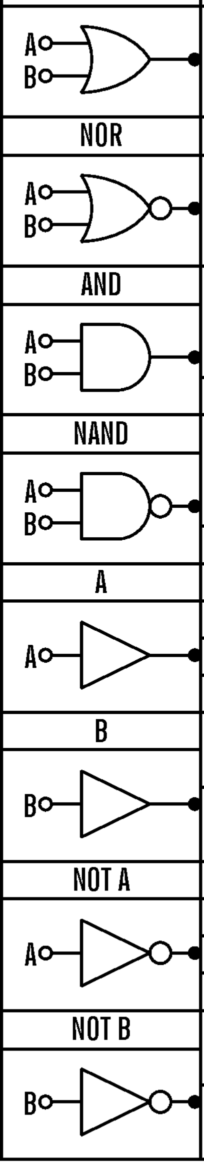
Figure 4:
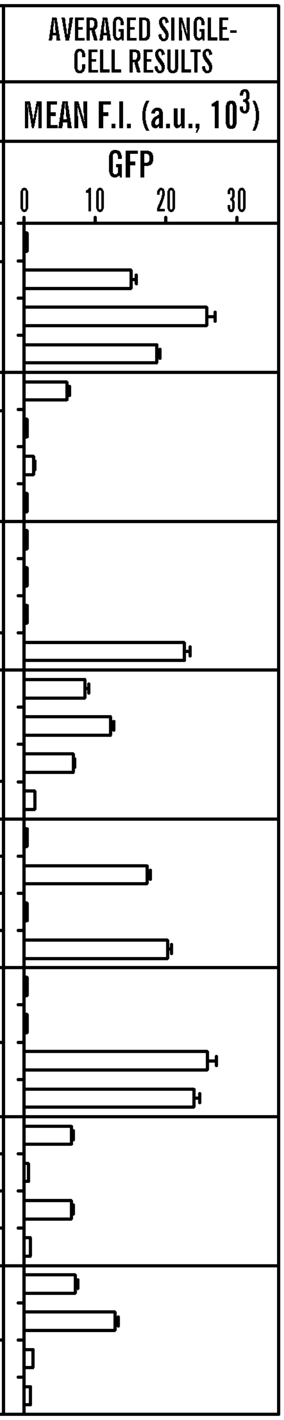
Figure 4:
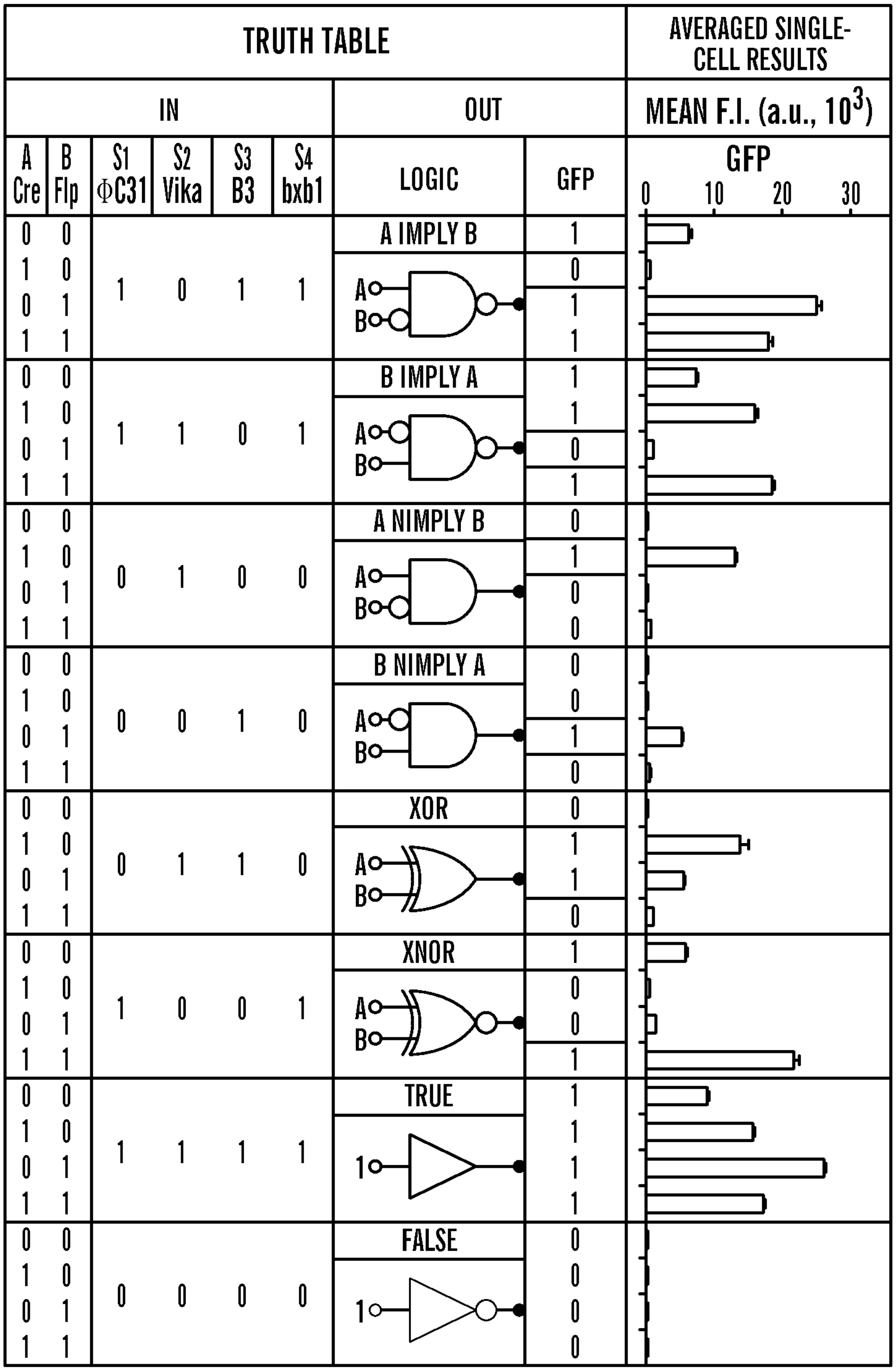

The inventors have constructed a plurality of nucleic acid logic cassettes capable of performing different logic functions. For example, FIG. 4 depicts an exemplary 6-input-one output genetic device which receives two data inputs, that is controlled by four select inputs $S_1$-$S_4$ to control the output of the GFP expression, where A and B are inputs. This circuit has two data inputs, A and B, and four select inputs, $S_1$, $S_2$, $S_3$, and $S_4$. Each select input can control which buffer gates are GFP ON or OFF. Thus, each combination of select inputs configures the device to a specific Boolean logic gate with up to two inputs and one output. Depicted in FIG. 4 shows A is input from Cre, B is input from Flp, $S_1$ is input from ϕC31 (phiC31), $S_2$ is input from Vika, $S_3$ is input from B3 and $S_4$ is input from bxb1 recombinases. It should be understood that these are exemplary recombinases for the inputs for the logic gates described herein. The invention contemplates the use of other inputs, which may be chosen by the end-user and used interchangeably with or in place of Cre, or Flp as A and B inputs, or ϕC31 (phiC31), Vika, B3 and bxb1 as S1-S4 recombinases respectively.

Figure 7:
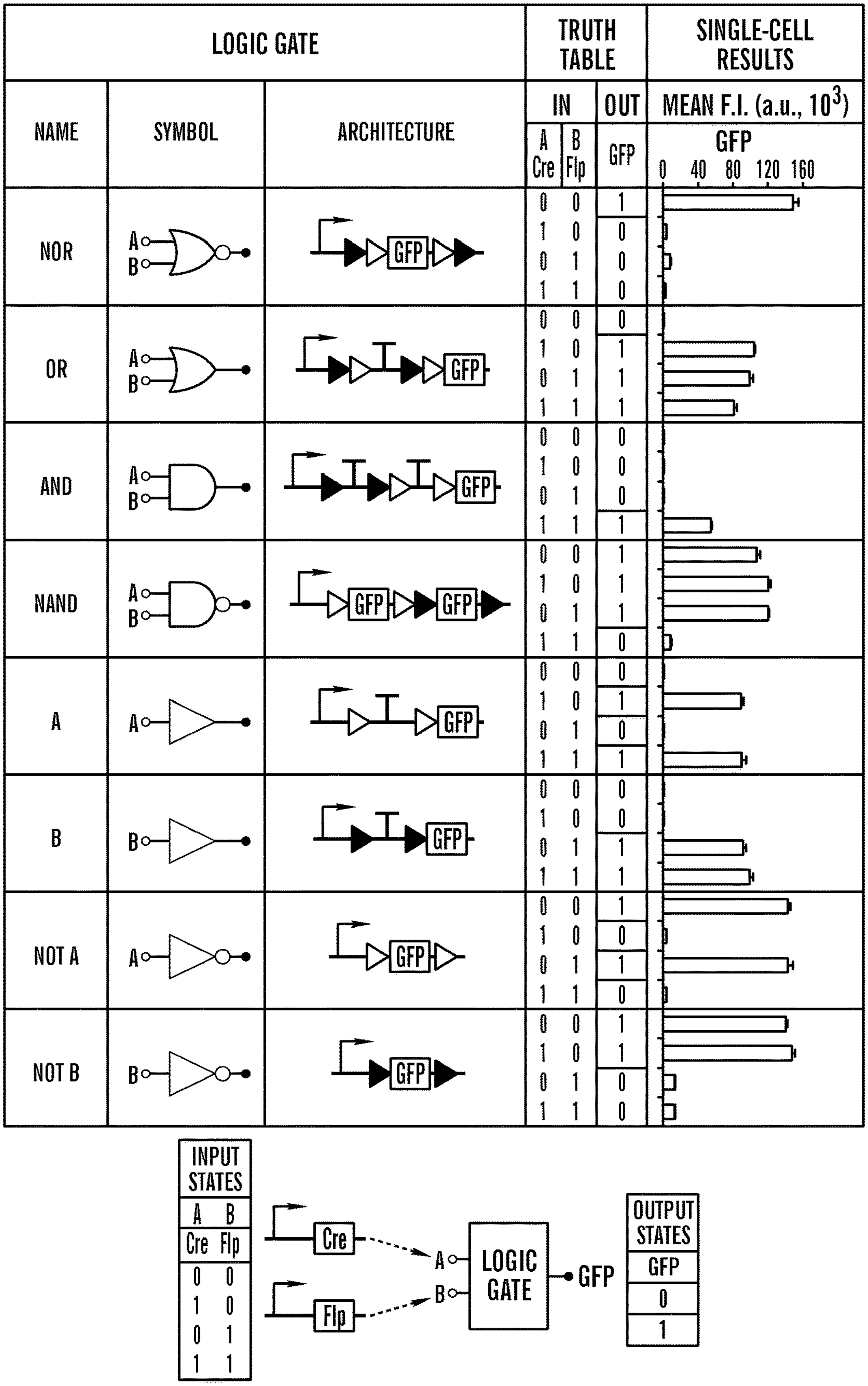
Figure 7:
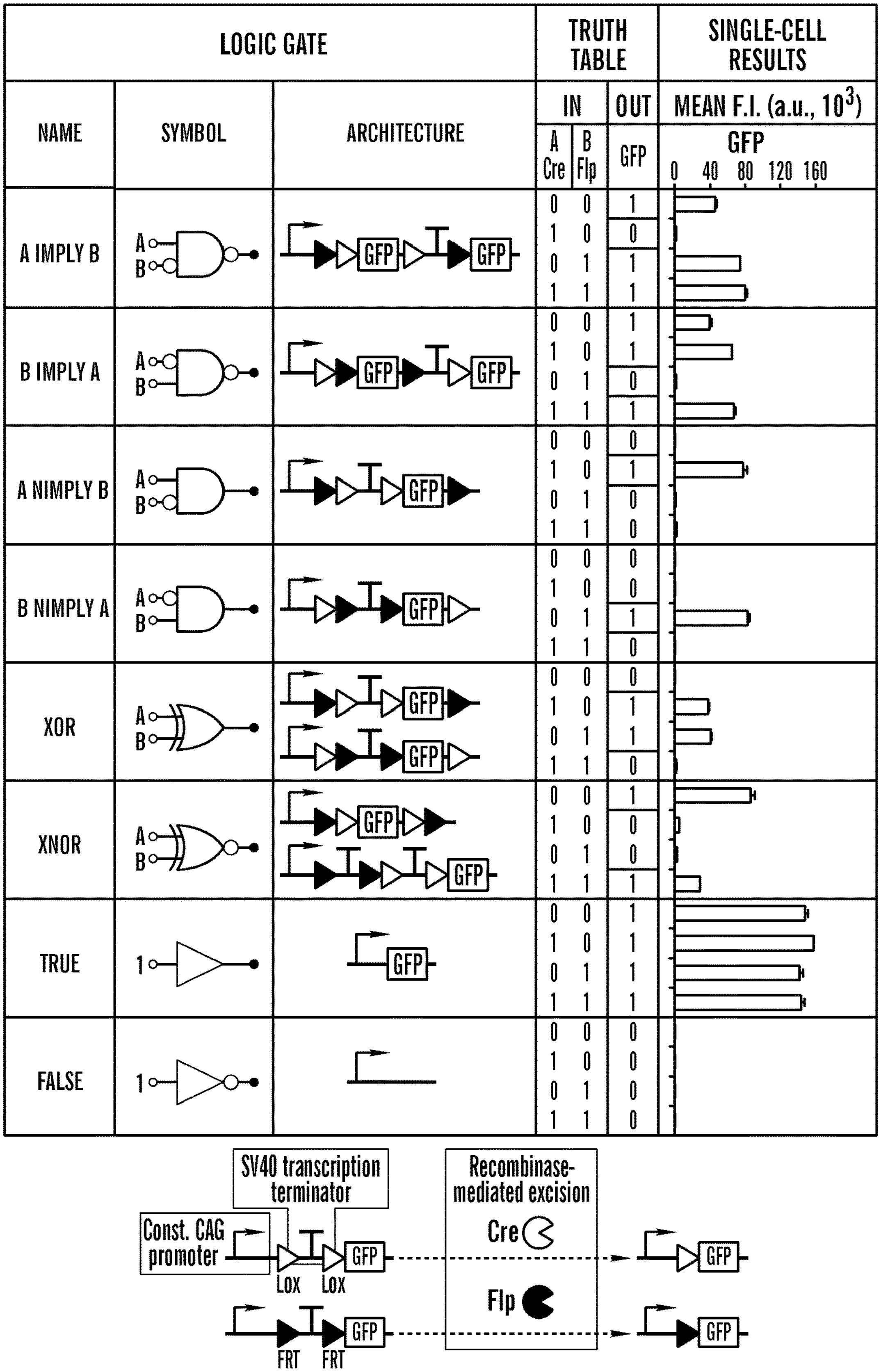

Sixteen logic gates of the invention (AND, OR, NOT A, NOT B, NOR, NAND, XOR, XNOR, A IMPLY B, B IMPLY A, A NIMPLY B, B NIMPLY A, A, B, FALSE and TRUE) are described below and depicted in FIGS. 4, 7, and 8A-8B, which depict two-input, 4-input, 6-input and 8-input Boolean logic functions. As shown in FIG. 7, logic gates that include "two-input" Boolean logic functions include AND, OR, NOR, NAND, XOR, XNOR, A IMPLY B, B IMPLY A, A NIMPLY B and B NIMPLY A. Thus, a logic gate or a plurality of logic gates is considered to provide all two-input Boolean logic functions if the logic gates or the plurality of logic gates includes AND, OR, NOR, NAND, XOR, XNOR, A IMPLY B, B IMPLY A, A NIMPLY B and B NIMPLY A logic gates. The individual logic gates of the invention, however, are not limited to the genetic circuits depicted in FIGS. 4, 7, and 8A-8B, but also encompass any of the genetic circuits depicted in all the figures disclosed herein. Any number of the genetic elements in FIG. 7 may be arranged in a variety of locations and orientations in a given genetic circuit construct of a logic gate to achieve the desired output. For example, alternative genetic circuit constructs for logic gates NOR, AND and XOR are depicted in FIG. 4 and FIGS. 7 and 8A-8B.

Herein, a promoter is considered to be "operatively linked" when it is in a functional location and orientation in relation to a nucleic acid sequence it regulates to control ("drive") transcriptional initiation and/or expression of that sequence. A promoter is said to be "conditionally operatively linked" when, upon a genetic recombination event, it is placed in a functional location and orientation in relation to a nucleic acid sequence it regulates.

An "inverted" genetic element (e.g., inverted promoter, inverted terminator, inverted target gene) is one that is in the reverse orientation, such that what was the coding (sense) strand is now the non-coding (antisense) strand. In its inverted, reverse orientation, a genetic element is non-functional (e.g., not operatively linked to another genetic element such as a target gene). Function of the genetic element can be restored upon recombination of flanking complementary recognition sites and subsequent inversion of the genetic element back to its correct orientation. Thus, an inverted promoter flanked by recombination recognition sites may be considered to be "conditionally operatively linked" to a downstream target gene if, upon recombination of the flanking complementary recognition sites, the promoter is oriented such that what was the non-coding strand is now the coding strand, and the promoter is able to control transcriptional initiation and/or expression of the target gene. Likewise, an inverted target gene flanked by recombination recognition sites may be "conditionally operatively linked" to an upstream promoter if, upon recombination of the flanking recognition sites, the target gene is oriented such that what was the non-coding strand is now the coding strand, and the upstream promoter is able to control transcriptional initiation and/or expression of the output nucleic acid.

Illustrative examples of a promoter operatively linked to a target gene are shown in the NOR, NAND, TRUE, NOT A, NOT B and XNOR logic gates of FIGS. 4, 7 and 8A-8B. Illustrative examples of a promoter conditionally operatively linked to a target gene are shown in the AND, OR, A, B, A NIMPLY B, B NIMPLY A and XOR logic gates of FIGS. 4 and 7, 8A-8B. Logic gates A IMPLY B and B IMPLY A contain both a promoter that is operatively linked to a target gene and a promoter that is conditionally operatively linked to a target gene.

Herein, a target gene is considered to be downstream of a genetic element if the target gene is located toward the 3' end and the genetic element is located toward the 5' end of the coding (sense) strand. One genetic element is considered to be "immediately downstream" of another genetic element the two are proximal to each other (e.g., no other genetic element is located between the two).

NOT Gates:

some embodiments of the nucleic acid logic cassettes are adapted to function as NOT gates. The simplest Boolean logic gate is referred to as a NOT gate. It takes one input and produces as output its opposite. Disclosed herein are exemplary NOT A and NOT B logic gates in the 6-input-one output genetic device which receives two data inputs, that is controlled by four select inputs S1-S4 to control the output of the GFP expression, where A and B are inputs (FIG. 4). In FIG. 4, where NOT A is used, GFP is expressed when input is received from $S_1$ and $S_3$ and input is received from B or when there is no input from either A or B. Similarly, where NOT B is used, GFP is expressed when input is received from $S_1$ and $S_2$ and input is received from A or when there is no input from either A or B.

One embodiment of the NOT gate is shown in FIG. 7. In FIG. 7, the NOT gate comprises a promoter and a recombination unit connected to and positioned downstream of the promoter. The recombination unit comprises a pair of RRS specific for a recombinase, each of the RRS flanks each side of a target gene. For a NOT A gate, where A is the recombinase, the target gene is expressed as long as the recombinase is not present; when the recombinase is present, the target gene is excised.

AND Gates:

some embodiments of the nucleic acid logic cassettes are adapted to function as AND gates. The AND gate is another simple Boolean logic gate. It performs a logical "and" operation on at least two inputs, A and B. Thus, in the LUT 6-input-one output genetic device shown in FIG. 4 which receives two inputs, that is controlled by four select inputs S1-S4 to control the output of the GFP expression, GFP is only expressed when inputs A and B are both present.

One embodiment of the AND gate is shown in FIG. 7, where the AND gate is adapted to receive two inputs. The AND gate comprises a promoter, a U1 connected to and positioned downstream of the promoter, a U2 connected to and positioned downstream of the U1, and a target gene connected to and positioned downstream of the U2. The U1 comprises a first pair of RRS1 specific for a R1, each of the RRS1 flanking each side of a first transcriptional terminator (TT1). The U2 comprises a second pair of RRS2 specific for a R2, each of the RRS2 flanking each side of a second transcriptional terminator (TT2). When both R1 and R2 are present, the TT1 and TT2 are excised, which operatively links the target gene to the promoter.

Figure 12A:
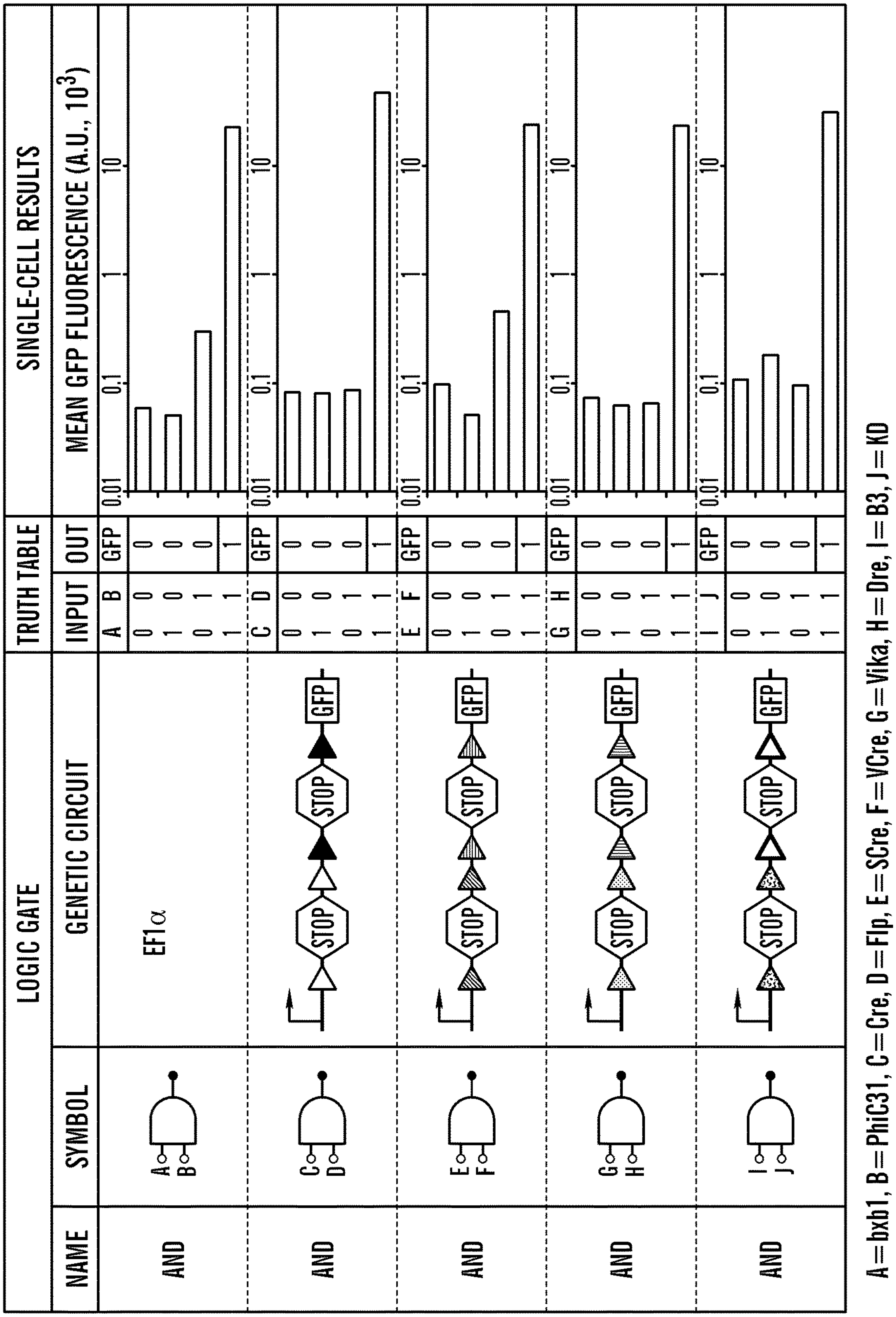
Figure 12B:
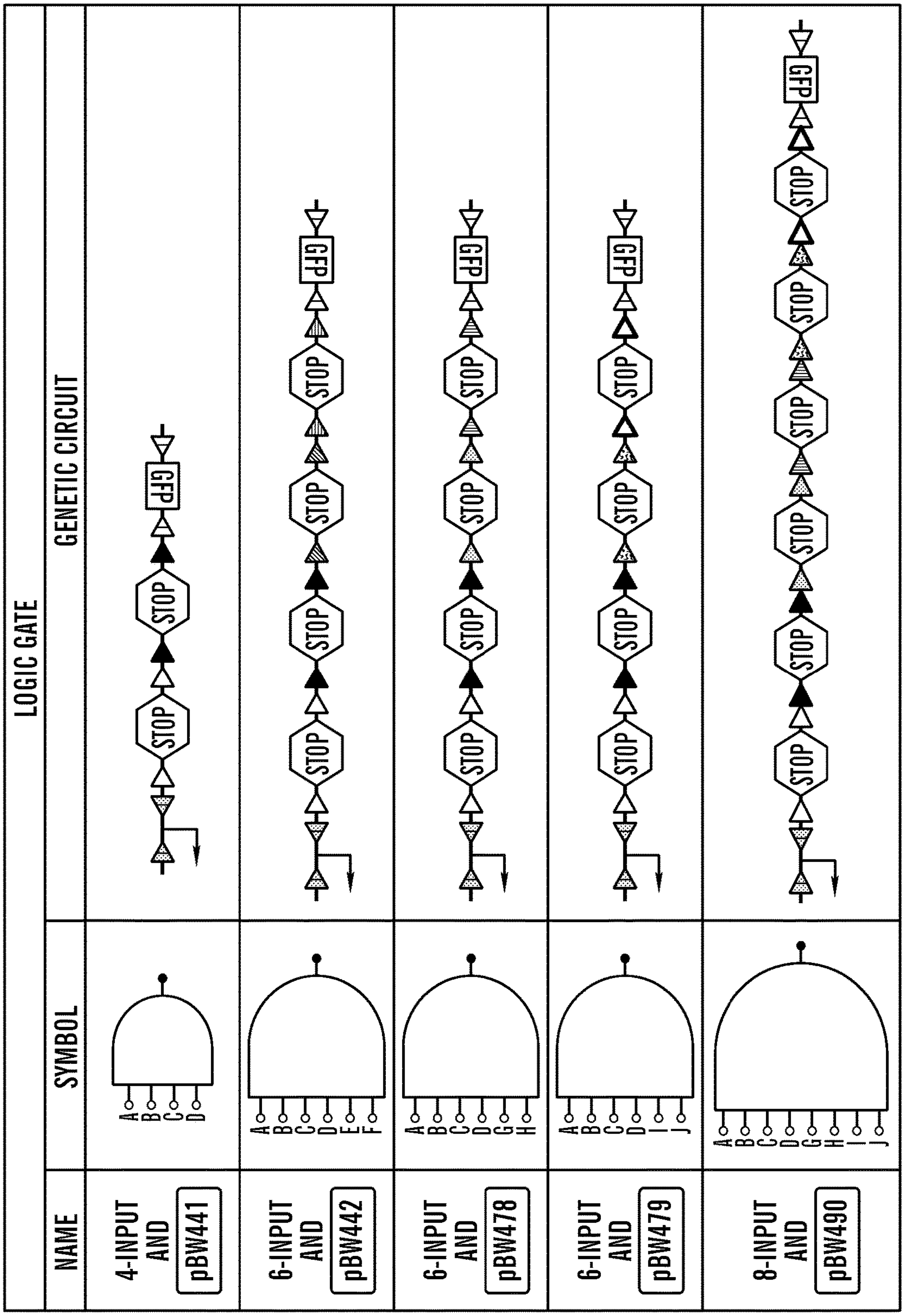

Some embodiments of the AND gates are adapted to receive at least three inputs (e.g., 3, 4, 5, 6, 7, 8, or more) as shown in FIG. 12B. In these embodiments, the U1, U2 and U3 are connected in series. In the U1, the RRS1 are in an inverse orientation with respect to each other and the first nucleic acid encodes the promoter in an inverted orientation; in the U2, the RRS2 are in the same orientation with respect to each other and the second nucleic acid comprises a transcriptional terminator sequence (TT); and in the U3, the RRS3 are in an inverse orientation with respect to each other and the third nucleic acid comprises a target gene (TG) in an inverted orientation. The RRS1, RRS2, and RRS3 are each recognized by R1, R2, and R3 respectively, and thus only in the presence of the R1, R2 and R3 is the TG operatively linked to the promoter.

More recombination units can be added in tandem with the U1, U2, and U3 if more inputs are needed. Accordingly, in some embodiments, the multi-input AND gate further comprises a fourth recombination unit (U4) comprising a fourth pair of recombinase recognition sequences (RRS4) for a fourth recombinase (R4) different from the R1, R2, and R3, the RRS4 being in the same orientation with respect to each other. Each of the RRS4 flanks each side of a fourth nucleic acid sequence comprising a second transcriptional terminator sequence (TT2), and the U4 is positioned in between the U2 and U3. Only in the presence of the R1, R2, R3, and R4 is the TG operatively linked to the promoter.

OR Gates:

some embodiments of the nucleic acid logic cassettes are adapted to function as OR gates. The OR gate performs a logical "or" operation on input A or input B. Thus, in the LUT 6-input-one output genetic device shown in FIG. 4 which receives two data inputs, that is controlled by four select inputs S1-S4 to control the output of the GFP expression, GFP is expressed when either inputs A or B, or A and B, are present.

One embodiment of the OR gate is shown in FIG. 7. The OR gate comprises a promoter, a U1 connected to and positioned downstream of the promoter, a U2 connected to and positioned downstream of the prompter, and a target gene. Each of the RRS1 of the U1 flanks each side of a transcriptional terminator, and each of the RRS2 of the U2 flanks each side of the same transcriptional terminator. The RRS1 are in the same orientation with respect to each other. The RRS2 are in the same orientation with respect to each other. When either the R1 or R2 is present, the transcriptional terminator is excised, thus operatively linking the target gene to the promoter.

NOR Gates:

some embodiments of the nucleic acid logic cassettes are adapted to function as NOR gates. The NOR gate is a combination of an OR gate with a NOT gate. Thus, in the LUT 6-input-one output genetic device shown in FIG. 4 which receives two data inputs, that is controlled by four select inputs S1-S4 to control the output of the GFP expression, GFP is only expressed when neither A and B inputs are present.

One embodiment of the NOR gate is shown in FIG. 7. The NOR gate comprises a promoter, a U1 connected to and positioned downstream of the promoter, a U2 connected to and positioned downstream of the prompter, and a target gene. The U1 comprises the U2. The RRS1 are in the same orientation with respect to each other. The RRS2 are in the same orientation with respect to each other. Each of the RRS2 of the U2 flanks each side of the same target gene. When neither the R1 nor R2 is present, the target gene is expressed. When at least one of the R1 and R2 is present, the target gene is excised.

NAND Gates:

some embodiments of the nucleic acid logic cassettes are adapted to function as NAND gates. The NAND gate is a combination of an AND gate with a NOT gate. Thus, in the LUT 6-input-one output genetic device shown in FIG. 4 which receives two data inputs, that is controlled by four select inputs S1-S4 to control the output of the GFP expression, GFP is expressed when inputs A or B are present, or when neither A and B inputs are present.

One embodiment of the NAND gate is shown in FIG. 7. The NAND gate comprises a promoter, a U1 connected to and positioned downstream of the promoter, and a U2 connected to and positioned downstream of the U1. The U1 comprises a pair of RRS1, wherein each of the RRS1 flanks each side of a TG1, and wherein the RRS1 are in the same orientation as each other. The U2 comprises a pair of RRS2, wherein each of the RRS2 flanks each side of a TG2, and wherein the RRS2 are in the same orientation as each other. The TG1 and TG2 encode the same molecule of interest. There is no or minimal output when both R1 and R2 are present. Under other input conditions, output of similar magnitude is produced.

IMPLY Gates:

some embodiments of the nucleic acid logic cassettes are adapted to function as A IMPLY B gates (A AND NOT B) and B IMPLY A gates (B AND NOT A). In A IMPLY B gates in the LUT 6-input-one output genetic device shown in FIG. 4 which receives two data inputs, that is controlled by four select inputs S1-S4 to control the output of the GFP expression, GFP is expressed in all circumstances except when input A is present alone. Similarly, In B IMPLY A gates, GFP is expressed in all circumstances except when input B is present alone.

One embodiment of the IMPLY gate is shown in FIG. 7. For example, the A IMPLY B gate comprises a promoter, a U1 connected to and positioned downstream of the promoter, and a TG1 connected to and positioned downstream of the U1. The U1 comprises a pair of RRS1 in the same orientation with respect to each other and also a first nucleic acid sequence. Each of the RRS1 flanks each side of the first nucleic acid sequence. The first nucleic acid sequence comprises a U2 and a transcriptional terminator positioned downstream of the U2. The U2 comprises a pair of RRS2 in the same orientation with respect to each other, each of the RRS2 flanking each side of a TG2. The TG1 and TG2 encode the same molecule of interest. When R1 is present and R2 is absent, there is no or minimal output. Under other input conditions, output of similar magnitude is produced.

NIMPLY Gates:

some embodiments of the nucleic acid logic cassettes are adapted to function as A NIMPLY B and B NIMPLY A gates. In A NIMPLY B gates in the LUT 6-input-one output genetic device shown in FIG. 4 which receives two data inputs, that is controlled by four select inputs S1-S4 to control the output of the GFP expression, GFP is only expressed when input A is present alone. Similarly, In B NIMPLY A gates, GFP is only expressed when input B is present alone.

One embodiment of the NIMPLY gate is shown in FIG. 7. For example, the A NIMPLY B gate comprises a promoter and a U1 connected to and positioned downstream of the promoter. The U1 comprises a pair of RRS1 in the same orientation with respect to each other and also a first nucleic acid sequence. Each of the RRS1 flanks each side of the first nucleic acid sequence. The first nucleic acid sequence comprises a U2 and a TG positioned downstream of the U2. The U2 comprises a pair of RRS2 in the same orientation with respect to each other, each of the RRS2 flanking each side of a transcriptional terminator. Output is produced only when R1 is present and R2 is absent.

XOR Gates:

some embodiments of the nucleic acid logic cassettes are adapted to function as XOR gates. The XOR gate is an "exclusive or" gate. Thus, in the LUT 6-input-one output genetic device shown in FIG. 4 which receives two data inputs, that is controlled by four select inputs S1-S4 to control the output of the GFP expression, GFP is expressed when either inputs A or input B is present, but not when neither are absent or both A and B inputs are present.

One embodiment of the XOR gate is shown in FIG. 7. The XOR gate comprises an A NIMPLY B gate and a B NIMPLY A gate.

XNOR Gates:

some embodiments of the nucleic acid logic cassettes are adapted to function as XNOR gates. The XNOR gate is an "exclusive nor" gate. Thus, in the LUT 6-input-one output genetic device shown in FIG. 4 which receives two data inputs, that is controlled by four select inputs S1-S4 to control the output of the GFP expression, GFP is expressed when either there are no inputs from both A and B, or when inputs from both A and B are present.

One embodiment of the XNOR gate is shown in FIG. 7. The XNOR gate comprises a NOR gate and an AND gate.

A and B Gates:

some embodiments of the nucleic acid logic cassettes are adapted to function as A and B gates. Thus, in an A gate in the LUT 6-input-one output genetic device shown in FIG. 4 which receives two data inputs, that is controlled by four select inputs S1-S4 to control the output of the GFP expression, GFP is expressed when A input is present, regardless of whether it is alone or whether B input is present. Similarly, in a B gate, GFP is expressed when B input is present, regardless of whether it is alone or whether A input is present.

One embodiment of the A gate or B gate is shown in FIG. 7. For example, the A gate comprises a promoter, a U1 connected to and positioned downstream of the promoter, and a TG connected to and positioned downstream of the U1. The U1 comprises a pair of RRS1 in the same orientation with respect to each other, wherein each of the RRS1 flanks each side of a transcriptional terminator. Output is produced only when R1 is present.

TRUE and FALSE Gates:

some embodiments of the nucleic acid logic cassettes are adapted to function as TRUE and FALSE gates. The TRUE gate in FIG. 4 results in GFP expression at all times. The FALSE gate in FIG. 4 results in no GFP expression at all times.

One embodiment of the TRUE gate or FALSE gate is shown in FIG. 7.

Figure 13A:
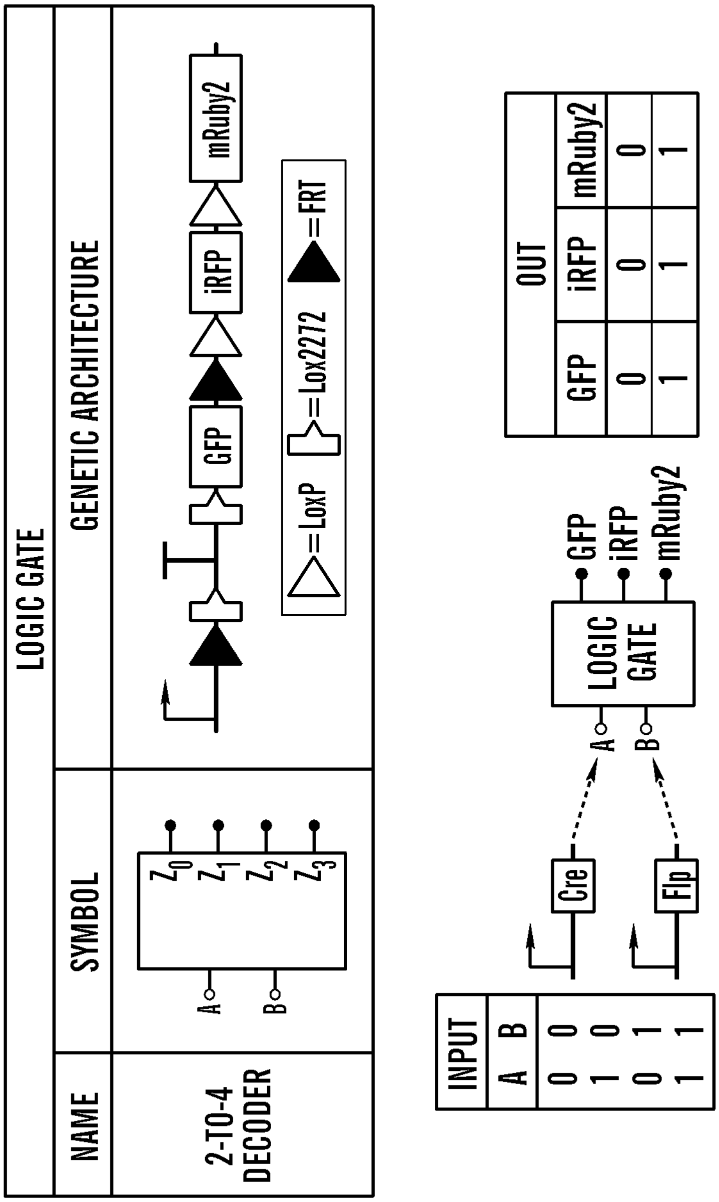
Figure 13A:
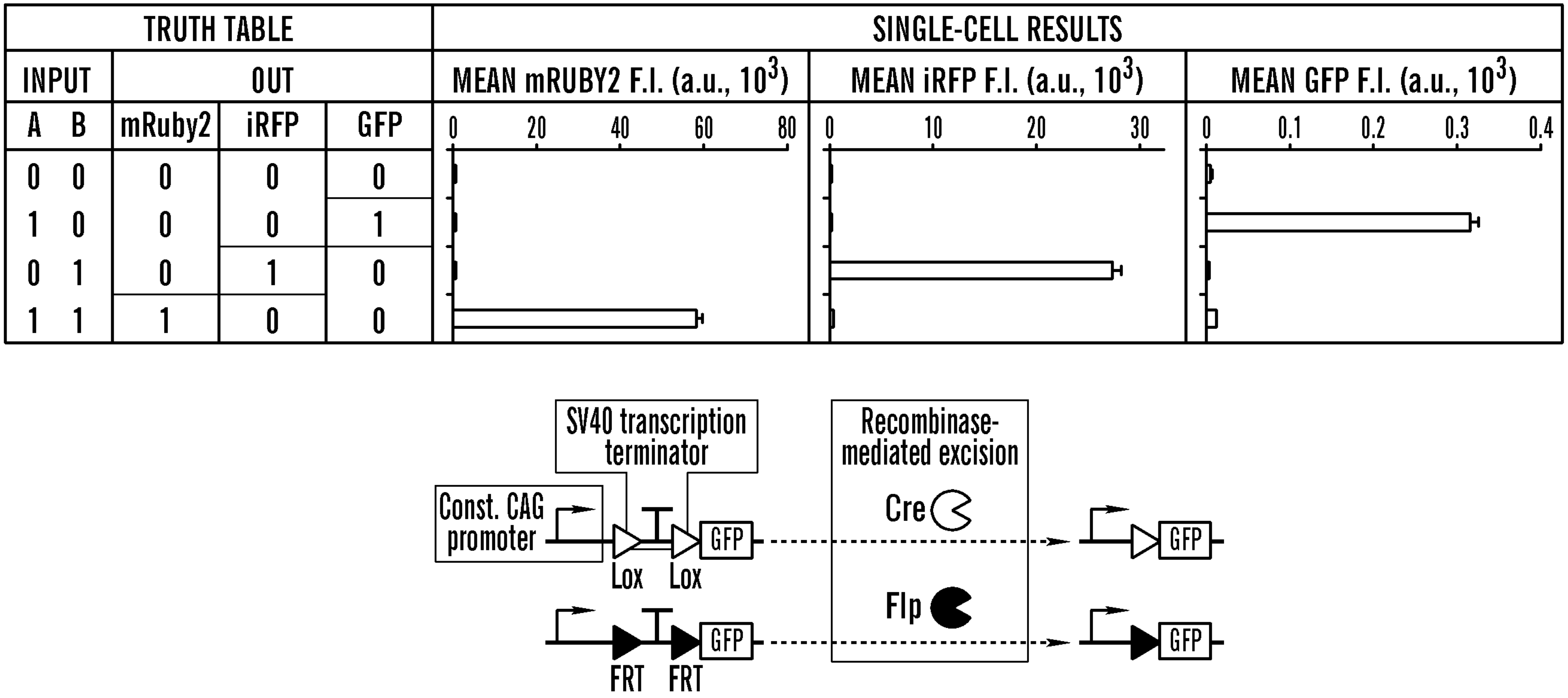
Figure 13B:
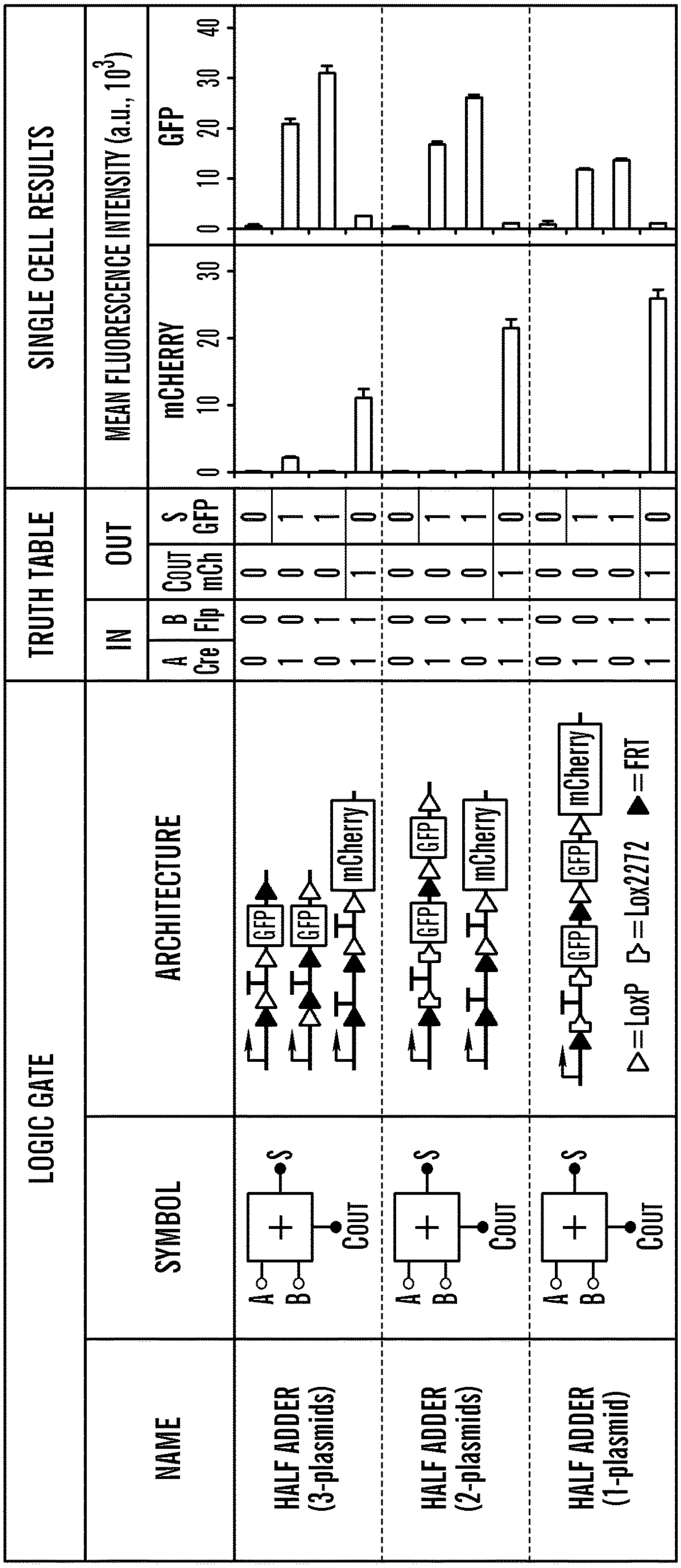

Half Adder:

some embodiments of the nucleic acid logic cassettes are adapted to function as Half Adders. The half adder adds two single binary digits A and B. It has two outputs, sum (S) and carry ($C_{out}$). The carry signal represents an overflow into the next digit of a multi-digit addition. The value of the sum is $2C_{out}+S$. For example, when the value of input A is 1, the value of input B is 0, the value of the sum is 1; when the value of input A is 1, the value of input B is 1, the value of the sum is 2. As shown in FIG. 13B, in some embodiments, the half adder can comprise two different reporter genes. In some embodiments, the half adder can comprise one plasmid, two plasmids, or three plasmids.

In some embodiments of the half adder being a single transcriptional unit, the first nucleic acid sequence of the U1 of the half adder comprises the U2 and a first target gene (TG1) positioned downstream of the U2. The RRS1 are in the same orientation with respect to each other, and the RRS2 are in the same orientation with respect to each other. The second nucleic acid sequence of the U2 encodes a transcriptional terminator. The U3 has the RRS3 in the same orientation with respect to each other, and the third nucleic acid sequence of the U3 comprises a second TG1. A second target gene (TG2) is positioned downstream of the U3. The RRS2 and RRS3 can be recognized by the same recombinase.

Figure 13C:
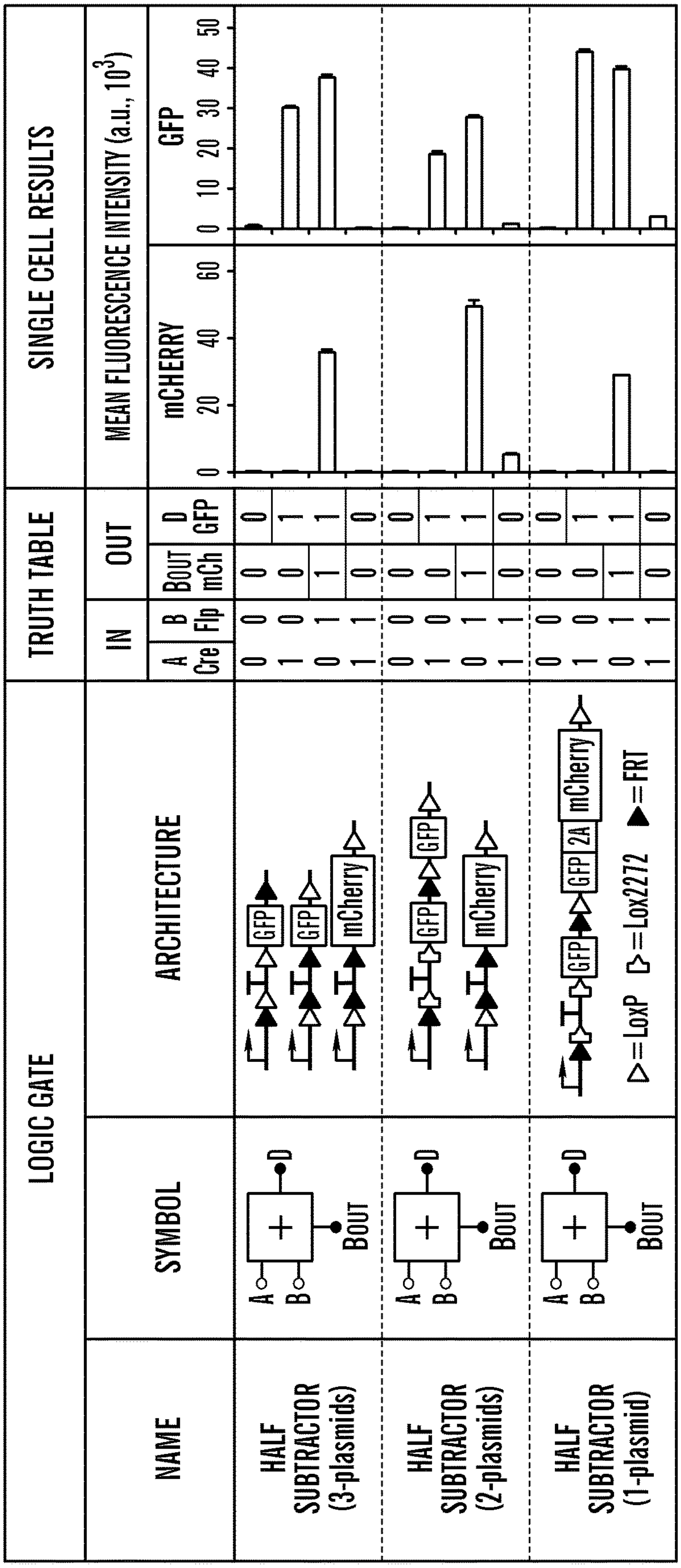

Half Subtractor:

some embodiments of the nucleic acid logic cassettes are adapted to function as Half Subtractors. The half subtractor is a combinational circuit which is used to perform subtraction of two bits. It has two inputs, A (minuend) and B (subtrahend) and two outputs D (difference) and $B_{out}$ (borrow). For example, when the value of input A is 1, the value of input B is 0, the value of the difference is 1; when the value of input A is 1, the value of input B is 1, the value of the difference is 0. As shown in FIG. 13C, in some embodiments, the half subtractor can comprise two different reporter genes. The half subtractor can comprise one plasmid, two plasmids, or three plasmids.

In some embodiments of the half subtractor being a single transcriptional unit, the first nucleic acid sequence of the U1 of the half subtractor comprises the U2 and a first target gene (TG1) positioned downstream of the U2. The RRS1 are in the same orientation with respect to each other, and the RRS2 are in the same orientation with respect to each other. The second nucleic acid sequence of the U2 encodes a transcriptional terminator. The U3 has the RRS3 in the same orientation with respect to each other, and the third nucleic acid sequence of the U3 comprises a second TG1 and a second target gene (TG2) separated by ribosomal skip sequences. The RRS2 and RRS3 can be recognized by the same recombinase.

Full Adder:

some embodiments of the nucleic acid logic cassettes are adapted to function as Full Adders. The full adder adds binary numbers and accounts for values carried in as well as out. A one-bit full adder adds three one-bit numbers, often written as A, B, and $C_{in}$; A and B are the operands, and is a bit carried in from the previous less significant stage. The circuit produces a two-bit output, output carry and sum typically represented by the signals $C_{out}$ and S, where $S=2\times C_{out}+S$.

Figures 16A, 16B, 16C:
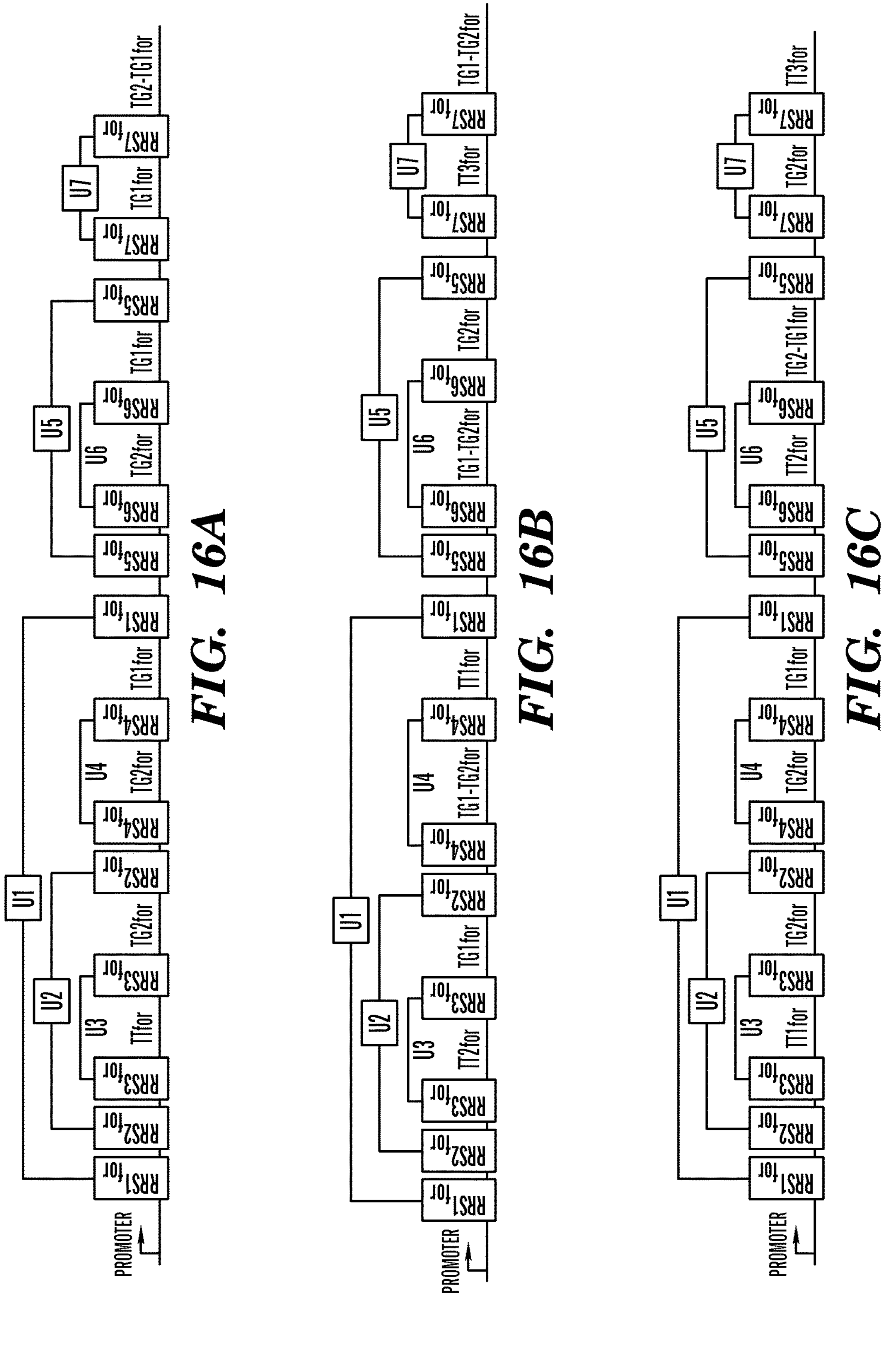

FIG. 5B shows one embodiment of the full adder. The corresponding genetic architecture is shown in both FIG. 5B and FIG. 16A. The U1 of the full adder has the RRS1 in the same orientation with respect to each other and the first nucleic acid sequence comprises the U2, a fourth recombination unit (U4) positioned downstream of the U2, and a first target gene (TG1) positioned downstream of the U4. The U2 has the RRS2 in the same orientation with respect to each other and the second nucleic acid comprises the U3 and a second target gene (TG2) positioned downstream of the U3. The U3 has the RRS3 in the same orientation with respect to each other and the third nucleic acid comprises a transcriptional terminator sequence. The U4 comprises a fourth pair of recombinase recognition sequences (RRS4) in the same orientation with respect to each other, wherein each of the RRS4 flanks each side of a second TG2. The full adder further comprises (i) a fifth recombination unit (U5) positioned downstream of the U1 and comprising a fifth pair of recombinase recognition sequences (RRS5) in the same orientation with respect to each other and a fifth nucleic acid sequence, each of the RRS5 flanking each side of the fifth nucleic acid sequence, the fifth nucleic acid sequence comprising a sixth recombination unit (U6) and a second TG1 positioned downstream of the U6, the U6 comprising a sixth pair of recombinase recognition sequences (RRS6) in the same orientation with respect to each other, wherein each of the RRS6 flanks each side of a third TG2; (ii) a seventh recombination unit (U7) positioned downstream of the U5, the U7 comprising a seventh pair of recombinase recognition sequences (RRS7) in the same orientation with respect to each other, wherein each of the RRS7 flanks each side of a third TG1; and (iii) a fourth TG2 connected to a fourth TG1 and positioned downstream of the U7. In some embodiments, the fourth TG2 is separated from the fourth TG1 by ribosomal skip sequences (2A). In some embodiments, the R1 recognizes the RRS1, the R2 recognizes the RRS2, RRS6, and RRS7, and the R3 recognized the RRS3, RRS4, and RRS5.

Full Subtractor:

some embodiments of the nucleic acid logic cassettes are adapted to function as Full Subtractors. The full subtractor is a combinational circuit which is used to perform subtraction of three bits. It has three inputs, A (minuend) and B (subtrahend) and C (subtrahend) and two outputs Q (difference) and P (borrow).

FIG. 5B shows one embodiment of the full subtractor. The corresponding genetic architecture is shown in both FIG. 5B and FIG. 16B. The U1 of the full subtractor has the RRS1 in the same orientation with respect to each other and the first nucleic acid sequence comprises the U2, a fourth recombination unit (U4) positioned downstream of the U2, and a first transcriptional terminator sequence (TT1) downstream of the U4. The U2 has the RRS2 in the same orientation with respect to each other and the second nucleic acid comprises the U3 and a first target gene (TG1) positioned downstream of the U3. The U3 has the RRS3 in the same orientation with respect to each other and the third nucleic acid comprises a second transcriptional terminator sequence (TT2). The U4 comprises a fourth pair of recombinase recognition sequences (RRS4) in the same orientation with respect to each other, wherein each of the RRS4 flanks each side of a second TG1 and a first TG2 connected together. In some embodiments, the second TG1 is separated from the first TG2 by ribosomal skip sequences (2A). The full subtractor further comprises (i) a fifth recombination unit (U5) positioned downstream of the U1 and comprising a fifth pair of recombinase recognition sequences (RRS5) in the same orientation with respect to each other and a fifth nucleic acid sequence, each of the RRS5 flanking each side of the fifth nucleic acid sequence, the fifth nucleic acid sequence comprising a sixth recombination unit (U6) and a second TG2 positioned downstream of the U6, the U6 comprising a sixth pair of recombinase recognition sequences (RRS6) in the same orientation with respect to each other, wherein each of the RRS6 flanks each side of a third TG1 and a third TG2 connected together; (ii) a seventh recombination unit (U7) positioned downstream of the U5, the U7 comprising a seventh pair of recombinase recognition sequences (RRS7) in the same orientation with respect to each other, wherein each of the RRS7 flanks each side of a third transcriptional terminator sequence (TT3); and (iii) a fourth TG2 connected to a fourth TG1 and positioned downstream of the U7. In some embodiments, the third TG1 is separated from the third TG2 by ribosomal skip sequences (2A). In some embodiments, the fourth TG1 is separated from the fourth TG2 by ribosomal skip sequences (2A). In some embodiments, the R1 recognizes the RRS1, the R2 recognizes the RRS2, RRS6, and RRS7, and the R3 recognized the RRS3, RRS4, and RRS5.

Half Adder-Subtractor:

some embodiments of the nucleic acid logic cassettes are adapted to function as Half Adder-Subtractors. The half adder-subtractor is a circuit that is capable of adding or subtracting numbers.

FIG. 5B shows one embodiment of the half adder-subtractor. The corresponding genetic architecture is shown in both FIG. 5B and FIG. 16C. The U1 of the half adder-subtractor has the RRS1 in the same orientation with respect to each other and the first nucleic acid sequence comprises the U2, a fourth recombination unit (U4) positioned downstream of the U2, and a first target gene (TG1) positioned downstream of the U4 The U2 has the RRS2 in the same orientation with respect to each other and the second nucleic acid comprises the U3 and a second target gene (TG2) positioned downstream of the U3. The U3 has the RRS3 in the same orientation with respect to each other and the third nucleic acid comprises a first transcriptional terminator sequence (TT1). The U4 comprises a fourth pair of recombinase recognition sequences (RRS4) in the same orientation with respect to each other, wherein each of the RRS4 flanks each side of a second TG2. The half adder-subtractor further comprises (i) a fifth recombination unit (U5) positioned downstream of the U1 and comprising a fifth pair of recombinase recognition sequences (RRS5) in the same orientation with respect to each other and a fifth nucleic acid sequence, each of the RRS5 flanking each side of the fifth nucleic acid sequence, the fifth nucleic acid sequence comprising a sixth recombination unit (U6) and a third TG2 and a second TG1 connected together and positioned downstream of the U6, the U6 comprising a sixth pair of recombinase recognition sequences (RRS6) in the same orientation with respect to each other, wherein each of the RRS6 flanks each side of a second transcriptional terminator sequence (TT2); (ii) a seventh recombination unit (U7) positioned downstream of the U5, the U7 comprising a seventh pair of recombinase recognition sequences (RRS7) in the same orientation with respect to each other, wherein each of the RRS7 flanks each side of a fourth TG2; and (iii) a third transcriptional terminator sequence (TT3) positioned downstream of the U7. In some embodiments, the third TG2 is separated from the second TG1 by ribosomal skip sequences (2A). In some embodiments, the R1 recognizes the RRS1, the R2 recognizes the RRS2, RRS6, and RRS7, and the R3 recognized the RRS3, RRS4, and RRS5.

Decoder:

some embodiments of the nucleic acid logic cassettes are adapted to function as binary decoders. A binary decoder is a combinational logic circuit that converts a binary integer value to an associated pattern of output bits. They are used in a wide variety of applications, including data demultiplexing, seven segment displays, and memory address decoding. Depending on its function, a binary decoder can convert binary information from n input signals to as many as 2' unique output signals. Some decoders have less than T output lines; in such cases, at least one output pattern will be repeated for different input values.

Figure 17A:
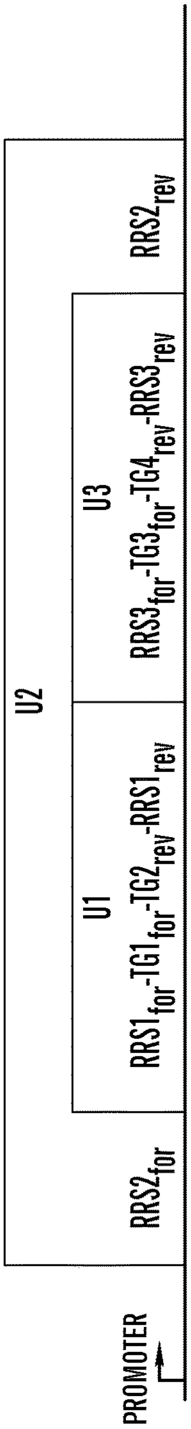
FIG. 17A is a schematic illustrating the architecture of a 2-input 4-output decoder in accordance with some embodiments of the invention.
Figure 17B:
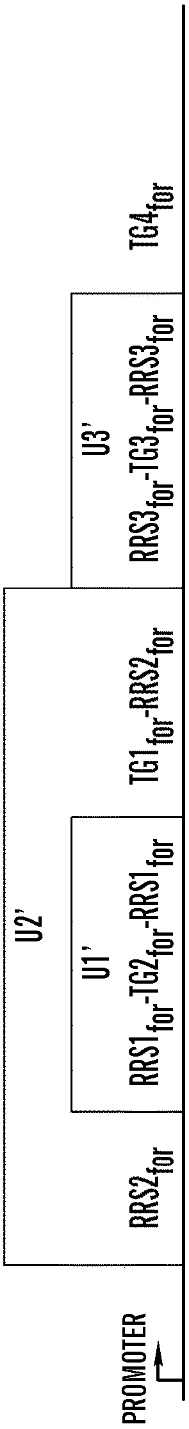
FIG. 17B is a schematic illustrating the architecture of a 2-input 4-output decoder in accordance with some embodiments of the invention.
Figure 17C:
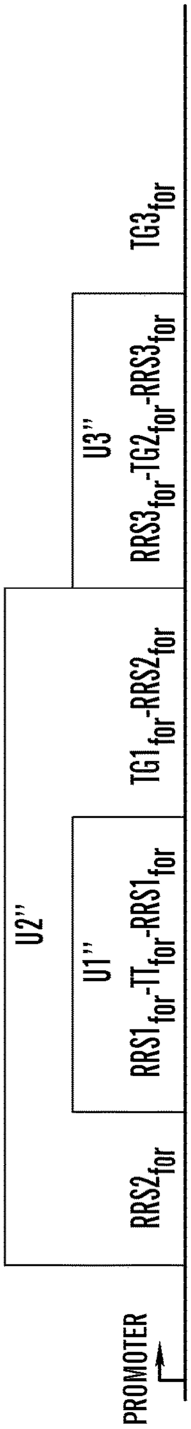
FIG. 17C is a schematic illustrating the architecture of a 2-input 3-output decoder in accordance with some embodiments of the invention.

In some embodiments, the decoder described herein is a 2-input 3-output decoder. An exemplary 2-input 3-output decoder is shown in FIG. 13A. The corresponding genetic architecture is shown in both FIG. 13A and FIG. 17C. In some embodiments, the 2-input 3-output decoder comprises a transcription terminator, a first target gene, a second target gene, and a third target gene connected in series, wherein the transcription terminator is operatively linked to the promoter, whereby (a) when both the R1 and R2 are absent, no output signal is produced; (b) when the R1 is present and the R2 is absent, the first target gene is operatively linked to the promoter, thereby expressing the first target gene to produce a first output signal; (c) when the R1 is absent and the R2 is present, the second target gene is operatively linked to the promoter, thereby expressing the second target gene to produce a second output signal; and (d) when both the R1 and R2 are present, the third target gene is operatively linked to the promoter, thereby expressing the third target gene to produce a third output signal.

In some embodiments, the U2 of the 2-input 3-output decoder has the RRS2 in same orientation with respect to each other and the second nucleic acid sequence comprises the U1 upstream of a first target gene (TG1). The TG1 is in the same orientation as the RRS2. And in the U1, each of the RRS1 are in same orientation with respect to each other and the first nucleic acid sequence comprises a transcriptional terminator sequence (TT), wherein the TT is in the same orientation as each of the RRS1. The U3 is located downstream of the U2, and the RRS3 are in the same orientation with respect to each other and the third nucleic acid sequence comprises a second target gene (TG2). The 2-input 3-output decoder optionally comprises a third target gene (TG3) located downstream of the U3. The TG3 is in the same orientation with respect to the RRS3. The RRS1 and RRS3 are recognized by the R1. The operation of the 2-input 3-output decoder adheres to the following rules: (a) absence of the R1 and R2, none of the TG1, TG2 or TG3 are operatively linked to the promoter, or (b) presence of the R1 and absence of the R2 operatively link the promoter to the TG1, or (c) absence of the R1 and presence of the R2 operatively link the promoter to the TG2, or (d) presence of the R1 and R2 operatively links the promoter to the TG3.

In some embodiments, the decoder described herein is a 2-input 4-output decoder. In some embodiments, the 2-input 4-output decoder comprises a first target gene (TG1), a second target gene (TG2), a third target gene (TG3), and a fourth target gene (TG4) connected in series, wherein the TG1 is operatively linked to the promoter. Expression of each of the target genes produces a distinct output signal. The operation of the 2-input 4-output decoder adheres to the following rules: (a) when both the R1 and R2 are absent, the TG1 is expressed to produce a first output signal; (b) when the R1 is present and the R2 is absent, the TG2 is operatively linked to the promoter, thereby expressing the TG2 to produce a second output signal; (c) when the R1 is absent and the R2 is present, the TG3 is operatively linked to the promoter, thereby expressing the TG3 to produce a third output signal; and (d) when both the R1 and R2 are present, the TG4 is operatively linked to the promoter, thereby expressing the TG4 to produce a fourth output signal.

Figure 15A:
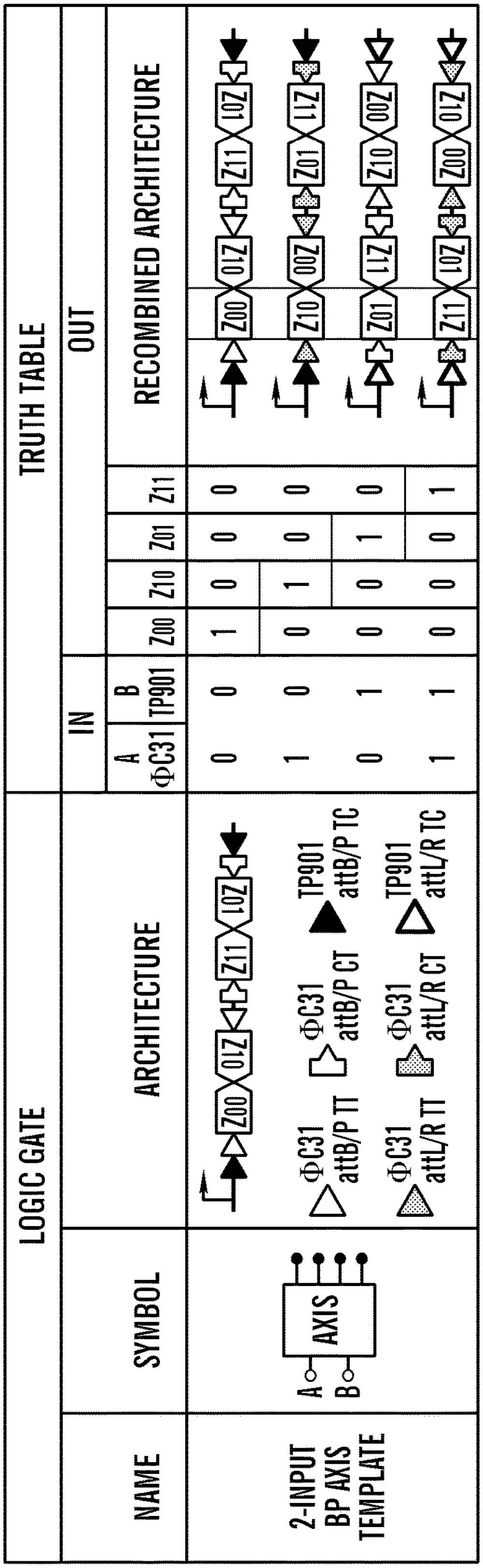
Figure 15B:
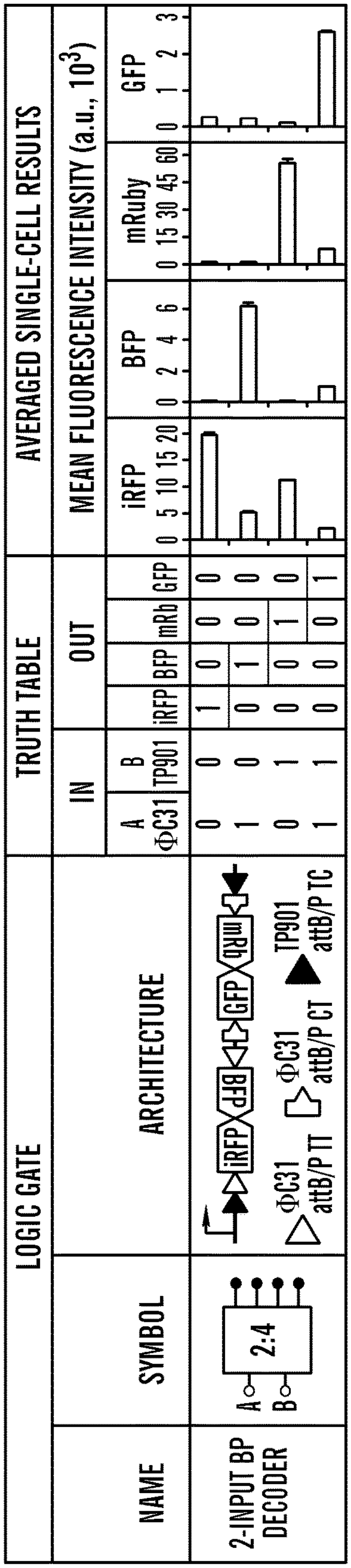

In some embodiments, an exemplary 2-input 4-output decoder is shown in FIG. 15B. The corresponding genetic architecture is shown in both FIG. 15B and FIG. 17A. The U2 of the 2-input 4-output decoder has the RRS2 in an inverse orientation with respect to each other and the second nucleic acid sequence comprises the nucleic acid sequences of the U1 and the U3. The U3 is positioned downstream of the U1. And in the U1, the RRS1 are in an inverse orientation with respect to each other and the first nucleic acid sequence comprises a first target gene (TG1) and a second target gene (TG2), wherein the TG1 and the TG2 are in an inverse orientation with respect to each other, and the TG1 is in the same orientation as the promoter. And in the U3, the RRS3 are in an inverse orientation with respect to each other and the third nucleic acid sequence comprises a third target gene (TG3) and a fourth target gene (TG4), wherein the TG3 and the TG4 are in an inverse orientation with respect to each other, and the TG3 is in the same orientation as the promoter. The RRS1 and RRS3 are recognized by the R1. The RRS2 are recognized by the R2. The operation of the 2-input 4-output decoder adheres to the following rules: (a) absence of the R1 and R2 operatively links the promoter to the TG1, or (b) presence of the R1 and absence of the R2 operatively link the promoter to the TG3, or (c) absence of the R1 and presence of the R2 operatively link the promoter to the TG4, or (d) presence of the R1 and R2 operatively links the promoter to the TG2.

Figure 2A:
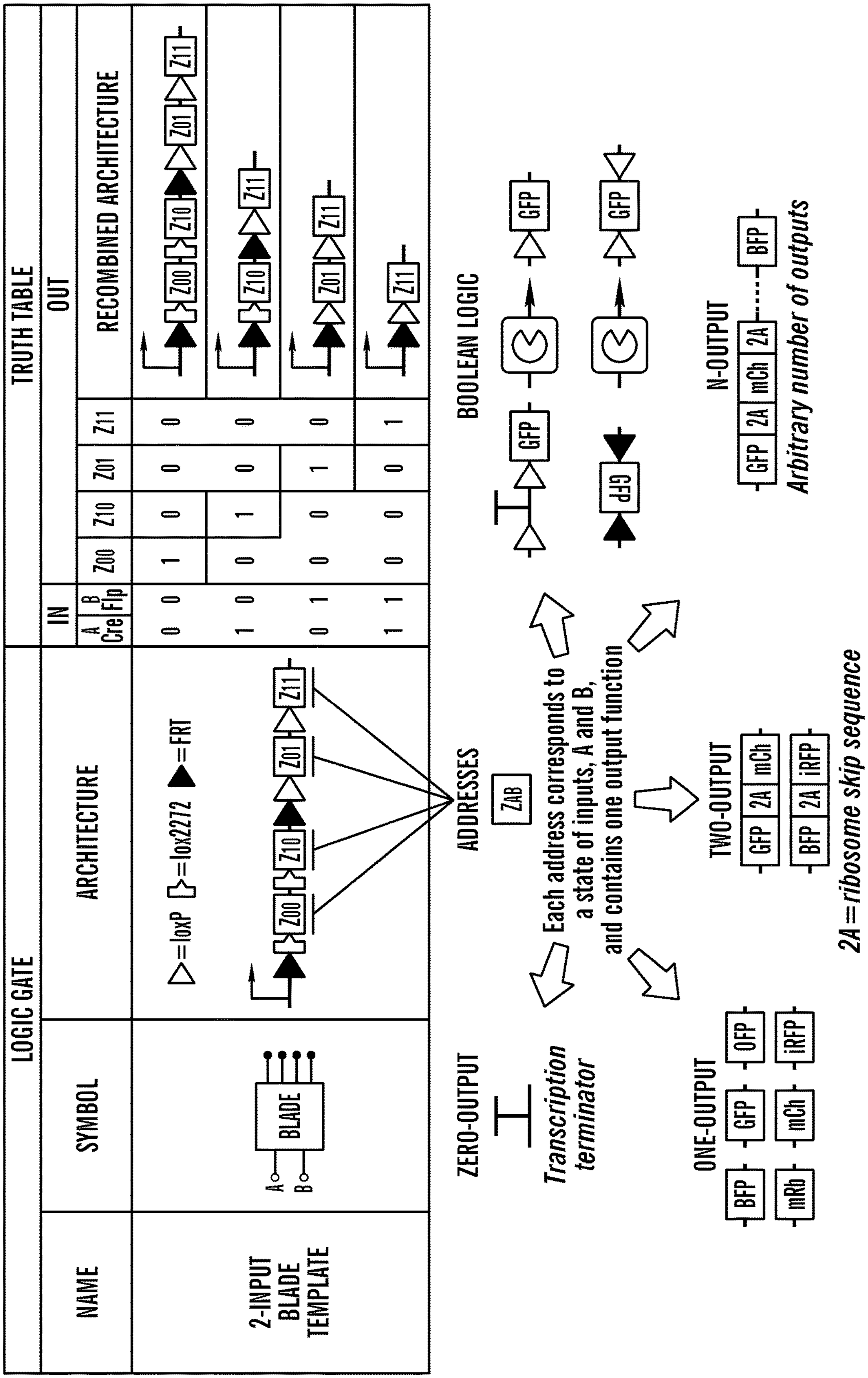
Figure 2B:
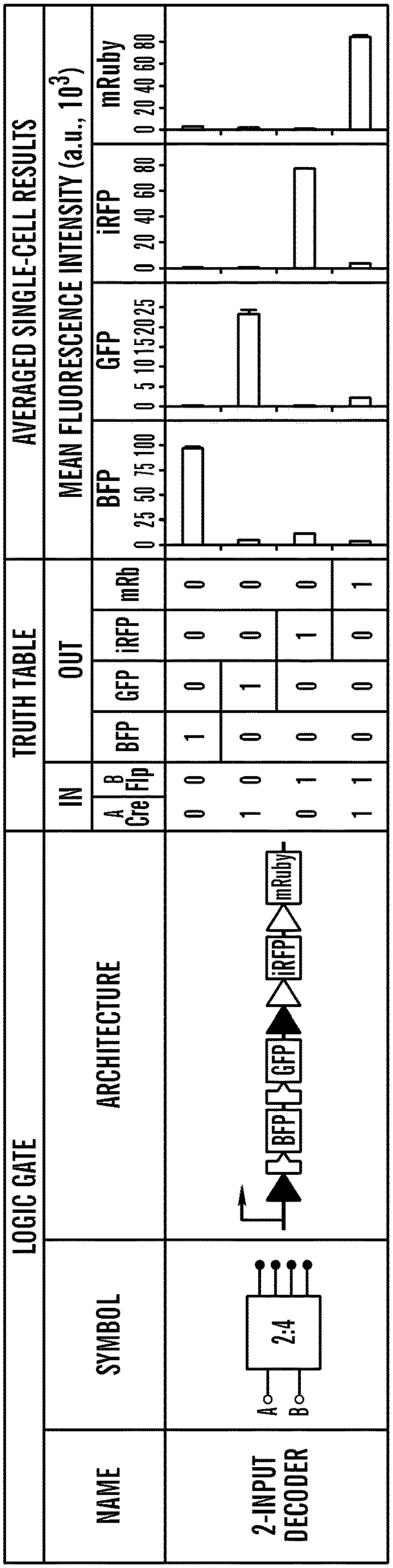

In some embodiments, an exemplary 2-input 4-output decoder is shown in FIG. 2B. The corresponding genetic architecture is shown in both FIG. 2B and FIG. 17B. In some embodiments, the RRS2 of the U2 of the 2-input 4-output decoder are in the same orientation with respect to each other and the second nucleic acid sequence comprises the U1 and a first target gene (TG1), wherein the U1 is upstream of the TG1, wherein the TG1 is in the same orientation as the RRS2. And in the U1, the RRS1 are in same orientation with respect to each other and the first nucleic acid sequence encodes a second target gene (TG2), wherein the TG2 is in the same orientation as the RRS1. And the U3 is located downstream of the U2, and the RRS3 are in the same orientation with respect to each other and the third nucleic acid sequence encodes a third target gene (TG3). The 2-input 4-output decoder optionally comprises a fourth target gene (TG4) positioned downstream of the U3. The TG4 is in the same orientation with respect to the RRS3, and the RRS1 and RRS3 are recognized by the R1. The operation of the 2-input 4-output decoder adheres to the following rules: absence of the R1 and R2 operatively links the promoter to the TG2, or presence of the R1 and absence of the R2 operatively link the promoter to the TG1, or absence of the R1 and presence of the R2 operatively link the promoter to the TG3, or presence of the R1 and R2 operatively links the promoter to the TG4.

Figure 14A:
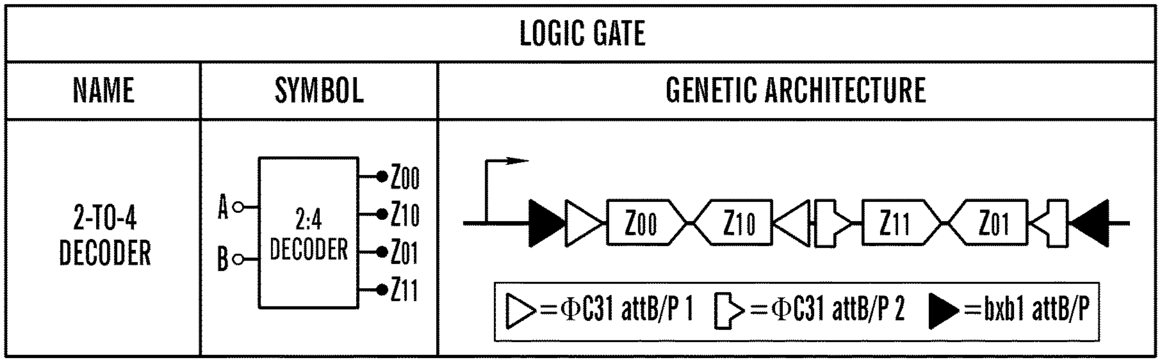
Figure 14B:
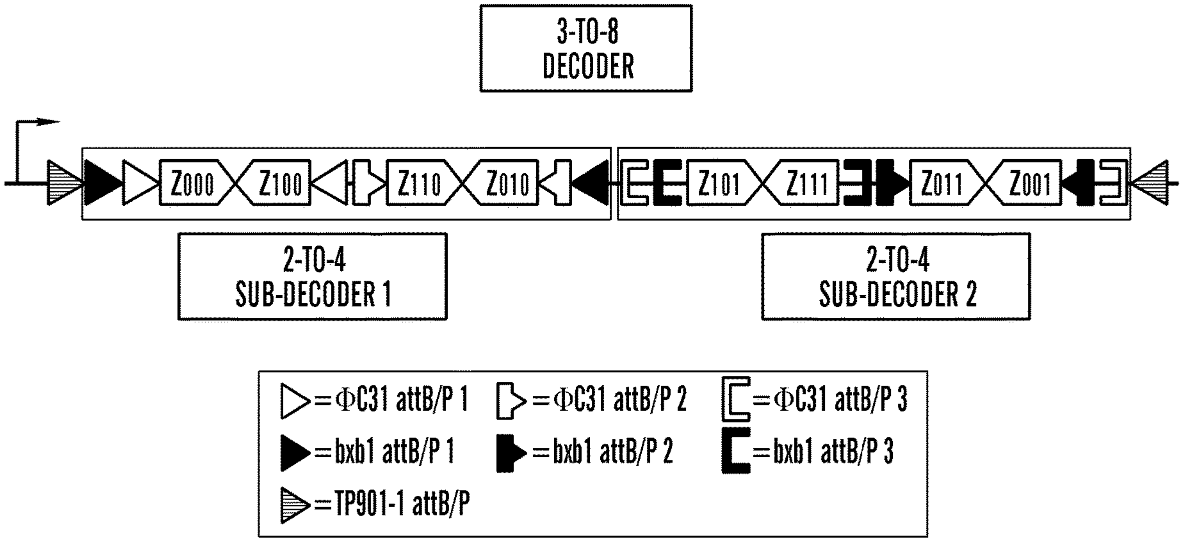

In some embodiments, the decoder described herein is a 3-input 8-output decoder. An embodiment of the 3-input 8-output decoder is shown in FIG. 14B. The corresponding genetic architecture is shown in both FIG. 14B and FIG.

Figure 17D:
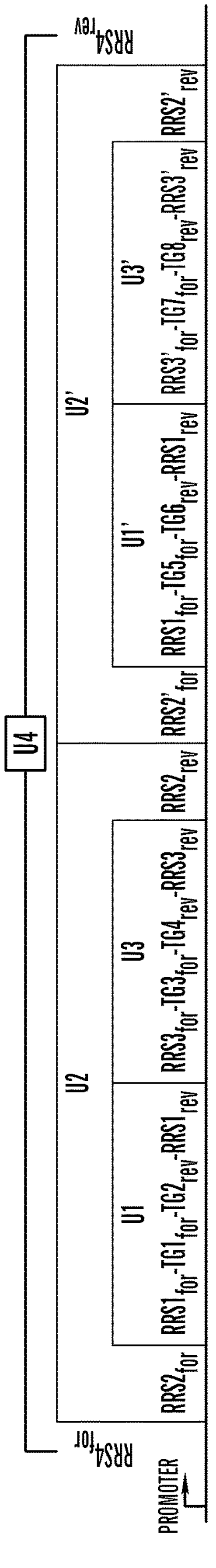
FIG. 17D is a schematic illustrating the architecture of a 3-input 8-output decoder in accordance with some embodiments of the invention.

17D. The 3-input 8-output decoder can comprise a first 2-input 4-output decoder connected with a second 2-input 4-output decoder in series. The first 2-input 4-output has the same genetic architecture as the second 2-input 4-output decoder. The first 2-input 4-output decoder and the second 2-input 4-output decoder are in the same orientation. The 3-input 8-output decoder can further comprise a pair of RRS specific for the R3. Each of the RRS specific for the R3 flanks each side of the two connected 2-input 4-output decoders. The RRS specific for the R3 are in an inverse orientation with respect to each other. And thus when the R3 recognizes the RRS specific for the R3, the nucleic acid sequence comprising the first 2-input 4-output decoder and second 2-input 4-output decoder is inverted with respect to the promoter. As shown in FIG. 17D, the recombinase that recognizes the RRS2 in the U2 also recognizes the RRS in the U1' and U3'; the recombinase that recognizes the RRS2' in the U2' also recognizes the RRS in the U1 and U3.

Figure 17E:
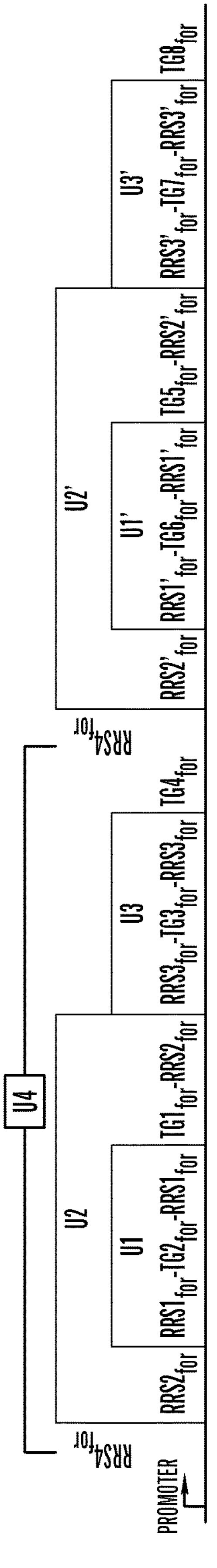
FIG. 17E is a schematic illustrating the architecture of a 3-input 8-output decoder in accordance with some embodiments of the invention.

Another embodiment of the 3-input 8-output decoder is shown in FIG. 5A. The corresponding genetic architecture is shown in both FIG. 5A and FIG. 17E. The 3-input 8-output decoder comprises (i) a first 2-input 4-output decoder and a second 2-input 4-output decoder connected together and in the same orientation, and (ii) a fourth recombination unit (U4) comprising a fourth pair of recombinase recognition sequence (RRS4) specific for the R3, wherein each of the RRS4 flanks each side of the first 2-input 4-output decoder, wherein the RRS4 are in the same orientation with respect to each other, whereby when R3 recognizes the RRS4, the first nucleic acid logic construct of the 2-input 4-output decoder is excised. As shown in FIG. 17E, the recombinase that recognizes the RRS2 in the U2 also recognizes the RRS in the U1' and U3'; the recombinase that recognizes the RRS2' in the U2' also recognizes the RRS in the U1 and U3.

Promoters

In some embodiments, the nucleic acid logic cassettes disclosed herein comprise a promoter sequence. Provided herein are promoter sequences ("promoters") for use in the recombinase-based synthetic logic and memory systems of the invention. As used herein, a "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific or any combination thereof. In some embodiments, the promoter is constitutive. In some embodiments, the promoter is inducible. In some embodiments, the promoter is a mammalian promoter. As discussed herein, a promoter can be applied in any type of cassettes.

A promoter drives expression or drives transcription of the nucleic acid sequence that it regulates. An "inverted promoter," as described above, is a promoter in which the nucleic acid sequence is in the reverse orientation, such that what was the coding strand is now the non-coding strand, and vice versa. Inverted promoter sequences can be used in various embodiments of the invention to regulate the state of a logic gate (e.g., high output, "ON," or low/no output, "OFF"). Thus, in some embodiments, the promoter is an inverted promoter, flanked by complementary recombinase recognition sites that, upon recombination of the sites, inverts to the correct orientation and drives expression of an operatively linked nucleic acid sequence. In some embodiments of the invention, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter and/or the encoded nucleic acid.

A promoter is classified as strong or weak according to its affinity for RNA polymerase (and/or sigma factor); this is related to how closely the promoter sequence resembles the ideal consensus sequence for the polymerase. The strength of a promoter may depend on whether initiation of transcription occurs at that promoter with high or low frequency. Different promoters with different strengths may be used to construct logic gates with different digitally settable levels of gene output expression (e.g., the level of gene expression initiated from a weak promoter is lower than the level of gene expression initiated from a strong promoter).

A promoter may be one naturally associated with a gene or sequence, as may be obtained by isolating the 5' non-coding sequences located upstream of the coding segment and/or exon of a given gene or sequence. Such a promoter can be referred to as "endogenous." Similarly, an enhancer may be one naturally associated with a nucleic acid sequence, located either downstream or upstream of that sequence.

In some embodiments, a coding nucleic acid segment may be positioned under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment. Such promoters or enhancers may include promoters or enhancers of other genes; promoters or enhancers isolated from any other prokaryotic, viral or eukaryotic cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including PCR, in connection with the logic gates disclosed herein (see U.S. Pat. Nos. 4,683,202 and 5,928,906). Furthermore, control sequences that direct transcription and/or expression of sequences within non-nuclear organelles such as mitochondria, chloroplasts and the like, may be used in accordance with the invention.

In some embodiments, the promoter in the cassette or switch is a constitutive or tissue-specific promoter. Tissue-specific promoters are active in a specific type of cells or tissues such as B cells, monocytic cells, leukocytes, macrophages, muscle, pancreatic acinar cells, endothelial cells, astrocytes, and lung. Tissue-specific promoters are available as native or composite promoter. Native promoters, also called minimal promoters, consist of a single fragment from the 5' region of a given gene. Each of them comprises a core promoter and its natural 5'UTR. In some cases, the 5'UTR contains an intron. Composite promoters combine promoter elements of different origins or were generated by assembling a distal enhancer with a minimal promoter of the same origin. Tissue-specific promoters are commercially available through vendors such as InvivoGen.

Non-limiting constitutive promoters include EF1alpha, SFFV, CMV, RSV, SV40, PGK, CAGGS, pTK, Ubc, Ubi, hU6, and H1.

In some embodiments, the promoter in the cassette is an inducible promoter.

Inducible Promoters

As used herein, an "inducible promoter" is one that is characterized by initiating or enhancing transcriptional activity when in the presence of, influenced by or contacted by an inducer or inducing agent. An "inducer" or "inducing agent" may be endogenous or a normally exogenous compound or protein that is administered in such a way as to be active in inducing transcriptional activity from the inducible promoter.

Inducible promoters for use in accordance with the invention may function in both prokaryotic and eukaryotic host organisms. In some embodiments, mammalian inducible promoters are used. Examples of mammalian inducible promoters for use herein include, without limitation, promoter type $P_{ACT}$:$P_{AIR}$, $P_{ART}$, $P_{BIT}$, $P_{CR5}$, $P_{CTA}$, $P_{ETR}$, $P_{NIC}$, $P_{PIP, PROP}$, $P_{SPA}$/$P_{SCA}$, $P_{TET}$, $P_{TtgR}$, promoter type $P_{Rep}$:$P_{CuO}$, $P_{ETR}$, ON8, $P_{NIC}$, $P_{PIR}$ ON, $P_{SCA}$ ON8, $P_{TetO}$, $P_{UREXS}$, promoter type $P_{Hyb}$:teto$_7$-ETR$_8$-$P_{hcMVmin}$, tet0$_7$-PIR$_3$-ETR$_8$-$P_{hCMVmin}$, and scbR$_8$-PIR$_3$-$P_{hCMVmin}$. In some embodiments, inducible promoters from other organisms, as well as synthetic promoters designed to function in a prokaryotic or eukaryotic host may be used. Examples of non-mammalian inducible promoters for use herein include, without limitation, Lentivirus promoters {e.g., EFa, CMV, Human Synapsinl (hSynl), CaMKIIa, hGFAP and TPH-2) and Adeno-Associated Virus promoters (e.g., CaMKIIa (AAV5), hSynl (AAV2), hThyl (AAV5), fSST (AAV1), hGFAP (AAV5, AAV8), MBP (AAV8), SST (AAV2)). One important functional characteristic of the inducible promoters of the present invention is their inducibility by exposure to an externally applied inducer. Other examples of inducible promoters include tetracycline inducible (pTRE), streptogramin inducible (pPIR), macrolide inducible (pETR), allolactose or isopropyl β-D-thiogalactopyranoside inducible (pLacO), ponasterone A inducible, coumermycin/novobiocin-regulated gene expression system, hypoxia inducible (hypoxia response elements), TGFbeta inducible (SMAD response elements), amino acid deprivation inducible (ATF3/ATF3/ATF2). More examples of inducible promoters can be found at http://www.sabiosciences.com/reporterassays.php.

The administration or removal of an inducer results in a switch between the "ON" or "OFF" states of the transcription of the operatively linked nucleic acid sequence (e.g., nucleic acid encoding a recombinase). Thus, as used herein, the "ON" state of a promoter operatively linked to a nucleic acid sequence refers to the state when the promoter is actively driving transcription of the nucleic acid sequence (i.e., the linked nucleic acid sequence is expressed). Conversely, the "OFF" state of a promoter operatively linked, or conditionally operatively linked, to a nucleic acid sequence refers to the state when the promoter is not actively driving transcription of the nucleic acid sequence (i.e., the linked nucleic acid sequence is not expressed). In some embodiments, the inducer can be doxycycline, tamoxifen, rapamycin, or abscisic acid for the promoter operative linked to a nucleic acid sequence encoding a recombinase.

An inducible promoter for use in accordance with the invention may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof. The condition(s) and/or agent(s) that induce or repress an inducible promoter can be input(s) of the logic gates described herein.

Promoters that are inducible by ionizing radiation can be used in certain embodiments, where gene expression is induced locally in a cell by exposure to ionizing radiation such as UV or x-rays. Radiation inducible promoters include the non-limiting examples of fos promoter, c-jun promoter or at least one CArG domain of an Egr-1 promoter. Further non-limiting examples of inducible promoters include promoters from genes such as cytochrome P450 genes, inducible heat shock protein genes, metallothionein genes, hormone-inducible genes, such as the estrogen gene promoter, and such. In further embodiments, an inducible promoter useful in the methods and systems as described herein can be Zn2+ metallothionein promoter, metallothionein-1 promoter, human metallothionein IIA promoter, lac promoter, lacO promoter, mouse mammary tumor virus early promoter, mouse mammary tumor virus LTR promoter, triose dehydrogenase promoter, herpes simplex virus thymidine kinase promoter, simian virus 40 early promoter or retroviral myeloproliferative sarcoma virus promoter. Examples of inducible promoters also include mammalian probasin promoter, lactalbumin promoter, GRP78 promoter, or the bacterial tetracycline-inducible promoter. Other examples include phorbol ester, adenovirus E1A element, interferon, and serum inducible promoters.

In some embodiments, the inducer or inducing agent, i.e., a chemical, a compound or a protein, can itself be the result of transcription or expression of a nucleic acid sequence (i.e., an inducer can be a transcriptional repressor protein, such as Lad), which itself can be under the control of an inducible promoter. In some embodiments, an inducible promoter is induced in the absence of certain agents, such as a repressor. In other words, in such embodiments, the inducible promoter drives transcription of an operably linked sequence except when the repressor is present. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

The promoters for use in the molecular/biological circuits described herein encompass the inducibility of a prokaryotic or eukaryotic promoter by, in part, either of two mechanisms. In some embodiments, the molecular/biological circuits comprise suitable inducible promoters that can be dependent upon transcriptional activators that, in turn, are reliant upon an environmental inducer. In other embodiments, the inducible promoters can be repressed by a transcriptional repressor which itself is rendered inactive by an environmental inducer, such as the product of a sequence driven by another promoter. Thus, unless specified otherwise, an inducible promoter can be either one that is induced by an inducing agent that positively activates a transcriptional activator, or one which is repressed by an inducing agent that negatively regulates a transcriptional repressor. In such embodiments of the various aspects described herein, where it is required to distinguish between an activating and a repressing inducing agent, explicit distinction will be made.

Inducible promoters that are useful in the molecular/biological circuits and methods of use described herein also include those controlled by the action of latent transcriptional activators that are subject to induction by the action of environmental inducing agents. Some non-limiting examples include the copper-inducible promoters of the yeast genes CUP1, CRS5, and SOD1 that are subject to copper-dependent activation by the yeast ACE1 transcriptional activator (see e.g. Strain and Culotta, 1996; Hottiger et al., 1994; Lapinskas et al., 1993; and Gralla et al., 1991). Alternatively, the copper inducible promoter of the yeast gene CTT1 (encoding cytosolic catalase T), which operates independently of the ACE1 transcriptional activator (Lapinskas et al., 1993), can be utilized. The copper concentrations required for effective induction of these genes are suitably low so as to be tolerated by most cell systems, including yeast and *Drosophila* cells. Alternatively, other naturally occurring inducible promoters can be used in the present invention including: steroid inducible gene promoters (see e.g. Oligino et al. (1998) Gene Ther. 5: 491-6); galactose inducible promoters from yeast (see e.g. Johnston (1987) Microbiol Rev 51: 458-76; Ruzzi et al. (1987) Mol Cell Biol 7: 991-7); and various heat shock gene promoters. Many eukaryotic transcriptional activators have been shown to function in a broad range of eukaryotic host cells, and so, for example, many of the inducible promoters identified in yeast can be adapted for use in a mammalian host cell as well. For example, a unique synthetic transcriptional induction system for mammalian cells has been developed based upon a GAL4-estrogen receptor fusion protein that induces mammalian promoters containing GAL4 binding sites (Braselmann et al. (1993) Proc Natl Acad Sci USA 90: 1657-61). These and other inducible promoters responsive to transcriptional activators that are dependent upon specific inducers are suitable for use with the cassettes, switches, and methods of use described herein.

Inducible promoters useful in some embodiments of the cassettes, switches, and methods of use disclosed herein also include those that are repressed by "transcriptional repressors" that are subject to inactivation by the action of environmental, external agents, or the product of another gene. Such inducible promoters can also be termed "repressible promoters" where it is required to distinguish between other types of promoters in a given module or component of a cassette or switch described herein. Examples include prokaryotic repressors that can transcriptionally repress eukaryotic promoters that have been engineered to incorporate appropriate repressor-binding operator sequences.

In some embodiments, repressors for use in the cassettes or switches described herein are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline or doxycycline will cause the dissociation of the tet repressor from the engineered promoter and allow transcription of the sequence downstream of the engineered promoter to occur.

Inducible promoters for use in accordance with the invention include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, the inducer used in accordance with the invention is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters. In some embodiments, the inducer used in accordance with the invention is anhydrotetracycline (aTc), which is a derivative of tetracycline that exhibits no antibiotic activity and is designed for use with tetracycline-controlled gene expression systems, for example, in bacteria. Other inducible promoter systems may be used in accordance with the invention.

Inducible promoters useful in the functional modules, cassettes, and switches as described herein for in vivo uses can include those responsive to biologically compatible agents, such as those that are usually encountered in defined animal tissues or cells. An example is the human PAI-1 promoter, which is inducible by tumor necrosis factor. Further suitable examples include cytochrome P450 gene promoters, inducible by various toxins and other agents; heat shock protein genes, inducible by various stresses; hormone-inducible genes, such as the estrogen gene promoter, and such.

The administration or removal of an inducer or repressor as disclosed herein results in a switch between the "on" or "off" states of the transcription of the operably linked heterologous target gene. Thus, as defined herein the "on" state, as it refers to a promoter operably linked to a nucleic acid sequence, refers to the state when the promoter is actively driving transcription of the operably linked nucleic acid sequence, i.e., the linked nucleic acid sequence is expressed. Several small molecule ligands have been shown to mediate regulated gene expressions, either in tissue culture cells and/or in transgenic animal models. These include the FK1012 and rapamycin immunosupressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference. By way of further example, Yao discloses in U.S. Pat. No. 6,444,871, which is incorporated herein by reference, prokaryotic elements associated with the tetracycline resistance (tet) operon, a system in which the tet repressor protein is fused with polypeptides known to modulate transcription in mammalian cells. The fusion protein is then directed to specific sites by the positioning of the tet operator sequence. For example, the tet repressor has been fused to a transactivator (VP16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP16 activator to the specific site where the induction of transcription is desired. An alternative approach has been to fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

One example of a repressible promoter useful in the cassettes and switches described herein is the Lac repressor (lacR)/operator/inducer system of *E. coli* that has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Baim et al., 1991). In one version of the Lac system, expression of lac operator-linked sequences is constitutively activated by a LacR-VP16 fusion protein and is turned off in the presence of isopropyl-D-1-thiogalactopyranoside (IPTG) (Labow et al. (1990), cited supra). In another version of the system, a lacR-VP16 variant is used that binds to lac operators in the presence of IPTG, which can be enhanced by increasing the temperature of the cells (Baim et al. (1991), cited supra).

Thus, in some embodiments described herein, components of the Lac system are utilized. For example, a lac operator (LacO) can be operably linked to tissue specific promoter, and control the transcription and expression of the heterologous target gene and another protein, such as a repressor protein for another inducible promoter. Accordingly, the expression of the heterologous target gene is inversely regulated as compared to the expression or presence of Lac repressor in the system.

Components of the tetracycline (Tc) resistance system of *E. coli* have also been found to function in eukaryotic cells and have been used to regulate gene expression. For example, the Tet repressor (TetR), which binds to tet operator (tetO) sequences in the absence of tetracycline or doxycycline and represses gene transcription, has been expressed in plant cells at sufficiently high concentrations to repress transcription from a promoter containing tet operator sequences (Gatz, C. et al. (1992) Plant J. 2:397-404). In some embodiments described herein, the Tet repressor system is similarly utilized in the molecular/biological circuits described herein.

A temperature- or heat-inducible gene regulatory system can also be used in the cassettes and switches described herein, such as the exemplary TIGR system comprising a cold-inducible transactivator in the form of a fusion protein having a heat shock responsive regulator, rheA, fused to the VP16 transactivator (Weber et al. 2003a). The promoter responsive to this fusion thermosensor comprises a rheO element operably linked to a minimal promoter, such as the minimal version of the human cytomegalovirus immediate early promoter. At the permissive temperature of 37° C., the cold-inducible transactivator transactivates the exemplary rheO-CMVmin promoter, permitting expression of the target gene. At 41° C., the cold-inducible transactivator no longer transactivates the rheO promoter. Any such heat-inducible or heat-regulated promoter can be used in accordance with the circuits and methods described herein, including but not limited to a heat-responsive element in a heat shock gene (e.g., hsp20-30, hsp27, hsp40, hsp60, hsp70, and hsp90). See Easton et al. (2000) Cell Stress Chaperones 5(4):276-290; Csermely et al. (1998) Pharmacol Ther 79(2): 129-1 68; Ohtsuka & Hata (2000) Int J Hyperthermia 16(3):231-245; and references cited therein. Sequence similarity to heat shock proteins and heat-responsive promoter elements have also been recognized in genes initially characterized with respect to other functions, and the DNA sequences that confer heat inducibility are suitable for use in the disclosed gene therapy vectors. For example, expression of glucose-responsive genes (e.g., grp94, grp78, mortalin/grp75) (Merrick et al. (1997) Cancer Lett 119(2): 185-1 90; Kiang et al. (1998) FASEB J 12(14):1571-16-579), calreticulin (Szewczenko-Pawlikowski et al. (1997) MoI Cell Biochem 177(1-2): 145-1 52); clusterin (Viard et al. (1999) J Invest Dermatol 112(3):290-296; Michel et al. (1997) Biochem J 328(Pt1):45-50; Clark & Griswold (1997) J Androl 18(3): 257-263), histocompatibility class I gene (HLA-G) (Ibrahim et al. (2000) Cell Stress Chaperones 5(3):207-218), and the Kunitz protease isoform of amyloid precursor protein (Shepherd et al. (2000) Neuroscience 99(2):31 7-325) are upregulated in response to heat. In the case of clusterin, a 14 base pair element that is sufficient for heat-inducibility has been delineated (Michel et al. (1997) Biochem J 328(Pt1):45-50). Similarly, a two sequence unit comprising a 10- and a 14-base pair element in the calreticulin promoter region has been shown to confer heat-inducibility (Szewczenko-Pawlikowski et al. (1997) MoI Cell Biochem 177(1-2): 145-1 52).

Other inducible promoters useful in the cassettes and switches described herein include the erythromycin-resistance regulon from *E. coli*, having repressible (Eoff) and inducible (Eon) systems responsive to macrolide antibiotics, such as erythromycin, clarithromycin, and roxithromycin (Weber et al., 2002). The Eoff system utilizes an erythromycin-dependent transactivator, wherein providing a macrolide antibiotic represses transgene expression. In the Eon system, the binding of the repressor to the operator results in repression of transgene expression. Thus, in the presence of macrolides, gene expression is induced.

Fussenegger et al. (2000) describe repressible and inducible systems using a Pip (pristinamycin-induced protein) repressor encoded by the streptogramin resistance operon of *Streptomyces coelicolor*, wherein the systems are responsive to streptogramin-type antibiotics (such as, for example, pristinamycin, virginiamycin, and Synercid). The Pip DNA-binding domain is fused to a VP16 transactivation domain or to the KRAB silencing domain, for example. The presence or absence of, for example, pristinamycin, regulates the PipON and PipOFF systems in their respective manners, as described therein.

Another example of a promoter expression system useful for the cassettes and switches described herein utilizes a quorum-sensing (referring to particular prokaryotic molecule communication systems having diffusible signal molecules that prevent binding of a repressor to an operator site, resulting in repression of a target regulon) system. For example, Weber et al. (2003b) employ a fusion protein comprising the *Streptomyces coelicolor* quorum-sending receptor to a transactivating domain that regulates a chimeric promoter having a respective operator that the fusion protein binds. The expression is fine-tuned with non-toxic butyrolactones, such as SCB1 and MP133.

In some embodiments, multiregulated, multigene gene expression systems that are functionally compatible with one another are utilized in the modules, cassettes, and switches described herein (see, for example, Kramer et al. (2003)). For example, in Weber et al. (2002), the macrolide-responsive erythromycin resistance regulon system is used in conjunction with a streptogramin (PIP)-regulated and tetracycline-regulated expression systems.

Other promoters responsive to non-heat stimuli can also be used. For example, the mortalin promoter is induced by low doses of ionizing radiation (Sadekova (1997) Int J Radiat Biol 72(6):653-660), the hsp27 promoter is activated by 17-β-estradiol and estrogen receptor agonists (Porter et al. (2001) J MoI Endocrinol 26(1):31-42), the HLA-G promoter is induced by arsenite, hsp promoters can be activated by photodynamic therapy (Luna et al. (2000) Cancer Res 60(6): 1637-1 644). A suitable promoter can incorporate factors such as tissue-specific activation. For example, hsp70 is transcriptionally impaired in stressed neuroblastoma cells (Drujan & De Maio (1999) 12(6):443-448) and the mortalin promoter is up-regulated in human brain tumors (Takano et al. (1997) Exp Cell Res 237(1):38-45). A promoter employed in methods described herein can show selective up-regulation in tumor cells as described, for example, for mortalin (Takano et al. (1997) Exp Cell Res 237(1):38-45), hsp27 and calreticulin (Szewczenko-Pawlikowski et al. (1997) MoI Cell Biochem 177(1-2): 145-1 52; Yu et al. (2000) Electrophoresis 2 1(14):3058-3068)), grp94 and grp78 (Gazit et al. (1999) Breast Cancer Res Treat 54(2): 135-146), and hsp27, hsp70, hsp73, and hsp90 (Cardillo et al. (2000) Anticancer Res 20(6B):4579-4583; Strik et al. (2000) Anticancer Res 20(6B):4457-4552).

In some exemplary embodiments, an inducible promoter is an arabinose-inducible promoter $P_{BAD}$ comprising the sequence:

(SEQ ID NO: 38)
AAGAAACCAATTGTCCATATTGCATCAGACATTGCCGTCACTGCGTCTTT

TACTGGCTCTTCTCGCTAACCAAACCGGTAACCCCGCTTATTAAAAGCAT

TCTGTAACAAAGCGGGACCAAAGCCATGACAAAAACGCGTAACAAAAGTG

TCTATAATCACGGCAGAAAAGTCCACATTGATTATTTGCACGGCGTCACA

CTTTGCTATGCCATAGCATTTTTATCCATAAGATTAGCGGATCCTACCTG

ACGCTTTTTATCGCAACTCTCTACTGTTTCTCCATA.

In some exemplary embodiments, an inducible promoter is a LuxR-inducible promoter $P_{LUXR}$ comprising the sequence:

(SEQ ID NO: 39)
ACCTGTAGGATCGTACAGGTTTACGCAAGAAAATGGTTTGTTATAGTCG

AATAAA.

In some exemplary embodiments, an inducible promoter is a mutated LuxR-targeted promoter with modulated binding efficiency for LuxR, such as, for example, pluxR3:

(SEQ ID NO: 40)
AATTTGGGGATCGTACAGGTTTACGCAAGAAAATGGTTTGTTATAGTCGA

ATAAA;

pluxR28:

(SEQ ID NO: 41)
CTGGCGGGGATCGTACAGGTTTACGCAAGAAAATGGTTTGTTATAGTCGA

ATAAA;

pluxR56:

(SEQ ID NO: 42)
TGGGGTAGGATCGTACAGGTTTACGCAAGAAAATGGTTTGTTATAGTCGA

ATAAA.

In some exemplary embodiments, the inducible promoter comprises an Anhydrotetracycline (aTc)-inducible promoter as provided in PLtetO-1 (Pubmed Nucleotide #U66309) with the sequence comprising:

(SEQ ID NO: 43)
GCATGCTCCCTATCAGTGATAGAGATTGACATCCCTATCAGTGATAGAGA

TACTGAGCACATCAGCAGGACGCACTGACCAGGA.

In some exemplary embodiments, the inducible promoter is an isopropyl β-D-1-thiogalactopyranoside (IPTG) inducible promoter. In one embodiment, the IPTG-inducible promoter comprises the $P_{TAC}$ sequence found in the vector encoded by PubMed Accession ID #EU546824. In one embodiment, the IPTG-inducible promoter sequence comprises the $P_{Trc-2}$ sequence:

(SEQ ID NO: 44)
CCATCGAATGGCTGAAATGAGCTGTTGACAATTAATCATCCGGCTCGTAT

AATGTGTGGAATTGTGAGCGGATAACAATTTCACACAGGA.

In some exemplary embodiments, the IPTG-inducible promoter comprises the $P_{LlacO-1}$ sequence:

(SEQ ID NO: 45)
ATAAATGTGAGCGGATAACATTGACATTGTGAGCGGATAACAAGATACTG

AGCACTCAGCAGGACGCACTGACC.

In some exemplary embodiments, the IPTG-inducible promoter comprises the $P_{AllacO-1}$ sequence:

(SEQ ID NO: 46)
AAAATTTATCAAAAAGAGTGTTGACTTGTGAGCGGATAACAATGATACTT

AGATTCAATTGTGAGCGGATAACAATTTCACACA.

In some exemplary embodiments, the IPTG-inducible promoter comprises the $P_{lac/ara-1}$ sequence (SEQ ID NO: 47)
CATAGCATTTTTATCCATAAGATTAGCGGATCCTAAGCTTTACAATTGTG

AGCGCTCACAATTATGATAGATTCAATTGTGAGCGGATAACAATTTCAC

ACA.

In some exemplary embodiments, the inducible promoter sequence comprises the $P_{Ls1com}$ sequence:

(SEQ ID NO: 48)
GCATGCACAGATAACCATCTGCGGTGATAAATTATCTCTGGCGGTGTTGA

CATAAATACCACTGGCGGTtATAaTGAGCACATCAGCAGG//GTATGCAA

AGGA.

Other non-limiting examples of promoters are provided in Tables 1-36.

TABLE 1

Examples of Constitutive *E. coli* $\sigma^{70}$ Promoters

| Name | Description | Promoter Sequence |
|---|---|---|
| BBa_I14018 | SEQ ID NO: 49 P(Bla) | . . . gtttatacataggcgagtactctgttatgg |
| BBa_I14033 | SEQ ID NO: 50 P(Cat) | . . . agaggttccaactttcaccataatgaaaca |
| BBa_I14034 | SEQ ID NO: 51 P(Kat) | . . . taaacaactaacggacaattctacctaaca |
| BBa_I732021 | SEQ ID NO: 52 Template for Building Primer Family Member | . . . acatcaagccaaattaaacaggattaacac |
| BBa_I742126 | SEQ ID NO: 53 Reverse lambda cI-regulated promoter | . . . gaggtaaaatagtcaacacgcacggtgtta |
| BBa_J01006 | SEQ ID NO: 54 Key Promoter absorbs 3 | . . . caggccggaataactccctataatgcgcca |
| BBa_J23100 | SEQ ID NO: 55 constitutive promoter family member | . . . ggctagctcagtcctaggtacagtgctagc |
| BBa_J23101 | SEQ ID NO: 56 constitutive promoter family member | . . . agctagctcagtcctaggtattatgctagc |
| BBa_J23102 | SEQ ID NO: 57 constitutive promoter family member | . . . agctagctcagtcctaggtactgtgctagc |
| BBa_J23103 | SEQ ID NO: 58 constitutive promoter family member | . . . agctagctcagtcctagggattatgctagc |
| BBa_J23104 | SEQ ID NO: 59 constitutive promoter family member | . . . agctagctcagtcctaggtattgtgctagc |
| BBa_J23105 | SEQ ID NO: 60 constitutive promoter family member | . . . ggctagctcagtcctaggtactatgctagc |
| BBa_J23106 | SEQ ID NO: 61 constitutive promoter family member | . . . ggctagctcagtcctaggtatagtgctagc |
| BBa_J23107 | SEQ ID NO: 62 constitutive promoter family member | . . . ggctagctcagccctaggtattatgctagc |
| BBa_J23108 | SEQ ID NO: 63 constitutive promoter family member | . . . agctagctcagtcctaggtataatgctagc |
| BBa_J23109 | SEQ ID NO: 64 constitutive promoter family member | . . . agctagctcagtcctagggactgtgctagc |
| BBa_J23110 | SEQ ID NO: 65 constitutive promoter family member | . . . ggctagctcagtcctaggtacaatgctagc |
| BBa_J23111 | SEQ ID NO: 66 constitutive promoter family member | . . . ggctagctcagtcctaggtatagtgctagc |
| BBa_J23112 | SEQ ID NO: 67 constitutive promoter family member | . . . agctagctcagtcctagggattatgctagc |
| BBa_J23113 | SEQ ID NO: 68 constitutive promoter family member | . . . ggctagctcagtcctagggattatgctagc |

TABLE 1-continued

Examples of Constitutive *E. coli* $\sigma^{70}$ Promoters

| Name | Description | Promoter Sequence |
|---|---|---|
| BBa_J23114 | SEQ ID NO: 69 constitutive promoter family member | ... ggctagctcagtcctaggtacaatgctagc |
| BBa_J23115 | SEQ ID NO: 70 constitutive promoter family member | ... agctagctcagcccttggtacaatgctagc |
| BBa_J23116 | SEQ ID NO: 71 constitutive promoter family member | ... agctagctcagtcctagggactatgctagc |
| BBa_J23117 | SEQ ID NO: 72 constitutive promoter family member | ... agctagctcagtcctagggattgtgctagc |
| BBa_J23118 | SEQ ID NO: 73 constitutive promoter family member | ... ggctagctcagtcctaggtattgtgctagc |
| BBa_J23119 | SEQ ID NO: 74 constitutive promoter family member | ... agctagctcagtcctaggtataatgctagc |
| BBa_J23150 | SEQ ID NO: 75 1bp mutant from J23107 | ... ggctagctcagtcctaggtattatgctagc |
| BBa_J23151 | SEQ ID NO: 76 1bp mutant from J23114 | ... ggctagctcagtcctaggtacaatgctagc |
| BBa_J44002 | SEQ ID NO: 77 pBAD reverse | ... aaagtgtgacgccgtgcaaataatcaatgt |
| BBa_J48104 | SEQ ID NO: 78 NikR promoter, a protein of the ribbon helix-helix family of transcription factors that repress expre | ...gacgaatacttaaaatcgtcatacttattt |
| BBa_J54200 | SEQ ID NO: 79 lacq_Promoter | ... aaacctttcgcggtatggcatgatagcgcc |
| BBa_J56015 | SEQ ID NO: 80 lacIQ—promoter sequence | ... tgatagcgcccggaagagagtcaattcagg |
| BBa_J64951 | SEQ ID NO: 81 *E. coli* CreABCD phosphate sensing operon promoter | ...ttatttaccgtgacgaactaattgctcgtg |
| BBa_K088007 | SEQ ID NO: 82 GlnRS promoter | ...catacgccgttatacgttgtttacgctttg |
| BBa_K119000 | SEQ ID NO: 83 Constitutive weak promoter of lacZ | ...ttatgcttccggctcgtatgttgtgtggac |
| BBa_K119001 | SEQ ID NO: 84 Mutated LacZ promoter | ... ttatgcttccggctcgtatggtgtgtggac |
| BBa_K137029 | SEQ ID NO: 85 constitutive promoter with (TA)10 between −10 and −35 elements | ...atatatatatatatataatggaagcgtttt |
| BBa_K137030 | SEQ ID NO: 86 constitutive promoter with (TA)9 between −10 and −35 elements | ...atatatatatatatataatggaagcgtttt |
| BBa_K137031 | SEQ ID NO: 87 constitutive promoter with (C)10 between −10 and −35 elements | ... ccccgaaagcttaagaatataattgtaagc |
| BBa_K137032 | SEQ ID NO: 88 constitutive promoter with (C)12 between −10 and −35 elements | ... ccccgaaagcttaagaatataattgtaagc |
| BBa_K137085 | SEQ ID NO: 89 optimized (TA) repeat constitutive promoter with 13 bp between −10 and −35 elements | ...tgacaatatatatatatatataatgctagc |
| BBa_K137086 | SEQ ID NO: 90 optimized (TA) repeat constitutive promoter with 15 bp between −10 and −35 elements | ...acaatatatatatatatatataatgctagc |
| BBa_K137087 | SEQ ID NO: 91 optimized (TA) repeat constitutive promoter with 17 bp between −10 and −35 elements | ...aatatatatatatatatatataatgctagc |
| BBa_K137088 | SEQ ID NO: 92 optimized (TA) repeat constitutive promoter with 19 bp between −10 and −35 elements | ...tatatatatatatatatatataatgctagc |
| BBa_K137089 | SEQ ID NO: 93 optimized (TA) repeat constitutive promoter with 21 bp between −10 and −35 elements | ...tatatatatatatatatatataatgctagc |

TABLE 1-continued

Examples of Constitutive *E. coli* $\sigma^{70}$ Promoters

| Name | Description | Promoter Sequence |
|---|---|---|
| BBa_K137090 | SEQ ID NO: 94 optimized (A) repeat constitutive promoter with 17 bp between -10 and -35 elements | ... aaaaaaaaaaaaaaaaaatataatgctagc |
| BBa_K137091 | SEQ ID NO: 95 optimized (A) repeat constitutive promoter with 18 bp between -10 and -35 elements | ... aaaaaaaaaaaaaaaaaatataatgctagc |
| BBa_K256002 | SEQ ID NO: 96 J23101:GFP | ... caccttcgggtgggcctttctgcgtttata |
| BBa_K256018 | SEQ ID NO: 97 J23119:IFP | ... caccttcgggtgggcctttctgcgtttata |
| BBa_K256020 | SEQ ID NO: 98 J23119:HO1 | ... caccttcgggtgggcctttctgcgtttata |
| BBa_K256033 | SEQ ID NO: 99 Infrared signal reporter (J23119:IFP:J23119:HO1) | ... caccttcgggtgggcctttctgcgtttata |
| BBa_K292000 | SEQ ID NO: 100 Double terminator + constitutive promoter | ... ggctagctcagtcctaggtacagtgctagc |
| BBa_K292001 | SEQ ID NO: 101 Double terminator + Constitutive promoter + Strong RBS | ... tgctagctactagagattaaagaggagaaa |
| BBa_M13101 | SEQ ID NO: 102 M13K07 gene I promoter | ...cctgtttttatgttattctctctgtaaagg |
| BBa_M13102 | SEQ ID NO: 103 M13K07 gene II promoter | ...aaatatttgcttatacaatcttcctgtttt |
| BBa_M13103 | SEQ ID NO: 104 M13K07 gene III promoter | ... gctgataaaccgatacaattaaaggctcct |
| BBa_M13104 | SEQ ID NO: 105 M13K07 gene IV promoter | ...ctcttctcagcgtcttaatctaagctatcg |
| BBa_M13105 | SEQ ID NO: 106 M13K07 gene V promoter | ... atgagccagttcttaaaatcgcataaggta |
| BBa_M13106 | SEQ ID NO: 107 M13K07 gene VI promoter | ...ctattgattgtgacaaaataaacttattcc |
| BBa_M13108 | SEQ ID NO: 108 M13K07 gene VIII promoter | ... gtttcgcgcttggtataatcgctgggggtc |
| BBa_M13110 | SEQ ID NO: 109 M13110 | ...ctttgcttctgactataatagtcagggtaa |
| BBa_M31519 | SEQ ID NO: 110 Modified promoter sequence of g3. | ... aaaccgatacaattaaaggctcctgctagc |
| BBa_R1074 | SEQ ID NO: 111 Constitutive Promoter I | ... gccggaataactccctataatgcgccacca |
| BBa_R1075 | SEQ ID NO: 112 Constitutive Promoter II | ... gccggaataactccctataatgcgccacca |
| BBa_S03331 | SEQ ID NO: 113 | ttgacaagcttttcctcagctccgtaaact |

TABLE 2

Examples of Constitutive *E. coli* $\sigma^{70}$ Promoters

| Identifier | | Sequence | |
|---|---|---|---|
| BBa_J23119 | SEQ ID NO: 114 | ttgacagctagctcagtcctaggtataatgctagc | n/a |
| BBa_J23100 | SEQ ID NO: 115 | ttgacggctagctcagtcctaggtacagtgctagc | 1 |
| BBa_J23101 | SEQ ID NO: 116 | tttacagctagctcagtcctaggtattatgctagc | 0.70 |
| BBa_J23102 | SEQ ID NO: 117 | ttgacagctagctcagtcctaggtactgtgctagc | 0.86 |
| BBa_J23103 | SEQ ID NO: 118 | ctgatagctagctcagtcctagggattatgctagc | 0.01 |
| BBa_J23104 | SEQ ID NO: 119 | ttgacagctagctcagtcctaggtattgtgctagc | 0.72 |

TABLE 2-continued

Examples of Constitutive *E. coli* $\sigma^{70}$ Promoters

| Identifier | | Sequence | |
|---|---|---|---|
| BBa_J23105 | SEQ ID NO: 120 | tttacggctagctcagtcctaggtactatgctagc | 0.24 |
| BBa_J23106 | SEQ ID NO: 121 | tttacggctagctcagtcctaggtatagtgctagc | 0.47 |
| BBa_J23107 | SEQ ID NO: 122 | tttacggctagctcagccctaggtattatgctagc | 0.36 |
| BBa_J23108 | SEQ ID NO: 123 | ctgacagctagctcagtcctaggtataatgctagc | 0.51 |
| BBa_J23109 | SEQ ID NO: 124 | tttacagctagctcagtcctagggactgtgctagc | 0.04 |
| BBa_J23110 | SEQ ID NO: 125 | tttacggctagctcagtcctaggtacaatgctagc | 0.33 |
| BBa_J23111 | SEQ ID NO: 126 | ttgacggctagctcagtcctaggtatagtgctagc | 0.58 |
| BBa_J23112 | SEQ ID NO: 127 | ctgatagctagctcagtcctagggattatgctagc | 0.00 |
| BBa_J23113 | SEQ ID NO: 128 | ctgatggctagctcagtcctagggattatgctagc | 0.01 |
| BBa_J23114 | SEQ ID NO: 129 | tttatggctagctcagtcctaggtacaatgctagc | 0.10 |
| BBa_J23115 | SEQ ID NO: 130 | tttatagctagctcagcccttggtacaatgctagc | 0.15 |
| BBa_J23116 | SEQ ID NO: 131 | ttgacagctagctcagtcctagggactatgctagc | 0.16 |
| BBa_J23117 | SEQ ID NO: 132 | ttgacagctagctcagtcctagggattgtgctagc | 0.06 |
| BBa_J23118 | SEQ ID NO: 133 | ttgacggctagctcagtcctaggtattgtgctagc | 0.56 |

TABLE 3

Examples of Constitutive *E. coli* $\sigma^{S}$ Promoters

| Name | Description | Promoter Sequence |
|---|---|---|
| BBa_J45992 | SEQ ID NO: 134 Full-length stationary phase osmY promoter | ... ggtttcaaaattgtgatctatatttaacaa |
| BBa_J45993 | SEQ ID NO: 135 Minimal stationary phase osmY promoter | ... ggtttcaaaattgtgatctatatttaacaa |

TABLE 4

Examples of Constitutive *E. coli* $\sigma^{32}$ Promoters

| Name | Description | Promoter Sequence |
|---|---|---|
| BBa_J45504 | SEQ ID NO: 136 htpG Heat Shock Promoter | ... tctattccaataaagaaat cttcctgcgtg |

TABLE 5

Examples of Constitutive *B. subtilis* $\sigma^{A}$ Promoters

| Name | Description | Promoter Sequence |
|---|---|---|
| BBa_K143012 | SEQ ID NO: 137 Promoter veg a constitutive promoter for *B. subtilis* | ... aaaaatgggctcgtgttgtacaataaatgt |
| BBa_K143013 | SEQ ID NO: 138 Promoter 43 a constitutive promoter for *B. subtilis* | ... aaaaaaagcgcgcgattatgtaaaatataa |

TABLE 6

| Examples of Constitutive *B. subtilis* $\sigma^B$ Promoters | | |
|---|---|---|
| Name | Description | Promoter Sequence |
| BBa_K143010 | SEQ ID NO: 139 Promoter etc for *B. subtilis* | ...atccttatcgttatgggtattgtttgtaat |
| BBa_K143011 | SEQ ID NO: 140 Promoter gsiB for *B. subtilis* | ... taaaagaattgtgagcgggaatacaacaac |
| BBa_K143013 | SEQ ID NO: 141 Promoter 43 a constitutive promoter for *B. subtilis* | ... aaaaaaagcgcgcgattatgtaaaatataa |

TABLE 7

| Examples of Constitutive Promoters from Miscellaneous Prokaryotes | | |
|---|---|---|
| Name | Description | Promoter Sequence |
| BBa_K112706 | SEQ ID NO: 142 Pspv2 from *Salmonella* | ...tacaaaataattcccctgcaaacattatca |
| BBa_K112707 | SEQ ID NO: 143 Pspv from *Salmonella* | ...tacaaaataattcccctgcaaacattatcg |

TABLE 8

| Examples of Constitutive Promoters from bacteriophage T7 | | |
|---|---|---|
| Name | Description | Promoter Sequence |
| BBa_I712074 | SEQ ID NO: 144 T7 promoter (strong promoter from T7 bacteriophage) | ...agggaatacaagctacttgttctttttgca |
| BBa_I719005 | SEQ ID NO: 145 T7 Promoter | taatacgactcactatagggaga |
| BBa_J34814 | SEQ ID NO: 146 T7 Promoter | gaatttaatacgactcactatagggaga |
| BBa_J64997 | SEQ ID NO: 147 T7 consensus -10 and rest | taatacgactcactatagg |
| BBa_K113010 | SEQ ID NO: 148 overlapping T7 promoter | ... gagtcgtattaatacgactcactatagggg |
| BBa_K113011 | SEQ ID NO: 149 more overlapping T7 promoter | ... agtgagtcgtactacgactcactatagggg |
| BBa_K113012 | SEQ ID NO: 150 weaken overlapping T7 promoter | ... gagtcgtattaatacgactctctatagggg |
| BBa_R0085 | SEQ ID NO: 151 T7 Consensus Promoter Sequence | taatacgactcactatagggaga |
| BBa_R0180 | SEQ ID NO: 152 T7 RNAP promoter | ttatacgactcactatagggaga |
| BBa_R0181 | SEQ ID NO: 153 T7 RNAP promoter | gaatacgactcactatagggaga |
| BBa_R0182 | SEQ ID NO: 154 T7 RNAP promoter | taatacgtctcactatagggaga |
| BBa_R0183 | SEQ ID NO: 155 T7 RNAP promoter | tcatacgactcactatagggaga |
| BBa_Z0251 | SEQ ID NO: 156 T7 strong promoter | ... taatacgactcactatagggagaccacaac |
| BBa_Z0252 | SEQ ID NO: 157 T7 weak binding and processivity | ... taattgaactcactaaagggagaccacagc |
| BBa_Z0253 | SEQ ID NO: 158 T7 weak binding promoter | ... cgaagtaatacgactcactattagggaaga |
| | SEQ ID NO: 159 T7 14.3 m | attaaccctcactaaagggaga |

TABLE 9

Examples of Constitutive Promoters from bacteriophage SP6

| Name | Description | Promoter Sequence |
|---|---|---|
| BBa_J64998 | SEQ ID NO: 160 consensus -10 and rest from SP6 | atttaggtgacactataga |

TABLE 10

Examples of Constitutive Promoters from Yeast

| Name | Description | Promoter Sequence |
|---|---|---|
| BBa_I766555 | SEQ ID NO: 161 pCyc (Medium) Promoter | ...acaaacacaaatacacacactaaattaata |
| BBa_I766556 | SEQ ID NO: 162 pAdh (Strong) Promoter | ...ccaagcatacaatcaactatctcatataca |
| BBa_I766557 | SEQ ID NO: 163 pSte5 (Weak) Promoter | ...gatacaggatacagcggaaacaactataa |
| BBa_J63005 | SEQ ID NO: 164 yeast ADH1 promoter | ...tttcaagctataccaagcatacaatcaact |
| BBa_K105027 | SEQ ID NO: 165 cyc100 minimal promoter | ...cctttgcagcataaattactatacttctat |
| BBa_K105028 | SEQ ID NO: 166 cyc70 minimal promoter | ...cctttgcagcataaattactatacttctat |
| BBa_K105029 | SEQ ID NO: 167 cyc43 minimal promoter | ...cctttgcagcataaattactatacttctat |
| BBa_K105030 | SEQ ID NO: 168 cyc28 minimal promoter | ...cctttgcagcataaattactatacttctat |
| BBa_K105031 | SEQ ID NO: 169 cyc16 minimal promoter | ...cctttgcagcataaattactatacttctat |
| BBa_K122000 | SEQ ID NO: 170 pPGK1 | ...ttatctactattacaacaaatataaaaca |
| BBa_K124000 | SEQ ID NO: 171 pCYC Yeast Promoter | ...acaaacacaaatacacacactaaattaata |
| BBa_K124002 | SEQ ID NO: 172 Yeast GPD (TDH3) Promoter | ...gtttcgaataaacacacataaacaaacaaa |
| BBa_M31201 | SEQ ID NO: 173 Yeast CLB1 promoter region, G2/M cell cycle specific | ...accatcaaaggaagattaatcttctcata |

TABLE 11

Examples of Constitutive Promoters from Miscellaneous Eukaryotes

| Name | Description | Promoter Sequence |
|---|---|---|
| BBa_I712004 | SEQ ID NO: 174 CMV promoter | ...agaacccactgcttactggcttatcgaaat |
| BBa_K076017 | SEQ ID NO: 175 Ubc Promoter | ...ggccgtttaggcttttttgttagacgaag |

TABLE 12

Examples of Cell Signaling Promoters

| Name | Description | Promoter Sequence |
|---|---|---|
| BBa_I1051 | SEQ ID NO: 176 Lux cassette right promoter | ...tgttatagtcgaatacctctggcggtgata |
| BBa_I14015 | SEQ ID NO: 177 P(Las) TetO | ...ttttggtacactccctatcagtgatagaga |

TABLE 12-continued

Examples of Cell Signaling Promoters

| Name | Description | Promoter Sequence |
|---|---|---|
| BBa_I14016 | SEQ ID NO: 178 P(Las) CIO | ... ctttttggtacactacctctggcggtgata |
| BBa_I14017 | SEQ ID NO: 179 P(Rhl) | ... tacgcaagaaaatggtttgttatagtcgaa |
| BBa_I739105 | SEQ ID NO: 180 Double Promoter (LuxR/HSL, positive/cI, negative) | ... cgtgcgtgttgataacaccgtgcgtgttga |
| BBa_I746104 | SEQ ID NO: 181 P2 promoter in agr operon from S. aureus | ... agattgtactaaatcgtataatgacagtga |
| BBa_I751501 | SEQ ID NO: 182 plux-cI hybrid promoter | ... gtgttgatgcttttatcaccgccagtggta |
| BBa_I751502 | SEQ ID NO: 183 plux-lac hybrid promoter | ... agtgtgtggaattgtgagcggataacaatt |
| BBa_I761011 | SEQ ID NO: 184 CinR, CinL and glucose controlled promoter | ...acatcttaaaagttttagtatcatattcgt |
| BBa_J06403 | SEQ ID NO: 185 RhIR promoter repressible by CI | ... tacgcaagaaaatggtttgttatagtcgaa |
| BBa_J64000 | SEQ ID NO: 186 rhlI promoter | ...atcctcctttagtcttccccctcatgtgtg |
| BBa_J64010 | SEQ ID NO: 187 lasI promoter | ...taaaattatgaaatttgcataaattcttca |
| BBa_J64067 | SEQ ID NO: 188 LuxR + 3OC6HSL independent R0065 | ...gtgttgactattttacctctggcggtgata |
| BBa_J64712 | SEQ ID NO: 189 LasR/LasI Inducible & RHLR/RHLI repressible Promoter | ... gaaatctggcagtttttggtacacgaaagc |
| BBa_K091107 | SEQ ID NO: 190 pLux/cI Hybrid Promoter | ... acaccgtgcgtgttgatatagtcgaataaa |
| BBa_K091117 | SEQ ID NO: 191 pLas promoter | ...aaaattatgaaatttgtataaattcttcag |
| BBa_K091143 | SEQ ID NO: 192 pLas/cI Hybrid Promoter | ... ggttattttggtacctctggcggtgataa |
| BBa_K091146 | SEQ ID NO: 193 pLas/Lux Hybrid Promoter | ... tgtaggatcgtacaggtataaattcttcag |
| BBa_K091156 | SEQ ID NO: 194 pLux | ... caagaaaatggtttgttatagtcgaataaa |
| BBa_K091157 | SEQ ID NO: 195 pLux/Las Hybrid Promoter | ...ctatctcatttgctagtatagtcgaataaa |
| BBa_K145150 | SEQ ID NO: 196 Hybrid promoter: HSL-LuxR activated, P22 C2 repressed | ...tagtttataatttaagtgttctttaatttc |
| BBa_K266000 | SEQ ID NO: 197 PAI + LasR -> LuxI (AI) | ... caccttcgggtgggcctttctgcgtttata |
| BBa_K266005 | SEQ ID NO: 198 PAI + LasR -> LasI & AI + LuxR --\| LasI | ... aataactctgatagtgctagtgtagatctc |
| BBa_K266006 | SEQ ID NO: 199 PAI + LasR -> LasI + GFP & AI + LuxR --\| LasI + GFP | ... caccttcgggtgggcctttctgcgtttata |
| BBa_K266007 | SEQ ID NO: 200 Complex QS -> LuxI & LasI circuit | ... caccttcgggtgggcctttctgcgtttata |
| BBa_R0061 | SEQ ID NO: 201 Promoter (HSL-mediated luxR repressor) | ttgacacctgtaggatcgtacaggtataat |
| BBa_R0062 | SEQ ID NO: 202 Promoter (luxR & HSL regulated -- lux pR) | ... caagaaaatggtttgttatagtcgaataaa |
| BBa_R0063 | SEQ ID NO: 203 Promoter (luxR & HSL regulated -- lux pL) | ... cacgcaaaacttgcgacaaacaataggtaa |
| BBa_R0071 | SEQ ID NO: 204 Promoter (RhlR & C4-HSL regulated) | ... gttagctttcgaattggctaaaaagtgttc |

TABLE 12-continued

| Examples of Cell Signaling Promoters | | |
|---|---|---|
| Name | Description | Promoter Sequence |
| BBa_R0078 | SEQ ID NO: 205 Promoter (cinR and HSL regulated) | ... ccattctgctttccacgaacttgaaaacgc |
| BBa_R0079 | SEQ ID NO: 206 Promoter (LasR & PAI regulated) | ... ggccgcgggttattttggtacacgaaagc |
| BBa_R1062 | SEQ ID NO: 207 Promoter, Standard (luxR and HSL regulated -- lux pR) | ... aagaaaatggtttgttgatactcgaataaa |

TABLE 13

| Examples of Metal Inducible Promoters | | |
|---|---|---|
| Name | Description | Promoter Sequence |
| BBa_I721001 | SEQ ID NO: 208 Lead Promoter | ...gaaaaccttgtcaatgaagagcgatctatg |
| BBa_I731004 | SEQ ID NO: 209 FecA promoter | ...ttctcgttcgactcatagctgaacacaaca |
| BBa_I760005 | SEQ ID NO: 210 Cu-sensitive promoter | atgacaaaattgtcat |
| BBa_I765000 | SEQ ID NO: 211 Fe promoter | ... accaatgctgggaacggccagggcacctaa |
| BBa_I765007 | SEQ ID NO: 212 Fe and UV promoters | ...ctgaaagcgcataccgctatggagggggtt |
| BBa_J3902 | SEQ ID NO: 213 PrFe (PI + PII rus operon) | ...tagatatgcctgaaagcgcataccgctatg |

TABLE 14

| Examples of T7 Promoters | | |
|---|---|---|
| Name | Description | Promoter Sequence |
| BBa_I712074 | SEQ ID NO: 214 T7 promoter (strong promoter from T7 bacteriophage) | ...agggaatacaagctacttgttctattgca |
| BBa_I719005 | SEQ ID NO: 215 T7 Promoter | taatacgactcactatagggaga |
| BBa_J34814 | SEQ ID NO: 216 T7 Promoter | gaatttaatacgactcactatagggaga |
| BBa_J64997 | SEQ ID NO: 217 T7 consensus-10 and rest | taatacgactcactatagg |
| BBa_J64998 | SEQ ID NO: 218 consensus-10 and rest from SP6 | atttaggtgacactataga |
| BBa_K113010 | SEQ ID NO: 219 overlapping T7 promoter | ... gagtcgtattaatacgactcactatagggg |
| BBa_K113011 | SEQ ID NO: 220 more overlapping T7 promoter | ... agtgagtcgtactacgactcactatagggg |
| BBa_K113012 | SEQ ID NO: 221 weaken overlapping T7 promoter | ... gagtcgtattaatacgactctctatagggg |
| BBa_R0085 | SEQ ID NO: 222 T7 Consensus Promoter Sequence | taatacgactcactatagggaga |
| BBa_R0180 | SEQ ID NO: 223 T7 RNAP promoter | ttatacgactcactatagggaga |
| BBa_R0181 | SEQ ID NO: 224 T7 RNAP promoter | gaatacgactcactatagggaga |
| BBa_R0182 | SEQ ID NO: 225 T7 RNAP promoter | taatacgtctcactatagggaga |
| BBa_R0183 | SEQ ID NO: 226 T7 RNAP promoter | tcatacgactcactatagggaga |

TABLE 14-continued

| Examples of T7 Promoters | | |
|---|---|---|
| Name | Description | Promoter Sequence |
| BBa_R0184 | SEQ ID NO: 227 T7 promoter (ladI repressible) | ... ataggggaattgtgagcggataacaattcc |
| BBa_R0185 | SEQ ID NO: 228 T7 promoter (ladI repressible) | ... ataggggaattgtgagcggataacaattcc |
| BBa_R0186 | SEQ ID NO: 229 T7 promoter (ladI repressible) | ... ataggggaattgtgagcggataacaattcc |
| BBa_R0187 | SEQ ID NO: 230 T7 promoter (ladI repressible) | ... ataggggaattgtgagcggataacaattcc |
| BBa_Z0251 | SEQ ID NO: 231 T7 strong promoter | ... taatacgactcactatagggagaccacaac |
| BBa_Z0252 | SEQ ID NO: 232 T7 weak binding and processivity | ... taattgaactcactaaagggagaccacagc |
| BBa_Z0253 | SEQ ID NO: 233 T7 weak binding promoter | ... cgaagtaatacgactcactattagggaaga |

TABLE 15

| Examples of Stress Kit Promoters | | |
|---|---|---|
| Name | Description | Promoter Sequence |
| BBa_K086017 | SEQ ID NO: 234 unmodified Lutz-Bujard LacO promoter | ... ttgtgagcggataacaagatactgagcaca |
| BBa_K086018 | SEQ ID NO: 235 modified Lutz-Bujard LacO promoter, with alternative sigma factor σ24 | ... ttgtgagcggataacaattctgaagaacaa |
| BBa_K086019 | SEQ ID NO: 236 modified Lutz-Bujard LacO promoter, with alternative sigma factor σ24 | ... ttgtgagcggataacaattctgataaaaca |
| BBa_K086020 | SEQ ID NO: 237 modified Lutz-Bujard LacO promoter, with alternative sigma factor σ24 | ... ttgtgagcggataacatctaaccattaga |
| BBa_K086021 | SEQ ID NO: 238 modified Lutz-Bujard LacO promoter, with alternative sigma factor σ24 | ... ttgtgagcggataacatagcagataagaaa |
| BBa_K086022 | SEQ ID NO: 239 modified Lutz-Bujard LacO promoter, with alternative sigma factor σ28 | ... gtttgagcgagtaacgccgaaaatcttgca |
| BBa_K086023 | SEQ ID NO: 240 modified Lutz-Bujard LacO promoter, with alternative sigma factor σ28 | ... gtgtgagcgagtaacgacgaaaatcttgca |
| BBa_K086024 | SEQ ID NO: 241 modified Lutz-Bujard LacO promoter, with alternative sigma factor σ28 | ... tttgagcgagtaacagccgaaaatcttgca |
| BBa_K086025 | SEQ ID NO: 242 modified Lutz-Bujard LacO promoter, with alternative sigma factor σ28 | ... tgtgagcgagtaacagccgaaaatcttgca |
| BBa_K086026 | SEQ ID NO: 243 modified Lutz-Bujard LacO promoter, with alternative sigma factor σ32 | ... ttgtgagcgagtggcaccattaagtacgta |
| BBa_K086027 | SEQ ID NO: 244 modified Lutz-Bujard LacO promoter, with alternative sigma factor σ32 | ... ttgtgagcgagtgacaccattaagtacgta |
| BBa_K086028 | SEQ ID NO: 245 modified Lutz-Bujard LacO promoter, with alternative sigma factor σ32 | ... ttgtgagcgagtaacaccattaagtacgta |
| BBa_K086029 | SEQ ID NO: 246 modified Lutz-Bujard LacO promoter, with alternative sigma factor σ32 | ... ttgtgagcgagtaacaccattaagtacgta |
| BBa_K086030 | SEQ ID NO: 247 modified Lutz-Bujard LacO promoter, with alternative sigma factor σ38 | ... cagtgagcgagtaacaactacgctgtttta |
| BBa_K086031 | SEQ ID NO: 248 modified Lutz-Bujard LacO promoter, with alternative sigma factor σ38 | ... cagtgagcgagtaacaactacgctgtttta |

TABLE 15-continued

| Examples of Stress Kit Promoters | | |
|---|---|---|
| Name | Description | Promoter Sequence |
| BBa_K086032 | SEQ ID NO: 249 modified Lutz-Bujard LacO promoter, with alternative sigma factor σ38 | . . . atgtgagcggataacactataattaataga |
| BBa_K086033 | SEQ ID NO: 250 modified Lutz-Bujard LacO promoter, with alternative sigma factor σ38 | . . . atgtgagcggataacactataattaataga |

TABLE 16

| Examples of Logic Promoters | | |
|---|---|---|
| Name | Description | Promoter Sequence |
| BBa_I732200 | SEQ ID NO: 251 NOT Gate Promoter Family Member (D001O1wt1) | . . . gaattgtgagcggataacaattggatccgg |
| BBa_I732201 | SEQ ID NO: 252 NOT Gate Promoter Family Member (D001O11) | . . . ggaattgtgagcgctcacaattggatccgg |
| BBa_I732202 | SEQ ID NO: 253 NOT Gate Promoter Family Member (D001O22) | . . . ggaattgtaagcgcttacaattggatccgg |
| BBa_I732203 | SEQ ID NO: 254 NOT Gate Promoter Family Member (D001O33) | . . . ggaattgtaaacgtttacaattggatccgg |
| BBa_I732204 | SEQ ID NO: 255 NOT Gate Promoter Family Member (D001O44) | . . . ggaattgtgaacgttcacaattggatccgg |
| BBa_I732205 | SEQ ID NO: 256 NOT Gate Promoter Family Member (D001O55) | . . . ggaattttgagcgctcaaaattggatccgg |
| BBa_I732206 | SEQ ID NO: 257 NOT Gate Promoter Family Member (D001O66) | . . . ggaattatgagcgctcataattggatccgg |
| BBa_I732207 | SEQ ID NO: 258 NOT Gate Promoter Family Member (D001O77) | . . . gggacgactgtatacagtcgtcggatccgg |
| BBa_I732270 | SEQ ID NO: 259 Promoter Family Member with Hybrid Operator (D001O12) | . . . ggaattgtgagcgcttacaattggatccgg |
| BBa_I732271 | SEQ ID NO: 260 Promoter Family Member with Hybrid Operator (D001O16) | . . . ggaattgtgagcgctcataattggatccgg |
| BBa_I732272 | SEQ ID NO: 261 Promoter Family Member with Hybrid Operator (D001O17) | . . . ggaattgtgagctacagtcgtcggatccgg |
| BBa_I732273 | SEQ ID NO: 262 Promoter Family Member with Hybrid Operator (D001O21) | . . . ggaattgtaagcgctcacaattggatccgg |
| BBa_I732274 | SEQ ID NO: 263 Promoter Family Member with Hybrid Operator (D001O24) | . . . ggaattgtaagcgttcacaattggatccgg |
| BBa_I732275 | SEQ ID NO: 264 Promoter Family Member with Hybrid Operator (D001O26) | . . . ggaattgtaagcgctcataattggatccgg |
| BBa_I732276 | SEQ ID NO: 265 Promoter Family Member with Hybrid Operator (D001O27) | . . . ggaattgtaagctacagtcgtcggatccgg |
| BBa_I732277 | SEQ ID NO: 266 Promoter Family Member with Hybrid Operator (D001O46) | . . . ggaattgtgaacgctcataattggatccgg |
| BBa_I732278 | SEQ ID NO: 267 Promoter Family Member with Hybrid Operator (D001O47) | . . . ggaattgtgaactacagtcgtcggatccgg |
| BBa_I732279 | SEQ ID NO: 268 Promoter Family Member with Hybrid Operator (D001O61) | . . . ggaattatgagcgctcacaattggatccgg |
| BBa_I732301 | SEQ ID NO: 269 NAND Candidate (U073O26D001O16) | . . . ggaattgtgagcgctcataattggatccgg |
| BBa_I732302 | SEQ ID NO: 270 NAND Candidate (U073O27D001O17) | . . . ggaattgtgagctacagtcgtcggatccgg |

TABLE 16-continued

| Examples of Logic Promoters | | |
|---|---|---|
| Name | Description | Promoter Sequence |
| BBa_I732303 | SEQ ID NO: 271 NAND Candidate (U073O22D001O46) | ... ggaattgtgaacgctcataattggatccgg |
| BBa_I732304 | SEQ ID NO: 272 NAND Candidate (U073O22D001O47) | ... ggaattgtgaactacagtcgtcggatccgg |
| BBa_I732305 | SEQ ID NO: 273 NAND Candidate (U073O22D059O46) | ... taaattgtgaacgctcataattggatccgg |
| BBa_I732306 | SEQ ID NO: 274 NAND Candidate (U073O11D002O22) | ... gaaattgtaagcgcttacaattggatccgg |
| BBa_I732351 | SEQ ID NO: 275 NOR Candidate (U037O11D002O22) | ... gaaattgtaagcgcttacaattggatccgg |
| BBa_I732352 | SEQ ID NO: 276 NOR Candidate (U035O44D001O22) | ... ggaattgtaagcgcttacaattggatccgg |
| BBa_I732400 | SEQ ID NO: 277 Promoter Family Member (U097NUL + D062NUL) | ... gccaaattaaacaggattaacaggatccgg |
| BBa_I732401 | SEQ ID NO: 278 Promoter Family Member (U097O11 + D062NUL) | ... gccaaattaaacaggattaacaggatccgg |
| BBa_I732402 | SEQ ID NO: 279 Promoter Family Member (U085O11 + D062NUL) | ... gccaaattaaacaggattaacaggatccgg |
| BBa_I732403 | SEQ ID NO: 280 Promoter Family Member (U073O11 + D062NUL) | ... gccaaattaaacaggattaacaggatccgg |
| BBa_I732404 | SEQ ID NO: 281 Promoter Family Member (U061O11 + D062NUL) | ... gccaaattaaacaggattaacaggatccgg |
| BBa_I732405 | SEQ ID NO: 282 Promoter Family Member (U049O11 + D062NUL) | ... gccaaattaaacaggattaacaggatccgg |
| BBa_I732406 | SEQ ID NO: 283 Promoter Family Member (U037O11 + D062NUL) | ... gccaaattaaacaggattaacaggatccgg |
| BBa_I732407 | SEQ ID NO: 284 Promoter Family Member (U097NUL + D002O22) | ... gaaattgtaagcgcttacaattggatccgg |
| BBa_I732408 | SEQ ID NO: 285 Promoter Family Member (U097NUL + D014O22) | ... taaattgtaagcgcttacaattggatccgg |
| BBa_I732409 | SEQ ID NO: 286 Promoter Family Member (U097NUL + D026O22) | ... gtaattgtaagcgcttacaattggatccgg |
| BBa_I732410 | SEQ ID NO: 287 Promoter Family Member (U097NUL + D038O22) | ... tcaattgtaagcgcttacaattggatccgg |
| BBa_I732411 | SEQ ID NO: 288 Promoter Family Member (U097NUL + D050O22) | ... aaaattgtaagcgcttacaattggatccgg |
| BBa_I732412 | SEQ ID NO: 289 Promoter Family Member (U097NUL + D062O22) | ... caaattgtaagcgcttacaattggatccgg |
| BBa_I732413 | SEQ ID NO: 290 Promoter Family Member (U097O11 + D002O22) | ... gaaattgtaagcgcttacaattggatccgg |
| BBa_I732414 | SEQ ID NO: 291 Promoter Family Member (U097O11 + D014O22) | ... taaattgtaagcgcttacaattggatccgg |
| BBa_I732415 | SEQ ID NO: 292 Promoter Family Member (U097O11 + D026O22) | ... gtaattgtaagcgcttacaattggatccgg |
| BBa_I732416 | SEQ ID NO: 293 Promoter Family Member (U097O11 + D038O22) | ... tcaattgtaagcgcttacaattggatccgg |
| BBa_I732417 | SEQ ID NO: 294 Promoter Family Member (U097O11 + D050O22) | ... aaaattgtaagcgcttacaattggatccgg |
| BBa_I732418 | SEQ ID NO: 295 Promoter Family Member (U097O11 + D062O22) | ... caaattgtaagcgcttacaattggatccgg |

TABLE 16-continued

Examples of Logic Promoters

| Name | Description | Promoter Sequence |
|---|---|---|
| BBa_I732419 | SEQ ID NO: 296 Promoter Family Member (U085O11 + D002O22) | ... gaaattgtaagcgcttacaattggatccgg |
| BBa_I732420 | SEQ ID NO: 297 Promoter Family Member (U085O11 + D014O22) | ... taaattgtaagcgcttacaattggatccgg |
| BBa_I732421 | SEQ ID NO: 298 Promoter Family Member (U085O11 + D026O22) | ... gtaattgtaagcgcttacaattggatccgg |
| BBa_I732422 | SEQ ID NO: 299 Promoter Family Member (U085O11 + D038O22) | ... tcaattgtaagcgcttacaattggatccgg |
| BBa_I732423 | SEQ ID NO: 300 Promoter Family Member (U085O11 + D050O22) | ... aaaattgtaagcgcttacaattggatccgg |
| BBa_I732424 | SEQ ID NO: 301 Promoter Family Member (U085O11 + D062O22) | ... caaattgtaagcgcttacaattggatccgg |
| BBa_I732425 | SEQ ID NO: 302 Promoter Family Member (U073O11 + D002O22) | ... gaaattgtaagcgcttacaattggatccgg |
| BBa_I732426 | SEQ ID NO: 303 Promoter Family Member (U073O11 + D014O22) | ... taaattgtaagcgcttacaattggatccgg |
| BBa_I732427 | SEQ ID NO: 304 Promoter Family Member (U073O11 + D026O22) | ... gtaattgtaagcgcttacaattggatccgg |
| BBa_I732428 | SEQ ID NO: 305 Promoter Family Member (U073O11 + D038O22) | ... tcaattgtaagcgcttacaattggatccgg |
| BBa_I732429 | SEQ ID NO: 306 Promoter Family Member (U073O11 + D050O22) | ... aaaattgtaagcgcttacaattggatccgg |
| BBa_I732430 | SEQ ID NO: 307 Promoter Family Member (U073O11 + D062O22) | ... caaattgtaagcgcttacaattggatccgg |
| BBa_I732431 | SEQ ID NO: 308 Promoter Family Member (U061O11 + D002O22) | ... gaaattgtaagcgcttacaattggatccgg |
| BBa_I732432 | SEQ ID NO: 309 Promoter Family Member (U061O11 + D014O22) | ... taaattgtaagcgcttacaattggatccgg |
| BBa_I732433 | SEQ ID NO: 310 Promoter Family Member (U061O11 + D026O22) | ... gtaattgtaagcgcttacaattggatccgg |
| BBa_I732434 | SEQ ID NO: 311 Promoter Family Member (U061O11 + D038O22) | ... tcaattgtaagcgcttacaattggatccgg |
| BBa_I732435 | SEQ ID NO: 312 Promoter Family Member (U061O11 + D050O22) | ... aaaattgtaagcgcttacaattggatccgg |
| BBa_I732436 | SEQ ID NO: 313 Promoter Family Member (U061O11 + D062O22) | ... caaattgtaagcgcttacaattggatccgg |
| BBa_I732437 | SEQ ID NO: 314 Promoter Family Member (U049O11 + D002O22) | ... gaaattgtaagcgcttacaattggatccgg |
| BBa_I732438 | SEQ ID NO: 315 Promoter Family Member (U049O11 + D014O22) | ... taaattgtaagcgcttacaattggatccgg |
| BBa_I732439 | SEQ ID NO: 316 Promoter Family Member (U049O11 + D026O22) | ... gtaattgtaagcgcttacaattggatccgg |
| BBa_I732440 | SEQ ID NO: 317 Promoter Family Member (U049O11 + D038O22) | ... tcaattgtaagcgcttacaattggatccgg |
| BBa_I732441 | SEQ ID NO: 318 Promoter Family Member (U049O11 + D050O22) | ... aaaattgtaagcgcttacaattggatccgg |
| BBa_I732442 | SEQ ID NO: 319 Promoter Family Member (U049O11 + D062O22) | ... caaattgtaagcgcttacaattggatccgg |
| BBa_I732443 | SEQ ID NO: 320 Promoter Family Member (U037O11 + D002O22) | ... gaaattgtaagcgcttacaattggatccgg |

TABLE 16-continued

| Examples of Logic Promoters | | |
|---|---|---|
| Name | Description | Promoter Sequence |
| BBa_I732444 | SEQ ID NO: 321 Promoter Family Member (U037O11 + D014O22) | ... taaattgtaagcgcttacaattggatccgg |
| BBa_I732445 | SEQ ID NO: 322 Promoter Family Member (U037O11 + D026O22) | ... gtaattgtaagcgcttacaattggatccgg |
| BBa_I732446 | SEQ ID NO: 323 Promoter Family Member (U037O11 + D038O22) | ... tcaattgtaagcgcttacaattggatccgg |
| BBa_I732447 | SEQ ID NO: 324 Promoter Family Member (U037O11 + D050O22) | ... aaaattgtaagcgcttacaattggatccgg |
| BBa_I732448 | SEQ ID NO: 325 Promoter Family Member (U037O11 + D062O22) | ... caaattgtaagcgcttacaattggatccgg |
| BBa_I732450 | SEQ ID NO: 326 Promoter Family Member (U073O26 + D062NUL) | ... gccaaattaaacaggattaacaggatccgg |
| BBa_I732451 | SEQ ID NO: 327 Promoter Family Member (U073O27 + D062NUL) | ... gccaaattaaacaggattaacaggatccgg |
| BBa_I732452 | SEQ ID NO: 328 Promoter Family Member (U073O26 + D062O61) | ... caaattatgagcgctcacaattggatccgg |

TABLE 17

| Examples of Positively Regulated *E. coli* σ70 Promoters | | |
|---|---|---|
| Name | Description | Promoter Sequence |
| BBa_I0500 | SEQ ID NO: 329 Inducible pBad/araC promoter | ...gatctccatacccgtttttttgggctagc |
| BBa_I1051 | SEQ ID NO: 330 Lux cassette right promoter | ...tgttatagtcgaatacctctggcggtgata |
| BBa_I12006 | SEQ ID NO: 331 Modified lamdba Prm promoter (repressed by 434 cI) | ...attacaaactttcttgtatagatttaacgt |
| BBa_I12007 | SEQ ID NO: 332 Modified lambda Prm promoter (OR-3 obliterated) | ...atttataaatagtggtgatagatttaacgt |
| BBa_I12036 | SEQ ID NO: 333 Modified lamdba Prm promoter (cooperative repression by 434 cI) | ...tttcttgtatagatttacaatgtatcttgt |
| BBa_I12040 | SEQ ID NO: 334 Modified lambda P(RM) promoter: -10 region from P(L) and cooperatively repressed by 434 cI | ...tttcttgtagatacttacaatgtatcttgt |
| BBa_I12210 | SEQ ID NO: 335 plac Or2-62 (positive) | ...ctttatgcttccggctcgtatgttgtgtgg |
| BBa_I13406 | SEQ ID NO: 336 Pbad/AraC with extra REN sites | ...ttttttgggctagcaagatttaccatggat |
| BBa_I13453 | SEQ ID NO: 337 Pbad promoter | ...tgtttctccataccgtttttttgggctagc |
| BBa_I14015 | SEQ ID NO: 338 P(Las) TetO | ...ttttggtacactccctatcagtgatagaga |
| BBa_I14016 | SEQ ID NO: 339 P(Las) CIO | ...ctttttggtacactacctctggcggtgata |
| BBa_I14017 | SEQ ID NO: 340 P(Rhl) | ...tacgcaagaaaatggtttgttatagtcgaa |
| BBa_I721001 | SEQ ID NO: 341 Lead Promoter | ...gaaaaccttgtcaatgaagagcgatctatg |
| BBa_I723020 | SEQ ID NO: 342 Pu | ...ctcaaagcgggccagccgtagccgttacgc |
| BBa_I731004 | SEQ ID NO: 343 FecA promoter | ...ttctcgttcgactcatagctgaacacaaca |
| BBa_I1739104 | SEQ ID NO: 344 Double Promoter (LuxR/HSL, positive/P22 cII, negative) | ...gttctttaattatttaagtgttctttaatt |
| BBa_I739105 | SEQ ID NO: 345 Double Promoter (LuxR/HSL, positive/cI, negative) | ...cgtgcgtgttgataacaccgtgcgtgttga |

TABLE 17-continued

Examples of Positively Regulated *E. coli* σ70 Promoters

| Name | Description | Promoter Sequence |
|---|---|---|
| BBa_I741018 | SEQ ID NO: 346 Right facing promoter (for xylF) controlled by xylR and CRP-cAMP | ...gttacgtttatcgcggtgattgttacttat |
| BBa_I741019 | SEQ ID NO: 347 Right facing promoter (for xylA) controlled by xylR and CRP-cAMP | ...gcaaaataaaatggaatgatgaaactgggt |
| BBa_I741020 | SEQ ID NO: 348 promoter to xylF without CRP and several binding sites for xylR | ...gttacgtttatcgcggtgattgttacttat |
| BBa_I741021 | SEQ ID NO: 349 promoter to xylA without CRP and several binding sites for xylR | ...atttcacactgctattgagataattcacaa |
| BBa_I746104 | SEQ ID NO: 350 P2 promoter in agr operon from *S. aureus* | ...agattgtactaaatcgtataatgacagtga |
| BBa_I746360 | SEQ ID NO: 351 PF promoter from P2 phage | ...gacatctccggcgcaactgaaaataccact |
| BBa_I746361 | SEQ ID NO: 352 PO promoter from P2 phage | ...gaggatgcgcatcgtcgggaaactgatgcc |
| BBa_I746362 | SEQ ID NO: 353 PP promoter from P2 phage | ...catccgggactgatggcggaggatgcgcat |
| BBa_I746363 | SEQ ID NO: 354 PV promoter from P2 phage | ...aacttttatatattgtgcaatctcacatgc |
| BBa_I746364 | SEQ ID NO: 355 Psid promoter from P4 phage | ...tgttgtccggtgtacgtcacaattttctta |
| BBa_I746365 | SEQ ID NO: 356 PLL promoter from P4 phage | ...aatggctgtgtgtttttttgttcatctccac |
| BBa_I751501 | SEQ ID NO: 357 plux-cI hybrid promoter | ...gtgttgatgcttttatcaccgccagtggta |
| BBa_I751502 | SEQ ID NO: 358 plux-lac hybrid promoter | ...agtgtgtggaattgtgagcggataacaatt |
| BBa_I760005 | SEQ ID NO: 359 Cu-sensitive promoter | atgacaaaattgtcat |
| BBa_I761011 | SEQ ID NO: 360 CinR, CinL and glucose controlled promoter | ...acatcttaaaagttttagtatcatattcgt |
| BBa_I765001 | SEQ ID NO: 361 UV promoter | ...ctgaaagcgcataccgctatggagggggtt |
| BBa_I765007 | SEQ ID NO: 362 Fe and UV promoters | ...ctgaaagcgcataccgctatggagggggtt |
| BBa_J01005 | SEQ ID NO: 363 pspoIIE promoter (spo0A J01004, positive) | ...aacgaatataacaggtgggagatgagagga |
| BBa_J03007 | SEQ ID NO: 364 Maltose specific promoter | ...aatatttcctcattttccacagtgaagtga |
| BBa_J06403 | SEQ ID NO: 365 RhIR promoter repressible by CI | ...tacgcaagaaaatggtttgttatagtcgaa |
| BBa_J07007 | SEQ ID NO: 366 ctx promoter | ...atttaattgttttgatcaattatttttctg |
| BBa_J13210 | SEQ ID NO: 367 pOmpR dependent POPS producer | ...attattctgcatttttggggagaatggact |
| BBa_J15502 | SEQ ID NO: 368 copA promoter | ...ccttgctggaaggtttaacctttatcacag |
| BBa_J16101 | SEQ ID NO: 369 BanAp - Banana-induced Promoter | atgatgtgtccatggatta |
| BBa_J16105 | SEQ ID NO: 370 HelPp - "Help" Dependant promoter | atgatagacgatgtgcggacaacgtg |
| BBa_J45503 | SEQ ID NO: 371 hybB Cold Shock Promoter | ...cattagccgccaccatggggttaagtagca |
| BBa_J58100 | SEQ ID NO: 372 AND-type promoter synergistically activated by cI and CRP | ...atttataaatagtggtgatagatttaacgt |

TABLE 17-continued

Examples of Positively Regulated *E. coli* σ70 Promoters

| Name | Description | Promoter Sequence |
|---|---|---|
| BBa_J61051 | SEQ ID NO: 373 [Psal1] | ...ataaagccatcacgagtaccatagaggatc |
| BBa_J61054 | SEQ ID NO: 374 [HIP-1] Promoter | ...tttgtcttttcttgcttaataatgttgtca |
| BBa_J61055 | SEQ ID NO: 375 [HIP-1 fnr] Promoter | ...tttgtcttttcttgcttaataatgttgtca |
| BBa_J64000 | SEQ ID NO: 376 rhlI promoter | ...atcctcctttagtcttccccctcatgtgtg |
| BBa_J64010 | SEQ ID NO: 377 lasI promoter | ...taaaattatgaaatttgcataaattcttca |
| BBa_J64712 | SEQ ID NO: 378 LasR/LasI Inducible & RHLR/RHLI repressible Promoter | ...gaaatctggcagtttttggtacacgaaagc |
| BBa_J64800 | SEQ ID NO: 379 RHLR/RHLI Inducible & LasR/LasI repressible Promoter | ...tgccagttctggcaggtctaaaaagtgttc |
| BBa_J64804 | SEQ ID NO: 380 The promoter region (inclusive of regulator binding sites) of the *B. subtilis* RocDEF operon | ...cacagaacttgcatttatataaagggaaag |
| BBa_K091107 | SEQ ID NO: 381 pLux/cI Hybrid Promoter | ...acaccgtgcgtgttgatatagtcgaataaa |
| BBa_K091117 | SEQ ID NO: 382 pLas promoter | ...aaaattatgaaatttgtataaattcttcag |
| BBa_K091143 | SEQ ID NO: 383 pLas/cI Hybrid Promoter | ...ggttctttttggtacctctggcggtgataa |
| BBa_K091146 | SEQ ID NO: 384 pLas/Lux Hybrid Promoter | ...tgtaggatcgtacaggtataaattcttcag |
| BBa_K091156 | SEQ ID NO: 385 pLux | ...caagaaaatggtttgttatagtcgaataaa |
| BBa_K091157 | SEQ ID NO: 386 pLux/Las Hybrid Promoter | ...ctatctcatttgctagtatagtcgaataaa |
| BBa_K100000 | SEQ ID NO: 387 Natural Xylose Regulated Bi-Directional Operator | ...gttacgtttatcgcggtgattgttacttat |
| BBa_K100001 | SEQ ID NO: 388 Edited Xylose Regulated Bi-Directional Operator 1 | ...gttacgtttatcgcggtgattgttacttat |
| BBa_K100002 | SEQ ID NO: 389 Edited Xylose Regulated Bi-Directional Operator 2 | ...gttacgtttatcgcggtgattgttacttat |
| BBa_K112118 | SEQ ID NO: 390 rrnB P1 promoter | ...ataaatgcttgactctgtagcgggaaggcg |
| BBa_K112320 | SEQ ID NO: 391 {<ftsAZ promoter>} in BBb format | ...aaaactggtagtaggactggagattggtac |
| BBa_K112322 | SEQ ID NO: 392 {Pdps} in BBb format | ...gggacacaaacatcaagaggatatgagatt |
| BBa_K112402 | SEQ ID NO: 393 promoter for FabA gene - Membrane Damage and Ultrasound Sensitive | ...gtcaaaatgaccgaaacgggtggtaacttc |
| BBa_K112405 | SEQ ID NO: 394 Promoter for CadA and CadB genes | ...agtaatcttatcgccagtttggtctggtca |
| BBa_K112406 | SEQ ID NO: 395 cadC promoter | ...agtaatcttatcgccagtttggtctggtca |
| BBa_K112701 | SEQ ID NO: 396 hns promoter | ...aattctgaacaacatccgtactcttcgtgc |
| BBa_K112900 | SEQ ID NO: 397 Pbad | ...tcgataagattaccgatcttacctgaagct |
| BBa_K116001 | SEQ ID NO: 398 nhaA promoter, which can be regulated by pH and nhaR protein. | ...cgatctattcacctgaaagagaaataaaaa |
| BBa_K116401 | SEQ ID NO: 399 external phosphate sensing promoter | ...atcgcaacctatttattacaacactagtgc |
| BBa_K116500 | SEQ ID NO: 400 OmpF promoter that is activated or repressed by OmpR according to osmolarity. | ...aaacgttagtttgaatggaaagatgcctgc |

TABLE 17-continued

| Examples of Positively Regulated *E. coli* σ70 Promoters | | |
|---|---|---|
| Name | Description | Promoter Sequence |
| BBa_K116603 | SEQ ID NO: 401 pRE promoter from λ phage | ...tttgcacgaaccatatgtaagtatttcctt |
| BBa_K117002 | SEQ ID NO: 402 LsrA promoter (indirectly activated by AI-2) | ...taacacttatttaattaaaaagaggagaaa |
| BBa_K118011 | SEQ ID NO: 403 PcstA (glucose-repressible promoter) | ...tagaaacaaaatgtaacatctctatggaca |
| BBa_K121011 | SEQ ID NO: 404 promoter (ladI regulated) | ...acaggaaacagctatgaccatgattacgcc |
| BBa_K135000 | SEQ ID NO: 405 pCpxR (CpxR responsive promoter) | ...agcgacgtctgatgacgtaatttctgcctc |
| BBa_K136010 | SEQ ID NO: 406 fliA promoter | ...gttcactctataccgctgaaggtgtaatgg |
| BBa_K145150 | SEQ ID NO: 407 Hybrid promoter: HSL-LuxR activated, P22 C2 repressed | ...tagtttataatttaagtgttctttaatttc |
| BBa_K180000 | SEQ ID NO: 408 Hybrid promoter (trp & lac regulated -- tac pR) | ...cgagcacttcaccaacaaggaccatagcat |
| BBa_K180002 | SEQ ID NO: 409 tac pR testing plasmid (GFP) | ...caccttcgggtgggcctttctgcgtttata |
| BBa_K180003 | SEQ ID NO: 410 PTAC testing plasmid (GFP) - basic | ...catggcatggatgaactatacaaataataa |
| BBa_K180004 | SEQ ID NO: 411 Game of Life - Primary plasmid | ...caccttcgggtgggcctttctgcgtttata |
| BBa_K180005 | SEQ ID NO: 412 GoL - Primary plasmid (part 1)/RPS - Paper primary plasmid (part 1) [LuxR generator] | ...caccttcgggtgggcctttctgcgtttata |
| BBa_K180006 | SEQ ID NO: 413 Game of Life - Primary plasmid (part 2) [lux pR, GFP and LacI generator] | ...caccttcgggtgggcctttctgcgtttata |
| BBa_K180007 | SEQ ID NO: 414 Game of Life - Secondary plasmid [tac pR, LuxI generator] | ...caccttcgggtgggcctttctgcgtttata |
| BBa_K180010 | SEQ ID NO: 415 Rock-paper-scissors - Rock primary plasmid | ...caccttcgggtgggcctttctgcgtttata |
| BBa_K180011 | SEQ ID NO: 416 Rock - Primary plasmid (part 1) [RhlR generator] | ...caccttcgggtgggcctttctgcgtttata |
| BBa_K180012 | SEQ ID NO: 417 Rock - Primary plasmid (part 2) [tac pR, mCherry and LasI generator] | ...caccttcgggtgggcctttctgcgtttata |
| BBa_K180013 | SEQ ID NO: 418 Rock-paper-scissors - Rock secondary plasmid [rhl pR, LacI generator] | ...caccttcgggtgggcctttctgcgtttata |
| BBa_K180014 | SEQ ID NO: 419 Rock-paper-scissors - Paper primary plasmid | ...caccttcgggtgggcctttctgcgtttata |
| BBa_K180015 | SEQ ID NO: 420 Paper - Primary plasmid (part 2) [tac pR, GFP and RhlI generator] | ...caccttcgggtgggcctttctgcgtttata |
| BBa_K180016 | SEQ ID NO: 421 Rock-paper-scissors - Paper secondary plasmid [lux pR, LacI generator] | ...caccttcgggtgggcctttctgcgtttata |
| BBa_K180017 | SEQ ID NO: 422 Rock-paper-scissors - Scissors primary plasmid | ...caccttcgggtgggcctttctgcgtttata |
| BBa_K180018 | SEQ ID NO: 423 Scissors - Primary plasmid (part 1) [LasR generator] | ...caccttcgggtgggcctttctgcgtttata |
| BBa_K180019 | SEQ ID NO: 424 Scissors - Primary plasmid (part 2) [tac pR, mBanana and LuxI generator] | ...caccttcgggtgggcctttctgcgtttata |

TABLE 17-continued

Examples of Positively Regulated *E. coli* σ70 Promoters

| Name | Description | Promoter Sequence |
|---|---|---|
| BBa_K180020 | SEQ ID NO: 425 Rock-paper-scissors - Scissors secondary plasmid [las pR, LacI generator] | ...caccttcgggtgggcctttctgcgtttata |
| BBa_K206000 | SEQ ID NO: 426 pBAD strong | ...tgtttctccataccgtttttttgggctagc |
| BBa_K206001 | SEQ ID NO: 427 pBAD weak | ...tgtttctccataccgtttttttgggctagc |
| BBa_K259005 | SEQ ID NO: 428 AraC Rheostat Promoter | ...ttttatcgcaactctctactgtttctccat |
| BBa_K259007 | SEQ ID NO: 429 AraC Promoter fused with RBS | ...gtttctccattactagagaaagaggggaca |
| BBa_K266000 | SEQ ID NO: 430 PAI + LasR -> LuxI (AI) | ...caccttcgggtgggcctttctgcgtttata |
| BBa_K266005 | SEQ ID NO: 431 PAI + LasR -> LasI & AI + LuxR--\| LasI | ...aataactctgatagtgctagtgtagatctc |
| BBa_K266006 | SEQ ID NO: 432 PAI + LasR -> LasI + GFP & AI + LuxR--\| LasI + GFP | ...caccttcgggtgggcctttctgcgtttata |
| BBa_K266007 | SEQ ID NO: 433 Complex QS -> LuxI & LasI circuit | ...caccttcgggtgggcctttctgcgtttata |

TABLE 18

Examples of Positively regulated *E. coli* σS promoters

| Name | Description | Promoter Sequence |
|---|---|---|
| BBa_K112322 | SEQ ID NO: 434 {Pdps} in BBb format | ...gggacacaaacatc aagaggatatgagatt |

TABLE 19

Examples of Positively regulated *E. coli* σ32 promoters

| Name | Description | Promoter Sequence |
|---|---|---|
| BBa_K112400 | SEQ ID NO: 435 Promoter for grpE | ... ataataagcgaagttag |

TABLE 19-continued

Examples of Positively regulated *E. coli* σ32 promoters

| Name | Description | Promoter Sequence |
|---|---|---|
| | gene - Heat Shock and Ultrasound Sensitive | cgagatgaatgcg |

TABLE 20

Examples of Positively regulated *E. coli* σ54 promoters

| Name | Description | Promoter Sequence |
|---|---|---|
| BBa_J64979 | SEQ ID NO: 436 glnAp2 | ...agttggcacagatttcgcttt atctttttt |

TABLE 21

Examples of Positively regulated *B. subtilis* σA promoters

| Name | Description | Promoter Sequence |
|---|---|---|
| BBa_R0062 | SEQ ID NO: 437 Promoter (luxR & HSL regulated -- lux pR) | ... caagaaaatggtttgttatagtcgaataaa |
| BBa_R0065 | SEQ ID NO: 438 Promoter (lambda cI and luxR regulated -- hybrid) | ...gtgttgactattttacctctggcggtgata |
| BBa_R0071 | SEQ ID NO: 439 Promoter (RhlR & C4-HSL regulated) | ... gttagctttcgaattggctaaaaagtgttc |
| BBa_R0078 | SEQ ID NO: 440 Promoter (cinR and HSL regulated) | ... ccattctgctttccacgaacttgaaaacgc |
| BBa_R0079 | SEQ ID NO: 441 Promoter (LasR & PAI regulated) | ... ggccgcgggttattttggtacacgaaagc |
| BBa_R0080 | SEQ ID NO: 442 Promoter (AraC regulated) | ...ttttatcgcaactctctactgtttctccat |

TABLE 21-continued

| Examples of Positively regulated *B. subtilis* σA promoters | | |
|---|---|---|
| Name | Description | Promoter Sequence |
| BBa_R0082 | SEQ ID NO: 443 Promoter (OmpR, positive) | ...attattctgcatttttggggagaatggact |
| BBa_R0083 | SEQ ID NO: 444 Promoter (OmpR, positive) | ...attattctgcatttttggggagaatggact |
| BBa_R0084 | SEQ ID NO: 445 Promoter (OmpR, positive) | ... aacgttagtttgaatggaaagatgcctgca |
| BBa_R1062 | SEQ ID NO: 446 Promoter, Standard (luxR and HSL regulated -- lux pR) | ... aagaaaatggtttgttgatactcgaataaa |

TABLE 22

| Examples of Miscellaneous Prokaryotic Induced Promoters | | |
|---|---|---|
| Name | Description | Promoter Sequence |
| BBa_J64001 | SEQ ID NO: 447 psicA from *Salmonella* | ...aacgcagtcgttaagttctacaaagtcggt |
| BBa_J64750 | SEQ ID NO: 448 SPI-1 TTSS secretion-linked promoter from *Salmonella* | ... gtcggtgacagataacaggagtaagtaatg |
| BBa_K112149 | SEQ ID NO: 449 PmgtCB Magnesium promoter from *Salmonella* | ...tattggctgactataataagcgcaaattca |
| BBa_K116201 | SEQ ID NO: 450 ureD promoter from *P mirabilis* | |
| BBa_K125100 | SEQ ID NO: 451 nir promoter from *Synechocystis* sp. PCC6803 | ...cgaaacgggaaccctatattgatctctact |
| BBa_K131017 | SEQ ID NO: 452 p_qrr4 from *Vibrio harveyi* | ...aagttggcacgcatcgtgctttatacagat |

TABLE 23

| Examples of Yeast Positive (Activatible) Promoters | | |
|---|---|---|
| Name | Description | Promoter Sequence |
| BBa_J63006 | SEQ ID NO: 453 yeast GAL1 promoter | . . . gaggaaactagacccgccgccaccatggag |
| BBa_K284002 | SEQ ID NO: 454 JEN1 Promoter from *Kluyveromyces lactis* | . . . gagtaaccaaaaccaaaacagatttcaacc |
| BBa_K106699 | SEQ ID NO: 455 Gal1 Promoter | . . . aaagtaagaatttttgaaaattcaatataa |
| BBa_K165041 | SEQ ID NO: 456 Zif268-HIV binding sites + TEF constitutive yeast promoter | . . . atacggtcaacgaactataattaactaaac |
| BBa_K165034 | SEQ ID NO: 457 Zif268-HIV bs + LexA bs + mCYC promoter | . . . cacaaatacacacactaaattaataactag |
| BBa_K165031 | SEQ ID NO: 458 mCYC promoter plus LexA binding sites | . . . cacaaatacacacactaaattaataactag |
| BBa_K165030 | SEQ ID NO: 459 mCYC promoter plus Zif268-HIV binding sites | . . . cacaaatacacacactaaattaataactag |
| BBa_K165001 | SEQ ID NO: 460 pGAL1 + w/XhoI sites | . . . atactttaacgtcaaggagaaaaaactata |
| BBa_K110016 | SEQ ID NO: 461 A-Cell Promoter STE2 (backwards) | . . . accgttaagaaccatatccaagaatcaaaa |
| BBa_K110015 | SEQ ID NO: 462 A-Cell Promoter MFA1 (RtL) | . . . cttcatatataaaccgccagaaatgaatta |

TABLE 23-continued

Examples of Yeast Positive (Activatible) Promoters

| Name | Description | Promoter Sequence |
|---|---|---|
| BBa_K110014 | SEQ ID NO: 463 A-Cell Promoter MFA2 (backwards) | . . . atcttcatacaacaataactaccaacctta |
| BBa_K110006 | SEQ ID NO: 464 Alpha-Cell Promoter MF(ALPHA)1 | . . . tttcatacacaatataaacgattaaaagaa |
| BBa_K110005 | SEQ ID NO: 465 Alpha-Cell Promoter MF(ALPHA)2 | . . . aaattccagtaaattcacatattggagaaa |
| BBa_K110004 | SEQ ID NO: 466 Alpha-Cell Promoter Ste3 | . . . gggagccagaacgcttctggtggtgtaaat |
| BBa_J24813 | SEQ ID NO: 467 URA3 Promoter from *S. cerevisiae* | . . . gcacagacttagattggtatatatacgcat |
| BBa_K284003 | SEQ ID NO: 468 Partial DLD Promoter from *Kluyveromyces lactis* | . . . aagtgcaagaaagaccagaaacgcaactca |

TABLE 24

Examples of Eukaryotic Positive (Activatible) Promoters

| Name | Description | Promoter Sequence |
|---|---|---|
| BBa_I10498 | SEQ ID NO: 469 Oct-4 promoter | ...taaaaaaaaaaaaaaaaaaaaaaaaaaaaa |
| BBa_J05215 | SEQ ID NO: 470 Regulator for R1-CREBH | ... ggggcgagggccccgcctccggaggcgggg |
| BBa_J05216 | SEQ ID NO: 471 Regulator for R3-ATF6 | ... gaggggacggctccggccccggggccggag |
| BBa_J05217 | SEQ ID NO: 472 Regulator for R2-YAP7 | ... ggggcgagggctccggccccggggccggag |
| BBa_J05218 | SEQ ID NO: 473 Regulator for R4-cMaf | ... gaggggacggccccgcctccggaggcgggg |

TABLE 25

Examples of Negatively regulated (repressible) *E. coli* σ70 promoters

| Name | Description | Promoter Sequence |
|---|---|---|
| BBa_I1051 | SEQ ID NO: 474 Lux cassette right promoter | ...tgttatagtcgaatacctctggcggtgata |
| BBa_I12001 | SEQ ID NO: 475 Promoter (PRM+) | ... gatttaacgtatcagcacaaaaaagaaacc |
| BBa_I12006 | SEQ ID NO: 476 Modified lamdba Prm promoter (repressed by 434 cI) | ...attacaaactttcttgtatagatttaacgt |
| BBa_I12036 | SEQ ID NO: 477 Modified lamdba Prm promoter (cooperative repression by 434 cI) | ...tttcttgtatagatttacaatgtatcttgt |
| BBa_I12040 | SEQ ID NO: 478 Modified lambda P(RM) promoter: -10 region from P(L) and cooperatively repressed by 434 cI | ...tttcttgtagatacttacaatgtatcttgt |
| BBa_I12212 | SEQ ID NO: 479 TetR - TetR-4C heterodimer promoter (negative) | ... actctgtcaatgatagagtggattcaaaaa |
| BBa_I14015 | SEQ ID NO: 480 P(Las) TetO | ...ttttggtacactccctatcagtgatagaga |
| BBa_I14016 | SEQ ID NO: 481 P(Las) CIO | ...ctttttggtacactacctctggcggtgata |
| BBa_I14032 | SEQ ID NO: 482 promoter P(Lac) IQ | ... aaacctttcgcggtatggcatgatagcgcc |

TABLE 25-continued

| Examples of Negatively regulated (repressible) *E. coli* σ70 promoters | | |
|---|---|---|
| Name | Description | Promoter Sequence |
| BBa_I714889 | SEQ ID NO: 483 OR21 of PR and PRM | ...tattttacctctggcggtgataatggttgc |
| BBa_I714924 | SEQ ID NO: 484 RecA_DlexO_DLacO1 | ... actctcggcatggacgagctgtacaagtaa |
| BBa_I715003 | SEQ ID NO: 485 hybrid pLac with UV5 mutation | ... ttgtgagcggataacaatatgttgagcaca |
| BBa_I718018 | SEQ ID NO: 486 dapAp promoter | ... cattgagacacttgtttgcacagaggatgg |
| BBa_I731004 | SEQ ID NO: 487 FecA promoter | ...ttctcgttcgactcatagctgaacacaaca |
| BBa_I732200 | SEQ ID NO: 488 NOT Gate Promoter Family Member (D001O1wt1) | ... gaattgtgagcggataacaattggatccgg |
| BBa_I732201 | SEQ ID NO: 489 NOT Gate Promoter Family Member (D001O11) | ... ggaattgtgagcgctcacaattggatccgg |
| BBa_I732202 | SEQ ID NO: 490 NOT Gate Promoter Family Member (D001O22) | ... ggaattgtaagcgcttacaattggatccgg |
| BBa_I732203 | SEQ ID NO: 491 NOT Gate Promoter Family Member (D001O33) | ... ggaattgtaaacgtttacaattggatccgg |
| BBa_I732204 | SEQ ID NO: 492 NOT Gate Promoter Family Member (D001O44) | ... ggaattgtgaacgttcacaattggatccgg |
| BBa_I732205 | SEQ ID NO: 493 NOT Gate Promoter Family Member (D001O55) | ... ggaattttgagcgctcaaaattggatccgg |
| BBa_I732206 | SEQ ID NO: 494 NOT Gate Promoter Family Member (D001O66) | ... ggaattatgagcgctcataattggatccgg |
| BBa_I732207 | SEQ ID NO: 495 NOT Gate Promoter Family Member (D001O77) | ... gggacgactgtatacagtcgtcggatccgg |
| BBa_I732270 | SEQ ID NO: 496 Promoter Family Member with Hybrid Operator (D001O12) | ... ggaattgtgagcgcttacaattggatccgg |
| BBa_I732271 | SEQ ID NO: 497 Promoter Family Member with Hybrid Operator (D001O16) | ... ggaattgtgagcgctcataattggatccgg |
| BBa_I732272 | SEQ ID NO: 498 Promoter Family Member with Hybrid Operator (D001O17) | ... ggaattgtgagctacagtcgtcggatccgg |
| BBa_I732273 | SEQ ID NO: 499 Promoter Family Member with Hybrid Operator (D001O21) | ... ggaattgtaagcgctcacaattggatccgg |
| BBa_I732274 | SEQ ID NO: 500 Promoter Family Member with Hybrid Operator (D001O24) | ... ggaattgtaagcgttcacaattggatccgg |
| BBa_I732275 | SEQ ID NO: 501 Promoter Family Member with Hybrid Operator (D001O26) | ... ggaattgtaagcgctcataattggatccgg |
| BBa_I732276 | SEQ ID NO: 502 Promoter Family Member with Hybrid Operator (D001O27) | ... ggaattgtaagctacagtcgtcggatccgg |
| BBa_I732277 | SEQ ID NO: 503 Promoter Family Member with Hybrid Operator (D001O46) | ... ggaattgtgaacgctcataattggatccgg |
| BBa_I732278 | SEQ ID NO: 504 Promoter Family Member with Hybrid Operator (D001O47) | ... ggaattgtgaactacagtcgtcggatccgg |
| BBa_I732279 | SEQ ID NO: 505 Promoter Family Member with Hybrid Operator (D001O61) | ... ggaattatgagcgctcacaattggatccgg |
| BBa_I732301 | SEQ ID NO: 506 NAND Candidate (U073O26D001O16) | ... ggaattgtgagcgctcataattggatccgg |
| BBa_I732302 | SEQ ID NO: 507 NAND Candidate (U073O27D001O17) | ... ggaattgtgagctacagtcgtcggatccgg |
| BBa_I732303 | SEQ ID NO: 508 NAND Candidate (U073O22D001O46) | ... ggaattgtgaacgctcataattggatccgg |

TABLE 25-continued

Examples of Negatively regulated (repressible) *E. coli* σ70 promoters

| Name | Description | Promoter Sequence |
| --- | --- | --- |
| BBa_I732304 | SEQ ID NO: 509 NAND Candidate (U073O22D001O47) | ...ggaattgtgaactacagtcgtcggatccgg |
| BBa_I732305 | SEQ ID NO: 510 NAND Candidate (U073O22D059O46) | ...taaattgtgaacgctcataattggatccgg |
| BBa_I732306 | SEQ ID NO: 511 NAND Candidate (U073O11D002O22) | ...gaaattgtaagcgcttacaattggatccgg |
| BBa_I732351 | SEQ ID NO: 512 NOR Candidate (U037O11D002O22) | ...gaaattgtaagcgcttacaattggatccgg |
| BBa_I732352 | SEQ ID NO: 513 NOR Candidate (U035O44D001O22) | ...ggaattgtaagcgcttacaattggatccgg |
| BBa_I732400 | SEQ ID NO: 514 Promoter Family Member (U097NUL + D062NUL) | ...gccaaattaaacaggattaacaggatccgg |
| BBa_I732401 | SEQ ID NO: 515 Promoter Family Member (U097O11 + D062NUL) | ...gccaaattaaacaggattaacaggatccgg |
| BBa_I732402 | SEQ ID NO: 516 Promoter Family Member (U085O11 + D062NUL) | ...gccaaattaaacaggattaacaggatccgg |
| BBa_I732403 | SEQ ID NO: 517 Promoter Family Member (U073O11 + D062NUL) | ...gccaaattaaacaggattaacaggatccgg |
| BBa_I732404 | SEQ ID NO: 518 Promoter Family Member (U061O11 + D062NUL) | ...gccaaattaaacaggattaacaggatccgg |
| BBa_I732405 | SEQ ID NO: 519 Promoter Family Member (U049O11 + D062NUL) | ...gccaaattaaacaggattaacaggatccgg |
| BBa_I732406 | SEQ ID NO: 520 Promoter Family Member (U037O11 + D062NUL) | ...gccaaattaaacaggattaacaggatccgg |
| BBa_I732407 | SEQ ID NO: 521 Promoter Family Member (U097NUL + D002O22) | ...gaaattgtaagcgcttacaattggatccgg |
| BBa_I732408 | SEQ ID NO: 522 Promoter Family Member (U097NUL + D014O22) | ...taaattgtaagcgcttacaattggatccgg |
| BBa_I732409 | SEQ ID NO: 523 Promoter Family Member (U097NUL + D026O22) | ...gtaattgtaagcgcttacaattggatccgg |
| BBa_I732410 | SEQ ID NO: 524 Promoter Family Member (U097NUL + D038O22) | ...tcaattgtaagcgcttacaattggatccgg |
| BBa_I732411 | SEQ ID NO: 525 Promoter Family Member (U097NUL + D050O22) | ...aaaattgtaagcgcttacaattggatccgg |
| BBa_I732412 | SEQ ID NO: 526 Promoter Family Member (U097NUL + D062O22) | ...caaattgtaagcgcttacaattggatccgg |
| BBa_I732413 | SEQ ID NO: 527 Promoter Family Member (U097O11 + D002O22) | ...gaaattgtaagcgcttacaattggatccgg |
| BBa_I732414 | SEQ ID NO: 528 Promoter Family Member (U097O11 + D014O22) | ...taaattgtaagcgcttacaattggatccgg |
| BBa_I732415 | SEQ ID NO: 529 Promoter Family Member (U097O11 + D026O22) | ...gtaattgtaagcgcttacaattggatccgg |
| BBa_I732416 | SEQ ID NO: 530 Promoter Family Member (U097O11 + D038O22) | ...tcaattgtaagcgcttacaattggatccgg |
| BBa_I732417 | SEQ ID NO: 531 Promoter Family Member (U097O11 + D050O22) | ...aaaattgtaagcgcttacaattggatccgg |
| BBa_I732418 | SEQ ID NO: 532 Promoter Family Member (U097O11 + D062O22) | ...caaattgtaagcgcttacaattggatccgg |
| BBa_I732419 | SEQ ID NO: 533 Promoter Family Member (U085O11 + D002O22) | ...gaaattgtaagcgcttacaattggatccgg |

TABLE 25-continued

| Name | Description | Promoter Sequence |
|---|---|---|
| Examples of Negatively regulated (repressible) *E. coli* σ70 promoters | | |
| BBa_I732420 | SEQ ID NO: 534 Promoter Family Member (U085O11 + D014O22) | ...taaattgtaagcgcttacaattggatccgg |
| BBa_I732421 | SEQ ID NO: 535 Promoter Family Member (U085O11 + D026O22) | ... gtaattgtaagcgcttacaattggatccgg |
| BBa_I732422 | SEQ ID NO: 536 Promoter Family Member (U085O11 + D038O22) | ...tcaattgtaagcgcttacaattggatccgg |
| BBa_I732423 | SEQ ID NO: 537 Promoter Family Member (U085O11 + D050O22) | ... aaaattgtaagcgcttacaattggatccgg |
| BBa_I732424 | SEQ ID NO: 538 Promoter Family Member (U085O11 + D062O22) | ... caaattgtaagcgcttacaattggatccgg |
| BBa_I732425 | SEQ ID NO: 539 Promoter Family Member (U073O11 + D002O22) | ... gaaattgtaagcgcttacaattggatccgg |
| BBa_I732426 | SEQ ID NO: 540 Promoter Family Member (U073O11 + D014O22) | ...taaattgtaagcgcttacaattggatccgg |
| BBa_I732427 | SEQ ID NO: 541 Promoter Family Member (U073O11 + D026O22) | ... gtaattgtaagcgcttacaattggatccgg |
| BBa_I732428 | SEQ ID NO: 542 Promoter Family Member (U073O11 + D038O22) | ...tcaattgtaagcgcttacaattggatccgg |
| BBa_I732429 | SEQ ID NO: 543 Promoter Family Member (U073O11 + D050O22) | ... aaaattgtaagcgcttacaattggatccgg |
| BBa_I732430 | SEQ ID NO: 544 Promoter Family Member (U073O11 + D062O22) | ... caaattgtaagcgcttacaattggatccgg |
| BBa_I732431 | SEQ ID NO: 545 Promoter Family Member (U061O11 + D002O22) | ... gaaattgtaagcgcttacaattggatccgg |
| BBa_I732432 | SEQ ID NO: 546 Promoter Family Member (U061O11 + D014O22) | ...taaattgtaagcgcttacaattggatccgg |
| BBa_I732433 | SEQ ID NO: 547 Promoter Family Member (U061O11 + D026O22) | ... gtaattgtaagcgcttacaattggatccgg |
| BBa_I732434 | SEQ ID NO: 548 Promoter Family Member (U061O11 + D038O22) | ...tcaattgtaagcgcttacaattggatccgg |
| BBa_I732435 | SEQ ID NO: 549 Promoter Family Member (U061O11 + D050O22) | ... aaaattgtaagcgcttacaattggatccgg |
| BBa_I732436 | SEQ ID NO: 550 Promoter Family Member (U061O11 + D062O22) | ... caaattgtaagcgcttacaattggatccgg |
| BBa_I732437 | SEQ ID NO: 551 Promoter Family Member (U049O11 + D002O22) | ... gaaattgtaagcgcttacaattggatccgg |
| BBa_I732438 | SEQ ID NO: 552 Promoter Family Member (U049O11 + D014O22) | ...taaattgtaagcgcttacaattggatccgg |
| BBa_I732439 | SEQ ID NO: 553 Promoter Family Member (U049O11 + D026O22) | ... gtaattgtaagcgcttacaattggatccgg |
| BBa_I732440 | SEQ ID NO: 554 Promoter Family Member (U049O11 + D038O22) | ...tcaattgtaagcgcttacaattggatccgg |
| BBa_I732441 | SEQ ID NO: 555 Promoter Family Member (U049O11 + D050O22) | ... aaaattgtaagcgcttacaattggatccgg |
| BBa_I732442 | SEQ ID NO: 556 Promoter Family Member (U049O11 + D062O22) | ... caaattgtaagcgcttacaattggatccgg |
| BBa_I732443 | SEQ ID NO: 557 Promoter Family Member (U037O11 + D002O22) | ... gaaattgtaagcgcttacaattggatccgg |
| BBa_I732444 | SEQ ID NO: 558 Promoter Family Member (U037O11 + D014O22) | ...taaattgtaagcgcttacaattggatccgg |

TABLE 25-continued

Examples of Negatively regulated (repressible) *E. coli* σ70 promoters

| Name | Description | Promoter Sequence |
|---|---|---|
| BBa_I732445 | SEQ ID NO: 559 Promoter Family Member (U037O11 + D026O22) | ... gtaattgtaagcgcttacaattggatccgg |
| BBa_I732446 | SEQ ID NO: 560 Promoter Family Member (U037O11 + D038O22) | ...tcaattgtaagcgcttacaattggatccgg |
| BBa_I732447 | SEQ ID NO: 561 Promoter Family Member (U037O11 + D050O22) | ... aaaattgtaagcgcttacaattggatccgg |
| BBa_I732448 | SEQ ID NO: 562 Promoter Family Member (U037O11 + D062O22) | ... caaattgtaagcgcttacaattggatccgg |
| BBa_I732450 | SEQ ID NO: 563 Promoter Family Member (U073O26 + D062NUL) | ... gccaaattaaacaggattaacaggatccgg |
| BBa_I732451 | SEQ ID NO: 564 Promoter Family Member (U073O27 + D062NUL) | ... gccaaattaaacaggattaacaggatccgg |
| BBa_I732452 | SEQ ID NO: 565 (U073O26 + D062O61) Promoter Family Member | ... caaattatgagcgctcacaattggatccgg |
| BBa_I739101 | SEQ ID NO: 566 Double Promoter (constitutive/ TetR, negative) | ...tgatagagattccctatcagtgatagagat |
| BBa_I739102 | SEQ ID NO: 567 Double Promoter (cI, negative/ TetR, negative) | ...tgatagagattccctatcagtgatagagat |
| BBa_I739103 | SEQ ID NO: 568 Double Promoter (lacI, negative/ P22 cII, negative) | ...gttctttaattatttaagtgttctttaatt |
| BBa_I739104 | SEQ ID NO: 569 Double Promoter (LuxR/HSL, positive/P22 cII, negative) | ...gttctttaattatttaagtgttctttaatt |
| BBa_I739105 | SEQ ID NO: 570 Double Promoter (LuxR/HSL, positive/cI, negative) | ... cgtgcgtgttgataacaccgtgcgtgttga |
| BBa_I739106 | SEQ ID NO: 571 Double Promoter (TetR, negative/ P22 cII, negative) | ...gtgttctttaatatttaagtgttctttaat |
| BBa_I739107 | SEQ ID NO: 572 Double Promoter (cI, negative/ LacI, negative) | ... ggaattgtgagcggataacaatttcacaca |
| BBa_I746665 | SEQ ID NO: 573 Pspac-hy promoter | ...tgtgtgtaattgtgagcggataacaattaa |
| BBa_I751500 | SEQ ID NO: 574 pcI (for positive control of pcI-lux hybrid promoter) | ...ttttacctctggcggtgataatggttgcag |
| BBa_I751501 | SEQ ID NO: 575 plux-cI hybrid promoter | ...gtgttgatgcttttatcaccgccagtggta |
| BBa_I751502 | SEQ ID NO: 576 plux-lac hybrid promoter | ... agtgtgtggaattgtgagcggataacaatt |
| BBa_I756014 | SEQ ID NO: 577 LexAoperator-MajorLatePromoter | ... agggggtgggggcgcgttggcgcgccacac |
| BBa_I761011 | SEQ ID NO: 578 CinR, CinL and glucose controlled promoter | ...acatcttaaaagttttagtatcatattcgt |
| BBa_J05209 | SEQ ID NO: 579 Modified Pr Promoter | ...tattttacctctggcggtgataatggttgc |
| BBa_J05210 | SEQ ID NO: 580 Modified Prm + Promoter | ...atttataaatagtggtgatagatttaacgt |
| BBa_J07019 | SEQ ID NO: 581 FecA Promoter (with Fur box) | ...acccttctcgttcgactcatagctgaacac |
| BBa_J15301 | SEQ ID NO: 582 Pars promoter from *Escherichia coli* chromosomal ars operon. | ... tgacttatccgcttcgaagagagacactac |
| BBa_J22052 | SEQ ID NO: 583 Pcya | ...aggtgttaaattgatcacgttttagaccat |
| BBa_J22106 | SEQ ID NO: 584 rec A (SOS) Promoter | ...caatttggtaaaggctccatcatgtaataa |
| BBa_J22126 | SEQ ID NO: 585 Rec A (SOS) promoter | ... gagaaacaatttggtaaaggctccatcatg |
| BBa_J31013 | SEQ ID NO: 586 pLac Backwards [cf. BBa_R0010] | ... aacgcgcggggagaggcggtttgcgtattg |

TABLE 25-continued

Examples of Negatively regulated (repressible) *E. coli* σ70 promoters

| Name | Description | Promoter Sequence |
| --- | --- | --- |
| BBa_J34800 | SEQ ID NO: 587 Promoter tetracycline inducible | ... cagtgatagagatactgagcacatcagcac |
| BBa_J34806 | SEQ ID NO: 588 promoter lac induced | ...ttatgcttccggctcgtataatgtttcaaa |
| BBa_J34809 | SEQ ID NO: 589 promoter lac induced | ... ggctcgtatgttgtgtcgaccgagctgcgc |
| BBa_J54016 | SEQ ID NO: 590 promoter_lacq | ... aaacctttcgcggtatggcatgatagcgcc |
| BBa_J54120 | SEQ ID NO: 591 EmrR_regulated promoter | ...atttgtcactgtcgttactatatcggctgc |
| BBa_J54130 | SEQ ID NO: 592 BetI_regulated promoter | ...gtccaatcaataaccgctttaatagataaa |
| BBa_J56012 | SEQ ID NO: 593 Invertible sequence of dna includes Ptrc promoter | ...actttattatcaataagttaaatcggtacc |
| BBa_J64065 | SEQ ID NO: 594 cI repressed promoter | ...gtgttgactattttacctctggcggtgata |
| BBa_J64067 | SEQ ID NO: 595 LuxR + 3OC6HSL independent R0065 | ...gtgttgactattttacctctggcggtgata |
| BBa_J64068 | SEQ ID NO: 596 increased strength R0051 | ...atacctctggcggtgatatataatggttgc |
| BBa_J64069 | SEQ ID NO: 597 R0065 with lux box deleted | ...gtgttgactattttacctctggcggtgata |
| BBa_J64712 | SEQ ID NO: 598 LasR/LasI Inducible & RHLR/RHLI repressible Promoter | ... gaaatctggcagtttttggtacacgaaagc |
| BBa_J64800 | SEQ ID NO: 599 RHLR/RHLI Inducible & LasR/LasI repressible Promoter | ... tgccagttctggcaggtctaaaaagtgttc |
| BBa_J64981 | SEQ ID NO: 600 OmpR-P strong binding, regulatory region for Team Challenge03-2007 | ...agcgctcacaatttaatacgactcactata |
| BBa_J64987 | SEQ ID NO: 601 LacI Consensus Binding Site in sigma 70 binding region | ...taataattgtgagcgctcacaattttgaca |
| BBa_J72005 | SEQ ID NO: 602 {Piet} promoter in BBb | ... atccctatcagtgatagagatactgagcac |
| BBa_K086017 | SEQ ID NO: 603 unmodified Lutz-Bujard LacO promoter | ... ttgtgagcggataacaagatactgagcaca |
| BBa_K091100 | SEQ ID NO: 604 pLac_lux hybrid promoter | ... ggaattgtgagcggataacaatttcacaca |
| BBa_K091101 | SEQ ID NO: 605 pTet_Lac hybrid promoter | ... ggaattgtgagcggataacaatttcacaca |
| BBa_K091104 | SEQ ID NO: 606 pLac/Mnt Hybrid Promoter | ... ggaattgtgagcggataacaatttcacaca |
| BBa_K091105 | SEQ ID NO: 607 pTet/Mnt Hybrid Promoter | ... agaactgtaatccctatcagtgatagagat |
| BBa_K091106 | SEQ ID NO: 608 LsrA/cI hybrid promoter | ...tgttgatttatctaacaccgtgcgtgttga |
| BBa_K091107 | SEQ ID NO: 609 pLux/cI Hybrid Promoter | ... acaccgtgcgtgttgatatagtcgaataaa |
| BBa_K091110 | SEQ ID NO: 610 LacI Promoter | ... cctttcgcggtatggcatgatagcgcccgg |
| BBa_K091111 | SEQ ID NO: 611 LacIQ promoter | ... cctttcgcggtatggcatgatagcgcccgg |
| BBa_K091112 | SEQ ID NO: 612 pLacIQ1 promoter | ... cctttcgcggtatggcatgatagcgcccgg |
| BBa_K091143 | SEQ ID NO: 613 pLas/cI Hybrid Promoter | ...ggttatttttggtacctctggcggtgataa |
| BBa_K091146 | SEQ ID NO: 614 pLas/Lux Hybrid Promoter | ...tgtaggatcgtacaggtataaattcttcag |

TABLE 25-continued

Examples of Negatively regulated (repressible) *E. coli* σ70 promoters

| Name | Description | Promoter Sequence |
|---|---|---|
| BBa_K091157 | SEQ ID NO: 615 pLux/Las Hybrid Promoter | ...ctatctcatttgctagtatagtcgaataaa |
| BBa_K093000 | SEQ ID NO: 616 pRecA with LexA binding site | ...gtatatatatacagtataattgcttcaaca |
| BBa_K093008 | SEQ ID NO: 617 reverse BBa_R0011 | ...cacaatgtcaattgttatccgctcacaatt |
| BBa_K094120 | SEQ ID NO: 618 pLacI/ara-1 | ... aattgtgagcggataacaatttcacacaga |
| BBa_K094140 | SEQ ID NO: 619 pLacIq | ... ccggaagagagtcaattcagggtggtgaat |
| BBa_K101000 | SEQ ID NO: 620 Dual-Repressed Promoter for p22 mnt and TetR | ... acggtgacctagatctccgatactgagcac |
| BBa_K101001 | SEQ ID NO: 621 Dual-Repressed Promoter for LacI and LambdacI | ... tggaattgtgagcggataaaatttcacaca |
| BBa_K101002 | SEQ ID NO: 622 Dual-Repressed Promoter for p22 cII and TetR | ...tagtagataatttaagtgttctttaatttc |
| BBa_K101017 | SEQ ID NO: 623 MioC Promoter (DNAa-Repressed Promoter) | ... ccaacgcgttcacagcgtacaattactagt |
| BBa_K109200 | SEQ ID NO: 624 AraC and TetR promoter (hybrid) | ... aacaaaaaaacggatcctctagttgcggcc |
| BBa_K112118 | SEQ ID NO: 625 rrnB P1 promoter | ... ataaatgcttgactctgtagcgggaaggcg |
| BBa_K112318 | SEQ ID NO: 626 {<bolA promoter>} in BBb format | ... atttcatgatgatacgtgagcggatagaag |
| BBa_K112401 | SEQ ID NO: 627 Promoter for recA gene - SOS and Ultrasound Sensitive | ... caaacagaaagcgttggcggcagcactggg |
| BBa_K112402 | SEQ ID NO: 628 promoter for FabA gene - Membrane Damage and Ultrasound Sensitive | ... gtcaaaatgaccgaaacgggtggtaacttc |
| BBa_K112405 | SEQ ID NO: 629 Promoter for CadA and CadB genes | ...agtaatcttatcgccagtttggtctggtca |
| BBa_K112406 | SEQ ID NO: 630 cadC promoter | ...agtaatcttatcgccagtttggtctggtca |
| BBa_K112701 | SEQ ID NO: 631 hns promoter | ...aattctgaacaacatccgtactcttcgtgc |
| BBa_K112708 | SEQ ID NO: 632 PfhuA | ...tttacgttatcattcactttacatcagagt |
| BBa_K113009 | SEQ ID NO: 633 pBad/araC | ...gtttctccatacccgtttttttgggctagc |
| BBa_K116001 | SEQ ID NO: 634 nhaA promoter that can be regulated by pH and nhaR protein. | ... cgatctattcacctgaaagagaaataaaaa |
| BBa_K116500 | SEQ ID NO: 635 OmpF promoter that is activated or repressed by OmpR according to osmolarity. | ... aaacgttagtttgaatggaaagatgcctgc |
| BBa_K119002 | SEQ ID NO: 636 RcnR operator (represses RcnA) | ...attgccgaattaatactaagaattattatc |
| BBa_K121011 | SEQ ID NO: 637 promoter (lacI regulated) | ... acaggaaacagctatgaccatgattacgcc |
| BBa_K121014 | SEQ ID NO: 638 promoter (lambda cI regulated) | ... actggcggttataatgagcacatcagcagg |
| BBa_K137046 | SEQ ID NO: 639 150 bp inverted tetR promoter | ... caccgacaaacaacagataaaacgaaaggc |
| BBa_K137047 | SEQ ID NO: 640 250 bp inverted tetR promoter | ...agtgttattaagctactaaagcgtagtttt |
| BBa_K137048 | SEQ ID NO: 641 350 bp inverted tetR promoter | ... gaataagaaggctggctctgcaccttggtg |
| BBa_K137049 | SEQ ID NO: 642 450 bp inverted tetR promoter | ...ttagcgacttgatgctcttgatcttccaat |
| BBa_K137050 | SEQ ID NO: 643 650 bp inverted tetR promoter | ...acatctaaaacttttagcgttattacgtaa |

TABLE 25-continued

| Examples of Negatively regulated (repressible) *E. coli* σ70 promoters | | |
|---|---|---|
| Name | Description | Promoter Sequence |
| BBa_K137051 | SEQ ID NO: 644 850 bp inverted tetR promoter | ... ttccgacctcattaagcagctctaatgcgc |
| BBa_K137124 | SEQ ID NO: 645 LacI-repressed promoter A81 | ...caatttttaaacctgtaggatcgtacaggt |
| BBa_K137125 | SEQ ID NO: 646 LacI-repressed promoter B4 | ...caatttttaaaattaaaggcgttacccaac |
| BBa_K145150 | SEQ ID NO: 647 Hybrid promoter: HSL-LuxR activated, P22 C2 repressed | ...tagtttataatttaagtgttctttaatttc |
| BBa_K145152 | SEQ ID NO: 648 Hybrid promoter: P22 c2, LacI NOR gate | ... gaaaatgtgagcgagtaacaacctcacaca |
| BBa_K256028 | SEQ ID NO: 649 placI: CHE | ...caccttcgggtgggcctttctgcgtttata |
| BBa_K259005 | SEQ ID NO: 650 AraC Rheostat Promoter | ...ttttatcgcaactctctactgtttctccat |
| BBa_K259007 | SEQ ID NO: 651 AraC Promoter fused with RBS | ... gtttctccattactagagaaagaggggaca |
| BBa_K266001 | SEQ ID NO: 652 Inverter TetR -> LuxR | ...caccttcgggtgggcctttctgcgtttata |
| BBa_K266003 | SEQ ID NO: 653 POPS -> Lac Inverter -> LasR | ...caccttcgggtgggcctttctgcgtttata |
| BBa_K266004 | SEQ ID NO: 654 Const Lac Inverter -> LasR | ...caccttcgggtgggcctttctgcgtttata |
| BBa_K266005 | SEQ ID NO: 655 PAI + LasR -> LasI & AI + LuxR--\| LasI | ...aataactctgatagtgctagtgtagatctc |
| BBa_K266006 | SEQ ID NO: 656 PAI + LasR -> LasI + GFP & AI + LuxR--\|LasI + GFP | ...caccttcgggtgggcctttctgcgtttata |
| BBa_K266007 | SEQ ID NO: 657 Complex QS -> LuxI & LasI circuit | ...caccttcgggtgggcctttctgcgtttata |
| BBa_K266008 | SEQ ID NO: 658 J23100 + Lac inverter | ... ttgtgagcggataacaagatactgagcaca |
| BBa_K266009 | SEQ ID NO: 659 J23100 + Lac inverter + RBS | ... actgagcacatactagagaaagaggagaaa |
| BBa_K266011 | SEQ ID NO: 660 Lac Inverter and strong RBS | ... actgagcacatactagagaaagaggagaaa |
| BBa_K292002 | SEQ ID NO: 661 pLac (LacI regulated) + Strong RBS | ... tcacacatactagagattaaagaggagaaa |
| BBa_M31370 | SEQ ID NO: 662 tacI Promoter | ... ggaattgtgagcggataacaatttcacaca |
| BBa_R0010 | SEQ ID NO: 663 promoter (lacI regulated) | ... ggaattgtgagcggataacaatttcacaca |
| BBa_R0011 | SEQ ID NO: 664 Promoter (lacI regulated, lambda pL hybrid) | ... ttgtgagcggataacaagatactgagcaca |
| BBa_R0040 | SEQ ID NO: 665 TetR repressible promoter | ... atccctatcagtgatagagatactgagcac |
| BBa_R0050 | SEQ ID NO: 666 Promoter (HK022 cI regulated) | ... ccgtcataatatgaaccataagttcaccac |
| BBa_R0051 | SEQ ID NO: 667 promoter (lambda cI regulated) | ...tattttacctctggcggtgataatggttgc |
| BBa_R0052 | SEQ ID NO: 668 Promoter (434 cI regulated) | ...attgtatgaaaatacaagaaagtttgttga |
| BBa_R0053 | SEQ ID NO: 669 Promoter (p22 cII regulated) | ...tagtagataatttaagtgttattaatttc |
| BBa_R0061 | SEQ ID NO: 670 Promoter (HSL-mediated luxR repressor) | ttgacacctgtaggatcgtacaggtataat |
| BBa_R0063 | SEQ ID NO: 671 Promoter (luxR & HSL regulated -- lux pL) | ... cacgcaaaacttgcgacaaacaataggtaa |
| BBa_R0065 | SEQ ID NO: 672 Promoter (lambda cI and luxR regulated -- hybrid) | ...gtgttgactattttacctctggcggtgata |

TABLE 25-continued

| Examples of Negatively regulated (repressible) *E. coli* σ70 promoters | | |
|---|---|---|
| Name | Description | Promoter Sequence |
| BBa_R0073 | SEQ ID NO: 673 Promoter (Mnt regulated) | ...tagatctcctatagtgagtcgtattaattt |
| BBa_R0074 | SEQ ID NO: 674 Promoter (PenI regulated) | ...tactttcaaagactacatttgtaagatttg |
| BBa_R0075 | SEQ ID NO: 675 Promoter (TP901 cI regulated) | ... cataaagttcatgaaacgtgaactgaaatt |
| BBa_R1050 | SEQ ID NO: 676 Promoter, Standard (HK022 cI regulated) | ... ccgtgatactatgaaccataagttcaccac |
| BBa_R1051 | SEQ ID NO: 677 Promoter, Standard (lambda cI regulated) | ...aattttacctctggcggtgatactggttgc |
| BBa_R1052 | SEQ ID NO: 678 Promoter, Standard (434 cI regulated) | ...attgtatgatactacaagaaagtttgttga |
| BBa_R1053 | SEQ ID NO: 679 Promoter, Standard (p22 cII regulated) | ...tagtagatactttaagtgttctttaatttc |
| BBa_R2000 | SEQ ID NO: 680 Promoter, Zif23 regulated, test: between | ... tggtcccacgcgcgtgggatactacgtcag |
| BBa_R2001 | SEQ ID NO: 681 Promoter, Zif23 regulated, test: after | ... attacggtgagatactcccacgcgcgtggg |
| BBa_R2002 | SEQ ID NO: 682 Promoter, Zif23 regulated, test: between and after | ... acgcgcgtgggatactcccacgcgcgtggg |
| BBa_R2108 | SEQ ID NO: 683 Promoter with operator site for C2003 | ...gattagattcataaatttgagagaggagtt |
| BBa_R2109 | SEQ ID NO: 684 Promoter with operator site for C2003 | ...acttagattcataaatttgagagaggagtt |
| BBa_R2110 | SEQ ID NO: 685 Promoter with operator site for C2003 | ...ggttagattcataaatttgagagaggagtt |
| BBa_R2111 | SEQ ID NO: 686 Promoter with operator site for C2003 | ...acttagattcataaatttgagagaggagtt |
| BBa_R2112 | SEQ ID NO: 687 Promoter with operator site for C2003 | ...aattagattcataaatttgagagaggagtt |
| BBa_R2113 | SEQ ID NO: 688 Promoter with operator site for C2003 | ...acttagattcataaatttgagagaggagtt |
| BBa_R2114 | SEQ ID NO: 689 Promoter with operator site for C2003 | ...atttagattcataaatttgagagaggagtt |
| BBa_R2201 | SEQ ID NO: 690 C2006-repressible promoter | ... cacgcgcgtgggaatgttataatacgtcag |
| BBa_S04209 | SEQ ID NO: 691 R0051:Q04121:B0034:C0079:B0015 | ... actgagcacatactagagaaagaggagaaa |

TABLE 26

| Examples of Negatively regulated (repressible) *E. coli* $\sigma^s$ promoters | | |
|---|---|---|
| Name | Description | Promoter Sequence |
| BBa_K086030 | SEQ ID NO: 692 modified Lutz-Bujard LacO promoter, with alternative sigma factor σ38 | ... cagtgagcgagtaacaactacgctgtttta |
| BBa_K086031 | SEQ ID NO: 693 modified Lutz-Bujard LacO promoter, with alternative sigma factor σ38 | ... cagtgagcgagtaacaactacgctgtttta |
| BBa_K086032 | SEQ ID NO: 694 modified Lutz-Bujard LacO promoter, with alternative sigma factor σ38 | ... atgtgagcggataacactataattaataga |

TABLE 26-continued

Examples of Negatively regulated (repressible) *E. coli* $\sigma^s$ promoters

| Name | Description | Promoter Sequence |
|---|---|---|
| BBa_K086033 | SEQ ID NO: 695 modified Lutz-Bujard LacO promoter, with alternative sigma factor σ38 | ... atgtgagcggataacactataattaataga |
| BBa_K112318 | SEQ ID NO: 696 {<bolA promoter>} in BBb format | ... atttcatgatgatacgtgagcggatagaag |

TABLE 27

Examples of Negatively regulated (repressible) *E. coli* σ32 promoters

| Name | Description | Promoter Sequence |
|---|---|---|
| BBa_K086026 | SEQ ID NO: 697 modified Lutz-Bujard LacO promoter, with alternative sigma factor σ32 | ... ttgtgagcgagtggcaccattaagtacgta |
| BBa_K086027 | SEQ ID NO: 698 modified Lutz-Bujard LacO promoter, with alternative sigma factor σ32 | ... ttgtgagcgagtgacaccattaagtacgta |
| BBa_K086028 | SEQ ID NO: 699 modified Lutz-Bujard LacO promoter, with alternative sigma factor σ32 | ... ttgtgagcgagtaacaccattaagtacgta |
| BBa_K086029 | SEQ ID NO: 700 modified Lutz-Bujard LacO promoter, with alternative sigma factor σ32 | ... ttgtgagcgagtaacaccattaagtacgta |

TABLE 28

Examples of Negatively regulated (repressible) *E. coli* σ54 promoters

| Name | Description | Promoter Sequence |
|---|---|---|
| BBa_J64979 | SEQ ID NO: 701 glnAp2 | ...agttggcacagatttcgctttatcttttt |

TABLE 29

Examples of Repressible *B. subtilis* $\sigma^A$ promoters

| Name | Description | Promoter Sequence |
|---|---|---|
| BBa_K090501 | SEQ ID NO: 702 Gram-Positive IPTG-Inducible Promoter | ... tggaattgtgagcggataacaattaagctt |
| BBa_K143014 | SEQ ID NO: 703 Promoter Xyl for *B. subtilis* | ... agtttgtttaaacaacaaactaataggtga |
| BBa_K143015 | SEQ ID NO: 704 Promoter hyper-spank for *B. subtilis* | ... aatgtgtgtaattgtgagcggataacaatt |

TABLE 30

Examples of T7 Repressible Promoters

| Name | Description | Promoter Sequence |
|---|---|---|
| BBa_R0184 | SEQ ID NO: 705 T7 promoter (lacI repressible) | .. ataggggaattgtgagcggataacaattcc |
| BBa_R0185 | SEQ ID NO: 706 T7 promoter (lacI repressible) | ... ataggggaattgtgagcggataacaattcc |

TABLE 30-continued

| Examples of T7 Repressible Promoters | | |
|---|---|---|
| Name | Description | Promoter Sequence |
| BBa_R0186 | SEQ ID NO: 707 T7 promoter (lacI repressible) | ... ataggggaattgtgagcggataacaattcc |
| BBa_R0187 | SEQ ID NO: 708 T7 promoter (lacI repressible) | ... ataggggaattgtgagcggataacaattcc |

TABLE 31

| Examples of Yeast Repressible Promoters | | |
|---|---|---|
| Name | Description | Promoter Sequence |
| BBa_I766558 | SEQ ID NO: 709 pFig1 (Inducible) Promoter | ... aaacaaacaaacaaaaaaaaaaaaaaaaaa |
| BBa_I766214 | SEQ ID NO: 710 pGal1 | ...atactttaacgtcaaggagaaaaaactata |
| BBa_K165000 | SEQ ID NO: 711 MET 25 Promoter | ...tagatacaattctattacccccatccatac |

TABLE 32

| Examples of Eukaryotic Repressible Promoters | | |
|---|---|---|
| Name | Description | Promoter Sequence |
| BBa_I756015 | SEQ ID NO: 712 CMV Promoter with lac operator sites | ...ttagtgaaccgtcagatcactagtctgcag |
| BBa_I756016 | SEQ ID NO: 713 CMV-tet promoter | ...ttagtgaaccgtcagatcactagtctgcag |
| BBa_I756017 | SEQ ID NO: 714 U6 promoter with tet operators | ... ggaaaggacgaaacaccgactagtctgcag |
| BBa_I756018 | SEQ ID NO: 715 Lambda Operator in SV-40 intron | ...attgtttgtgtattttagactagtctgcag |
| BBa_I756019 | SEQ ID NO: 716 Lac Operator in SV-40 intron | ...attgtttgtgtattttagactagtctgcag |
| BBa_I756020 | SEQ ID NO: 717 Tet Operator in SV-40 intron | ...attgtttgtgtattttagactagtctgcag |
| BBa_I756021 | SEQ ID NO: 718 CMV promoter with Lambda Operator | ...ttagtgaaccgtcagatcactagtctgcag |

TABLE 33

| Examples of Combination Inducible & Repressible *E. coli* Promoters | | |
|---|---|---|
| Name | Description | Promoter Sequence |
| BBa_I1051 | SEQ ID NO: 719 Lux cassette right promoter | ... tgttatagtcgaatacctctggcggtgata |
| BBa_I12006 | SEQ ID NO: 720 Modified lambda Prm promoter (repressed by 434 cI) | ...attacaaactttcttgtatagatttaacgt |
| BBa_I12036 | SEQ ID NO: 721 Modified lambda Prm promoter (cooperative repression by 434 cI) | ...tttcttgtatagatttacaatgtatcttgt |
| BBa_I12040 | SEQ ID NO: 722 modified lambda P(RM) promoter: -10 region from P(L) and cooperatively repressed by 434 cI | ...tttcttgtagatacttacaatgtatcttgt |

TABLE 33-continued

Examples of Combination Inducible & Repressible *E. coli* Promoters

| Name | Description | Promoter Sequence |
|---|---|---|
| BBa_I14015 | SEQ ID NO: 723 P(Las) TetO | ... ttttggtacactccctatcagtgatagaga |
| BBa_I14016 | SEQ ID NO: 724 P(Las) CIO | ... ctttttggtacactacctctggcggtgata |
| BBa_I714924 | SEQ ID NO: 725 RecA DlexO_DLacO1 | ... actctcggcatggacgagctgtacaagtaa |
| BBa_I731004 | SEQ ID NO: 726 FecA promoter | ... ttctcgttcgactcatagctgaacacaaca |
| BBa_I732301 | SEQ ID NO: 727 NAND Candidate (U073O26D001O16) | ... ggaattgtgagcgctcataattggatccgg |
| BBa_I732302 | SEQ ID NO: 728 NAND Candidate (U073O27D001O17) | ... ggaattgtgagctacagtcgtcggatccgg |
| BBa_I732303 | SEQ ID NO: 729 NAND Candidate (U073O22D001O46) | ... ggaattgtgaacgctcataattggatccgg |
| BBa_I732304 | SEQ ID NO: 730 NAND Candidate (U073O22D001O47) | ... ggaattgtgaactacagtcgtcggatccgg |
| BBa_I732305 | SEQ ID NO: 731 NAND Candidate (U073O22D059O46) | ... taaattgtgaacgctcataattggatccgg |
| BBa_I732306 | SEQ ID NO: 732 NAND Candidate (U073O11D002O22) | ... gaaattgtaagcgcttacaattggatccgg |
| BBa_I732351 | SEQ ID NO: 733 NOR Candidate (U037O11D002O22) | ... gaaattgtaagcgcttacaattggatccgg |
| BBa_I732352 | SEQ ID NO: 734 NOR Candidate (U035O44D001O22) | ... ggaattgtaagcgcttacaattggatccgg |
| BBa_I732400 | SEQ ID NO: 735 Promoter Family Member (U097NUL + D062NUL) | ... gccaaattaaacaggattaacaggatccgg |
| BBa_I732401 | SEQ ID NO: 736 Promoter Family Member (U097O11 + D062NUL) | ... gccaaattaaacaggattaacaggatccgg |
| BBa_I732402 | SEQ ID NO: 737 Promoter Family Member (U085O11 + D062NUL) | ... gccaaattaaacaggattaacaggatccgg |
| BBa_I732403 | SEQ ID NO: 738 Promoter Family Member (U073O11 + D062NUL) | ... gccaaattaaacaggattaacaggatccgg |
| BBa_I732404 | SEQ ID NO: 739 Promoter Family Member (U061O11 + D062NUL) | ... gccaaattaaacaggattaacaggatccgg |
| BBa_I732405 | SEQ ID NO: 740 Promoter Family Member (U049O11 + D062NUL) | ... gccaaattaaacaggattaacaggatccgg |
| BBa_I732406 | SEQ ID NO: 741 Promoter Family Member (U037O11 + D062NUL) | ... gccaaattaaacaggattaacaggatccgg |
| BBa_I732407 | SEQ ID NO: 742 Promoter Family Member (U097NUL + D002O22) | ... gaaattgtaagcgcttacaattggatccgg |
| BBa_I732408 | SEQ ID NO: 743 Promoter Family Member (U097NUL + D014O22) | ... taaattgtaagcgcttacaattggatccgg |
| BBa_I732409 | SEQ ID NO: 744 Promoter Family Member (U097NUL + D026O22) | ... gtaattgtaagcgcttacaattggatccgg |
| BBa_I732410 | SEQ ID NO: 745 Promoter Family Member (U097NUL + D038O22) | ... tcaattgtaagcgcttacaattggatccgg |
| BBa_I732411 | SEQ ID NO: 746 Promoter Family Member (U097NUL + D050O22) | ... aaaattgtaagcgcttacaattggatccgg |
| BBa_I732412 | SEQ ID NO: 747 Promoter Family Member (U097NUL + D062O22) | ... caaattgtaagcgcttacaattggatccgg |

TABLE 33-continued

| Examples of Combination Inducible & Repressible *E. coli* Promoters | | |
|---|---|---|
| Name | Description | Promoter Sequence |
| BBa_I732413 | SEQ ID NO: 748 Promoter Family Member (U097O11 + D002O22) | ... gaaattgtaagcgcttacaattggatccgg |
| BBa_I732414 | SEQ ID NO: 749 Promoter Family Member (U097O11 + D014O22) | ... taaattgtaagcgcttacaattggatccgg |
| BBa_I732415 | SEQ ID NO: 750 Promoter Family Member (U097O11 + D026O22) | ... gtaattgtaagcgcttacaattggatccgg |
| BBa_I732416 | SEQ ID NO: 751 Promoter Family Member (U097O11 + D038O22) | ... tcaattgtaagcgcttacaattggatccgg |
| BBa_I732417 | SEQ ID NO: 752 Promoter Family Member (U097O11 + D050O22) | ... aaaattgtaagcgcttacaattggatccgg |
| BBa_I732418 | SEQ ID NO: 753 Promoter Family Member (U097O11 + D062O22) | ... caaattgtaagcgcttacaattggatccgg |
| BBa_I732419 | SEQ ID NO: 754 Promoter Family Member (U085O11 + D002O22) | ... gaaattgtaagcgcttacaattggatccgg |
| BBa_I732420 | SEQ ID NO: 755 Promoter Family Member (U085O11 + D014O22) | ... taaattgtaagcgcttacaattggatccgg |
| BBa_I732421 | SEQ ID NO: 756 Promoter Family Member (U085O11 + D026O22) | ... gtaattgtaagcgcttacaattggatccgg |
| BBa_I732422 | SEQ ID NO: 757 Promoter Family Member (U085O11 + D038O22) | ... tcaattgtaagcgcttacaattggatccgg |
| BBa_I732423 | SEQ ID NO: 758 Promoter Family Member (U085O11 + D050O22) | ... aaaattgtaagcgcttacaattggatccgg |
| BBa_I732424 | SEQ ID NO: 759 Promoter Family Member (U085O11 + D062O22) | ... caaattgtaagcgcttacaattggatccgg |
| BBa_I732425 | SEQ ID NO: 760 Promoter Family Member (U073O11 + D002O22) | ... gaaattgtaagcgcttacaattggatccgg |
| BBa_I732426 | SEQ ID NO: 761 Promoter Family Member (U073O11 + D014O22) | ... taaattgtaagcgcttacaattggatccgg |
| BBa_I732427 | SEQ ID NO: 762 Promoter Family Member (U073O11 + D026O22) | ... gtaattgtaagcgcttacaattggatccgg |
| BBa_I732428 | SEQ ID NO: 763 Promoter Family Member (U073O11 + D038O22) | ... tcaattgtaagcgcttacaattggatccgg |
| BBa_I732429 | SEQ ID NO: 764 Promoter Family Member (U073O11 + D050O22) | ... aaaattgtaagcgcttacaattggatccgg |
| BBa_I732430 | SEQ ID NO: 765 Promoter Family Member (U073O11 + D062O22) | ... caaattgtaagcgcttacaattggatccgg |
| BBa_I732431 | SEQ ID NO: 766 Promoter Family Member (U061O11 + D002O22) | ... gaaattgtaagcgcttacaattggatccgg |
| BBa_I732432 | SEQ ID NO: 767 Promoter Family Member (U061O11 + D014O22) | ... taaattgtaagcgcttacaattggatccgg |
| BBa_I732433 | SEQ ID NO: 768 Promoter Family Member (U061O11 + D026O22) | ... gtaattgtaagcgcttacaattggatccgg |
| BBa_I732434 | SEQ ID NO: 769 Promoter Family Member (U061O11 + D038O22) | ... tcaattgtaagcgcttacaattggatccgg |
| BBa_I732435 | SEQ ID NO: 770 Promoter Family Member (U061O11 + D050O22) | ... aaaattgtaagcgcttacaattggatccgg |
| BBa_I732436 | SEQ ID NO: 771 Promoter Family Member (U061O11 + D062O22) | ... caaattgtaagcgcttacaattggatccgg |
| BBa_I732437 | SEQ ID NO: 772 Promoter Family Member (U049O11 + D002O22) | ... gaaattgtaagcgcttacaattggatccgg |

TABLE 33-continued

| Examples of Combination Inducible & Repressible *E. coli* Promoters | | |
|---|---|---|
| Name | Description | Promoter Sequence |
| BBa_I732438 | SEQ ID NO: 773 Promoter Family Member (U049O11+D014O22) | ... taaattgtaagcgcttacaattggatccgg |
| BBa_I732439 | SEQ ID NO: 774 Promoter Family Member (U049O11 + D026O22) | ... gtaattgtaagcgcttacaattggatccgg |
| BBa_I732440 | SEQ ID NO: 775 Promoter Family Member (U049O11 + D038O22) | ... tcaattgtaagcgcttacaattggatccgg |
| BBa_I732441 | SEQ ID NO: 776 Promoter Family Member (U049O11 + D050O22) | ... aaaattgtaagcgcttacaattggatccgg |
| BBa_I732442 | SEQ ID NO: 777 Promoter Family Member (U049O11 + D062O22) | ... caaattgtaagcgcttacaattggatccgg |
| BBa_I732443 | SEQ ID NO: 778 Promoter Family Member (U037O11 + D002O22) | ... gaaattgtaagcgcttacaattggatccgg |
| BBa_I732444 | SEQ ID NO: 779 Promoter Family Member (U037O11 + D014O22) | ... taaattgtaagcgcttacaattggatccgg |
| BBa_I732445 | SEQ ID NO: 780 Promoter Family Member (U037O11 + D026O22) | ... gtaattgtaagcgcttacaattggatccgg |
| BBa_I732446 | SEQ ID NO: 781 Promoter Family Member (U037O11 + D038O22) | ... tcaattgtaagcgcttacaattggatccgg |
| BBa_I732447 | SEQ ID NO: 782 Promoter Family Member (U037O11 + D050O22) | ... aaaattgtaagcgcttacaattggatccgg |
| BBa_I732448 | SEQ ID NO: 783 Promoter Family Member (U037O11 + D062O22) | ... caaattgtaagcgcttacaattggatccgg |
| BBa_I732450 | SEQ ID NO: 784 Promoter Family Member (U073O26 + D062NUL) | ... gccaaattaaacaggattaacaggatccgg |
| BBa_I732451 | SEQ ID NO: 785 Promoter Family Member (U073O27 + D062NUL) | ... gccaaattaaacaggattaacaggatccgg |
| BBa_I732452 | SEQ ID NO: 786 Promoter Family Member (U073O26 + D062O61) | ... caaattatgagcgctcacaattggatccgg |
| BBa_I739102 | SEQ ID NO: 787 Double Promoter (cI, negative/ TetR, negative) | ... tgatagagattccctatcagtgatagagat |
| BBa_I739103 | SEQ ID NO: 788 Double Promoter (lacI, negative/P22 cII, negative) | ...gttctttaattatttaagtgttctttaatt |
| BBa_I739104 | SEQ ID NO: 789 Double Promoter (LuxR/HSL, positive/P22 cII, negative) | ...gttctttaattatttaagtgttctttaatt |
| BBa_I739105 | SEQ ID NO: 790 Double Promoter (LuxR/HSL, positive/cI, negative) | ... cgtgcgtgttgataacaccgtgcgtgttga |
| BBa_I739106 | SEQ ID NO: 791 Double Promoter (TetR, negative/P22 cII, negative) | ...gtgttctttaatatttaagtgttctttaat |
| BBa_I739107 | SEQ ID NO: 792 Double Promoter (cI, negative/ LacI, negative) | ... ggaattgtgagcggataacaatttcacaca |
| BBa_I741018 | SEQ ID NO: 793 Right facing promoter (for xylF) controlled by xylR and CRP-cAMP | ...gttacgtttatcgcggtgattgttacttat |
| BBa_I741019 | SEQ ID NO: 794 Right facing promoter (for xylA) controlled by xylR and CRP-cAMP | ... gcaaaataaaatggaatgatgaaactgggt |
| BBa_I742124 | SEQ ID NO: 795 Reverse complement Lac promoter | ... aacgcgcggggagaggcggtttgcgtattg |
| BBa_I751501 | SEQ ID NO: 796 plux-cI hybrid promoter | ... gtgttgatgcttttatcaccgccagtggta |
| BBa_I751502 | SEQ ID NO: 797 plux-lac hybrid promoter | ... agtgtgtggaattgtgagcggataacaatt |

TABLE 33-continued

| Examples of Combination Inducible & Repressible *E. coli* Promoters | | |
|---|---|---|
| Name | Description | Promoter Sequence |
| BBa_I761011 | SEQ ID NO: 798 CinR, CinL and glucose controlled promoter | ...acatcttaaaagttttagtatcatattcgt |
| BBa_I765007 | SEQ ID NO: 799 Fe and UV promoters | ... ctgaaagcgcataccgctatggagggggtt |
| BBa_J05209 | SEQ ID NO: 800 Modified Pr Promoter | ... tattttacctctggcggtgataatggttgc |
| BBa_J05210 | SEQ ID NO: 801 Modified Prm + Promoter | ...atttataaatagtggtgatagatttaacgt |
| BBa_J58100 | SEQ ID NO: 802 AND-type promoter synergistically activated by cI and CRP | ...atttataaatagtggtgatagatttaacgt |
| BBa_J64712 | SEQ ID NO: 803 LasR/LasI Inducible & RHLR/RHLI repressible Promoter | ... gaaatctggcagtttttggtacacgaaagc |
| BBa_J64800 | SEQ ID NO: 804 RHLR/RHLI Inducible & LasR/LasI repressible Promoter | ... tgccagttctggcaggtctaaaaagtgttc |
| BBa_J64804 | SEQ ID NO: 805 The promoter region (inclusive of regulator binding sites) of the B. subtilis RocDEF operon | ... cacagaacttgcatttatataaagggaaag |
| BBa_J64979 | SEQ ID NO: 806 glnAp2 | ...agttggcacagatttcgctttatcttttt |
| BBa_J64981 | SEQ ID NO: 807 OmpR-P strong binding, regulatory region for Team Challenge03-2007 | ... agcgctcacaatttaatacgactcactata |
| BBa_K091100 | SEQ ID NO: 808 pLac_lux hybrid promoter | ... ggaattgtgagcggataacaatttcacaca |
| BBa_K091101 | SEQ ID NO: 809 pTet_Lac hybrid promoter | ... ggaattgtgagcggataacaatttcacaca |
| BBa_K091104 | SEQ ID NO: 810 pLac/Mnt Hybrid Promoter | ... ggaattgtgagcggataacaatttcacaca |
| BBa_K091105 | SEQ ID NO: 811 pTet/Mnt Hybrid Promoter | ... agaactgtaatccctatcagtgatagagat |
| BBa_K091106 | SEQ ID NO: 812 LsrA/cI hybrid promoter | ...tgttgatttatctaacaccgtgcgtgttga |
| BBa_K091107 | SEQ ID NO: 813 pLux/cI Hybrid Promoter | ... acaccgtgcgtgttgatatagtcgaataaa |
| BBa_K091143 | SEQ ID NO: 814 pLas/cI Hybrid Promoter | ... ggttctttttggtacctctggcggtgataa |
| BBa_K091146 | SEQ ID NO: 815 pLas/Lux Hybrid Promoter | ... tgtaggatcgtacaggtataaattcttcag |
| BBa_K091157 | SEQ ID NO: 816 pLux/Las Hybrid Promoter | ...ctatctcatttgctagtatagtcgaataaa |
| BBa_K094120 | SEQ ID NO: 817 pLacI/ara-1 | ... aattgtgagcggataacaatttcacacaga |
| BBa_K100000 | SEQ ID NO: 818 Natural Xylose Regulated Bi-Directional Operator | ...gttacgtttatcgcggtgattgttacttat |
| BBa_K101000 | SEQ ID NO: 819 Dual-Repressed Promoter for p22 mnt and TetR | ... acggtgacctagatctccgatactgagcac |
| BBa_K101001 | SEQ ID NO: 820 Dual-Repressed Promoter for LacI and LambdacI | ... tggaattgtgagcggataaaatttcacaca |
| BBa_K101002 | SEQ ID NO: 821 Dual-Repressed Promoter for p22 cII and TetR | ...tagtagataatttaagtgttctttaatttc |
| BBa_K109200 | SEQ ID NO: 822 AraC and TetR promoter (hybrid) | ... aacaaaaaaacggatcctctagttgcggcc |
| BBa_K112118 | SEQ ID NO: 823 rrnB P1 promoter | ... ataaatgcttgactctgtagcgggaaggcg |

TABLE 33-continued

| Examples of Combination Inducible & Repressible *E. coli* Promoters | | |
|---|---|---|
| Name | Description | Promoter Sequence |
| BBa_K112318 | SEQ ID NO: 824 {<bolA promoter>} in BBb format | ... atttcatgatgatacgtgagcggatagaag |
| BBa_K112322 | SEQ ID NO: 825 {Pdps} in BBb format | ... gggacacaaacatcaagaggatatgagatt |
| BBa_K112402 | SEQ ID NO: 826 promoter for FabA gene—Membrane Damage and Ultrasound Sensitive | ... gtcaaaatgaccgaaacgggtggtaacttc |
| BBa_K112405 | SEQ ID NO: 827 Promoter for CadA and CadB genes | ... agtaatcttatcgccagtttggtctggtca |
| BBa_K112406 | SEQ ID NO: 828 cadC promoter | ... agtaatcttatcgccagtttggtctggtca |
| BBa_K112701 | SEQ ID NO: 829 hns promoter | ... aattctgaacaacatccgtactcttcgtgc |
| BBa_K116001 | SEQ ID NO: 830 nhaA promoter, that can be regulated by pH and nhaR protein. | ... cgatctattcacctgaaagagaaataaaaa |
| BBa_K116500 | SEQ ID NO: 831 OmpF promoter that is activated or repressed by OmpR according to osmolarity. | ... aaacgttagtttgaatggaaagatgcctgc |
| BBa_K121011 | SEQ ID NO: 832 promoter (lacI regulated) | ... acaggaaacagctatgaccatgattacgcc |
| BBa_K136010 | SEQ ID NO: 833 fliA promoter | ... gttcactctataccgctgaaggtgtaatgg |
| BBa_K145150 | SEQ ID NO: 834 Hybrid promoter: HSL-LuxR activated, P22 C2 repressed | ...tagtttataatttaagtgttctttaatttc |
| BBa_K145152 | SEQ ID NO: 835 Hybrid promoter: P22 c2, LacI NOR gate | ... gaaaatgtgagcgagtaacaacctcacaca |
| BBa_K259005 | SEQ ID NO: 836 AraC Rheostat Promoter | ...ttttatcgcaactctctactgtttctccat |
| BBa_K259007 | SEQ ID NO: 837 AraC Promoter fused with RBS | ... gtttctccattactagagaaagaggggaca |
| BBa_K266005 | SEQ ID NO: 838 PAI + LasR -> LasI & AI + LuxR -- LasI | ... aataactctgatagtgctagtgtagatctc |
| BBa_K266006 | SEQ ID NO: 839 PAI + LasR -> LasI + GFP & AI + LuxR -- LasI + GFP | ... caccttcgggtgggcctttctgcgtttata |
| BBa_K266007 | SEQ ID NO: 840 Complex QS -> LuxI & LasI circuit | ... caccttcgggtgggcctttctgcgtttata |
| BBa_R0065 | SEQ ID NO: 841 Promoter (lambda cI and luxR regulated -- hybrid) | ... gtgttgactattttacctctggcggtgata |

TABLE 34

| Examples of Combination Inducible & Repressible Miscellaneous Prokaryotic Promoters | | |
|---|---|---|
| Name | Description | Promoter Sequence |
| BBa_K125100 | SEQ ID NO: 842 nir promoter from *Synechocystis* sp. PCC6803 | ... cgaaacgggaaccctatattgatctctact |

TABLE 35

Examples of Combination Inducible & Repressible Miscellaneous Yeast Promoters

| Name | Description | Promoter Sequence |
|---|---|---|
| BBa_I766200 | SEQ ID NO: 843 pSte2 | ... accgttaagaaccatatccaagaatcaaaa |
| BBa_K110016 | SEQ ID NO: 844 A-Cell Promoter STE2 (backwards) | ... accgttaagaaccatatccaagaatcaaaa |
| BBa_K165034 | SEQ ID NO: 845 Zif268-HIV bs + LexA bs + mCYC promoter | ... cacaaatacacacactaaattaataactag |
| BBa_K165041 | SEQ ID NO: 846 Zif268-HIV binding sites + TEF constitutive yeast promoter | ... atacggtcaacgaactataattaactaaac |
| BBa_K165043 | SEQ ID NO: 847 Zif268-HIV binding sites + MET25 constitutive yeast promoter | ... tagatacaattctattacccccatccatac |

TABLE 36

Examples of Combination Inducible & Repressible Miscellaneous Eukaryotic Promoters

| Name | Description | Promoter Sequence |
|---|---|---|
| BBa_J05215 | SEQ ID NO: 848 Regulator for R1-CREBH | ... ggggcgagggccccgcctccggaggcgggg |
| BBa_J05216 | SEQ ID NO: 849 Regulator for R3-ATF6 | ... gaggggacggctccggccccggggccggag |
| BBa_J05217 | SEQ ID NO: 850 Regulator for R2-YAP7 | ... ggggcgagggctccggccccggggccggag |
| BBa_J05218 | SEQ ID NO: 851 Regulator for R4-cMaf | ... gaggggacggccccgcctccggaggcgggg |

In addition to the above-described promoter sequences, the cassettes and switches described herein can comprise, in addition, one or more molecular species, including, but not limited to, ribosome binding sequences, degradation tag sequences, translational terminator sequences, and anti-sense sequences, that are added to, for example, enhance translation of mRNA sequences for protein synthesis, prevent further transcription downstream of the an encoded protein, or enhance degradation of an mRNA sequence or protein sequence. Such additional molecular species, by enhancing the fidelity and accuracy of the molecular circuits described herein permit, for example, increased numbers and combinations of molecular circuits and improve the capabilities of the molecular circuits described herein. Known enhancer and repressor sequences from promoter regions or intronic regions and their corresponding regulatory proteins or RNAs can also be used to regulate, e.g., transcription.

Terminators

Provided herein are terminator sequences for use in some embodiments of the invention. A "terminator", "transcriptional terminator", "terminator sequence," as used herein, is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. A terminator may be necessary in vivo to achieve desirable output expression levels (e.g., low output levels).

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only.

In prokaryotic systems, terminators usually fall into two categories (1) rho-independent terminators and (2) rho-dependent terminators. Rho-independent terminators are generally composed of palindromic sequence that forms a stem loop rich in G-C base pairs followed by several T bases. Without wishing to be bound by theory, the conventional model of transcriptional termination is that the stem loop causes RNA polymerase to pause, and transcription of the poly-A tail causes the RNA:DNA duplex to unwind and dissociate from RNA polymerase.

In eukaryotic systems, the terminator region may comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently.

Thus, in some embodiments involving eukaryotes, a terminator may comprise a signal for the cleavage of the RNA. In some embodiments, the terminator signal promotes polyadenylation of the message. The terminator and/or polyadenylation site elements may serve to enhance output nucleic acid levels and/or to minimize read through between nucleic acids.

Terminators for use in accordance with the invention include any terminator of transcription described herein or known to one of ordinary skill in the art. Examples of terminators include, without limitation, the termination sequences of genes such as, for example, the bovine growth hormone terminator, and viral termination sequences such as, for example, the SV40 terminator, spy, yejM, secG-leuU, thrLABC, rrnB Tl, hisLGDCBHAFI, metZWV, rrnC, xapR, aspA and arcA terminator. In some embodiments, the termination signal may be a sequence that cannot be transcribed or translated, such as those resulting from a sequence truncation.

Terminators for use as molecular species in the molecular circuits and modular functional blocks described herein can be selected from the non-limiting examples of Tables 37-41.

TABLE 37

Examples of Forward Terminators

| Name | Description | Direction | Efficiency Fwd. | Efficiency Rev. | Length |
|---|---|---|---|---|---|
| BBa_B0010 | T1 from *E. coli* rrnB | Forward | | | 80 |
| BBa_B0012 | TE from coliphageT7 | Forward | 0.309[CC] | −0.368[CC] | 41 |
| BBa_B0013 | TE from coliphage T7 (+/−) | Forward | 0.6[CC] | −1.06[CC] | 47 |
| BBa_B0015 | double terminator (B0010-B0012) | Forward | 0.984[CC]<br>0.97[JK] | 0.295[CC]<br>0.62[JK] | 129 |
| BBa_B0017 | double terminator (B0010-B0010) | Forward | | | 168 |
| BBa_B0053 | Terminator (His) | Forward | | | 72 |
| BBa_B0055 | -- No description -- | | | | 78 |
| BBa_B1002 | Terminator (artificial, small, % T~=85%) | Forward | 0.98[CH] | | 34 |
| BBa_B1003 | Terminator (artificial, small, % T~=80) | Forward | 0.83[CH] | | 34 |
| BBa_B1004 | Terminator (artificial, small, % T~=55) | Forward | 0.93[CH] | | 34 |
| BBa_B1005 | Terminator (artificial, small, % T~=25% | Forward | 0.86[CH] | | 34 |
| BBa_B1006 | Terminator (artificial, large, % T~>90) | Forward | 0.99[CH] | | 39 |
| BBa_B1010 | Terminator (artificial, large, % T~<10) | Forward | 0.95[CH] | | 40 |
| BBa_I11013 | Modification of biobricks part BBa_B0015 | | | | 129 |
| BBa_I51003 | -- No description -- | | | | 110 |
| BBa_J61048 | [rnpB-T1] Terminator | Forward | 0.98[JCA] | | 113 |

TABLE 38

Examples of Bidirectional Terminators

| Name | Description | Direction | Efficiency Fwd. | Efficiency Rev. | Length |
|---|---|---|---|---|---|
| BBa_B0011 | LuxICDABEG (+/−) | Bidirectional | 0.419[CC]/<br>0.95[JK] | 0.636[CC]/<br>0.86[JK] | 46 |
| BBa_B0014 | double terminator (B0012-B0011) | Bidirectional | 0.604[CC]/<br>0.96[JK] | 0.86[JK] | 95 |
| BBa_B0021 | LuxICDABEG (+/−), reversed | Bidirectional | 0.636[CC]/<br>0.86[JK] | 0.419[CC]/<br>0.95[JK] | 46 |
| BBa_B0024 | double terminator (B0012-B0011), reversed | Bidirectional | 0.86[JK] | 0.604[CC]/<br>0.96[JK] | 95 |
| BBa_B0050 | Terminator (pBR322, +/−) | Bidirectional | | | 33 |
| BBa_B0051 | Terminator (yciA/tonA, +/−) | Bidirectional | | | 35 |
| BBa_B1001 | Terminator (artificial, small, % T~=90) | Bidirectional | 0.81[CH] | | 34 |
| BBa_B1007 | Terminator (artificial, large, % T~=80) | Bidirectional | 0.83[CH] | | 40 |
| BBa_B1008 | Terminator (artificial, large, % T~=70) | Bidirectional | | | 40 |
| BBa_B1009 | Terminator (artificial, large, % T~=40%) | Bidirectional | | | 40 |
| BBa_K259006 | GFP-Terminator | Bidirectional | 0.604[CC]/<br>0.96[JK] | 0.86[JK] | 823 |

TABLE 39

Examples of Reverse Terminators

| Name | Description | Direction | Efficiency Fwd. | Efficiency Rev. | Length |
|---|---|---|---|---|---|
| BBa_B0020 | Terminator (Reverse B0010) | Reverse | | | 82 |
| BBa_B0022 | TE from coliphageT7, reversed | Reverse | −0.368[CC] | 0.309[CC] | 41 |
| BBa_B0023 | TE from coliphage T7, reversed | Reverse | −1.06[CC] | 0.6[CC] | 47 |
| BBa_B0025 | double terminator (B0015), reversed | Reverse | 0.295[CC]/ 0.62[JK] | 0.984[CC]/ 0.97[JK] | 129 |
| BBa_B0052 | Terminator (rrnC) | Forward | | | 41 |
| BBa_B0060 | Terminator (Reverse B0050) | Bidirectional | | | 33 |
| BBa_B0061 | Terminator (Reverse B0051) | Bidirectional | | | 35 |
| BBa_B0063 | Terminator (Reverse B0053) | Reverse | | | 72 |

TABLE 40

Examples of Yeast Terminators

| Name | Description | Direction | Efficiency Fwd. | Efficiency Rev. | Length |
|---|---|---|---|---|---|
| BBa_J63002 | ADH1 terminator from *S. cerevisiae* | Forward | | | 225 |
| BBa_K110012 | STE2 terminator | Forward | | | 123 |
| BBa_Y1015 | CycE1 | | | | 252 |

TABLE 41

Examples of Eukaryotic Terminators

| Name | Description | Direction | Efficiency Fwd. | Efficiency Rev. | Chassis | Length |
|---|---|---|---|---|---|---|
| BBa_J52016 | eukaryotic - derived from SV40 early poly A signal sequence | Forward | | | | 238 |
| BBa_J63002 | ADH1 terminator from *S. cerevisiae* | Forward | | | | 225 |
| BBa_K110012 | STE2 terminator | Forward | | | | 123 |
| BBa_Y1015 | CycE1 | | | | | 252 |

Target Genes and Output Products

A variety of target genes and output products are provided for use in accordance with the invention. As used herein, "output products" refer to gene products that may be used as markers of specific states of the logic gates and systems described herein. A target gene of the invention can encode for a protein or RNA that is used to track or mark the state of the cell upon receiving a particular input. Such output products can be used to distinguish between various states (e.g., "ON" or "OFF") of a cell. Representative output products for the logic cassettes and systems of the invention include, without limitation, reporter proteins, transcriptional repressors, transcriptional activators, selection markers, enzymes, receptor proteins, ligand proteins, RNAs, riboswitches, short-hairpin RNAs and recombinases. Aspects of the invention relate to logic cassettes and systems that include a plurality of logic gates {e.g., at least two logic gates). It should be understood that in such systems, each logic gate may include one or more different output nucleic acid (e.g., that encode(s) different, or unique, output product (s)). Thus, a single cell or system may include at least 2, 3, 4, 5, 6, 7, 8, 9, 10 or more different output nucleic acids.

In some embodiments, the target gene of the invention may encode a "reporter" or "reporter molecule." Such target gene is also called the reporter gene. As used herein, a reporter refers to a protein that can be used to measure gene expression and generally produce a measurable signal such as fluorescence, luminescence or color. The presence of a reporter in a cell or organism is readily observed. For example, fluorescent proteins (e.g., GFP, red fluorescent protein such as mCherry) cause a cell to fluoresce when excited with light of a particular wavelength, luciferases cause a cell to catalyze a reaction that produces light, and enzymes such as β-galactosidase convert a substrate to a colored product. In some embodiments, reporters may be used to quantify the strength or activity of the input received by the systems of the invention. In some embodiments, reporters can be fused in-frame to other protein coding sequences to identify where a protein is located in a cell or organism. Reporters for use in accordance with the invention include any reporter described herein or known to one of ordinary skill in the art.

There are several different ways to measure or quantify a reporter depending on the particular reporter and what kind of characterization data is desired. In some embodiments, microscopy can be a useful technique for obtaining both spatial and temporal information on reporter activity, particularly at the single cell level. In some embodiments, flow cytometers can be used for measuring the distribution in reporter activity across a large population of cells. In some embodiments, plate readers may be used for taking population average measurements of many different samples over time. In some embodiments, instruments that combine such various functions, may be used, such as multiplex plate readers designed for flow cytometers, and combination microscopy and flow cytometric instruments.

Fluorescent proteins may be used for visualizing or quantifying the output of logic gates/systems. Fluorescence can be readily quantified using a microscope, plate reader or flow cytometer equipped to excite the fluorescent protein with the appropriate wavelength of light. Several different fluorescent proteins are available, thus multiple gene expression measurements can be made in parallel. Examples of genes encoding fluorescent proteins that may be used in accordance with the invention include, without limitation, those proteins provided in U.S. Patent Application No. 2012/0003630 (see Table 59), incorporated herein by reference.

Examples of UV fluorescent proteins include, but are not limited to, Sirius. Examples of blue fluorescent proteins include, but are not limited to, Azurite, EBFP2, mKalama1, mTagBFP2, and tagBFP. Examples of cyan fluorescent proteins include, but are not limited to, ECFP, Cerulean, mCerulean3, SCFP3A, CyPet, mTurquoise, mTurquoise2, TagCFP, Mtfp1, monomeric Midoriishi-Cyan, and Aquamarine. Examples of green fluorescent proteins include, but are not limited to, TurboGFP, TagGFP2, mUKG, Superfolder GFP, Emerald, EGFP, Monomeric Azami Green, mWasabi, Clover, and mNeonGreen. Examples of yellow fluorescent proteins include, but are not limited to, TagYFP, EYFP, Topaz, Venus, SYFP2, Citrine, Ypet, IanRFP-Δ583, and mPapayal. Examples of orange fluorescent proteins include, but are not limited to, Monomeric Kusabira-Orange, mOrange, mOrange2, mKOκ, and Mko2. Examples of red fluorescent proteins include, but are not limited to, TagRFP, TagRFP-T, mRuby, mRuby2, mTangerine, mApple, mStrawberry, FusionRed, mCherry, and mNectarine. Examples of far red fluorescent proteins include, but are not limited to, mKate2, HcRed-Tandem, mPlum, mRaspberry, mNeptune, NirFP, TagRFP657, TagRFP675, and mCardinal. Examples of near IR fluorescent proteins include, but are not limited to, iFP1.4, iRFP713 (iRFP), iRFP670, iRFP682, iRFP702, iRFP720, and iFP2.0. Examples of sapphire-type fluorescent proteins include, but are not limited to, Sapphire, T-Sapphire, and mAmetrine. Examples of long Stokes shift fluorescent proteins include, but are not limited to, mKeima Red, mBeRFP, LSS-mKate2, LSS-mKate1, and LSSmOrange.

Luciferases may also be used for visualizing or quantifying the output of logic gates/systems, particularly for measuring low levels of gene expression, as cells tend to have little to no background luminescence in the absence of a luciferase Luminescence can be readily quantified using a plate reader or luminescence counter. Examples of genes encoding luciferases for that may be used in accordance with the invention include, without limitation, dmMyD88-linker-Rluc, dmMyD88-linker-Rluc-linker-PEST191, *Renilla luciferase*, and firefly luciferase (from Photinus pyralis).

Enzymes that produce colored substrates ("colorimetric enzymes") may also be used for visualizing or quantifying the output of logic gates/systems. Enzymatic products may be quantified using spectrophotometers or other instruments that can take absorbance measurements including plate readers. Like luciferases, enzymes such as β-galactosidase can be used for measuring low levels of gene expression because they tend to amplify low signals. Examples of genes encoding colorimetric enzymes that may be used in accordance with the invention include, without limitation, lacZ alpha fragment, lacZ (encoding beta-galactosidase, full-length), and xylE.

In some embodiments, the reporter molecule is chloramphenicol acetyltransferase. In some embodiments, the reporter molecule is neomycin phosphotransferase. In some embodiments, the reporter molecule is Secreted Placental Alkaline Phosphatase (SEAP). In some embodiments, the reporter molecule is secreted α-amylase (SAMY).

Transcriptional Outputs

In some embodiments, the target gene of the invention may encode a transcriptional activator or repressor, the production of which by an output gene can result in a further change in state of the cell, and provide additional input signals to subsequent or additional logic gates. Transcriptional regulators either activate or repress transcription from cognate promoters. Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators serve as either an activator or a repressor depending on where it binds and cellular conditions. Transcriptional regulators for use in accordance with the invention include any transcriptional regulator described herein or known to one of ordinary skill in the art. Examples of genes encoding transcriptional regulators that may be used in accordance with the invention include, without limitation, those regulators provided in U.S. Patent Application No. 2012/0003630, incorporated herein by reference.

Selection Marker Outputs

In some embodiments, the target gene of the invention may encode a selection marker. As used herein, a "selection marker" refers to protein coding sequence that confers a selective advantage or disadvantage to a biological unit, such as a cell. For example, a common type of prokaryotic selection marker is one that confers resistance to a particular antibiotic. Thus, cells that carry the selection marker can grow in media despite the presence of antibiotic. For example, most plasmids contain antibiotic selection markers so that it is ensured that the plasmid is maintained during cell replication and division, as cells that lose a copy of the plasmid will soon either die or fail to grow in media supplemented with antibiotic. A second common type of selection marker, often termed a positive selection marker, is toxic to the cell. Positive selection markers are frequently used during cloning to select against cells transformed with the cloning vector and ensure that only cells transformed with a plasmid containing the insert. Selection markers for use in accordance with the invention include any selection marker described herein or known to one of ordinary skill in the art. Examples of genes encoding selection markers that may be used in accordance with the invention include, without limitation, those markers provided in U.S. Patent Application No. 2012/0003630, incorporated herein in its entirety by reference.

Enzyme Outputs

In some embodiments, the target gene of the invention may encode an enzyme. In some embodiments, an enzyme is used as a response to a particular input. For example, in response to a particular input received by a logic and memory system of the invention, such as a certain range of toxin concentration present in the environment, the system may turn "ON" a logic gate containing a target gene that encodes an enzyme that can degrade or otherwise destroy the toxin.

In some embodiments, output products may be "biosynthetic enzymes" that catalyze the conversion of substrates to products. For example, such biosynthetic enzymes can be used in accordance with the invention to assemble pathways that produce or degrade useful chemicals and materials, in response to specific signals. These combinations of enzymes can reconstitute either natural or synthetic biosynthetic pathways. These enzymes have applications in specialty chemicals, biofuels and bioremediation. Enzymes for use in accordance with the invention include any enzyme described herein or known to one of ordinary skill in the art. Examples of genes encoding enzymes that may be used in accordance with the invention include, without limitation, those provided in U.S. Patent Application No. 2012/0003630, incorporated herein by reference.

Receptors, Ligands and Lytic Proteins

In some embodiments, the target gene of the invention may encode a receptor, ligand or lytic protein. Receptors tend to have three domains: an extracellular domain for binding ligands such as proteins, peptides or small molecules, a transmembrane domain and an intracellular or cytoplasmic domain, which frequently can participate in some sort of signal transduction event such as phosphorylation. In some embodiments, transporters, channels or pumps are used as output products. Transporters are membrane proteins responsible for transport of substances across the cell membrane. Channels are made up of proteins that form transmembrane pores through which selected ions can diffuse.

Pumps are membrane proteins that can move substances against their gradients in an energy-dependent process known as active transport. In some embodiments, nucleic acid sequences encoding proteins and protein domains whose primary purpose is to bind other proteins, ions, small molecules, and other ligands may be used in accordance with the invention. Receptors, ligands and lytic proteins for use in accordance with the invention include any receptor, ligand and lytic protein, described herein or known to one of ordinary skill in the art.

Examples of genes encoding receptors, ligands and lytic proteins that may be used in accordance with the invention include, without limitation, those provided in U.S. Patent Application No. 2012/0003630, incorporated herein by reference.

A target gene can be any gene of interest, e.g., a gene that encodes a therapeutic protein or peptide of interest, a therapeutic protein inhibitor, miRNA, siRNA, etc., nucleic acid inhibitor (e.g., RNAi) etc., antibody or fragment thereof. Exemplary therapeutic proteins include, but are not limited to, antibodies or fragments thereof, CAR for cancer therapy as disclosed herein.

In some embodiments, the target gene of the invention may encode a RNA molecule of interest. For example, the RNA molecule of interest can be an sgRNA from the CRISPR/Cas9 system.

Genetic Engineering of Logic Gates and Systems

A cell to be engineered for use with the logic cassettes, switches, and systems of the invention may be any cell or host cell. As defined herein, a "cell" or "cellular system" is the basic structural and functional unit of all known independently living organisms. It is the smallest unit of life that is classified as a living thing. Some organisms, such as most bacteria, are unicellular (consist of a single cell). Other organisms, such as humans, are multicellular. The logic cassettes, switches, and systems described herein can be used in a cell of a variety of organisms. Preferably, the host cell is a mammalian cell. More preferably, the host cell is a human cell. The logic cassettes, switches, and systems described herein can be used in a variety of cell types. Exemplary cell types include, but are not limited to, liver cells, gastrointestinal cells, epithelial cells, endothelial cells, kidney cells, cancer cells, blood cells, stem cells, bone cells, smooth muscle cells, striated muscle cells, cardiac muscle cells, immune cells and nerve cells. Blood cells include, e.g., leukocytes, such as neutrophils, lymphocytes, monocytes, eosinophils, basophils, macrophages Immune cells include, but are not limited to, monocytes, Natural Killer (NK) cells, dendritic cells (which could be immature or mature), subsets of dendritic cells including myeloid, plasmacytoid (also called lymphoid) or Langerhans; macrophages such as histiocytes, Kupffer's cells, alveolar macrophages or peritoneal macrophages; neutrophils, eosinophils, mast cells, basophils; B cells including plasma B cells, memory B cells, B-1 cells, B-2 cells; CD45RO (naive T), CD45RA (memory T); CD4 Helper T Cells including Th1, Th2 and Tr1/Th3; CD8 Cytotoxic T Cells, Regulatory T Cells and Gamma Delta T Cells.

In some embodiments, a cell for use in accordance with the invention is an eukaryotic cell, which comprises membrane-bound compartments in which specific metabolic activities take place, such as a nucleus. Examples of eukaryotic cells for use in accordance with the invention include, without limitation, mammalian cells, insect cells, yeast cells {e.g., *Saccharomyces cerevisiae*) and plant cells. In some embodiments, the eukaryotic cells are from a vertebrate animal. Examples of vertebrate cells for use in accordance with the invention include, without limitation, reproductive cells including sperm, ova and embryonic cells, and non-reproductive cells, including kidney, lung, spleen, lymphoid, cardiac, gastric, intestinal, pancreatic, muscle, bone, neural, brain and epithelial cells. Stem cells, including embryonic stem cells, can also be used.

In some embodiments, a cell for use in accordance with the invention is a prokaryotic cell, which may comprise a cell envelope and a cytoplasmic region that contains the cell genome (DNA) and ribosomes and various sorts of inclusions. In some embodiments, the cells are bacterial cells. As used herein, the term "bacteria" encompasses all variants of bacteria, for example, prokaryotic organisms and cyanobacteria. Bacteria are small (typical linear dimensions of around 1 micron), non-compartmentalized, with circular DNA and ribosomes of 70S. The term "bacteria" also includes bacterial subdivisions of Eubacteria and Archaebacteria. Eubacteria can be further subdivided into gram-positive and gram-negative Eubacteria, which depend upon a difference in cell wall structure. Also included herein are those classified based on gross morphology alone (e.g., cocci, bacilli). In some embodiments, the bacterial cells are gram-negative cells, and in some embodiments, the bacterial cells are gram-positive cells. Examples of bacterial cells that may be used in accordance with the invention include, without limitation, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Stremtomyces* spp. In some embodiments, the bacterial cells are from *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides, cyanobacteria, Escherichia coli, Helobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus planta rum, Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferns, Lactobacillus pentosus, Bacteroides fragilis, Staphylococcus epidermidis, Zymomonas mobilis, Streptomyces phaechromo* genes, *Streptomyces ghanaenis, Halobacterium* strain GRB, or *Halobaferax* sp. strain Aa2.2.

In some embodiments, a non-cellular system such as a virus or phage may be used in accordance with the invention. For examples, any one or more component(s) of the synthetic logic and memory systems may be introduced, by direct integration of logic system nucleic acids, for example, into a viral genome. A virus for use as described herein may be a double-stranded DNA (dsDNA) virus (e.g., Adenoviruses, Herpesviruses, Poxviruses), a single-stranded DNA (ssDNA) viruses ((+)sense DNA) (e.g. Parvoviruses); a double-stranded RNA (dsRNA) virus (e.g., Reoviruses); a (+)ssRNA viruses ((+)sense RNA) (e.g. Picornaviruses, Togaviruses); (−)ssRNA virus ((−)sense RNA) (e.g., Orthomyxoviruses, Rhabdo viruses); a single-stranded RNA (ssRNA)-Reverse Transcriptase viruses ((+)sense RNA with DNA intermediate in life-cycle) (e.g., Retroviruses); or a dsDNA-Reverse Transcriptase virus (e.g., Hepadnaviruses).

Viruses may also include plant viruses and bacteriophages or phages. Examples of phage families that may be used in accordance with the invention include, without limitation, Myoviridae (T4-like viruses; P1-like viruses; P2-like viruses; Mu-like viruses; SPO1-like viruses; phiH-like viruses); Siphoviridae γ-like viruses (T1-like viruses; T5-like viruses; c2-like viruses; L5-like viruses; .psi.M1-like viruses; phiC31-like viruses; N15-like viruses); Podoviridae (T7-like viruses; phi29-like viruses; P22-like viruses; N4-like viruses); Tectiviridae (*Tecti* virus); Corticoviridae (Corticovirus); Lipothrixviridae (Alphalipothrixvirus, Betalipothrixvirus, Gammalipothrixvirus, Deltalipothrixvirus); Plasmaviridae (Plasmavirus); Rudiviridae (Rudi virus); Fuselloviridae (Fusellovirus); Inoviridae (Inovirus, Plectro virus); Microviridae (Micro virus, Spiromicro virus, Bdellomicro virus, Chlamydiamicro virus); Leviviridae (Levi virus, Allolevivirus) and Cystoviridae (Cysto virus). Such phages may be naturally occurring or engineered phages.

In some embodiments, the cell or cellular system is a "natural cell" (e.g., found in nature; not artificial or synthetic). In some embodiments, the cell or cellular system is an artificial cell or synthetic cell. As used herein, an "artificial cell" or a "synthetic cell" is a minimal cell formed from artificial parts that can function in ways that a natural cell can function (e.g., transcribe and translate proteins and generate ATP).

A host cell in accordance with the invention includes any host cell that, upon transformation or transfection with one or more component(s) of the synthetic logic system (e.g., logic gates) is capable of supporting the activation and expression of the synthetic logic and memory system component(s).

In some embodiments, one or more component(s) of the synthetic logic and memory systems of the invention may be introduced into a cellular or non-cellular system using a vector or plasmid. As used herein, a "vector" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors." In general, expression vectors described herein are often in the form of plasmids, which are circular double-stranded DNA loops not bound to chromosome. Expression vectors may be vectors for stable or transient expression of the DNA. A vector may be either a self-replicating extrachromosomal vector or a vector which integrates into a host genome. Other expression vectors may be used in accordance with the invention including, without limitation, episomes, bacteriophages and viral vectors, and such vectors can integrate into the host's genome or replicate autonomously in the particular cellular system used. Other forms of expression vectors known by those skilled in the art which serve the equivalent functions may also be used.

Vectors comprising nucleic acid sequences of the invention (e.g., those encoding logic gates) may be "introduced" into cells as polynucleotides by techniques well-known in the art for introducing DNA and RNA into cells. As used herein, "transfection" refers to the introduction of genetic material (e.g., a vector comprising nucleic acid sequences) into a cell, tissue or organism. Transfection of a cell may be stable or transient. A host cell is considered to be transiently transfected when nucleic acid is introduced into the cell and does not integrate into the host cell's genome. Transient transfection may be detected by, for example, enzyme linked immunosorbent assay (ELISA), which detects the presence of a polypeptide encoded by the nucleic acid, or it may be detected by detecting the activity of a protein encoded by the nucleic acid. By contrast, a host cell is considered to be stably transfected when nucleic acid is introduced into the cell and does integrate into the host cell's genome. Stably transfected cells pass the introduced nucleic acid to their progeny (i.e., stable heritability through meiosis). Stable transfection of a cell may be detected by Southern blot hybridization of genomic DNA of the cell with nucleic acid sequences, which are capable of binding to one or more of the transgenes, or by polymerase chain reaction of genomic DNA of the cell to amplify transgene sequences.

In some embodiments, a synthetic RNA-processing platform may be used to process mRNAs to separate the 5' untranslated region (UTR) from the downstream gene. For example, a sequence encoding a recombinase as disclosed herein may be inserted upstream (e.g., directly upstream) of the output nucleic acid to improve expression of the gene. In some embodiments, the bacterial clustered regularly interspaced short palindromic repeat (CRISPR) pathway may be used to process mRNAs to separate the 5' UTR from the downstream gene. In some embodiments, a coupled translational system with an upstream "throwaway" open reading frame (ORF) and downstream ORF may be used to generate mRNAs with more reliable and programmable translation of the downstream. Other synthetic RNA-processing platforms are also contemplated herein.

Uses of Synthetic Cassettes, Switches, and Systems

The components of the nucleic acid logic cassettes or switches shown are exemplary. One skilled in the art can readily substitute the different genetic elements such as promoters and RRS in the cassettes or switches. For example, one can readily substitute the recombinases and integrases depending on the RRS and/or the cell into which the cassette is to be inserted. The different examples of genetic elements such as promoters, RRS, and recombinases as discussed can be used in any combinations to construct a cassette or switch capable of a desirable logic function. The target genes used can readily be selected based upon the cell and desired use. For example, the target gene used in the cassettes or switches can be a regulatory gene, a marker gene, or a therapeutic gene.

The nucleic acid logic cassettes and switches of the invention can be constructed using methods known in the art. In some embodiments, a Gibson isothermal assembly method can be used.

The nucleic acid logic cassettes, switches, and systems of the invention are useful for, inter alia, engineering complex behavioral phenotypes in cellular systems, such as prokaryotic, eukaryotic and synthetic cells, or in non-cellular systems, including cell-free systems, test tubes, viruses and phages. The logic cassettes and systems described herein combine the power of nucleic acid-based engineering methods with computational and systems biology approaches for programming cellular, or biological, state machines, behaviors and pathways for therapeutic, diagnostic and basic science applications. As used herein, a "state machine" refers to any tool that stores the status (or state) of something at a given time and can operate on input(s) to change the status and/or cause an action(s) or output(s) to take place for any given change. Typically, a state machine includes a set of input events, a set of output events, a set of states, a function that maps states and input(s) to output(s), a function that maps states and inputs to new states (which is referred to as a state transition function), and a description of the initial state.

The synthetic logic cassettes, switches, systems of the invention may be used for a variety of applications and in many different types of methods, including, but not limited to, bioremediation, biosensing and biomedical therapeutics. In some embodiments, the logic and memory systems may be used to build multiplexed cellular switches for gene expression or synthetic differentiation cascades. Cellular signals can be integrated as inputs to the logic and memory systems by linking the signals to recombinase expression. Multicellular systems endowed with the synthetic logic cassettes, switches, systems of the invention may also implement distributed computation or synthetic cellular consortia.

The nucleic acid logic cassettes, switches, and systems of the invention are useful to control gene expression for cell-based immunotherapy (e.g., adoptive T-cell therapy). Exemplary target genes of interest include, but are not limited to, chimeric antigen receptor, T cell receptor, cytokines (e.g., IL-2, IL-12, IL-15), and suicide genes (e.g., HSV-TK, iCasp9).

In some embodiments, the synthetic logic cassettes, switches, and systems of the invention may also be used to build "digital-to-analog converters," which translate digital representations back into analog outputs. Such systems may be used to reliably set internal system states. For example, instead of fine-tuning transcriptional activity with varying amounts of chemical inducers, a digital-to-analog converter, composed of a bank of genetic switches (different recombinases and logic gates), each of which is sensitive to a different inducer, provides better control. By enabling, through each activated switch, transcription from promoters of varying strengths (e.g., P output,3>P output,2>P output,1), digital combinations of inducers may be used to program defined levels of transcriptional activities. Such a circuit may be used in biotechnology applications, where reliable expression of different pathways is needed for programming different modes of operation in engineered cells. In addition, digital-to-analog converters are useful for providing a multiplexed method for probing synthetic circuits. For example, because each analog level is associated with a distinct digital state, a single analog output can allow one to infer the internal digital state of a synthetic gene network.

Further, in some embodiments, the synthetic logic cassettes, switches, and systems of the invention may be used for detection of arsenic in drinking water and/or a range of toxins and/or heavy metals. The systems may be coupled to genetically engineered bacteria, which are capable of digesting and neutralizing toxins and heavy metals. This may be achieved, for example, by the bacteria sensing a specific toxin or heavy metal, and the sensor being directly linked as input for an inducible promoter that controls recombinase expression, which in turn activates the logic/memory system by flipping (e.g., activating or de-activating) the gene, promoter or terminator. As a result, the pathway that controls digesting and neutralizing toxins and heavy metals is turned on.

The methods and uses of the synthetic logic cassettes, switches, and systems of the invention may involve in vivo, ex vivo, or in vitro systems. The term "in vivo" refers to assays or processes that occur in or within an organism, such as a multicellular animal. In some embodiments, a method or use can be said to occur in vivo when a unicellular organism, such as a bacteria, is used. The term "ex vivo" refers to methods and uses that are performed using a living cell with an intact membrane that is outside of the body of a multicellular animal or plant (e.g., explants, cultured cells, including primary cells and cell lines, transformed cell lines, and extracted tissue or cells, including blood cells, among others). The term "in vitro" refers to assays and methods that do not require the presence of a cell with an intact membrane, such as cellular extracts, and may refer to introducing an engineered genetic counter in a non-cellular system, such as a media not comprising cells or cellular systems, such as cellular extracts.

It should be understood that this invention is not limited to the particular methodology, protocols, and reagents, etc., disclosed herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are disclosed herein.

Some embodiments of the invention are listed in the following numbered paragraphs:

1. A nucleic acid logic cassette comprising:
   - (i) a nucleic acid sequence encoding a mammalian promoter;
   - (ii) a first recombination unit (U1) comprising a first pair of recombinase recognition sequences (RRS1) for a first recombinase (R1), wherein each of the RRS1 flanks each side of a first nucleic acid sequence, and wherein the RRS1 are in the same orientation or in an inverse orientation with respect to each other, and wherein at least one of the RRS1 is positioned downstream of the promoter,
     whereby when the R1 recognizes the RRS1, the first nucleic acid sequence is excised when the RRS1 are in the same orientation or is inverted when the RRS1 are in the inverse orientation;
   - (iii) a second recombination unit (U2) comprising a second pair of recombinase recognition sequences (RRS2) for a second recombinase (R2), wherein each of the RRS2 flanks each side of a second nucleic acid sequence, and wherein the RRS2 are in the same orientation or in an inverse orientation with respect to each other, and wherein at least one of the RRS2 is positioned downstream of at least one of the RRS1, whereby when the R2 recognizes the RRS2, the second nucleic acid sequence is excised when the RRS2 are in the same orientation or is inverted when the RRS2 are in the inverse orientation;

(iv) a third recombination unit (U3) comprising a third pair of recombinase recognition sequences (RRS3) adapted to be recognized by the R1, R2, or a third recombinase (R3), wherein each of the RRS3 flanks each side of a third nucleic acid sequence, wherein the RRS3 are in the same orientation or in an inverse orientation with respect to each other, and wherein at least one of the RRS3 is positioned downstream of at least one of the RRS2, whereby when the R1, R2, or R3 recognizes the RRS3, the third nucleic acid sequence is excised when the RRS3 are in the same orientation, or is inverted when the RRS3 are in the inverse orientation;

wherein the first, second or third nucleic acid sequence comprises a target gene, and wherein presence or absence of at least one of the R1, R2, and R3 operatively links the promoter to at least one of the first, second or third nucleic acid sequence, thereby driving expression of the first, second or third nucleic acid sequence; and (v) a pair of flanking nucleic acid sequences, wherein each of the flanking nucleic acid sequences flanks each side of the nucleic acid logic cassette, permitting the cassette to be inserted into a mammalian cell.

2. The nucleic acid logic cassette of paragraph 1, wherein the mammalian cell is a human cell.

3. The nucleic acid logic cassette of paragraph 1 or 2, wherein the R2 does not recognize the RRS1 or RRS3.

4. The nucleic acid logic cassette of any one of the above paragraphs, wherein the R3 does not recognize the RRS1 or RRS2.

5. The nucleic acid logic cassette of any one of the above paragraphs, adapted to function as a decoder, wherein the decoder can receive n input signals and produce $2^n$ output signals, wherein n is an integer greater than 1.

6. The nucleic acid logic cassette of paragraph 5, wherein the decoder is a 2-input 4-output decoder.

7. The nucleic acid logic cassette of paragraph 6, wherein the 2-input 4-output decoder comprises a first target gene (TG1), a second target gene (TG2), a third target gene (TG3), and a fourth target gene (TG4) connected in series, wherein the TG1 is operatively linked to the promoter, whereby (a) when both the R1 and R2 are absent, the TG1 is expressed to produce a first output signal; (b) when the R1 is present and the R2 is absent, the TG2 is operatively linked to the promoter, thereby expressing the TG2 to produce a second output signal; (c) when the R1 is absent and the R2 is present, the TG3 is operatively linked to the promoter, thereby expressing the TG3 to produce a third output signal; and (d) when both the R1 and R2 are present, the TG4 is operatively linked to the promoter, thereby expressing the TG4 to produce a fourth output signal.

8. The nucleic acid logic cassette of paragraph 6 or 7, wherein the RRS2 are in the same orientation with respect to each other and the second nucleic acid sequence comprises the U1 and a first target gene (TG1), wherein the U1 is upstream of the TG1, wherein the TG1 is in the same orientation as the RRS2, and wherein in U1, the RRS1 are in same orientation with respect to each other and the first nucleic acid sequence encodes a second target gene (TG2), wherein the TG2 is in the same orientation as the RRS1; and wherein the U3 is located downstream of the U2, and the RRS3 are in the same orientation with respect to each other and the third nucleic acid sequence encodes a third target gene (TG3), the cassette optionally comprising a fourth target gene (TG4) positioned downstream of the U3, wherein the TG4 is in the same orientation with respect to the RRS3, and wherein the RRS1 and RRS3 are recognized by the R1, and whereby (a) absence of the R1 and R2 operatively links the promoter to the TG2, or (b) presence of the R1 and absence of the R2 operatively link the promoter to the TG1, or (c) absence of the R1 and presence of the R2 operatively link the promoter to the TG3, or (d) presence of the R1 and R2 operatively links the promoter to the TG4.

9. The nucleic acid logic cassette of paragraph 6 or 7, wherein the U2 has the RRS2 in an inverse orientation with respect to each other and the second nucleic acid sequence comprises the U1 and the U3, wherein the U3 is positioned downstream of the U1, and wherein in the U1, the RRS1 are in an inverse orientation with respect to each other and the first nucleic acid sequence comprises a first target gene (TG1) and a second target gene (TG2), wherein the TG1 and the TG2 are in an inverse orientation with respect to each other, and the TG1 is in the same orientation as the promoter, and wherein in the U3, the RRS3 are in an inverse orientation with respect to each other and the third nucleic acid sequence comprises a third target gene (TG3) and a fourth target gene (TG4), wherein the TG3 and the TG4 are in an inverse orientation with respect to each other, and the TG3 is in the same orientation as the promoter, and wherein the RRS1 and RRS3 are recognized by the R1, and whereby (a) absence of the R1 and R2 operatively links the promoter to the TG1, or (b) presence of the R1 and absence of the R2 operatively link the promoter to the TG3, or (c) absence of the R1 and presence of the R2 operatively link the promoter to the TG4, or (d) presence of R1 and R2 operatively links the promoter to the TG2.

10. The nucleic acid logic cassette of paragraph 6 or 7, wherein the U2 has the RRS2 in same orientation with respect to each other and the second nucleic acid sequence comprises the U1 upstream of a first target gene (TG1), wherein the TG1 is in the same orientation as the RRS2, and wherein in U1, each of the RRS1 are in same orientation with respect to each other and the first nucleic acid sequence comprises a transcriptional terminator sequence (TT), wherein the TT is in the same orientation as each of the RRS1; and wherein the U3 is located downstream of the U2, and the RRS3 are in the same orientation with respect to each other and the third nucleic acid sequence comprises a second target gene (TG2), the cassette optionally comprising a fourth nucleic acid sequence comprising a third target gene (TG3) located downstream of the U3, wherein the TG3 is in the same orientation with respect to the RRS3, and wherein the RRS1 and RRS3 are recognized by the R1, and whereby (a) absence of the R1 and R2, none of the TG1, TG2 or TG3 are operatively linked to the promoter, or (b) presence of the R1 and absence of the R2 operatively link the promoter to the TG1, or (c) absence of the R1 and presence of the R2 operatively link the promoter to the TG3, or (d) presence of the R1 and R2 operatively links the promoter to the TG2.

11. The nucleic acid logic cassette of paragraph 6, wherein the 2-input 4-output decoder comprises a transcription terminator, a first target gene, a second target gene, and a third target gene connected in series, wherein the transcription terminator is operatively linked to the promoter, whereby (a) when both the R1 and R2 are absent, no output signal is produced; (b) when the R1 is present and the R2 is absent, the first target gene is operatively linked to the promoter, thereby expressing the first target gene to produce a first output signal; (c) when the R1 is absent and the R2 is present, the second target gene is operatively linked to the promoter, thereby expressing the second target gene to produce a second output signal; and (d) when both the R1 and R2 are present, the third target gene is operatively linked to the promoter, thereby expressing the third target gene to produce a third output signal.

12. The nucleic acid logic cassette of paragraph 5, wherein the decoder is a 3-input 8-output decoder.

13. The nucleic acid logic cassette of paragraph 12, further comprising (i) a first 2-input 4-output decoder of paragraph 8; (ii) a second 2-input 4-output decoder of paragraph 8 positioned downstream of the first 2-input 4-output decoder and in the same orientation as the first 2-input 4-output decoder, (ii) a fourth recombination unit (U4) comprising a fourth pair of recombinase recognition sequences (RRS4) specific for the R3, wherein each of the RRS4 flanks each side of the first 2-input 4-output decoder, and (iii) a target gene positioned downstream of the second 2-input 4-output decoder, wherein the RRS4 are in the same orientation with respect to each other, whereby when R3 recognizes the RRS4, the first nucleic acid logic construct of the 2-input 4-output decoder is excised.

14. The nucleic acid logic cassette of paragraph 12, further comprising (i) a nucleic acid sequence comprising a first 2-input 4-output decoder of paragraph 9 and a second 2-input 4-output decoder of paragraph 9 connected together and in the same orientation, and (ii) a fourth recombination unit (U4) comprising a fourth pair of recombinase recognition sequence (RRS4) specific for a third recombinase (R3), wherein each of the RRS4 flanks each side of the nucleic acid sequence of (i), and wherein the RRS4 are in an inverse orientation with respect to each other, whereby when R3 recognizes the RRS4, the nucleic acid sequence of (i) inverted with respect to the promoter.

15. The nucleic acid logic cassette of any one of paragraphs 1-4, adapted to function as a multi-input AND gate configured to receive at least three inputs, wherein the U1, U2 and U3 are connected in series, wherein:

in U1, the RRS1 are in an inverse orientation with respect to each other and the first nucleic acid encodes the promoter in an inverted orientation;

in U2, the RRS2 are in the same orientation with respect to each other and the second nucleic acid comprises a transcriptional terminator sequence (TT);

in U3, the RRS3 are in an inverse orientation with respect to each other and the third nucleic acid comprises a target gene (TG) in an inverted orientation;

wherein the RRS1, RRS2, and RRS3 are each recognized by a different recombinase, whereby only in the presence of the R1, R2 and R3 is the TG operatively linked to the promoter.

16. The nucleic acid logic cassette of paragraph 15, further comprising a fourth recombination unit (U4) comprising a fourth pair of recombinase recognition sequences (RRS4) for a fourth recombinase (R4) different from the R1, R2, and R3, the RRS4 being in the same orientation with respect to each other, wherein each of the RRS4 flanks each side of a fourth nucleic acid sequence comprising a second transcriptional terminator sequence (TT2), wherein the U4 is positioned in between the U2 and U3, whereby only in the presence of the R1, R2, R3, and R4 is the TG operatively linked to the promoter.

17. The nucleic acid logic cassette of any one of paragraphs 1-4, adapted to function as a full adder.

18. The nucleic acid logic cassette of paragraph 17, wherein the U1 has the RRS1 in the same orientation with respect to each other and the first nucleic acid sequence comprises the U2, a fourth recombination unit (U4) positioned downstream of the U2, and a first target gene (TG1) positioned downstream of the U4, wherein the U2 has the RRS2 in the same orientation with respect to each other and the second nucleic acid comprises the U3 and a second target gene (TG2) positioned downstream of the U3, wherein the U3 has the RRS3 in the same orientation with respect to each other and the third nucleic acid comprises a transcriptional terminator sequence, wherein the U4 comprises a fourth pair of recombinase recognition sequences (RRS4) in the same orientation with respect to each other, wherein each of the RRS4 flanks each side of a second TG2, further comprising (i) a fifth recombination unit (U5) positioned downstream of the U1 and comprising a fifth pair of recombinase recognition sequences (RRS5) in the same orientation with respect to each other and a fifth nucleic acid sequence, each of the RRS5 flanking each side of the fifth nucleic acid sequence, the fifth nucleic acid sequence comprising a sixth recombination unit (U6) and a second TG1 positioned downstream of the U6, the U6 comprising a sixth pair of recombinase recognition sequences (RRS6) in the same orientation with respect to each other, wherein each of the RRS6 flanks each side of a third TG2; (ii) a seventh recombination unit (U7) positioned downstream of the U5, the U7 comprising a seventh pair of recombinase recognition sequences (RRS7) in the same orientation with respect to each other, wherein each of the RRS7 flanks each side of a third TG1; (iii) a fourth TG2 connected to a fourth TG1 and positioned downstream of the U7, and wherein the R1 recognizes the RRS1, the R2 recognizes the RRS2, RRS6, and RRS7, and the R3 recognized the RRS3, RRS4, and RRS5.

19. The nucleic acid logic cassette of any one of paragraphs 1-4, adapted to function as a full subtractor.

20. The nucleic acid logic cassette of paragraph 19, wherein the U1 has the RRS1 in the same orientation with respect to each other and the first nucleic acid sequence comprises the U2, a fourth recombination unit (U4) positioned downstream of the U2, and a first transcriptional terminator sequence (TT1) downstream of the U4,
   wherein the U2 has the RRS2 in the same orientation with respect to each other and the second nucleic acid comprises the U3 and a first target gene (TG1) positioned downstream of the U3, wherein the U3 has the RRS3 in the same orientation with respect to each other and the third nucleic acid comprises a second transcriptional terminator sequence (TT2), wherein the U4 comprises a fourth pair of recombinase recognition sequences (RRS4) in the same orientation with respect to each other, wherein each of the RRS4 flanks each side of a second TG1 and a first TG2 connected in series,
   further comprising (i) a fifth recombination unit (U5) positioned downstream of the U1 and comprising a fifth pair of recombinase recognition sequences (RRS5) in the same orientation with respect to each other and a fifth nucleic acid sequence, each of the RRS5 flanking each side of the fifth nucleic acid sequence, the fifth nucleic acid sequence comprising a sixth recombination unit (U6) and a second TG2 positioned downstream of the U6, the U6 comprising a sixth pair of recombinase recognition sequences (RRS6) in the same orientation with respect to each other, wherein each of the RRS6 flanks each side of a third TG1 and a third TG2 connected in series; (ii) a seventh recombination unit (U7) positioned downstream of the U5, the U7 comprising a seventh pair of recombinase recognition sequences (RRS7) in the same orientation with respect to each other, wherein each of the RRS7 flanks each side of a third transcriptional terminator sequence (TT3); (iii) a fourth TG2 connected to a fourth TG1 and positioned downstream of the U7,
   and wherein the R1 recognizes the RRS1, the R2 recognizes the RRS2, RRS6, and RRS7, and the R3 recognizes the RRS3, RRS4, and RRS5.
21. The nucleic acid logic cassette of any one of paragraphs 1-4, adapted to function as a half adder-subtractor.
22. The nucleic acid logic cassette of paragraph 21, wherein the U1 has the RRS1 in the same orientation with respect to each other and the first nucleic acid sequence comprises the U2, a fourth recombination unit (U4) positioned downstream of the U2, and a first target gene (TG1) positioned downstream of the U4,
   wherein the U2 has the RRS2 in the same orientation with respect to each other and the second nucleic acid comprises the U3 and a second target gene (TG2) positioned downstream of the U3, wherein the U3 has the RRS3 in the same orientation with respect to each other and the third nucleic acid comprises a first transcriptional terminator sequence (TT1), wherein the U4 comprises a fourth pair of recombinase recognition sequences (RRS4) in the same orientation with respect to each other, wherein each of the RRS4 flanks each side of a second TG2,
   further comprising (i) a fifth recombination unit (U5) positioned downstream of the U1 and comprising a fifth pair of recombinase recognition sequences (RRS5) in the same orientation with respect to each other and a fifth nucleic acid sequence, each of the RRS5 flanking each side of the fifth nucleic acid sequence, the fifth nucleic acid sequence comprising a sixth recombination unit (U6) and a third TG2 and a second TG1 connected in series and positioned downstream of the U6, the U6 comprising a sixth pair of recombinase recognition sequences (RRS6) in the same orientation with respect to each other, wherein each of the RRS6 flanks each side of a second transcriptional terminator sequence (TT2); (ii) a seventh recombination unit (U7) positioned downstream of the U5, the U7 comprising a seventh pair of recombinase recognition sequences (RRS7) in the same orientation with respect to each other, wherein each of the RRS7 flanks each side of a fourth TG2; (iii) a third transcriptional terminator sequence (TT3) positioned downstream of the U7,
   and wherein the R1 recognizes the RRS1, the R2 recognizes the RRS2, RRS6, and RRS7, and the R3 recognizes the RRS3, RRS4, and RRS5.
23. The nucleic acid logic cassette of any one of the above paragraphs, wherein the target gene encodes a reporter molecule, a protein of interest, an RNA of interest, or an enzyme of interest.
24. The nucleic acid logic cassette of paragraph 23, wherein the reporter molecule is selected from the group consisting of β-galactosidase, chloramphenicol acetyltransferase, neomycin phosphotransferase, green fluorescent protein, mCherry, red fluorescent protein, and secreted placental alkaline phosphatase (SEAP), secreted a-amylase (SAMY), firefly luciferase, and *Renilla* luciferase.
25. The nucleic acid logic cassette of any one of the above paragraphs, wherein the R1, R2, and R3 are each a tyrosine recombinase or a serine recombinase.
26. The nucleic acid logic cassette of any one of the above paragraphs, wherein the R1, R2, and R3 are each selected from the group consisting of Cre, Flp, Dre, SCre, VCre, Vika, B2, B3, KD, ΦC31, Bxb1, λ, HK022, HP1, γδ, ParA, Tn3, Gin, R4, TP901-1, TG1, PhiRv1, PhiBT1, SprA, XisF, TnpX, R, A118, spoIVCA, PhiMR11, SCCmec, TndX, XerC, XerD, XisA, Hin, Cin, mrpA, beta, PhiFC1, Fre, Clp, sTre, FimE, and HbiF.

27. The nucleic acid logic cassette of any one of the above paragraphs, wherein each pair of recombinase recognition sequences is selected from the group consisting of loxP, loxN, lox 511, lox 5171, lox 2272, M2, M3, M7, M11, lox71, lox66, FRT, rox, SloxM1, VloxP, vox, B3RT, KDRT, F3, F14, attB/P, F5, F13, Vlox2272, Slox2272, SloxP, RSRT, and B2RT.
28. The nucleic acid logic cassette of any one of the above paragraphs, wherein the promoter is an inducible promoter.
29. The nucleic acid logic cassette of any one of the above paragraphs, wherein the promoter is an constitutive promoter.
30. A nucleic acid logic system comprising:
   (i) at least one nucleic acid sequence encoding at least one inducible promoter operatively linked to at least one recombinase, whereby expression of the at least one recombinase provides an input to a nucleic acid logic cassette adapted to perform a logic function as a function of the input, and
   (ii) the nucleic acid logic cassette of any one of paragraphs 1-29.
31. The nucleic acid logic system of paragraph 30, wherein the logic function is selected from the group consisting of NOR, OR, AND, NAND, A IMPLY B, B IMPLY A, A NIMPLY B, B NIMPLY A, XOR, XNOR, decoder, half adder, half subtractor, half adder-subtractor, full adder, full subtractor, Feynman gate, logic selector, Ripple carry adder, array multiplier, arithmetic logic unit, and any combinations thereof.

32. A mammalian cell containing the nucleic acid logic cassette of any one of paragraphs 1-29.

33. A mammalian cell containing a nucleic acid logic system of paragraph 30 or 31.

34. A mammalian immune cell containing a nucleic acid logic cassette, the cassette comprising:
   (i) a nucleic acid sequence encoding a mammalian promoter;
   (ii) a first recombination unit (U1) comprising a first pair of recombinase recognition sequences (RRS1) for a first recombinase (R1), wherein each of the RRS1 flanks each side of a first nucleic acid sequence, and wherein the RRS1 are in the same orientation or in an inverse orientation with respect to each other, and wherein at least one of the RRS1 is positioned downstream of the promoter,
      whereby when the R1 recognizes the RRS1, the first nucleic acid sequence is excised when the RRS1 are in the same orientation or is inverted when the RRS1 are in the inverse orientation;
   (iii) a second recombination unit (U2) comprising a second pair of recombinase recognition sequences (RRS2) for a second recombinase (R2), wherein each of the RRS2 flanks each side of a second nucleic acid sequence, and wherein the RRS2 are in the same orientation or in an inverse orientation with respect to each other, and wherein at least one of the RRS2 is positioned downstream of at least one of the RRS1,
      whereby when the R2 recognizes the RRS2, the second nucleic acid sequence is excised when the RRS2 are in the same orientation or is inverted when the RRS2 are in the inverse orientation,
   wherein the first or second nucleic acid sequence comprises a target gene, and wherein presence or absence of at least one of the R1 and R2 operatively links the promoter to at least one of the first and second nucleic acid sequence, thereby driving expression of the first or second nucleic acid sequence.

35. The mammalian cell of paragraph 34, wherein the immune cell is a T cell.

36. The mammalian cell of paragraph 34, wherein the immune cell is a B cell.

37. The mammalian cell of any one of paragraphs 34-36, wherein the target gene encodes a reporter molecule, a protein of interest, an RNA of interest, or an enzyme of interest.

38. The mammalian cell of paragraph 37, wherein the reporter molecule is selected from the group consisting of β-galactosidase, chloramphenicol acetyltransferase, neomycin phosphotransferase, green fluorescent protein, mCherry, red fluorescent protein, secreted placental alkaline phosphatase (SEAP), secreted a-amylase (SAMY), firefly luciferase, and *Renilla* luciferase.

39. The mammalian cell of any one of paragraphs 34-38, wherein the R1 and R2 are each a tyrosine recombinase or a serine recombinase.

40. The mammalian cell of any one of paragraphs 34-39, wherein the R1 and R2 are each selected from the group consisting of Cre, Flp, Dre, SCre, VCre, Vika, B2, B3, KD, ΦC31, Bxb1, λ, HK022, HP1, γδ, ParA, Tn3, Gin, R4, TP901-1, TG1, PhiRv1, PhiBT1, SprA, XisF, TnpX, R, A118, spoIVCA, PhiMR11, SCCmec, TndX, XerC, XerD, XisA, Hin, Cin, mrpA, beta, PhiFC1, Fre, Clp, sTre, FimE, and HbiF.

41. The mammalian cell of any one of paragraphs 34-40, wherein the RRS1 and RRS2 are each selected from the group consisting of loxP, loxN, lox 511, lox 5171, lox 2272, M2, M3, M7, M11, lox71, lox66, FRT, rox, SloxM1, VloxP, vox, B3RT, KDRT, F3, F14, attB/P, F5, F13, Vlox2272, Slox2272, SloxP, RSRT, and B2RT.

42. The mammalian cell of any one of paragraphs 34-41, wherein the nucleic acid logic cassette is adapted to perform a logic function.

43. The mammalian cell of paragraph 42, wherein the logic function is selected from the group consisting of NOR, OR, AND, NAND, A IMPLY B, B IMPLY A, A NIMPLY B, B NIMPLY A, XOR, XNOR, decoder, half adder, half subtractor, half adder-subtractor, full adder, full subtractor, Feynman gate, logic selector, Ripple carry adder, array multiplier, arithmetic logic unit, and any combinations thereof.

44. A switch operable in a mammalian immune cell, comprising:
   (i) a nucleic acid sequence encoding a mammalian promoter;
   (ii) a first pair of recombinase recognition sequences (RRS1) for a first recombinase (R1), wherein each of the RRS1 flanks each side of a first nucleic acid sequence, and wherein the RRS1 are in an inverse orientation with respect to each other, and wherein at least one of the RRS1 is positioned downstream of the promoter;
   (iii) a second pair of recombinase recognition sequences (RRS2) for a second recombinase (R2), wherein each of the RRS2 flanks each side of a second nucleic acid sequence, and wherein the RRS2 are in an inverse orientation with respect to each other, and wherein at least one of the RRS2 is positioned downstream of at least one of the RRS1; and
   (iv) at least one target gene positioned downstream of at least one of the RRS1, whereby expression of the target gene is controlled by the presence or absence of at least one of the R1 and R2.

45. The switch of paragraph 44, wherein the immune cell is a B cell.

46. The switch of paragraph 44, wherein the immune cell is a T cell.

47. The switch of any one of paragraphs 44-46, wherein the target gene encodes a chimeric antigen receptor (CAR).

48. The switch of any one of paragraphs 44-47, wherein the switch is selected from the group consisting of an On switch, an Off switch, an Expression Level switch, an Affinity Switch, and a Target switch.

49. The switch of paragraph 48, wherein the switch is the Off switch, wherein the first nucleic acid sequence comprises one of the RRS2 and the target gene, and wherein the second nucleic acid sequence comprises the target gene and one of the RRS1, and wherein the target gene is in the same orientation as the promoter, whereby in the presence of the R2 and then the R1, the target gene is inverted, thereby turning off the expression of the target gene.

50. The switch of paragraph 48, wherein the switch is the On switch, wherein the first nucleic acid sequence comprises one of the RRS2 and the target gene, and wherein the second nucleic acid sequence comprises the target gene and one of the RRS1, and wherein the target gene is in an inverted orientation, whereby in the presence of the R2 and then the R1, the target gene is inverted, thereby turning on the expression of the target gene.

51. The switch of paragraph 48, wherein the switch is the Expression Level switch, wherein the promoter is in an inverted orientation, wherein the first nucleic acid sequence comprises the promoter and one of the RRS2, and wherein the second nucleic acid sequence comprises the promoter and one of the RRS1, and wherein the target gene is positioned downstream of the RRS1 and RRS2, whereby in the presence of the R1 and R2, the promoter is inverted, thereby turning on the expression of the target gene.
52. The switch of paragraph 48, wherein the switch is the Target switch, wherein the first nucleic acid sequence comprises a first target gene in the same orientation as the promoter, one of the RRS2, and a second target gene in an inverted orientation, and wherein the second nucleic acid sequence comprises the second target gene and one of the RRS1, whereby in the presence of the R1 and R2, the second target gene is operatively linked to the promoter, thereby turning on the expression of the second target gene and turning off the expression of the first target gene.
53. The switch of paragraph 52, wherein the switch is the Affinity switch, wherein the first target gene encodes a low-affinity CAR, and wherein the second target gene encodes a high-affinity CAR.
54. The switch of any one of paragraphs 44-53, wherein the R1 and R2 are each a tyrosine recombinase or a serine recombinase.
55. The switch of any one of paragraphs 44-54, wherein the R1 and R2 are each selected from the group consisting of Cre, Flp, Dre, SCre, VCre, Vika, B2, B3, KD, ΦC31, Bxb1, λ, HK022, HP1, γδ, ParA, Tn3, Gin, R4, TP901-1, TG1, PhiRv1, PhiBT1, SprA, XisF, TnpX, R, A118, spoIVCA, PhiMR11, SCCmec, TndX, XerC, XerD, XisA, Hin, Cin, mrpA, beta, PhiFC1, Fre, Clp, sTre, FimE, and HbiF.
56. The switch of any one of paragraphs 44-55, wherein the RRS1 and RRS2 are each selected from the group consisting of loxP, loxN, lox 511, lox 5171, lox 2272, M2, M3, M7, M11, lox71, lox66, FRT, rox, SloxM1, VloxP, vox, B3RT, KDRT, F3, F14, attB/P, F5, F13, Vlox2272, Slox2272, SloxP, RSRT, and B2RT.
57. The switch of any one of paragraphs 44-56, adapted to be activated by a compound selected from the group consisting of doxycycline, tamoxifen, rapamycin, and abscisic acid.
58. A method of treating cancer in a subject, the method comprising
    (i) incorporating a switch of any one of paragraphs 44-57 into T cells, thereby permitting the T cells to express the switch; and
    (ii) administering the T cells to the subject.
59. The method of paragraph 58, further comprising expanding the T cells prior to the administering.
60. The method of paragraph 58 or 59, further comprising administering a compound selected from the group consisting of doxycycline, tamoxifen, rapamycin, and abscisic acid to activate the switch.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the term "comprising" or "comprises" is used in reference to compositions, methods, and respective component(s) thereof, that are useful to an embodiment, yet open to the inclusion of unspecified elements, whether useful or not.

As used herein, the term "consisting essentially of" refers to those elements required for a given embodiment. The term permits the presence of elements that do not materially affect the basic and novel or functional characteristic(s) of that embodiment of the invention.

As used herein, the term "cassette" refers to a nucleic acid molecule, or a fragment thereof, that can be introduced to a host cell and incorporated into the host cell's genome. A cassette can comprise a target gene. A cassette can be an isolated nucleotide fragment, e.g. a dsDNA or can be comprised by a vector, e.g. a plasmid, cosmid, and/or viral vector. In some embodiments, a cassette is a single nucleic acid construct, e.g., an engineered nucleic acid sequence.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of lupus nephritis. A subject can be male or female.

As used herein, the term "administering," refers to the placement of a compound or a cell into a subject by a method or route which results in at least partial delivery of the agent at a desired site. Any appropriate route which results in an effective treatment in the subject can be used.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intrahepatic, intraperitoneal, transtracheal, subcutaneous, subcuticular, intraarticular, sub capsular, subarachnoid, intraspinal, intracerebro spinal, and intrasternal injection and infusion. The administration can be systemic or local.

A cell for use with the cassettes and switches described herein can be any cell or host cell. As defined herein, a "cell" or "cellular system" is the basic structural and functional unit of all known independently living organisms. It is the smallest unit of life that is classified as a living thing, and is often called the building block of life. Some organisms, such as most bacteria, are unicellular (consist of a single cell). Other organisms, such as humans, are multicellular. A "natural cell," as defined herein, refers to any prokaryotic or eukaryotic cell found naturally. A "prokaryotic cell" can comprise a cell envelope and a cytoplasmic region that contains the cell genome (DNA) and ribosomes and various sorts of inclusions.

In some embodiments, the cell is a eukaryotic cell, preferably a mammalian cell. A eukaryotic cell comprises membrane-bound compartments in which specific metabolic activities take place, such as a nucleus. In other embodiments, the cell or cellular system is an artificial or synthetic cell. As defined herein, an "artificial cell" or a "synthetic cell" is a minimal cell formed from artificial parts that can do many things a natural cell can do, such as transcribe and translate proteins and generate ATP.

Cells of use in the various aspects described herein upon transformation or transfection with the cassettes or switches described herein include any cell that is capable of supporting the activation and expression of the molecular circuits. In some embodiments of the aspects described herein, a cell can be from any organism or multi-cell organism. Examples of eukaryotic cells that can be useful in aspects described herein include eukaryotic cells selected from, e.g., mammalian, insect, yeast, or plant cells. The molecular circuits described herein can be introduced into a variety of cells including, e.g., fungal, plant, or animal (nematode, insect, plant, bird, reptile, or mammal (e.g., a mouse, rat, rabbit, hamster, gerbil, dog, cat, goat, pig, cow, horse, whale, monkey, or human)). The cells can be primary cells, immortalized cells, stem cells, or transformed cells. In some preferred embodiments, the cells comprise stem cells. Expression vectors for the components of the molecular circuit will generally have a promoter and/or an enhancer suitable for expression in a particular host cell of interest. The present invention contemplates the use of any such vertebrate cells for the molecular circuits, including, but not limited to, reproductive cells including sperm, ova and embryonic cells, and non-reproductive cells, such as kidney, lung, spleen, lymphoid, cardiac, gastric, intestinal, pancreatic, muscle, bone, neural, brain, and epithelial cells.

As used herein, the term "gene" refers to a nucleic acid sequence comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments will also encompass an additional strand that is partially, substantially or fully complementary to the single-stranded molecule. Thus, a nucleic acid sequence can encompass a double-stranded molecule or a double-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts."

The term "expression" as used herein refers to the biosynthesis of a gene product, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into mRNA and, optionally, the subsequent translation of mRNA into one or more polypeptides. Expression also refers to biosynthesis of a microRNA or RNAi molecule, which refers to expression and transcription of an RNAi agent such as siRNA, shRNA, and antisense DNA but does not require translation to polypeptide sequences. The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a prokaryotic cell, eukaryotic cell, or mammalian cell). If translation of the desired heterologous target gene is required, it also typically comprises sequences required for proper translation of the nucleotide sequence. The coding region can code for a protein of interest but can also code for a functional RNA of interest, for example, microRNA, microRNA target sequence, antisense RNA, dsRNA, or a nontranslated RNA, in the sense or antisense direction. The nucleic acid construct as disclosed herein can be chimeric, meaning that at least one of its components is heterologous with respect to at least one of its other components.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those disclosed herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology disclosed herein is further illustrated by the following examples which in no way should be construed as being further limiting.

Materials and Methods:

DNA Assembly.

All constructs were transformed and maintained in Top10 competent cells (Life technologies) at 37° C. or 30° C. prior to miniprep (Epoch Life Sciences) or midiprep (Macherey Nagel). All plasmids were created using standard molecular biology practices of ligation, digestion and transformation, in addition to Gibson isothermal assembly and Unique Nucleotide Sequence Guided assembly (a modular extension of Gibson assembly), where DNA fragments that are to be connected to each other are flanked by short homology sequences and are then fused together by a one-pot isothermal digestion, polymerization, and ligation reaction.

Construction Details of DNA Assembly.

Most genetic reporters were created using an extension of Gibson isothermal assembly called Unique Nucleotide Sequence (UNS) Guided Assembly. This strategy permits a modular, easy, efficient and fast framework for construction of DNA. In UNS-guided assembly, the homology sequences have been standardized (e.g. U1, U2, U3 . . . UK) and have been computationally optimized for proper assembly (reduction of hairpins, sequence homology, and GC tracts) and ease of use (no start codons or useful restriction sites). Genetic cassettes that are to be connected are cloned into part vectors, which contain the UNSes that surround the insert. Restriction digests and gel purifications are then performed to isolate the cassettes flanked with the UNSes. Finally, these products are joined to a linearized destination vector via Gibson isothermal assembly (see also FIGS. 9 and 10).

Transient DNA Transfection into HEK293FT Cells.

DNA was transfected into the human embryonic kidney cell line (HEK293FT) using a polyethylenimine (PEI) protocol. Cells were plated onto 48- or 96-well plates the day prior to transfection, such that the cells were 50-70% confluent the day of transfection. Cells were kept in a humidified incubator at 37° C. and 5% $CO_2$ and maintained in DMEM medium (Corning) with 10% Heat Inactivated Fetal Bovine Serum (Life technologies), 50 U.I./mL penicillin/50 μg/mL streptomycin (Corning), 2 mM glutamine (Corning) and 1 mM sodium pyruvate (Lonza).

Flow Cytometry.

Two days post-transfection and after trypsinization (0.05% T sin/0.53 mM EDTA, Corning) and resuspension, all cell populations were analyzed using a Becton Dickinson (BD) LSRFortessa SORP flow cytometer with HTS, except for data in FIG. 2B and FIG. 4, which were recorded on a BD LSRII. The LSRFortessa was equipped for detection of EGFP (488 nm laser, 530/30 emission filter, 505 longpass filter), tagBFP (405 nm laser, 450/50 emission filter), mCherry or mRuby2 (561 nm, 610/20 emission filter, 595 longpass filter), iRFP-720 (637 nm laser, 730/45 emission filter, 685 longpass filter) and LSS-mOrange (405 nm, 610/20 emission filter, 535 longpass filter). The LSRII was similarly equipped for detection of EGFP, tagBFP, mCherry and mRuby2, but with additional channels for iRFP-720 (633 nm laser, 720/40 emission filter, 710 longpass filter) and LSS-mOrange (405 nm, 590/35 emission filter, 505 longpass filter).

Transient Transfection into HEK293 Cells Using Polyethylenimine.

Polyethylenimine (PEI) stocks were made from linear polyethylenimine (Polysciences 23966-2) and were dissolved at a concentration of 0.323 g/L in deionized water with the assistance of concentrated hydrochloric acid and sodium hydroxide and then filtered sterilized (0.24 m). PEI stocks were stored at −80° C. until use and warmed to room temperature prior to usage. For 48-well plate transfections, DNA (1000 ng) was dissolved and brought up to a volume of 50 μL using 0.15 M sodium chloride (NaCl, Fisher Scientific). DNA-NaCl solutions were then mixed with 50 μL of a PEI-NaCl mixture (8 uL PEI: 42 uL NaCl). These solutions were then incubated at room temperature for ten minutes and 25 μL was carefully dropped into individual wells of HEK293FT cells (250 ng DNA/well). Similarly for 96-well plate transfections, DNA (500 ng) was dissolved and brought up to a volume of 25 μL using 0.15 M sodium chloride (NaCl). DNA-NaCl solutions were then mixed with 25 μL of a PEI-NaCl (4 uL PEI: 21 uL NaCl) mixture. These solutions were then incubated at room temperature for ten minutes and 10 μL was carefully dropped into individual wells of HEK293FT cells (100 ng DNA/well).

Example 1

Figure 1A:
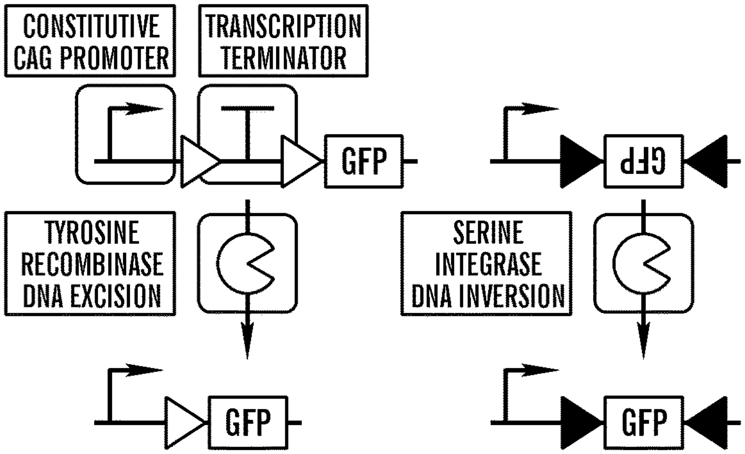

A useful feature of site-specific recombinases is that they can act as transcription activators or repressors depending on the placement of recombination sites. For instance, buffer (BUF) gates permit recombinase-mediated gene expression through tyrosine recombinase-mediated excision of a transcription terminator or serine integrase-mediated inversion (FIG. 1A). Conversely, NOT gates function to terminate gene expression via placement of recombination sites around a gene of interest and elimination of expression through tyrosine recombinase-mediated excision or serine integrase inversion. Increasingly, optogenetics, animal disease models, and study of stem cell generation and differentiation have relied on recombinase-based strategies to achieve tissue-specific gene expression or knockout, utilizing a tissue-specific promoter (TSP) to drive the recombinase expression in combination with a BUF or NOT gate containing a gene of interest (GOI)[18,20-23]. Although these tools have been instrumental in many studies, targeting a specific tissue with only one TSP often resulted in off-target expression[2,24]. To improve specificity, 2-input AND logical integration of two recombinases driven from two separate TSP's has been employed. Realizing that many cell types cannot be adequately specified with a 2-input AND gate, the inventors developed a powerful yet intuitive platform for rapidly creating genetic multi-input logic computation circuits in mammalian cells.

Figure 1B:
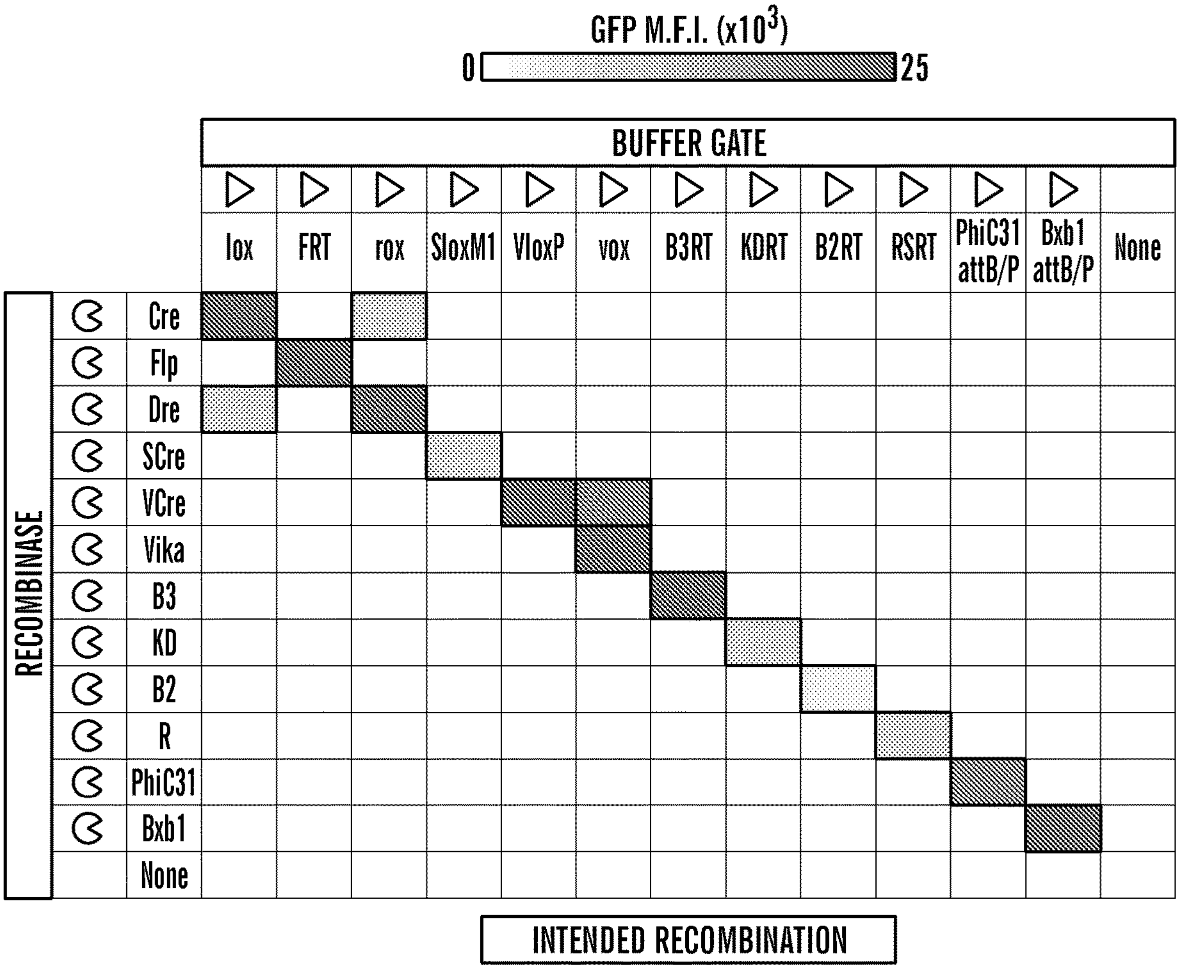

Multi-input recombinase-based logic gates require robust and orthogonal genetic components. Here, twelve recombinases, including both tyrosine recombinase and serine integrase families were tested for activity and orthogonality in a human embryonic kidney cell line (HEK293FT). Through transient transfection of recombinases and their BUF gates, ten of the enzymes were found to be highly active and sufficiently orthogonal to each other for the desired circuit design (FIG. 1B).

Figure 1C:
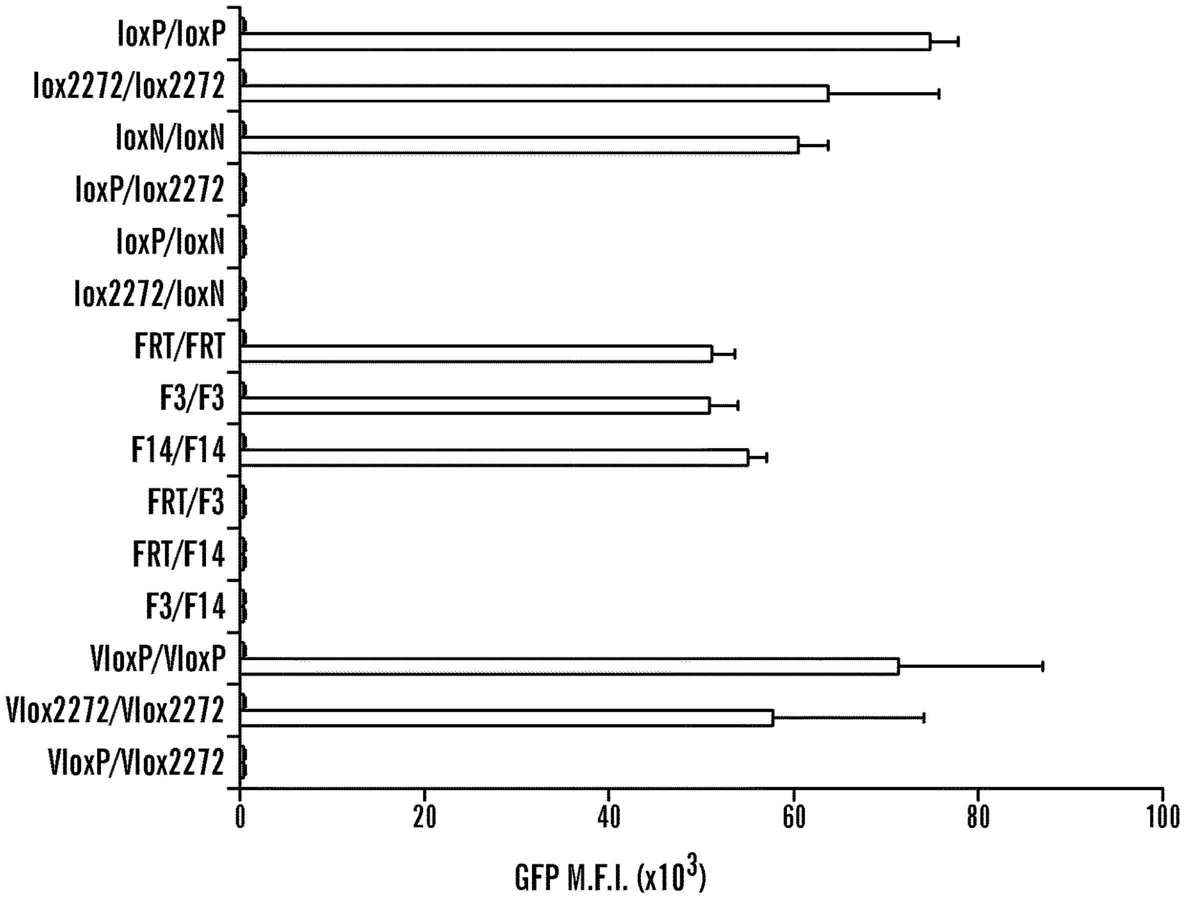
Figure 6A:
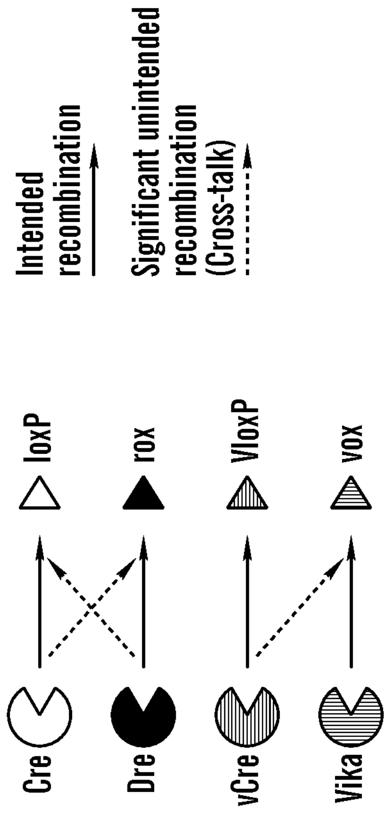
Figure 6B:
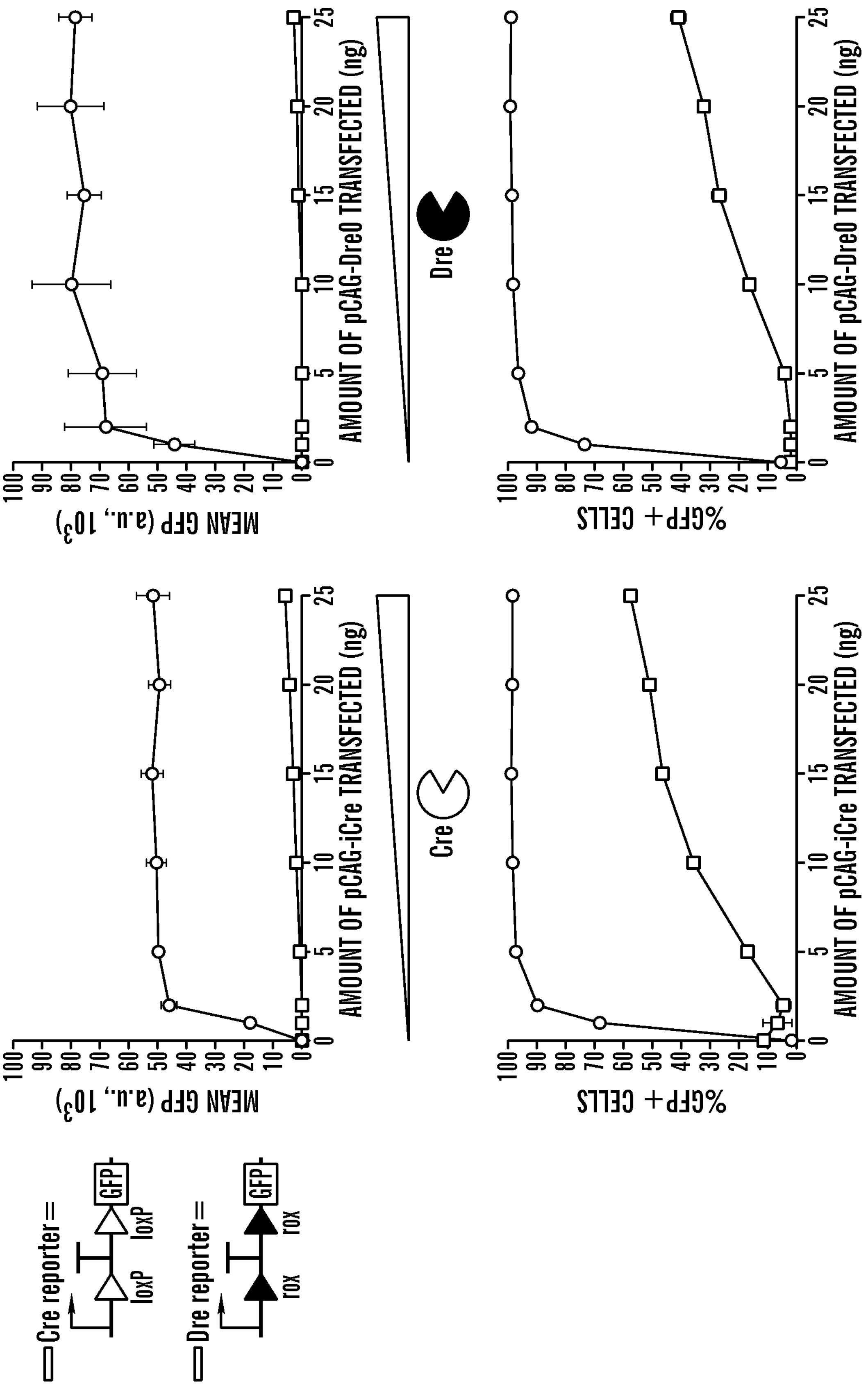
Figure 6C:
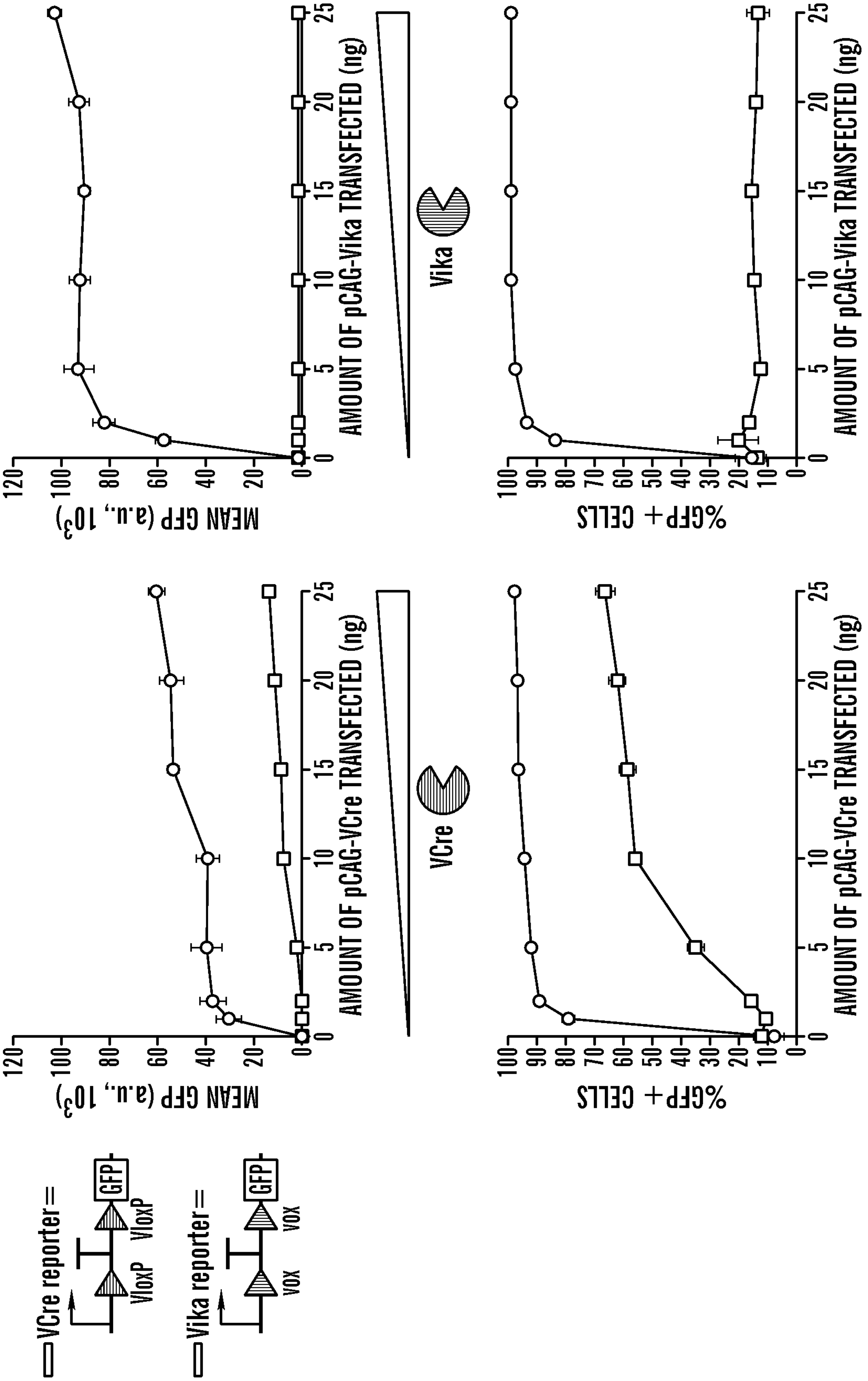

Surprisingly, some of the reportedly orthogonal recombinases, such as Dre, Cre, Vika, and VCre[25-28] showed cross reactivity in a dose-dependent manner (FIG. 6). Therefore, when using these recombinases for circuit design, a lower dose was required to minimize crosstalk. By applying these properties to Cre and Flp, two of the most commonly used recombinases in mammalian genetics literature, the inventors created all sixteen possible two-input Boolean logic gates (FIG. 7). Note that the 2-input AND is created by placing two transcription termination sequences in tandem. Due to the orthogonality of recombinases, it becomes possible to generate multi-input AND gates simply by placing more termination sequences in tandem between a promoter and GFP. Indeed, the inventors developed a 6-input AND gate that expresses GFP upon the excision of four termination sequences by tyrosine recombinases and the inversion of the EF1α promoter and GFP by two serine integrases (FIG. 1C). In contrast to earlier multi-layer 4-input AND gate work in *E. coli*[13], this multi-input AND gate was on a single layer, which could facilitate implementation in mammalian genetic systems.

A key element that allows complex computation on a single transcriptional unit is the usage of heterospecific recombination sites. Heterospecific sites, such as loxP and lox2272, differ from one another by only a few base pairs,[29] but they retain DNA excision capability in the presence of Cre, as long as two of the same sites are present, i.e. loxP with loxP. This feature allows the excision of more than one non-connected region of DNA simultaneously.

Example 2

The inventors exploited these characteristics to establish a platform for generation of N-input order-independent logic gates called Boolean Logic and Arithmetic through DNA Excision (BLADE). All logic computation for BLADE circuits is done on a single transcriptional layer and circuit construction is based on a BLADE template. N-input BLADE templates feature $2^N$ distinct regions of DNA termed addresses (Z). Each address is accessible only via a specific combination of inputs. For example, the 2-input BLADE template contains four addresses, $Z=Z_{AB}=Z_{00}$, $Z_{10}$, $Z_{01}$, and $Z_{11}$, corresponding to each state of A and B inputs (FIG. 2A). Each address contains one output function, which ranges from having zero outputs (transcription terminator), through arbitrary numbers of outputs separated by ribosomal skip sequences (2A), to Boolean functions like BUF.

Figure 3A:
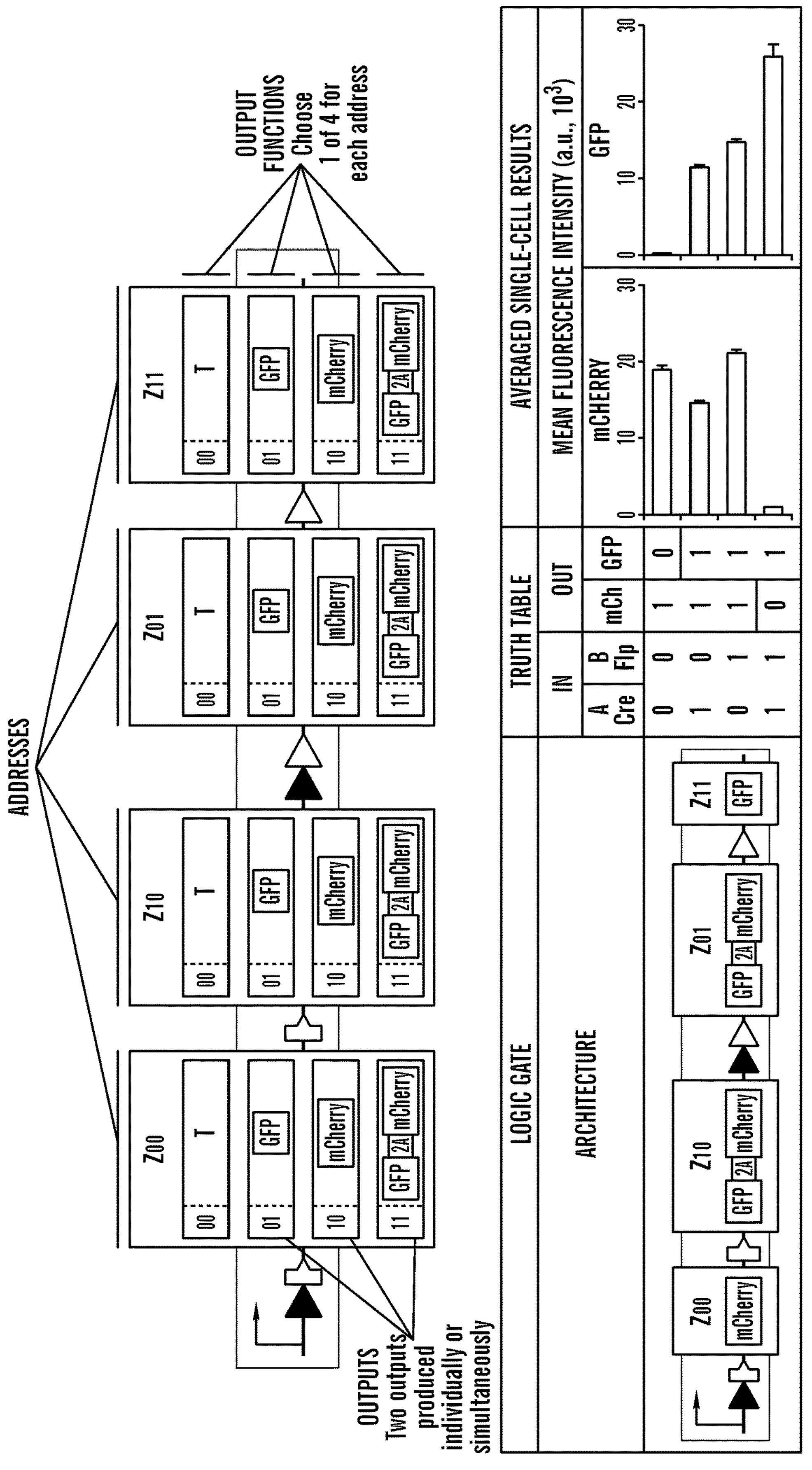
Figure 9:
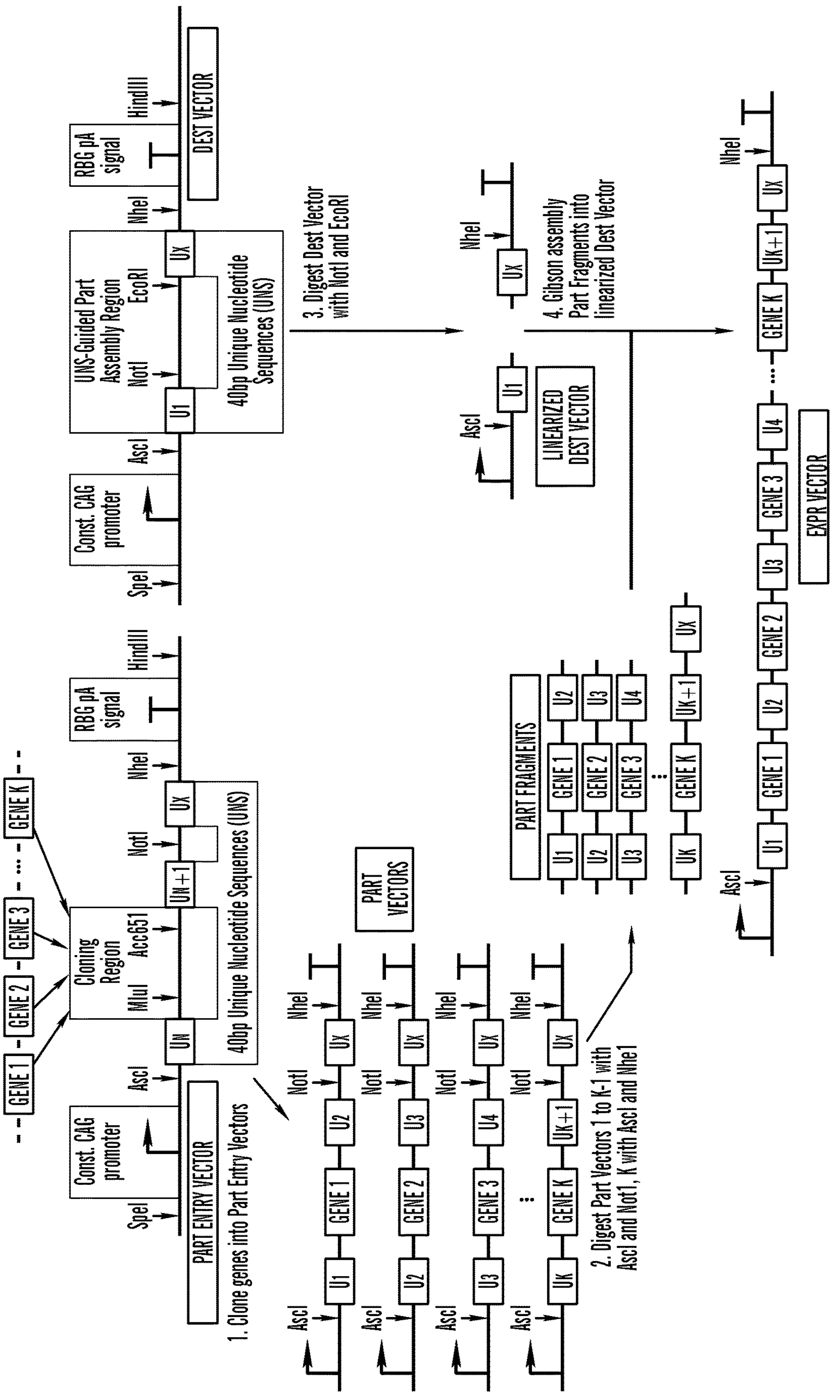
Figure 10A:
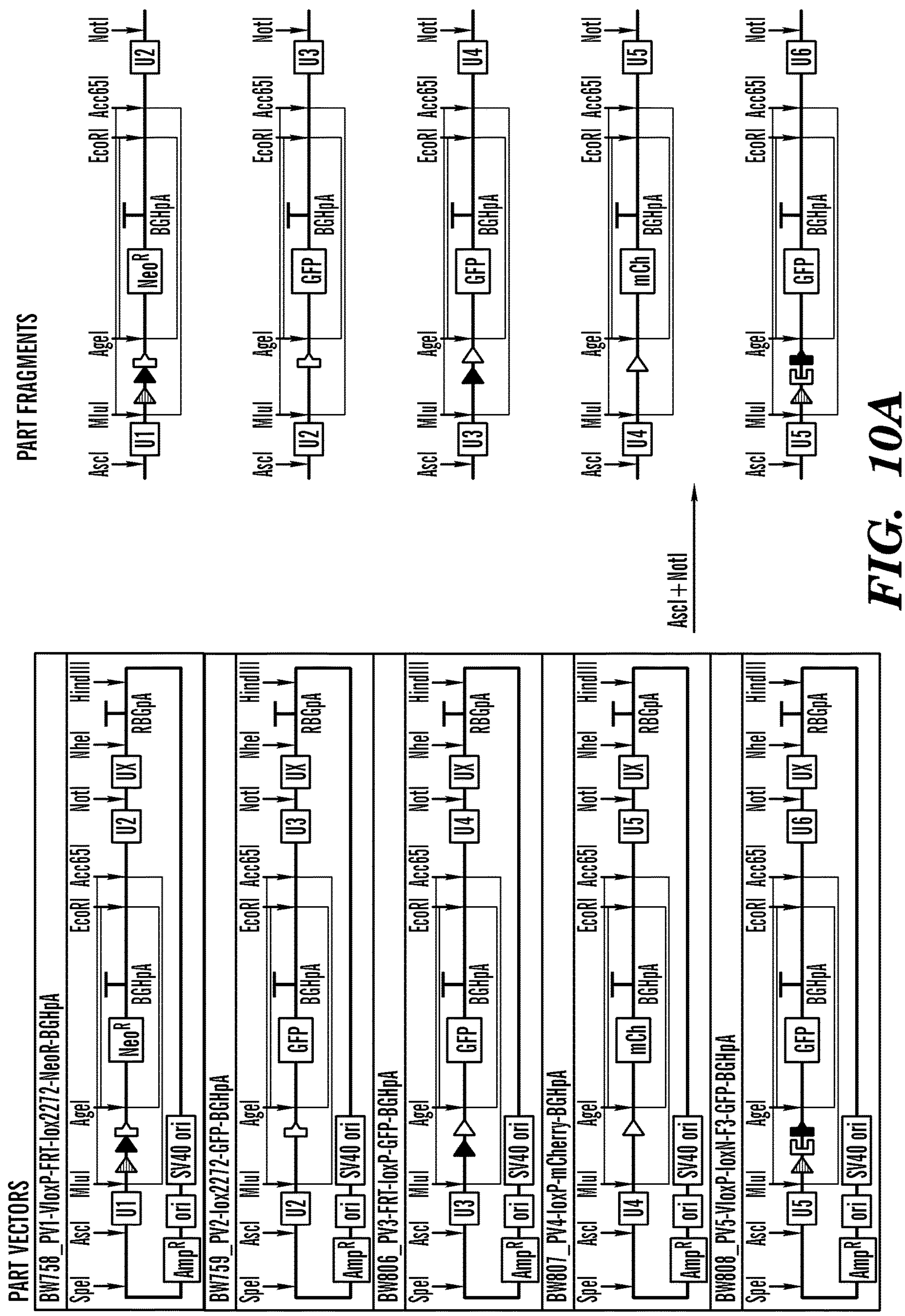
Figure 10A:
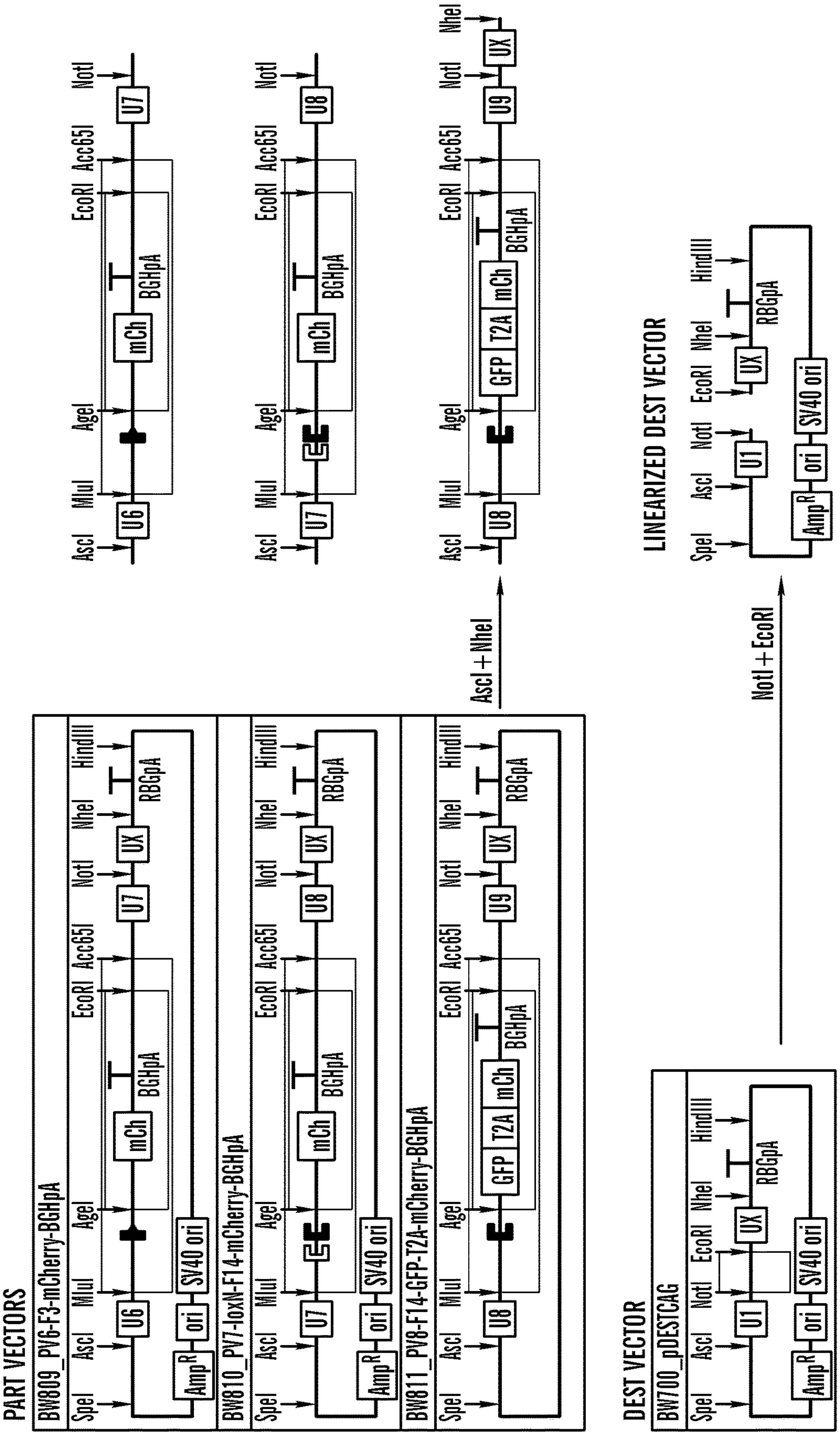
Figure 10B:
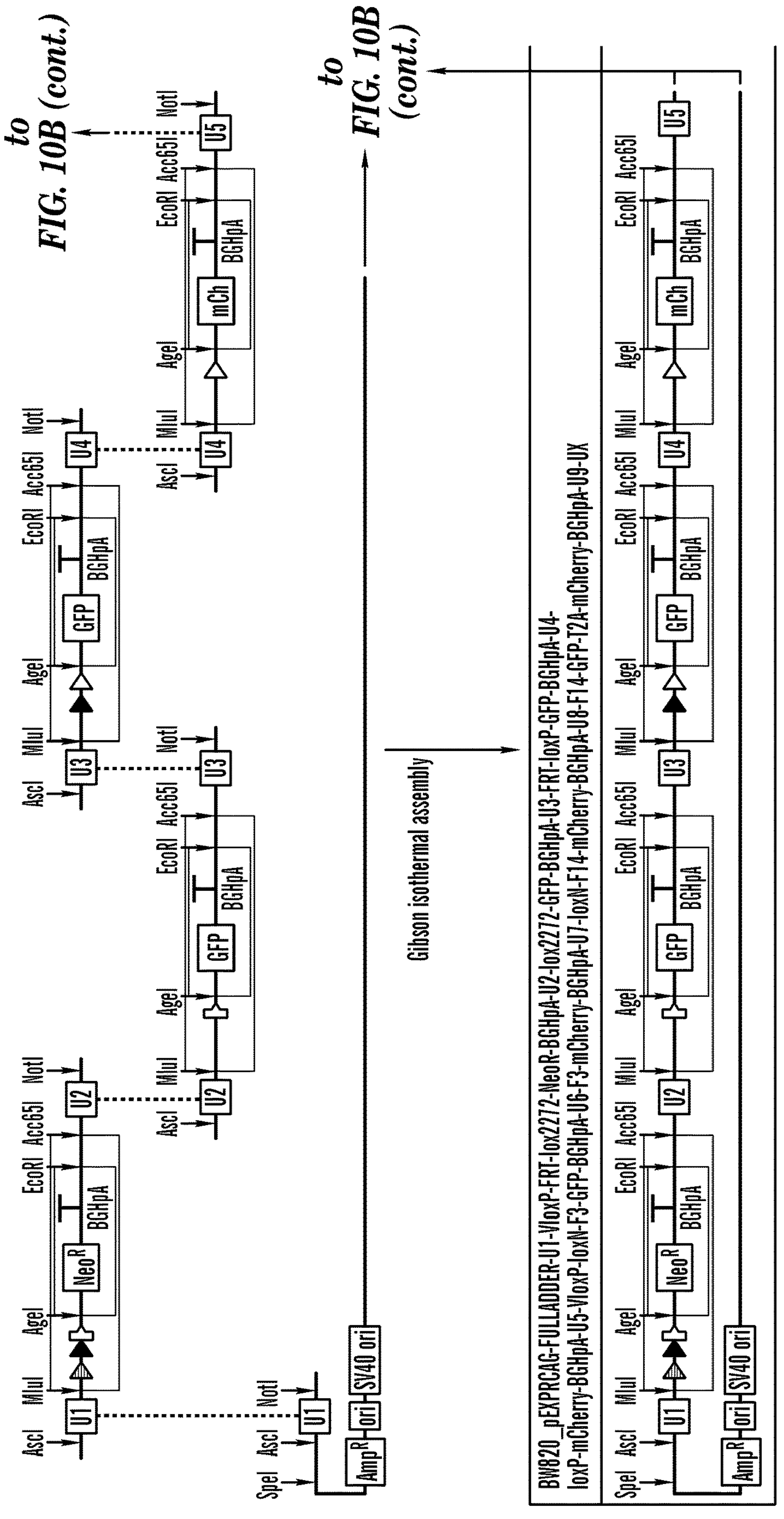
Figure 10B:
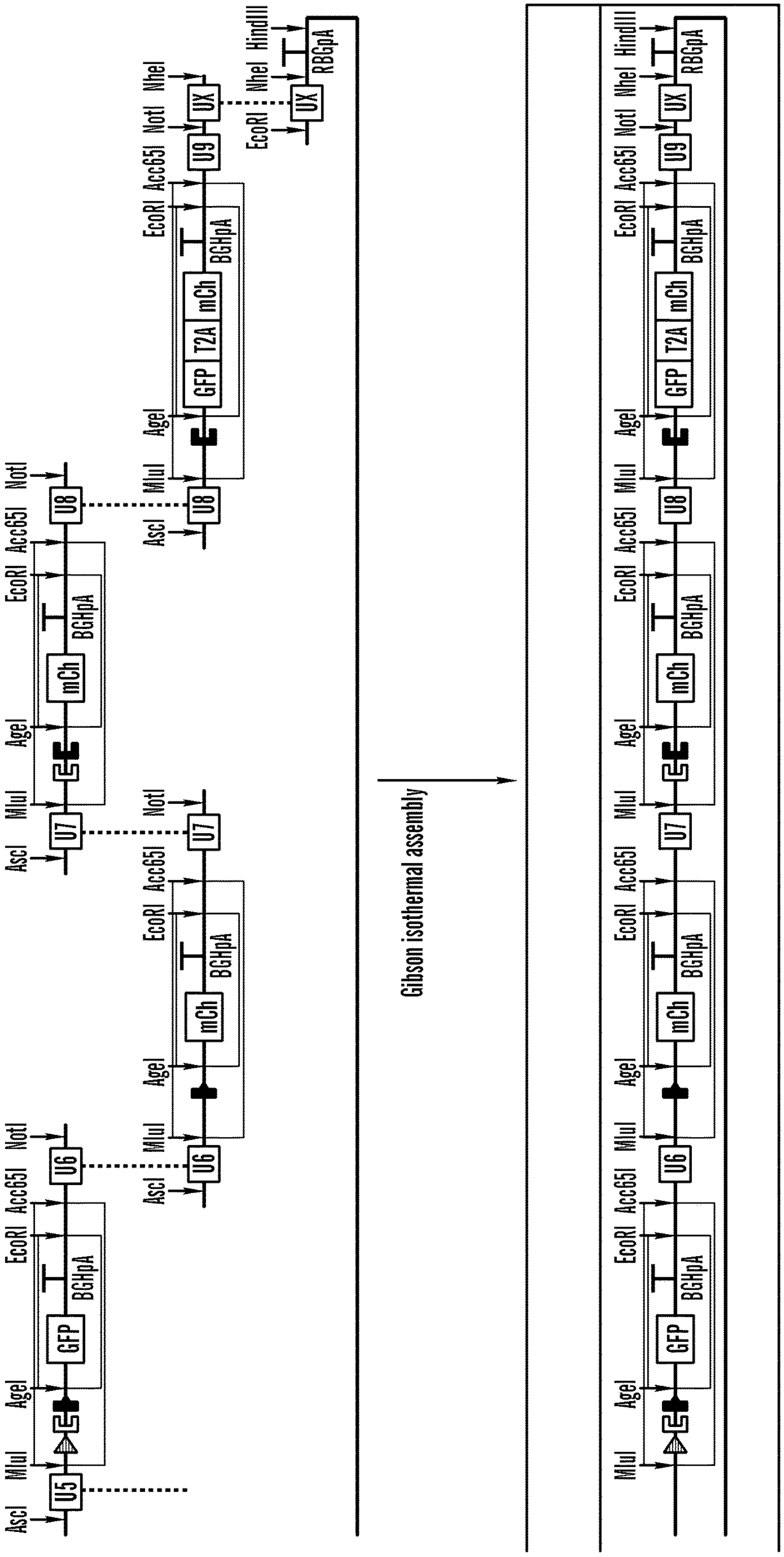

For initial characterization of the 2-input BLADE platform, single-output functions were tested. The inventors constructed a 2-input decoder circuit in which each address coincides with a distinct output function. Blue, green, infrared and red fluorescent proteins (tagBFP, EGFP, iRFP720, and mRuby2, respectively) were placed into the four addresses of the 2-input BLADE template (FIG. 2B). The circuit performed as predicted with strong fluorescent protein expression for each state of inputs, though there was a small degree of spill over between states, due to transient, basal gene expression that occurred prior to and following the recombination reactions. This circuit may be particularly useful as it could permit targeted expression of four different genes in four distinct cell types simultaneously using only two tissue-specific promoters. Furthermore, to test the robustness of this circuit design on a large scale, the inventors then produced a library of >100 circuits with up to two inputs and outputs using Unique Nucleotide Sequence-Guided Assembly, a modular and rapid Gibson isothermal assembly method[30,31] (FIG. 3A and FIG. 9). Of note, are three 2-input devices: the half adder (Gate 11) and half subtractor (Gate 17), which both perform 2-input arithmetic and the Controlled Not Feynman gate (Gate 55), which exhibits interesting logic behavior.

Figure 8A:
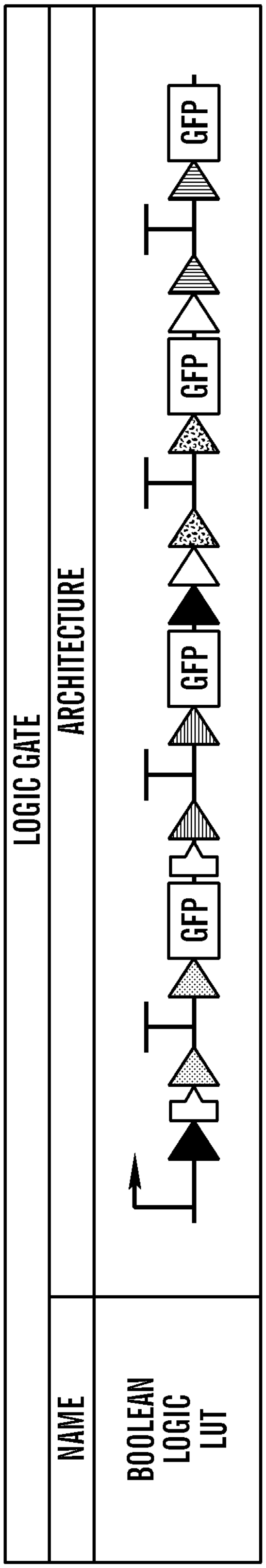
Figure 8A:
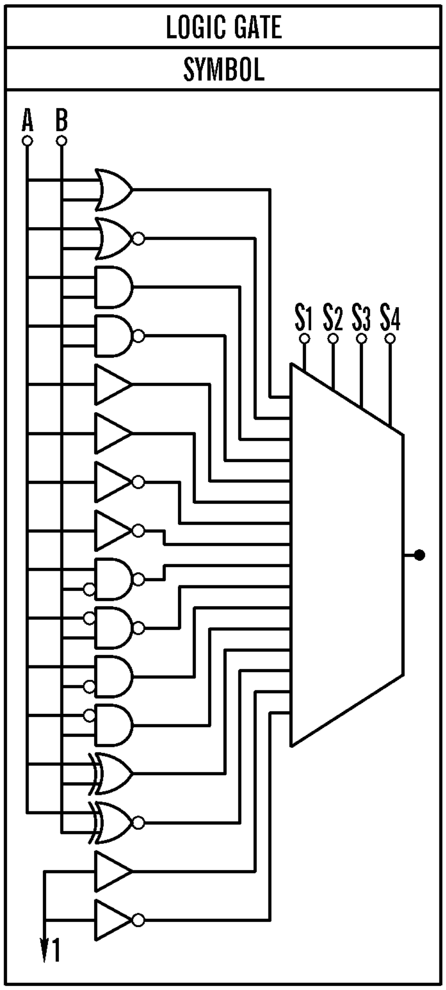
Figure 8A:
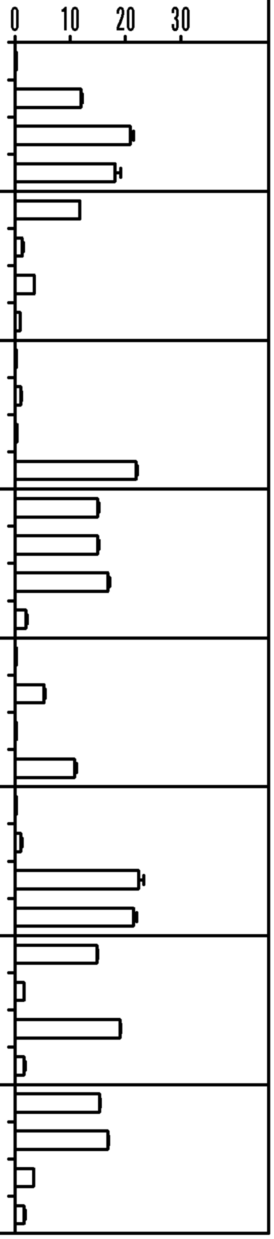
Figure 8A:
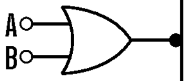
Figure 8A:
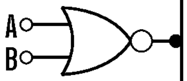
Figure 8A:
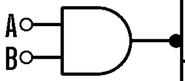
Figure 8A:
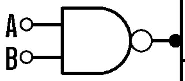
Figure 8A:
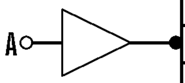
Figure 8A:
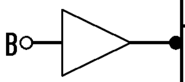
Figure 8A:
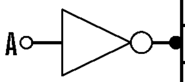
Figure 8A:
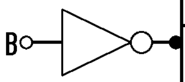
Figure 8A:
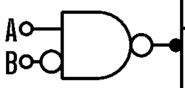
Figure 8A:
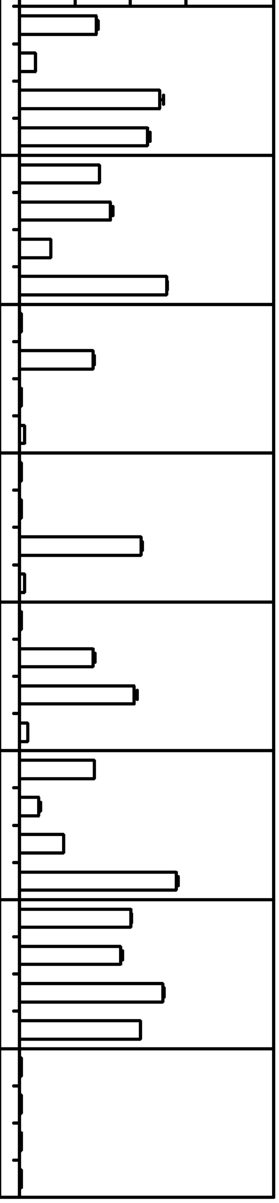
Figure 8A:
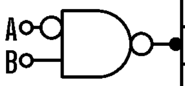
Figure 8A:
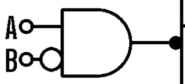
Figure 8A:
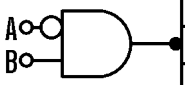
Figure 8A:
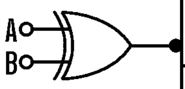
Figure 8A:
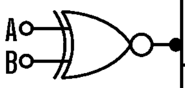
Figure 8A:
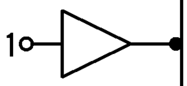
Figure 8A:
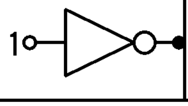
Figure 8B:
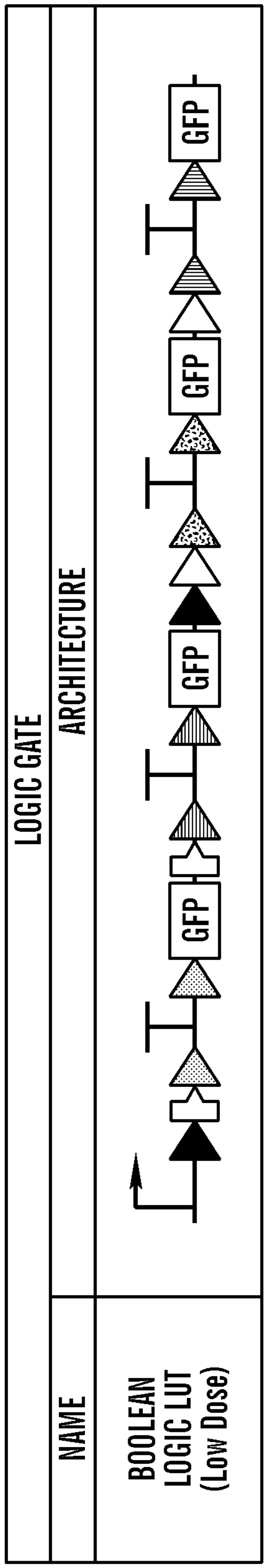
Figure 8B:
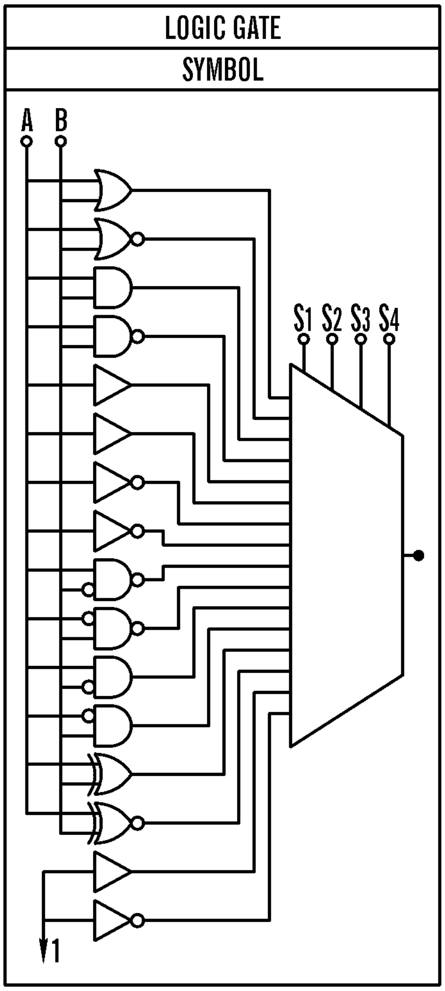
Figure 8B:
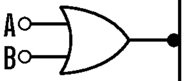
Figure 8B:
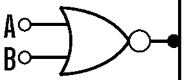
Figure 8B:
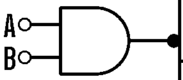
Figure 8B:
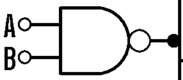
Figure 8B:
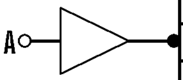
Figure 8B:
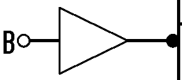
Figure 8B:
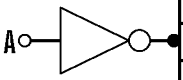
Figure 8B:
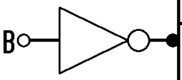
Figure 8B:
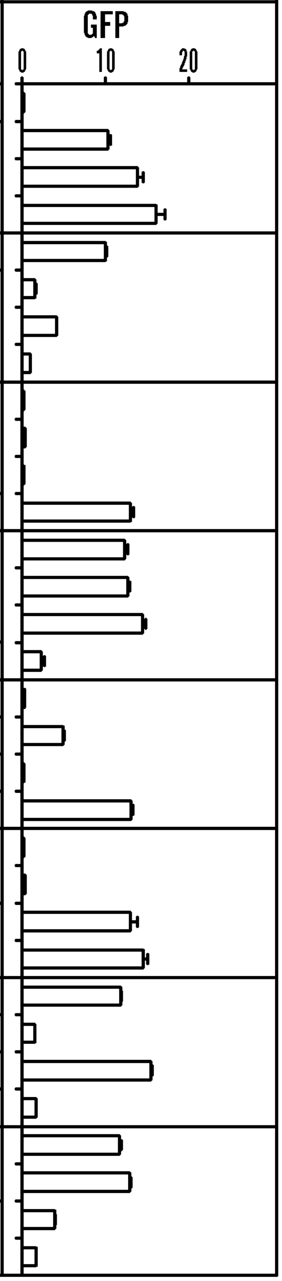
Figure 8B:
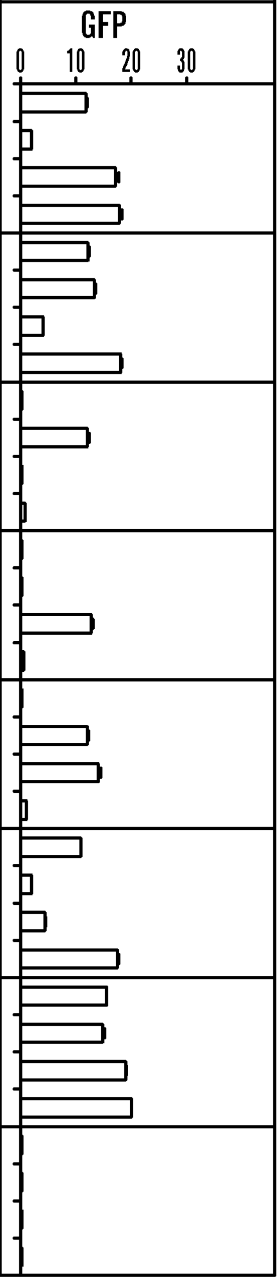
Figure 8B:
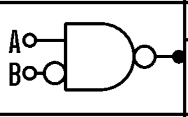
Figure 8B:
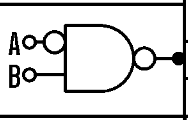
Figure 8B:
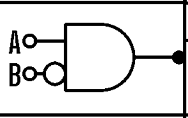
Figure 8B:
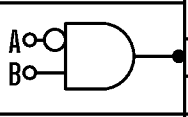
Figure 8B:
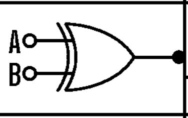
Figure 8B:
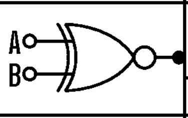
Figure 8B:
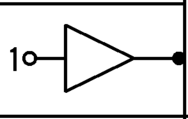
Figure 8B:
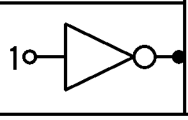

One important class of devices found in electronics is Field-Programmable Read-Only Memory (FPROM). The input-output behavior of these circuits can be configured in the field post-manufacturing, allowing users to customize their devices at a later time. The inventors built a FPROM device termed a Boolean Logic Look-up Table (LUT) that is based on placing BUF gates into the four addresses of the 2-input BLADE template (FIG. 4). This circuit has two data inputs, A and B, and four select inputs, $S_1$, $S_2$, $S_3$, and $S_4$. Each select input can control which buffer gates are GFP ON or OFF. Thus, each combination of select inputs configures the device to a specific Boolean logic gate with up to two inputs and one output. For instance, an OR function can be achieved using select inputs $S_2$, $S_3$, and $S_4$, keeping address $Z_{00}$ GFP OFF and setting addresses $Z_{10}$, $Z_{01}$, and $Z_{11}$ GFP ON. This circuit behaves as expected in mammalian cells. To illustrate the flexibility of the gene circuit platform in terms of recombinase choices, the inventors created an alternative Boolean Logic LUT (FIGS. 8A-8B).

Extending the BLADE framework further, the inventors then developed a 3-input BLADE template for constructing sophisticated arithmetic functions in human cells (FIG. 5A). This template responds to three inputs (Cre, Flp, and VCre) and contains eight addresses for expression of up to eight distinct output functions. This design utilizes three different heterospecific sites for Cre and Flp, but just one site for VCre. Three 3-input-2-ouput arithmetic computational circuits were made and tested in mammalian cells from the 3-input BLADE template (FIG. 5B). The full adder and full subtractor can perform either binary addition or subtraction of three 1-bit inputs, respectively. Furthermore, the half adder-subtractor is an arithmetic FPROM circuit that can compute addition or subtraction on two data inputs, A and B, depending on the presence of one select input C.

Example 3

Figure 11B:
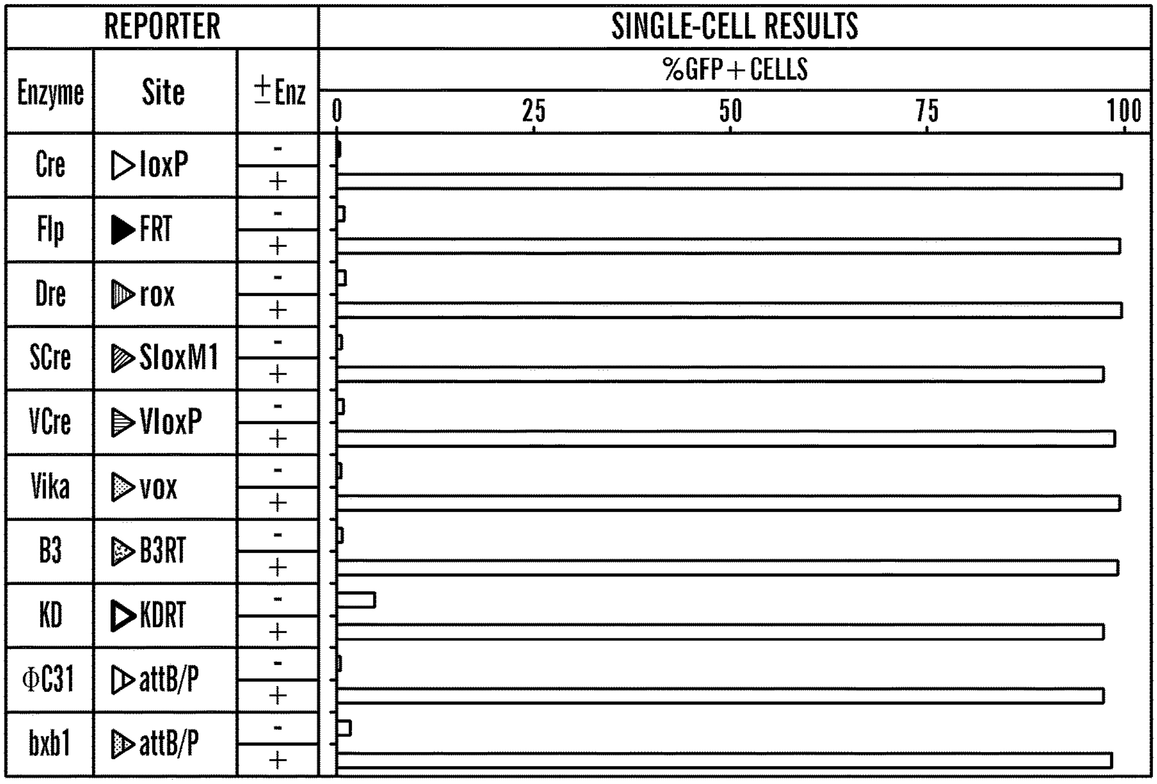

The development of multi-input logic gates requires robust and orthogonal recombinases. The inventors tested more than 10 different recombinases, including both the tyrosine and serine recombinase family in HEK 293T, a human embryonic kidney cell line. To test the tyrosine recombinases, a reporter plasmid for every recombinase was constructed where the corresponding recombination sites flanking a neomycin resistance gene followed by a SV40 polyA sequence (ref) is placed between a CAG promoter and a GFP. The neomycin and SV40 polyA sequence forms a transcriptional stop cassette and prevent the transcription of GFP. When the proper recombinase is expressed, it will bind to the two recombination sites and excise the stop cassette between the recombination sites (FIG. 11A). This reporter construct is also known as a buffer gate and will be used in other circuit design detailed later in this text. For serine recombinases, the recombination sites are placed between a GFP that is in antisense direction. The expression of the corresponding serine recombinase inverts the DNA fragment between the recombination sites, thus inverting the GFP into the sense direction and allowing GFP to be expressed (FIG. 11A). Through transient transfection of the recombinase and the reporter plasmid, most of the enzymes tested are found to be highly active and sufficiently orthogonal for the desired circuit design (FIG. 11B).

Figure 12C:
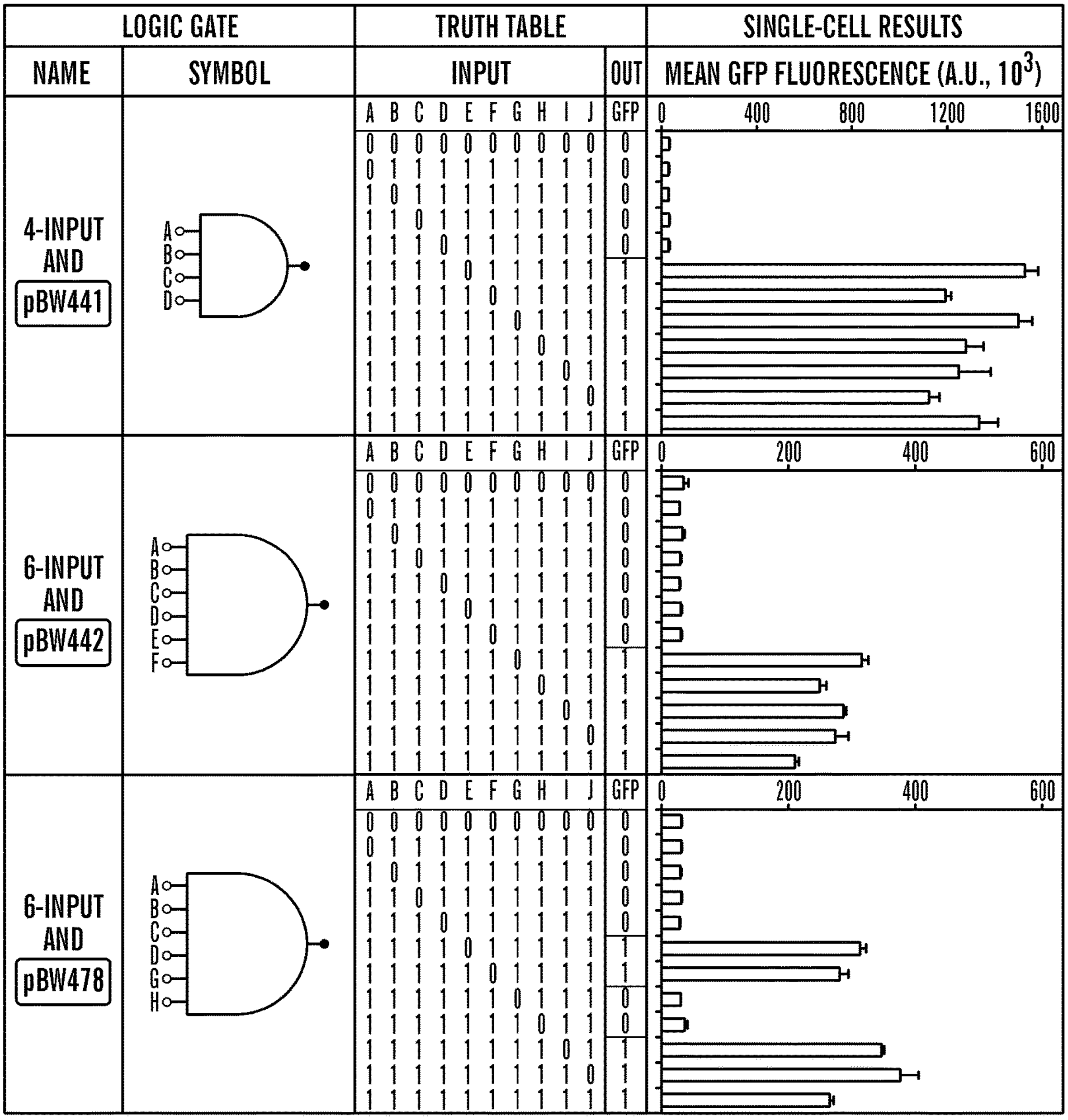
Figure 12C:
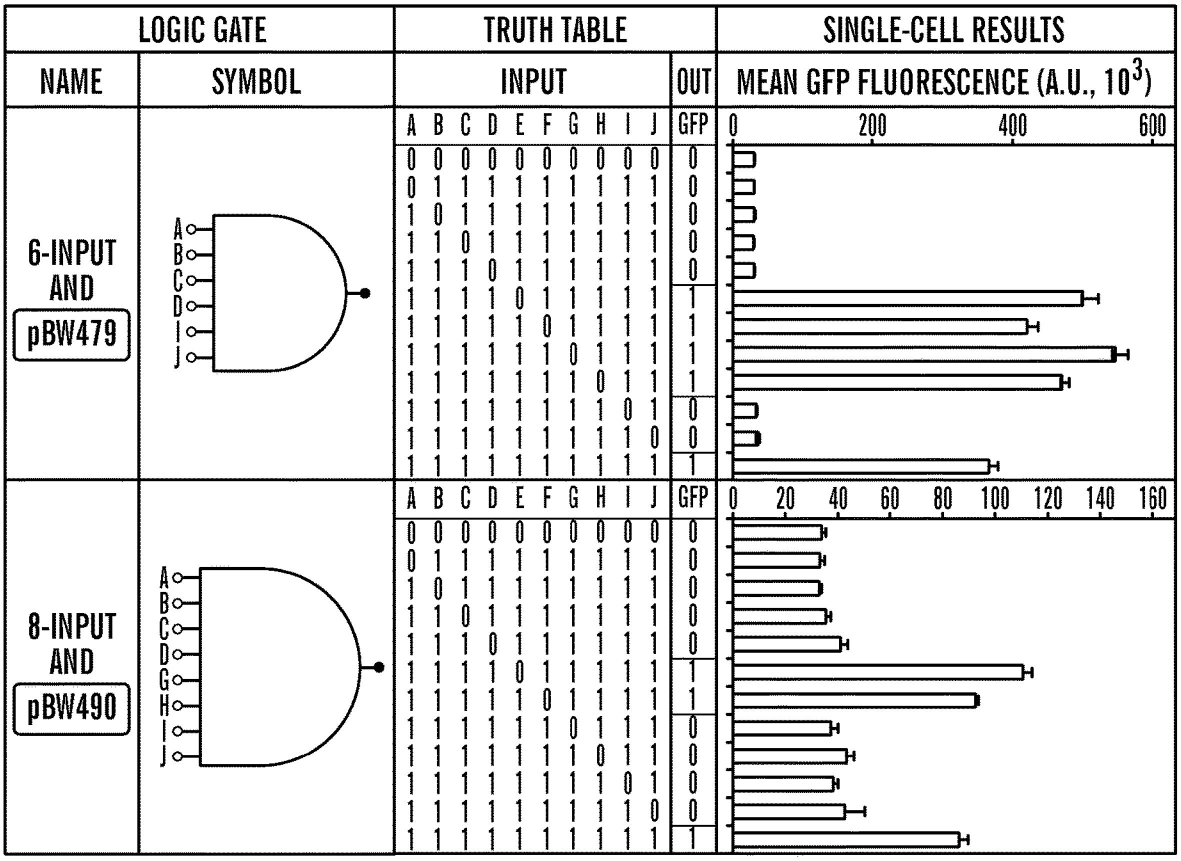

A unique feature of recombinase is that it can act as both a transcription initiator (i.e., activators) and suppressors (i.e. repressors), depending on the placement of the recombination site. For instance, by placing a stop cassette between recombination sites, the expression of the corresponding recombinase excises the transcription stop sequences and allows transcription to occur. Similarly, flanking the gene of interest with recombinase allow the recombinase to remove the gene, thus serve as suppressor of gene expression. Using these unique properties of recombinase, the inventors successfully created all 16 possible 2-Input Boolean logic gates (FIG. 7) using the most commonly used recombinases in mammalian genetics, Cre and Flp. Note that the AND is created by placing two stop cassette in tandem. Because of the othogonality of recombinases, it becomes possible to generate multi-Input AND gates simply by placing more stop cassettes in tandem between a GFP and the promoter. Indeed, the inventors have created several version of 4- and 6-Input AND gates using different enzymes and one 8-Input AND gates (FIGS. 12A-12C). In contrast to earlier multi-layer 4-Input AND gate work in *E. coli*, these multi-Input AND gates are single layer and will greatly facilitate implementation in mammalian genetic systems.

Any 2-Input logic gates has 4 distinct states. When each state generates either 0 or 1, they form the traditional 2-Input Boolean logic gates mentioned above. However, when each state generates a distinct output, this creates a 2-4 decorder (FIG. 13A). A genetically encodable 2-4 decoder will allow targeted gene expression in 4 distinct cell types simultaneously using just two recombinases input. In addition, realizing the advantage of the single transcription unit design for implementation in mammalian system, the inventors therefore sought to create a recombinase-based decorder in a single transcription unit. To achieve this goal, the inventors designed a decoder circuit where there are 4 distinct DNA fragment slots downstream of the promoter. Each slot is surrounded by different permutation of recombination sites configurations and corresponds to a unique state. A key enabling element that allows this design to work is the heterospecific recombination sites available for some of the recombinase, such as Cre and Flp. Heterospecific sites, such as loxP and lox2272, differ from each other by a few base pairs. However, they retain the ability to excise DNA in the presence of Cre, but will only react with the same type of site—loxP with loxP and lox2272 with lox2272. This feature allows the excision of more than one non-connected slot simultaneously. Without using heterospecific sites, decoder circuit can still be implemented, albeit requires several transcription unit.

To illustrate how this design work, consider the first slot ($Z_{0,0}$), which is the closest to the promoter. The Z00 correspond to a state where no recombinase is expressed (0,0). If the slot Z00 contains a protein coding sequence, then that gene will be expressed. Gene expression from the other slots downstream of Z00 will be blocked by the presence of Z00. In the presence of recombinase A, which correspond to state (1,0), slot Z0,0 and Z0,1 will be removed, thus moving slot Z1,0 directly downstream of the promoter and allow gene expression of slot Z1,0 and only Z1,0, to occur. Similarly, when recombinase B is presence, which correspond to state (0,1), slot Z00 and Z10 are removed, allowing Z01 to be moved directly downstream of the promoter. Finally, when both recombinases are expressed, slot Z00, Z01, Z10 are all excised, thus placing Z11 downstream of the promoter unobstructed by other slots. Note that each slot is not limited to the expression of just one gene/output. For example, an IRES or 2A type of sequence can be used to link multiple genes together in one slot, thus allowing arbitrary number of outputs. To demonstrate this decoder design experimentally, the inventors placed a stop cassette, mRuby2, iRFP, and GFP into slot Z00, Z10, Z01, and Z11 respectively, and transfected into HEK293T along with Cre and Flp expressing plasmids. The decorder output is highly digital with a signal to noise ratio over 100 for each state (FIG. 13A).

This 2-4 decoder design theoretically allow the generation of all possible 2-Input n-output devices in a single layer. Some of the more important 2-Input devices are the half adder and half subtractor, which are 2-Input 2-Output devices that can perform arithmetic. A half adder generates an output in the Sum (S) when either one of the input is presence. When both inputs are presence, it generates a carry out signal (Cout) and no S. To generate a half-adder, the inventors placed a stop cassette in the Z00 slot, a GFP in Z10 and Z01, and a GFP-2A-mCherry cassette in Z11 (FIG. 13B). In this case, the GFP is the S and mCherry is the Cout. Similar to the decoder, half adder performs as expected in mammalian cell with high signal to noise ratio (FIG. 4*b*). To create the half subtractor, a stop cassette is placed in the Z00 slot, a GFP in Z01, and a GFP-P2A-mCherry in Z10. Since there is no output in both the S and Cout, therefore nothing is required in the Z11 slot. Again, the half subtractor behaved as expected (FIG. 13C).

If heterospecific sites are not available for the enzyme of choice, it is still possible to create half adder or half subtractor using multiple transcription units. The inventors noticed that half adder or half subtractor can be composed from some of the simpler 2-Input 1 output Boolean logic gates. For example, a half adder is composed of an A-NIMPLYB and BNIMPLY with a GFP as output and a AND gate with mCherry as output. The inventors can achieve a half adder simply by co-transfecting three plasmids, each containing a transcription unit for a logic gate. The inventors can also combine the two NIMPLY logic gates into one unit to form a XOR gate and reduces the design into a two transcription unit system. Note that although it may be easier to implement a multi-transcription unit design in transient transfection because one can mix different number of plasmids readily, single transcription unit will facilitate integration into genome.

Figure 13D:
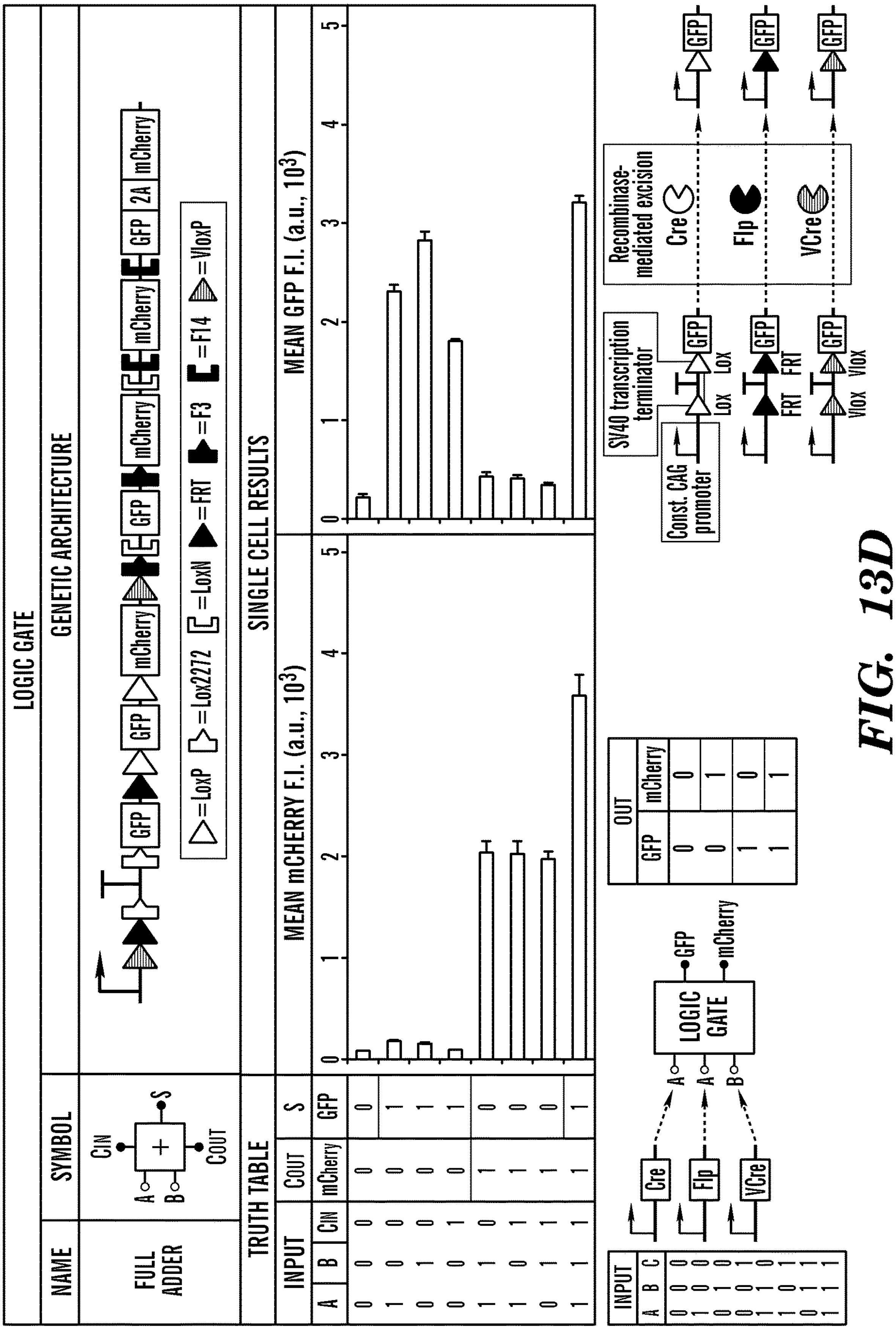

To test whether one can construct more sophisticated circuits, the inventors developed a Full-Adder, a 3-Input 2-output logic gates, using Cre, Flp and Vcre as input. Similar to the half-adder, a full adder is one of the permutations of the 3-8 decoder. A 3-8 decoder has 8 unique states, thus requires 8 different slots. This design requires 3 different heterospecific sites for Cre and Flp, but just one site for Vcre. Again, each slot corresponds to a specific state. To achieve a full adder, the inventors filled the slots with either a stop cassette, GFP, mCherry or GFP-2A-mCherry, depending on the out of the full adder truth table. This single layer design displayed the expected logic output in mammalian cells (FIG. 13D).

An important class of circuit found in modern computer is a Programmable Read Only Memory (PROM) device where depending on the input selection signal, the circuit will adopt one of the 16 2-Input 1 Output Boolean logic gates. In essence, this is a 6-Input 1-Output logic gate. To create the PROM, the Cre-Flp decoder framework is employed. Each slot is created with recombination sites from Cre and Flp. However, in each slot, a buffer gate for different selector input recombinase is inserted. In the present version, buffer gate for Dre, Vox, VCre and B3 is in the slot Z00, Z10, Z01, and Z11 respectively. Therefore, the selector input will dictate whether a stop cassette or a GFP is dominant in that slot. For instance, within a decoder framework, an OR can be achieved with a stop cassette in the Z00 slot and a GFP in the other three slots. Therefore, in the presence of Vox, VCre, and B3, slot Z10, Z01, and Z11 will have GFP while Z00 will still have a stop cassette, thus generating the OR gate. As shown in FIG. 8A, the logic gate selector can display the output logic of all 16 Boolean logic gates depending on the selector input recombinase.

In electronic circuit design, many of the more sophisticated logic circuits were created by connecting several simpler circuits together, often times in multiple layers. This is a robust design strategy in electronic, because the connection between different device is easy to implement and the resulting performance is predictable. However, following this strategy from electronic in synthetic biology has proven to be difficult because of the lack of understanding of how different components will behave when connected together. Large efforts are underway to provide detail characterization of components and develop standard to allow better predictability of the interoperability of different parts.

Here, a complementary approach is provided where a single layer platform can be used to create a large variety of complex circuits. This platform is highly robust, such that all of the inventors demonstrated that designed and developed circuits performed as expected on first attempt without iteration. To characterize the robustness of this platform, a library of 2-Input 2-Output circuit can be used by using a combinatorial Gibson assembly strategy (FIG. 9). Using the 2-4 decoder framework as the basis, 4 parts can be constructed for each slot—stop cassette, GFP, mCherry, and GFP-2A-mCherry. Since the 2-4 decoder has 4 slots, a total of 16 components can be used. Then a combinatorial assembly strategy can be employed to create all 256 possible 2-Input 2-Output circuits. Characterizing the percentage of the 256 circuits that behave as expected will characterize the robustness of the platform. Similar libraries can be created for all other n-Input m-Output circuit, thus providing a foundation to generate an enormous amount of functionally distinct circuits.

All the circuits designed in the work are single use system. While this single use system as disclosed herein is sufficient for many biotechnological applications, such as in animal model development, it can also be constructed to use a reversible system for other occasions. While both tyrosine and serine recombinase can perform excision and inversion, only serine recombinase can perform stable inversion. More importantly, some serine recombinase has a complementary directionality factor that when expressed together with the recombinase, will revert the inversion generated by the recombinase back to the original configuration. Using this property, the inventors also designed a decoder frame work based on inversion of serine recombinase, and depending on the presence of directionality factor or not, can revert the system back to the original state (FIGS. 14A-14B). Similar to the tyrosine recombinase design, such decoder framework also relies on the availability of heterospecific sites.

Example 4

In electronic circuit design, connecting several simple circuits together, often times in multiple layers, was applied in order to generate many sophisticated computational circuits. This is a robust design strategy in electronics, because the connections between different components are easy to implement and the resulting performance is predictable. However, applying this strategy from electrical engineering to synthetic biology has proven to be difficult because of the lack of a complete understanding of how different components will behave when connected together. Efforts are underway to provide detailed characterization of components and develop standards to allow for better predictability of the interoperability of different parts[32-34]. Furthermore, multi-layer design requires more orthogonal biological "wires", which drives effort toward parts development[35-38] at the expense of circuit design. Here, the inventors have demonstrated a simple and flexible approach in which a single layer platform can be used to create a large variety of complex circuits. This platform is highly robust, such that the developed circuits performed as expected on the first attempt without iteration. Coupled with the recent discoveries of many orthogonal serine integrases[39], the BLADE platform provides the foundation for creating advanced genetic computational devices in living cells and opens the doors for complex animal model development.

Example 5

TABLE 42-1

Setup of buffer gates and recombinase expression plasmids for recombinase cross-reactivity table as detailed in FIG. 1B, in addition to co-transfection with 62.5 ng pCAG-tagBFP (pBW462) and 62.5 ng pCAG-FALSE (pBW363).

| | | Reporter | | | | | | | |
|---|---|---|---|---|---|---|---|---|---|
| Enz | Plasmid ID | loxP pBW338 | FRT pBW339 | rox pBW364 | SloxM1 pBW271 | VloxP pBW273 | vox pBW275 | B3RT pBW276 | KDRT pBW277 |
| iCre | pBW390 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| FlpO | pBW391 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| DreO | pBW431 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| SCre | pBW432 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| VCre | pBW433 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| Vika | pBW434 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| B3 | pBW435 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| KD | pBW436 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| B2 | pBW437 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| R | pBW438 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| ϕC31 | pBW440 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| bxb1 | pBW439 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |
| None | pBW363 | 62.5 ng ea. | 62.5 ng ea. | 62.5 ng ea. | 62.5 ng ea. | 62.5 ng ea. | 62.5 ng ea. | 62.5 ng ea. | 62.5 ng ea. |

TABLE 42-2

| | | Reporter | | | | |
|---|---|---|---|---|---|---|
| Enz | Plasmid ID | B2RT pBW278 | RSRT pBW279 | ϕC31 attB/P pBW409 | bxb1 attB/P pBW406 | None pBW363 |
| iCre | pBW390 | 62.5 ng ea. | 62.5 ng ea. | 62.5 ng ea. | 62.5 ng ea. | 62.5 ng ea. |
| FlpO | pBW391 | 62.5 ng ea. | 62.5 ng ea. | 62.5 ng ea. | 62.5 ng ea. | 62.5 ng ea. |

TABLE 42-2-continued

| | | Reporter | | | | |
|---|---|---|---|---|---|---|
| Enz | Plasmid ID | B2RT pBW278 | RSRT pBW279 | φC31 attB/P pBW409 | bxb1 attB/P pBW406 | None pBW363 |
| DreO | pBW431 | 62.5 ng ea. | 62.5 ng ea. | 62.5 ng ea. | 62.5 ng ea. | 62.5 ng ea. |
| SCre | pBW432 | 62.5 ng ea. | 62.5 ng ea. | 62.5 ng ea. | 62.5 ng ea. | 62.5 ng ea. |
| VCre | pBW433 | 62.5 ng ea. | 62.5 ng ea. | 62.5 ng ea. | 62.5 ng ea. | 62.5 ng ea. |
| Vika | pBW434 | 62.5 ng ea. | 62.5 ng ea. | 62.5 ng ea. | 62.5 ng ea. | 62.5 ng ea. |
| B3 | pBW435 | 62.5 ng ea. | 62.5 ng ea. | 62.5 ng ea. | 62.5 ng ea. | 62.5 ng ea. |
| KD | pBW436 | 62.5 ng ea. | 62.5 ng ea. | 62.5 ng ea. | 62.5 ng ea. | 62.5 ng ea. |
| B2 | pBW437 | 62.5 ng ea. | 62.5 ng ea. | 62.5 ng ea. | 62.5 ng ea. | 62.5 ng ea. |
| R | pBW438 | 62.5 ng ea. | 62.5 ng ea. | 62.5 ng ea. | 62.5 ng ea. | 62.5 ng ea. |
| φC31 | pBW440 | 62.5 ng ea. | 62.5 ng ea. | 62.5 ng ea. | 62.5 ng ea. | 62.5 ng ea. |
| bxb1 | pBW439 | 62.5 ng ea. | 62.5 ng ea. | 62.5 ng ea. | 62.5 ng ea. | 62.5 ng ea. |
| None | pBW363 | 62.5 ng ea. | 62.5 ng ea. | 62.5 ng ea. | 62.5 ng ea. | 62.5 ng ea. |

TABLE 43

Figure 1D:
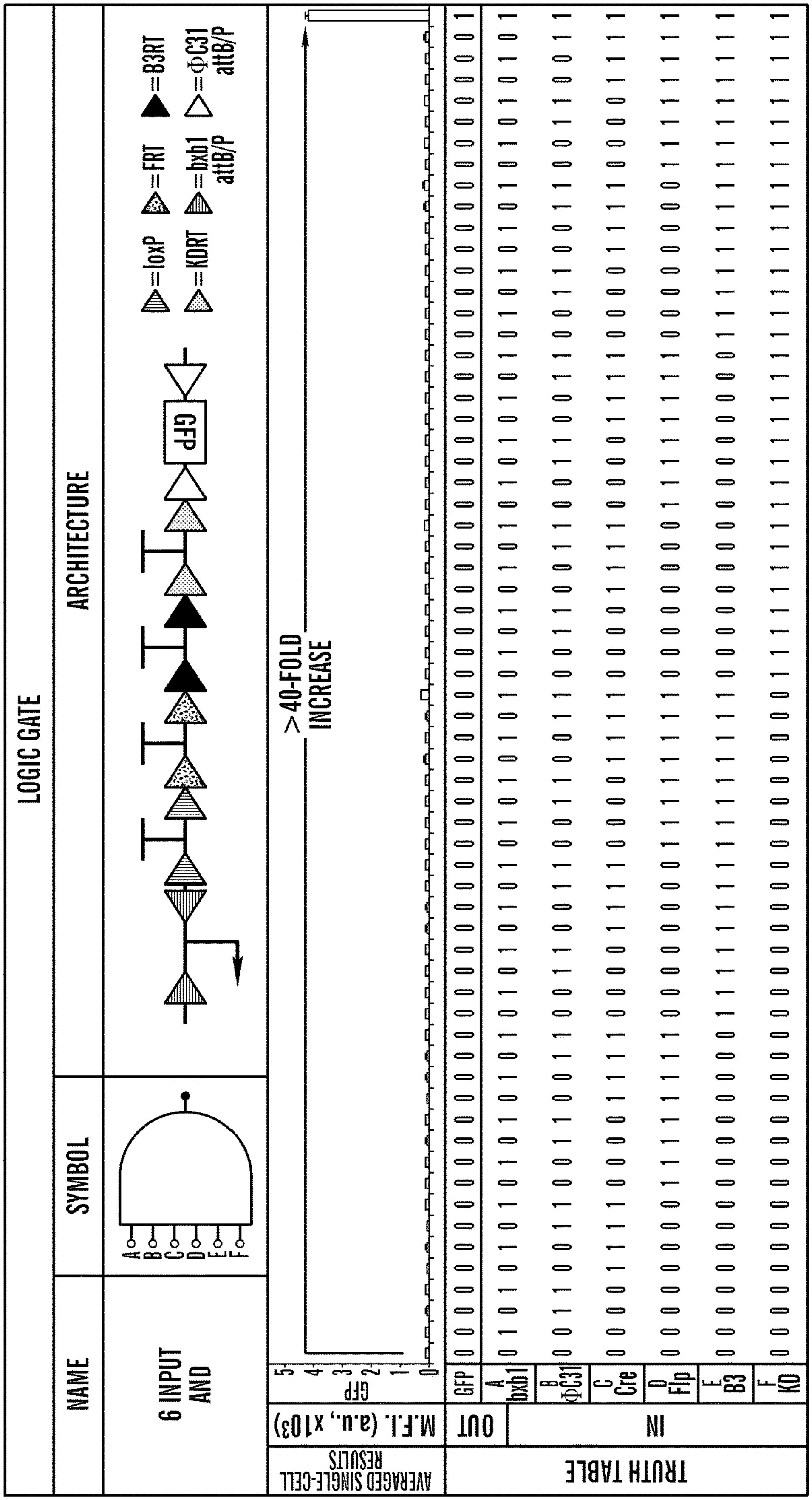

Transient transfection setup of six-input AND gate as detailed in FIG. 1D.

| AND GATE, ng pCAG-6AND (pBW479) | Enzyme 1, ng pCAG-PhiC31 (pBW440) | Enzyme 2, ng pCAG-bxb1 (pBW439) | Enzyme 3, ng pCAG-iCre (pBW390) | Enzyme 4, ng pCAG-FlpO (pBW391) | Enzyme 5, ng pCAG-B3 (pBW435) | Enzyme 6, ng pCAG-KD (pBW436) | Blank, ng pCAG-FALSE (pBW363) | Marker, ng pCAG-tagBFP (pBW462) |
|---|---|---|---|---|---|---|---|---|
| 150 | 0 or 12.5 | 0 or 12.5 | 0 or 12.5 | 0 or 12.5 | 0 or 12.5 | 0 or 12.5 | Fill to total DNA amount = 250 ng | 25 |

TABLE 44

Setup of buffer gates and recombinase expression plasmids for recombinase heterospecificity table as detailed in FIG. 1C, in addition to co-transfection with 62.5 ng pCAG-tagBFP (pBW462), 62.5 ng pCAG-FALSE (pBW363), and 62.5 ng corresponding recombinase expression plasmid.
Buffer Gate

| Buffer Gate | pBW | ng |
|---|---|---|
| pCAG-loxP-STOP-loxP-GFP | 338 | 25 |
| pCAG-lox2272-STOP-lox2272-GFP | 427 | 25 |
| pCAG-loxN-STOP-loxN-GFP | 428 | 25 |

TABLE 44-continued

Setup of buffer gates and recombinase expression plasmids for recombinase heterospecificity table as detailed in FIG. 1C, in addition to co-transfection with 62.5 ng pCAG-tagBFP (pBW462), 62.5 ng pCAG-FALSE (pBW363), and 62.5 ng corresponding recombinase expression plasmid.
Buffer Gate

| Buffer Gate | pBW | ng |
|---|---|---|
| pCAG-loxP-STOP-lox2272-GFP | 451 | 25 |
| PCAG-loxP-STOP-loxN-GFP | 452 | 25 |
| pCAG-lox2272-STOP-loxN-GFP | 453 | 25 |

TABLE 44-continued

Setup of buffer gates and recombinase expression plasmids for recombinase heterospecificity table as detailed in FIG. 1C, in addition to co-transfection with 62.5 ng pCAG-tagBFP (pBW462), 62.5 ng pCAG-FALSE (pBW363), and 62.5 ng corresponding recombinase expression plasmid.
Buffer Gate

| Buffer Gate | pBW | ng |
|---|---|---|
| pCAG-FRT-STOP-FRT-GFP | 339 | 25 |
| pCAG-F3-STOP-F3-GFP | 429 | 25 |
| PCAG-F14-STOP-F14-GFP | 430 | 25 |
| pCAG-FRT-STOP-F3-GFP | 454 | 25 |
| pCAG-FRT-STOP-F14-GFP | 455 | 25 |
| pCAG-F3-STOP-F14-GFP | 456 | 25 |
| pCAG-VloxP-STOP-VloxP-GFP | 273 | 25 |
| pCAG-Vlox2272-STOP-Vlox2272-GFP | 274 | 25 |
| pCAG-VloxP-STOP-Vlox2272-GFP | 331 | 25 |

Table 45A-45C: Transient transfection setup for 2-input, 1-output logic gates detailed in FIG. 6.

TABLE 45A

| Re-porter, ng | Input state A B | Enzyme 1, ng pCAG-iCre (pBW390) | Enzyme 2, ng pCAG-FlpO (pBW391) | Blank, ng pCAG-FALSE (pBW363) | Marker, ng pCAG-tagBFP (pBW462) |
|---|---|---|---|---|---|
| Values | 0 0 | 0 | 0 | 50 | 25 |
| shown | 1 0 | 25 | 0 | 25 | 25 |
| below | 0 1 | 0 | 25 | 25 | 25 |
| | 1 1 | 25 | 25 | 0 | 25 |

TABLE 45B

Logic gate

| Gate | Plasmid ID | ng |
|---|---|---|
| HALF ADDER 3 p | pBW344 | 8.3 |
| | pBW345 | 8.3 |
| | pBW403 | 8.3 |
| HALF ADDER 2 p | pBW448 | 12.5 |
| | pBW403 | 12.5 |
| HALF ADDER 1 p | pBW457 | 25 |
| HALF SUBTRACTOR 3 p | pBW344 | 8.3 |
| | pBW345 | 8.3 |
| | pBW206 | 8.3 |

TABLE 45B-continued

Logic gate

| Gate | Plasmid ID | ng |
|---|---|---|
| HALF SUBTRACTOR 2 p | pBW448 | 12.5 |
| | pBW206 | 12.5 |
| HALF SUBTRACTOR 1 p | pBW570 | 25 |

TABLE 45C

Logic gate

| Gate | Plasmid ID | ng |
|---|---|---|
| NOR | pBW334 | 25 |
| OR | pBW335 | 25 |
| AND | pBW336 | 25 |
| NAND | pBW337 | 25 |
| A | pBW338 | 25 |
| B | pBW339 | 25 |
| NOTA | pBW340 | 25 |
| NOTB | pBW341 | 25 |
| A IMPLY B | pBW342 | 25 |
| B IMPLY A | pBW343 | 25 |
| A NIMPLY B | pBW344 | 25 |
| B NIMPLY A | pBW345 | 25 |
| XOR | pBW344 | 12.5 |
| | pBW345 | 12.5 |
| XNOR | pBW334 | 12.5 |
| | pBW336 | 12.5 |
| TRUE | pBW361 | 25 |
| FALSE | pBW363 | 25 |
| XOR | pBW448 | 25 |
| XNOR | pBW450 | 25 |

TABLE 46

Transient transfection setup for 2-input, 4-output decoder circuit detailed in FIG. 2.

| Reporter pEXPRCAG-DECODER (pBW842) | Input State A B | Enzyme 1, ng pCAG-iCre (pBW390) | Enzyme 2, ng pCAG-FlpO (pBW391) | Blank, ng pCAG-FALSE (pBW363) | Marker, ng pCAG-Lss-mOrange (pBW474) |
|---|---|---|---|---|---|
| 62.5 | 0 0 | 0 | 0 | 125 | 62.5 |
| | 1 0 | 62.5 | 0 | 62.5 | 62.5 |
| | 0 1 | 0 | 62.5 | 62.5 | 62.5 |
| | 1 1 | 62.5 | 62.5 | 0 | 62.5 |

Figure 3B:
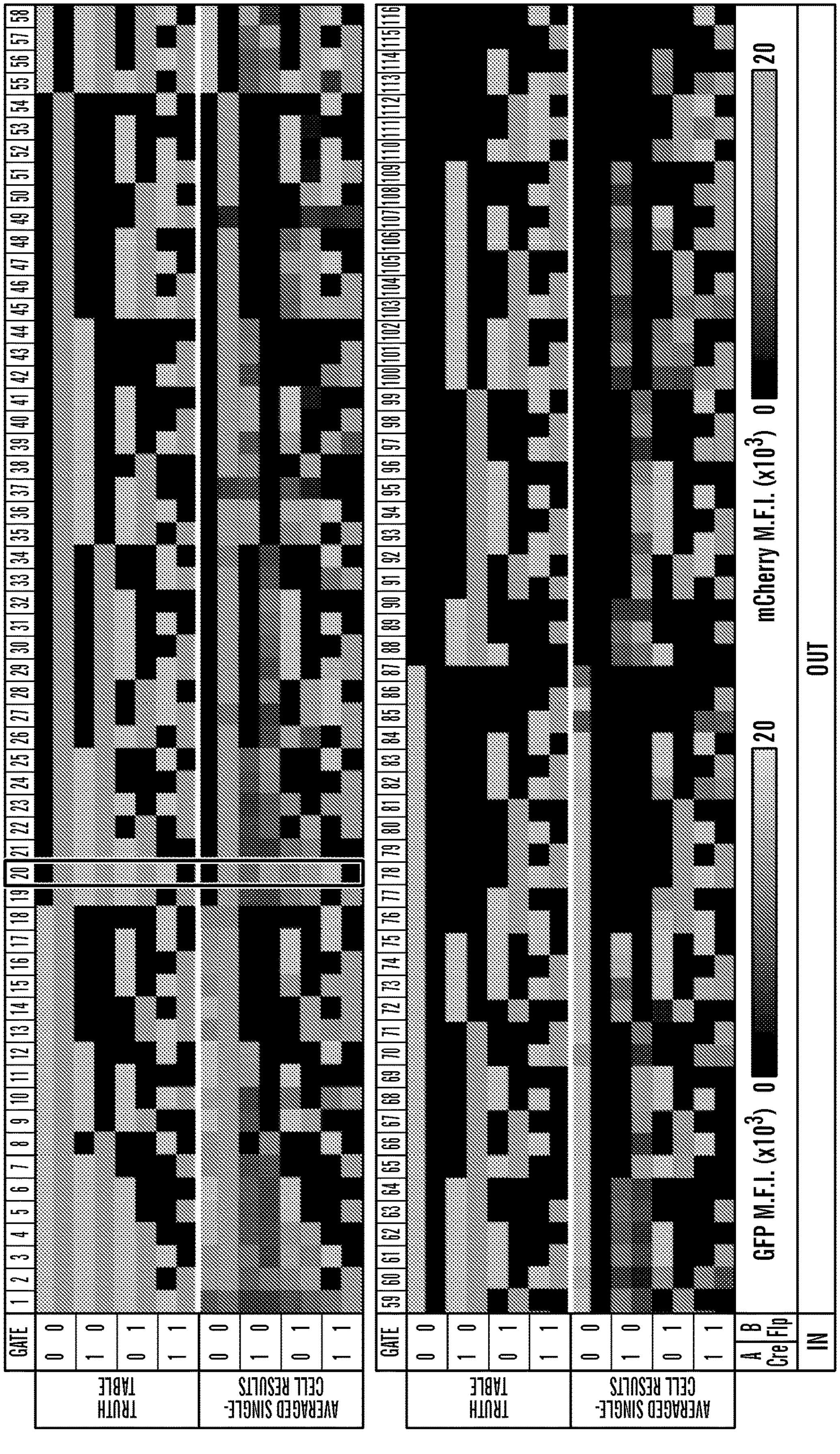

Tables 47A-47B: Transient transfection setup for 3-input logic gates detailed in FIG. 3.

TABLE 47A

| Reporter | Input State A B C | Enzyme 1, ng pCAG-iCre (pBW390) | Enzyme 2, ng pCAG-FlpO (pBW391) | Enzyme 3, ng pCAG-VCre (pBW433) | Blank, ng pCAG-FALSE (pBW363) | Marker, ng pCAG-tagBFP (pBW462) |
|---|---|---|---|---|---|---|
| Values | 0 0 0 | 0 | 0 | 0 | 0 | 62.5 |
| Shown | 1 0 0 | 41.7 | 0 | 0 | 83.3 | 62.5 |
| below | 0 1 0 | 0 | 41.7 | 0 | 83.3 | 62.5 |
| | 0 0 1 | 0 | 0 | 41.7 | 83.3 | 62.5 |
| | 1 1 0 | 41.7 | 41.7 | 0 | 41.7 | 62.5 |
| | 1 0 1 | 41.7 | 0 | 41.7 | 41.7 | 62.5 |
| | 0 1 1 | 0 | 41.7 | 41.7 | 41.7 | 62.5 |
| | 1 1 1 | 41.7 | 41.7 | 41.7 | 0 | 62.5 |

TABLE 47B

| Logic gate | | |
|---|---|---|
| Gate | Plasmid ID | ng |
| FULL ADDER | pBW820 | 62.5 |
| FULL SUBTRACTOR | pBW840 | 62.5 |
| HALF ADDER-SUBTRACTOR | pBW841 | 62.5 |

TABLE 48

Transient transfection setup for six-input Boolean logic Look-up (LUT) Table genetic device.

| OOLEAN LOGIC LUT, ng PEXPRCAG-LUT pBW829) | Input State A B | Enzyme 1, ng pCAG-iCre (pBW390) | Enzyme 2, ng pCAG-FlpO (pBW391) | Enzyme 3, ng pCAG-PhiC31 (pBW440) | Enzyme 4, ng pCAG-Vika (pBW434) | Enzyme 5, ng pCAG-B3 (pBW435) | Enzyme 6, ng pCAG-bxb1 (pBW439) | Blank, ng pCAG-FALSE (pBW363) | Marker, ng pCAG-tagBFP (pBW462) |
|---|---|---|---|---|---|---|---|---|---|
| 75 | 0 0 | 0 | 0 | 0 or 25 | 0 or 25 | 0 or 25 | 0 or 25 | Fill to total DNA amount = 250 ng | 25 |
|  | 1 0 | 25 | 0 |  |  |  |  |  |  |
|  | 0 1 | 0 | 25 |  |  |  |  |  |  |
|  | 1 1 | 25 | 25 |  |  |  |  |  |  |

Example 6

The switches are designed using DNA recombinase systems. DNA recombinases are enzymes derived from bacteria and fungi that recognize pairs of specific DNA sequences that are 30-40 base pairs long. The recombinase can perform either an excision or inversion on the sequence between these recognition sites based on the relative orientation of these sequences. Cre is a recombinase that acts upon pairs of sites called lox sites. A version of the stable inversion switch has also been constructed that responds to activity of the Flp recombinase, which acts on frt recognition sites.

There are several parameters that can guide the design of these switches. (1) Drug inducible: the switches can be controlled at bedside using the transient addition of a drug so that a doctor can easily change the therapy with minimal stress to the patient. (2) Stable switching: T cells undergo rapid proliferation upon activation, so it is important that the switches provide stable memory of switching from one state to another even under conditions of rapid expansion. (3) Lentiviral compatibility.

The stable inversion switch allows for control over whether a cell should stay in some initial state (State 1) or to switch to another state (State 2). These states can be encoded by different genes or promoters. The control over switching from State 1 to State 2 is effected by recombinase activity on the switch. We have constructed several variants of this switch (FIG. 18): 1.) Target switch: Directs T-cell to a new target. 2.) Affinity switch: Tunes the dynamics of T-cell activation by changing between CARS with different affinity to same target. 3.) Expression level switch: Tunes dynamics of T-cell activity by changing expression level of CAR. 4.) "On" or "Off" switch: Controls when the therapy is active.

As part of the design, drug-inducible recombinases can be implemented, which allow one to control recombinase activity through drug addition. There are several drugs available for use to control the action of recombinases, including doxycycline, tamoxifen, and abscisic acid. These drugs can control recombinase activity through different mechanisms: transcriptional control (doxycycline, abscisic acid, rapamycin), dimerization (rapamycin), and nuclear localization (tamoxifen). With the exception of rapamycin-induced dimerization, which has only been developed for Cre, all of these mechanisms can be used to control both Cre and Hp activity.

Figure 19:
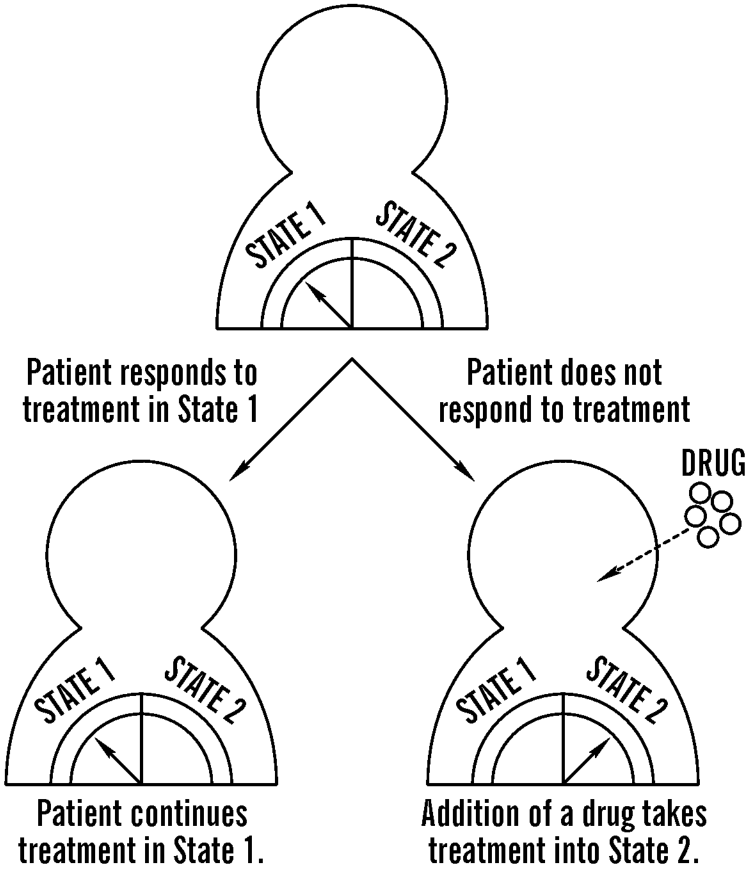
FIG. 19 shows a strategy to improve the flexibility and strength of adoptive T-cell therapy. Using dials that respond to the addition of a drug to tune the therapy to a patient's needs.

Using the drug-inducible recombinases to act on the stable inversion designs described above, doctors will be allowed greater control over adoptive T-cell therapy. With these circuits, the therapy can be tuned to an individual patient's needs. For example, patient can begin the therapy in its safest iteration. The doctor can then evaluate the patient's response and use a drug to drive recombination and advance the T-cells to a more aggressive form of therapy (FIG. 19).

Figure 20:
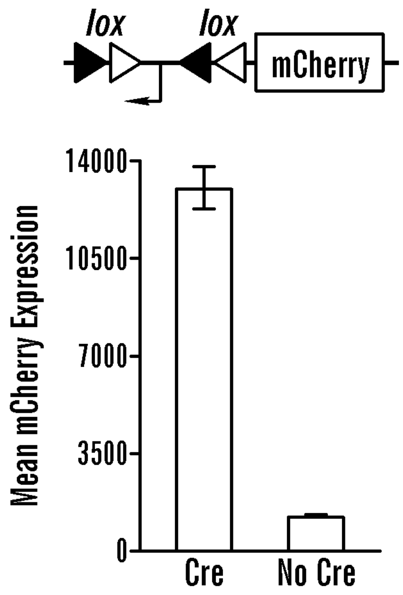
FIG. 20 shows stable inversion switching of a Cre/lox promoter switch controlling mCherry expression.

In preliminary tests using a lox-based expression level switch to control mCherry expression human embryonic kidney (HEK) cells, expression of mCherry was increased by 10-fold through Cre activity upon the switch (FIG. 20), Thus this design can be to create a stable change in expression of a gene, and we will use it to control CAR expression.

Figure 21A:
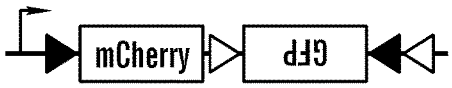
Figure 21B:
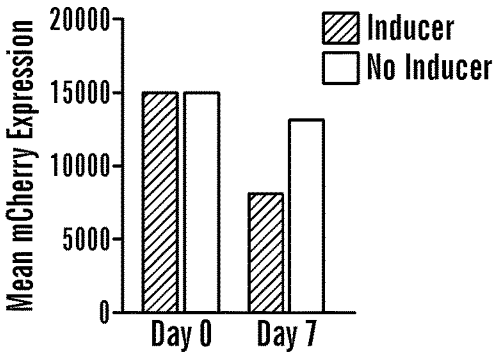
Figure 21C:
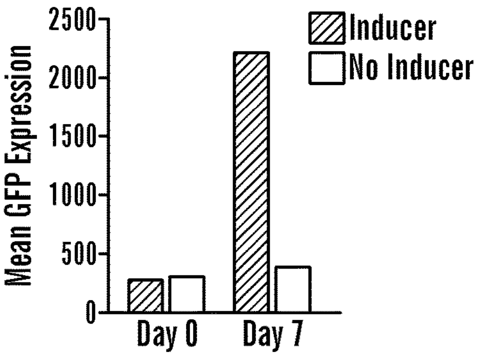

To create T-cells that express our circuit components, lentiviral integration can be used to stably integrate the switch and inducible recombinases into the genome. This lentiviral integration has been used successfully to express a fluorescent reporter stable inversion switch and a tamoxifen-inducible Cre in Jurkat T-cells. The reporter switch causes a cell to switch from mCherry expression to GET expression, and one were then able to induce this switch (FIGS. 21A-21C), These results indicate a drug can be used to control recombinase activity upon the stable inversion switch design.

Figure 22A:
FIGS. 22A-22C show drug-induced activation of Jurkat in response to the Her2 antigen using (FIG. 22A) an On switch that turns on expression of a Her2-specific CAR tagged to mCherry.
Figure 22B:
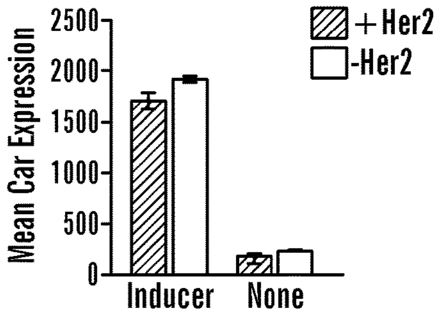
Figure 22C:
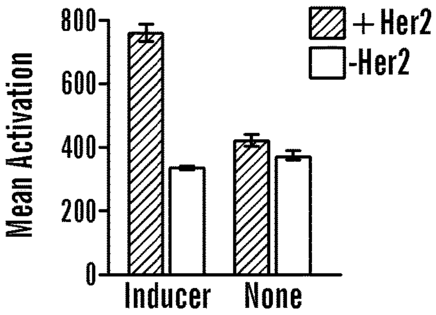
Figure 23A:
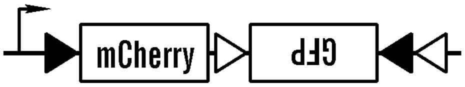
FIGS. 23A-23C show the implementation of fluorescent stable inversion switch in primary T-cells.
Figure 23B:
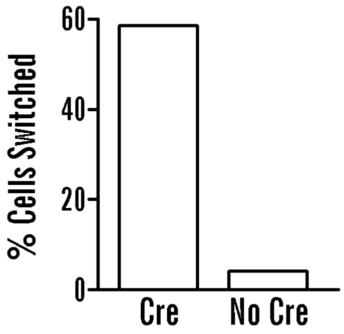
Figure 23C:
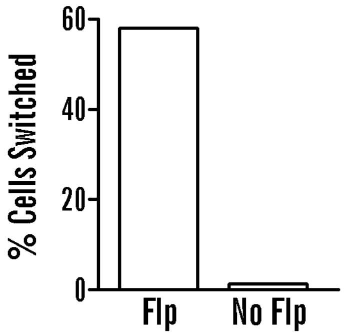

A Jurkat line that expresses GFP under an NFAT promoter has also been used to monitor activation. With this line, the inventors have stably expressed the tamoxifen-inducible Cre and an "ON" switch that turns on expression of a Her2-specific CAR, Using this switch, the inventors were able to control the response of the T-cell to Her2 through the addition of tamoxifen (FIGS. 22A-22C).

These switches can be implemented in a patient's own T-cells. Constitutively active Cre and Flp are used to act on the fluorescent reporter stable inversion switch in CD4 primary T-cells.

Testing switches in HEK cell.

To track the efficacy and dynamics of the switches, fluorescent-tagged recombinases and CARs can be used in testing the switches. This tagging can allow one to use fluorescence-activated cell sorting (FACS) to track the expression of the switch components. The switches can be tested first in human embryonic kidney (HEK) cells due to the ease of transfection, which will allow for quick verification that all components function in mammalian cells. This testing can also involve the construction of a simple fluorescence circuit that expresses red fluorescence until recombinase activity causes the red fluorescence to turn off and green fluorescence to turn on. The red and green fluorescence provides an easy read-out that can provide one with information of how different inducers effect recombinase activity.

Constructing and Testing Stable Circuit Lines in Jurkat T-Cells.

As the goal is to be able to use these switches in T-cells, lentiviral integration can be used to create lines of Jurkat T-cells that stably express the switches and inducible recombinase components. The fluorescent switch is first tested with inducible recombinases to characterize recombinase activity and refine the induction protocol. There are several aspects of inducible recombination activity that these stable lines can help to characterize. (I) Basal activity: While the recombinases should only act when the designated inducer is added to the media, the level of control may not always be tight enough to restrict recombinases from acting when there is no inducer present. This leakiness can lead to leaky basal recombination activity. It is important to minimize this basal activity so that the switches can be used safely. (II) inducibility: While keeping the basal activity low is important, it is also important that upon drug induction, the recombinase is able to work efficiently to convert the cell to the desired state.

Different parameters of the protocol for inducible recombinase activity can be varied to determine the best method to achieve a safe and effective treatment, using the basal activity and inducibility to characterize the outcome. These parameters include the volume of inducible recombinase lentivirus used to transduce cells, the drug dosage used to induce recombinase activity, and the amount of time the cells are exposed to the drug.

To create stable lines expressing our CAR-expressing switches, a Jurkat line that expresses a GFP reporter under the NEAT promoter can be used, NFAT turns on during T-cell activation, so this line can be used to track Jurkat activation by measuring GFP expression. Plate-bound antigen as well as artificial antigen presenting cells can be used to activate the T-cell. The fluorescent-tagged recombinases and CARs can then be used to monitor induction and switching from State 1 to State 2, and the NEAT-GFP reporter to monitor T-cell activation. This tracking can allow one to characterize the dynamics of switching, and correlate these changes in CAR expression to the activity of the T-cell, which can allow one to explore questions like how long it takes to switch from State 1 to State 2, how different parameters of CAR expression affect activation, and how the presence of different CARs on one T-cell affects overall response.

Constructing and Testing Stable Circuit Lines in Primary T-Cells.

Lentiviral integration can be used to express our circuits in primary T-cells, using fluorescent read-outs to track the switching of the cells from State 1 to State 2. The response of the primary T-cells to the target antigen can be measured by measuring proliferation, interleukin-2 (IL2), and Interferon gamma (IFN-γ), and by monitoring the ability of the primary T-cells to kill artificial antigen presenting cells.

Testing Switches in Mice.

A Mouse xenograft tumor model can be developed using 6-8 week old female NOD/Scid mice. They are maintained under pathogen-free conditions. Ten female mice are subcutaneously inoculated on the flank with cells from cancer cell lines expressing different levels of antigen, and the T-cells will be added via retraorbital injection. To induce switching, drugs can be added to the food. Tumor dimensions can be measured using calipers, and the animals can be euthanized if the tumor reaches 2 cm in diameter.

A transduction and induction strategy can be designed that minimizes the toxicity of the recombinases while still maintaining their activity. These strategies can include expressing the inducible recombinase at low levels, tagging the recombinases with degradation tags, or introducing the inducer in pulses so that the recombinase activity is induced for only short periods of time. These strategies are oriented around lowering the amount of recombinase present in the system or limiting their exposure to the DNA. While immunogenicity and genotoxicity are important challenges to consider in our design, they are only toxic to the cells the circuit is expressed in. While this will reduce the efficacy of the therapy, it should not kill other cells.

Packaging. The size of the circuits described is limited by the amount of DNA that can be successfully packaged into a lentiviral, and transduction of switches decrease as they become larger. Several strategies can be explored to overcome the challenge of limited payload delivery. For switches like the affinity switch, where the circuit is designed to switch from the expression of one CAR to another, one can split the design into two separate viruses: one that encodes the first CAR in an "OFF" switch and another that encodes the second CAR in an "ON switch". DNA transposon systems like PiggyBac and Sleeping Beauty can also be used to integrate the switches into T-cells. PiggyBac has been used to integrate CARs into T-cells.

With these components in place, the switches described herein can allow for increased control over the activity of CARs in T-cells, enabling adoptive T-cell therapy to become more personalized to an individual patient's needs.

Example 7

An ON/OFF toggle switch has been developed that can stably switch to either the ON or OFF state with the transient addition of drugs. This improvement can simplify treatment and avoid the potential long term effect of the drug on the patient. A quick OFF switch, an ON/OFF toggle switch, and a kill switch can all be implemented together to afford high level of control and safety.

To construct the ON/OFF toggle switch, several serine recombinases and corresponding recombinase directionality factors (RDFs, e.g., gp47 for bxb1, gp3 for phiC, ORF7 for TP901-1, gp25 for TG1, and gp3 for PhiRv1) that perform stable and reversible site specific DNA recombination were first used. Some of these enzymes (e.g., PhiC31 or bxb1) had been shown to be efficient in performing recombination reactions in mammalian cells. When the recombination sites, attB and attP are placed in the antiparallel orientation, the presence of recombinases will stably invert the DNA sequence between the two sites and generate an attL and attR site ("BP reaction"). This inversion remains stable unless a RDF is also expressed along with bxb1 or phiC, which will invert the sequence between attL and attR and regenerate attB and attP site ("LR reaction"). This reversible reaction has been demonstrated in *E. coli* to be repeatable for many cycles.

Experiments were performed to verify whether these recombinases with RDF can invert the sequence between attL and attR and regenerate attB and attP site (LR reaction) as well as BP reaction because not all recombinases and RDFs had been tested in mammalian cells to achieve 13P & LR reaction. It turned out that every recombinase including PhiC31, TP901-1, TG1, and PhiRV1 can successfully undergo BP & LR reaction. Among the recombinases and RDFs that can undergo BP and LR reaction, several inducible systems were screened for (e.g., ERT2, Destabilizing Domain (DD) from FKBP, DD from dihydrofolate reductase (DHFR), doxycycline inducible promoter) that can induce either recombinases ear RDFs and achieve BP & LR reaction successfully. For recombinases (PhiC31, TP901-1, and TG1), both destabilizing domains (one from FKBP and the other from dihydrofolate reductase) worked well in inducing expression of recombinases, but did not work well in inducing RDFs. However, PhiRv1 did not get induced with two DD domains efficiently. Also, location of destabilizing domain matters. When DD was fused to the C-terminus, it worked better than when it was fused to the N-terminus. When DD was fused to both the N and C terminus, low basal expression was observed. In addition, DD from DHFR (up to 8~9 fold difference) worked better than DD from FKBP (up to 3~4 fold difference). Shield1 ligand was used to induce DD from FKBP domain and trimethoprim (TMP) was used to induce DD from dihydrofolate reductase). Doxycycline inducible promoter (both Tet-on system and Tet-on-3G) system was used to induce recombinases and RDFs, but doxycycline inducible promoter was not efficient at expressing recombinases and RDFs. Also, ERT2 domain which is induced by 4-hydrotamoxifen (40HT) was used. ERT2 was primarily tested to induce different RDFs (e.g., gp3, gp25, and ORF7) and ERT2 can be used to induce gp3, gp25 and ORF7. Location of ERT2 domain matters. Most of the time when ERT2 was fused both the N and C terminus, basal expression was low and gave high fold change (~8). Location of NLS can be changed (either the Nor C terminus or both) to give better expression level.

The inventors have demonstrated the use of three widely used recombinases and corresponding RDFs (parenthesis), PhiC31 (gp3), TG1 (gp25) and TP901-1 (ORF7) in mammalian cells. These recombinases and corresponding RDFs were induced by different drugs (Shield1, TMP, and 40HT) to make On/Off toggle switch. Recombinases (PhiC13, TG1, and TP901-1) were induced by (Shield1, and TMP) and corresponding RDFs were induced by 40HT.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

REFERENCES

The references disclosed herein are incorporated in their entirety by reference.

Auslander, S., Auslander, D., Muller, M., Wieland, M., and Fussenegger, M. (2012). Programmable single-cell mammalian biocomputers. Nature 487, 123-127.

Bonnet, J., Yin, P., Ortiz, M. E., Subsoontorn, P., and Endy, D. (2013). Amplifying Genetic Logic Gates. Science.

Gaber, R., Lebar, T., Majerle, A., Ster, B., Dobnikar, A., Bencina, M., and Jerala, R. (2014). Designable DNA-binding domains enable construction of logic circuits in mammalian cells. Nat Chem Biol 10, 203-208.

Moon, T. S., Lou, C., Tamsir, A., Stanton, B. C., and Voigt, C. A. (2012). Genetic programs constructed from layered logic gates in single cells. Nature 491, 249-253.

Siuti, P., Yazbek, J., and Lu, T. K. (2013). Synthetic circuits integrating logic and memory in living cells. Nat Biotechnol.

1 Wei, P. et al. Bacterial virulence proteins as tools to rewire kinase pathways in yeast and immune cells. Nature 488, 384-388, doi:10.1038/nature11259 (2012).

2 Fenno, L. E. et al. Targeting cells with single vectors using multiple-feature Boolean logic. Nature methods 11, 763-772, doi:10.1038/nmeth.2996 (2014).

3 Zhang, F., Carothers, J. M. & Keasling, J. D. Design of a dynamic sensor-regulator system for production of chemicals and fuels derived from fatty acids. Nature biotechnology 30, 354-359, doi:10.1038/nbt.2149 (2012).

4 Ro, D. K. et al. Production of the antimalarial drug precursor artemisinic acid in engineered yeast. Nature 440, 940-943, doi:10.1038/nature04640 (2006).

5 Dueber, J. E. et al. Synthetic protein scaffolds provide modular control over metabolic flux. Nature biotechnology 27, 753-759, doi:10.1038/nbt.1557 (2009).

6 Bogorad, I. W., Lin, T. S. & Liao, J. C. Synthetic non-oxidative glycolysis enables complete carbon conservation. Nature 502, 693-697, doi:10.1038/nature12575 (2013).

7 Brophy, J. A. & Voigt, C. A. Principles of genetic circuit design. Nature methods 11, 508-520, doi:10.1038/nmeth.2926 (2014).

8 Gardner, T. S., Cantor, C. R. & Collins, J. J. Construction of a genetic toggle switch in *Escherichia coli*. Nature 403, 339-342, doi:10.1038/35002131 (2000).

9 Elowitz, M. B. & Leibler, S. A synthetic oscillatory network of transcriptional regulators. Nature 403, 335-338, doi:10.1038/35002125 (2000).

10 Stricker, J. et al. A fast, robust and tunable synthetic gene oscillator. Nature 456, 516-519, doi:10.1038/nature07389 (2008).

11 Gaber, R. et al. Designable DNA-binding domains enable construction of logic circuits in mammalian cells. Nature chemical biology 10, 203-208, doi:10.1038/nchembio.1433 (2014).

12 Daniel, R., Rubens, J. R., Sarpeshkar, R. & Lu, T. K. Synthetic analog computation in living cells. Nature 497, 619-623, doi:10.1038/nature12148 (2013).

13 Moon, T. S., Lou, C., Tamsir, A., Stanton, B. C. & Voigt, C. A. Genetic programs constructed from layered logic gates in single cells. Nature 491, 249-253, doi:10.1038/nature11516 (2012).

14 Leisner, M., Bleris, L., Lohmueller, J., Xie, Z. & Benenson, Y. Rationally designed logic integration of regulatory signals in mammalian cells. Nature nanotechnology 5, 666-670, doi:10.1038/nnano 2010.135 (2010).

15 Xie, Z., Wroblewska, L., Prochazka, L., Weiss, R. & Benenson, Y. Multi-input RNAi-based logic circuit for identification of specific cancer cells. Science 333, 1307-1311, doi:10.1126/science.1205527 (2011).

16 Guinn, M. & Bleris, L. Biological 2-input decoder circuit in human cells. ACS synthetic biology 3, 627-633, doi:10.1021/sb4001596 (2014).

17 Lapique, N. & Benenson, Y. Digital switching in a biosensor circuit via programmable timing of gene availability. Nature chemical biology, doi:10.1038/nchembio.1680 (2014).

18 Ventura, A. et al. Restoration of p53 function leads to tumour regression in vivo. Nature 445, 661-665, doi:10.1038/nature05541 (2007).

19 Heffner, C. S. et al. Supporting conditional mouse mutagenesis with a comprehensive cre characterization resource. Nature communications 3, 1218, doi:10.1038/ncomms2186 (2012).

20 Sauer, B. Inducible gene targeting in mice using the Cre/lox system. Methods 14, 381-392, doi:10.1006/meth.1998.0593 (1998).

21 Madisen, L. et al. A toolbox of Cre-dependent optogenetic transgenic mice for light-induced activation and silencing. Nature neuroscience 15, 793-802, doi:10.1038/nn.3078 (2012).

22 Olive, K. P. et al. Mutant p53 gain of function in two mouse models of Li-Fraumeni syndrome. Cell 119, 847-860, doi:10.1016/j.cell.2004.11.004 (2004).

23 Zhu, L. et al. Prominin 1 marks intestinal stem cells that are susceptible to neoplastic transformation. Nature 457, 603-607, doi:10.1038/nature07589 (2009).

24 Awatramani, R., Soriano, P., Rodriguez, C., Mai, J. J. & Dymecki, S. M. Cryptic boundaries in roof plate and choroid plexus identified by intersectional gene activation. Nature genetics 35, 70-75, doi:10.1038/ng1228 (2003).

25 Sauer, B. & McDermott, J. DNA recombination with a heterospecific Cre homolog identified from comparison of the pac-c1 regions of P1-related phages. Nucleic Acids Res 32, 6086-6095, doi:32/20/6086 [pii]
10.1093/nar/gkh941 (2004).

26 Sajgo, S. et al. Dre-Cre sequential recombination provides new tools for retinal ganglion cell labeling and manipulation in mice. PloS one 9, e91435, doi:10.1371/journal.pone.0091435 (2014).

27 Suzuki, E. & Nakayama, M. VCre/VloxP and SCre/SloxP: new site-specific recombination systems for genome engineering. Nucleic acids research 39, e49, doi:10.1093/nar/gkq1280 (2011).

28 Karimova, M. et al. Vika/vox, a novel efficient and specific Cre/loxP-like site-specific recombination system. Nucleic acids research 41, e37, doi:10.1093/nar/gks1037 (2013).

29 Lee, G. & Saito, I. Role of nucleotide sequences of loxP spacer region in Cre-mediated recombination. Gene 216, 55-65 (1998).

30 Torella, J. P. et al. Rapid construction of insulated genetic circuits via synthetic sequence-guided isothermal assembly. Nucleic acids research 42, 681-689, doi:10.1093/nar/gkt860 (2014).

31 Torella, J. P. et al. Unique nucleotide sequence-guided assembly of repetitive DNA parts for synthetic biology applications. Nature protocols 9, 2075-2089, doi:10.1038/nprot.2014.145 (2014).

32 Mutalik, V. K. et al. Precise and reliable gene expression via standard transcription and translation initiation elements. Nature methods 10, 354-360, doi:10.1038/nmeth.2404 (2013).

33 Mutalik, V. K. et al. Quantitative estimation of activity and quality for collections of functional genetic elements. Nature methods 10, 347-353, doi:10.1038/nmeth.2403 (2013).

34 Canton, B., Labno, A. & Endy, D. Refinement and standardization of synthetic biological parts and devices. Nature biotechnology 26, 787-793, doi:10.1038/nbt1413 (2008).

35 Khalil, A. S. et al. A synthetic biology framework for programming eukaryotic transcription functions. Cell 150, 647-658, doi:10.1016/j.cell.2012.05.045 (2012).

36 Keung, A. J., Bashor, C. J., Kiriakov, S., Collins, J. J. & Khalil, A. S. Using targeted chromatin regulators to engineer combinatorial and spatial transcriptional regulation. Cell 158, 110-120, doi:10.1016/j.cell.2014.04.047 (2014).

37 Chen, Y. J. et al. Characterization of 582 natural and synthetic terminators and quantification of their design constraints. Nature methods 10, 659-664, doi:10.1038/nmeth.2515 (2013).

38 Stanton, B. C. et al. Systematic transfer of prokaryotic sensors and circuits to mammalian cells. ACS synthetic biology, doi:10.1021/sb5002856 (2014).

39 Yang, L. et al. Permanent genetic memory with >1-byte capacity. Nature methods, doi:10.1038/nmeth.3147 (2014).

The invention claimed is:

1. A nucleic acid logic cassette comprising a mammalian promoter sequence operatively linked to a logic gate, wherein the logic gate comprises at least one target gene and at least two pairs of recombinase recognition sequences (RRS), wherein each pair of RRS is recognized by a different recombinase enzyme, and wherein the RRS of each pair can be the same sequence or a different sequence recognized by the same recombinase enzyme, wherein RRS1 is a recombinase recognition sequence (RRS) for a first recombinase enzyme (R1), RRS2 is a recombinase recognition sequence for a second recombinase enzyme (R2), RRS3 is a recombinase recognition sequence for a third recombinase enzyme (R3), RRS4 is a recombinase recognition sequence for a fourth recombinase enzyme (R4), RRS5 is a recombinase recognition sequence for a fifth recombinase enzyme (R5), RRS6 is a recombinase recognition sequence for a sixth recombinase enzyme (R6), and RRS7 is a recombinase recognition sequence for a seventh recombinase enzyme (R7), wherein when pair of RRS for the same recombinase enzyme are in the same orientation, the intervening nucleic acid sequence between RRS pair is excised in the presence of the recombinase enzyme, and when a pair of RRS for the same recombinase are in the inverse orientation with respect to each other, the intervening nucleic acid sequence between the RRS pair is inverted in the presence of the recombinase enzyme, and wherein the logic gate is selected from any of the following logic gates having in a 5' to 3' direction:

a) a first RRS1, a first RRS2, a nucleic acid sequence encoding a target gene, a second RRS2 and a second RRS1, wherein the RRS1 and RRS2 are all in the same orientation;

b) a first RRS1, a first RRS2, a stop sequence, a second RRS1, a second RRS2, and a nucleic acid sequence encoding a target gene, wherein the RRS1 and RRS2 are all in the same orientation;

c) a first RRS1, a stop sequence, a second RRS1, a first RRS2, a stop sequence, a second RRS2, and a nucleic acid sequence encoding a target gene, wherein the RRS1 and RRS2 are all in the same orientation;

d) a first RRS2, a first nucleic acid sequence encoding a target gene, a second RRS2, a first RRS1, and second nucleic acid sequence encoding the same target gene, a second RRS1, wherein the RRS1 and RRS2 are all in the same orientation;

e) a first RRS1, a first RRS2, a first nucleic acid sequence encoding a target gene, a second RRS2, a stop sequence, a second RRS1, a second nucleic acid sequence encoding the same target gene, wherein the RRS1 and RRS2 are all in the same orientation;

f) a first RRS2, a first RRS1, a first nucleic acid sequence encoding a target gene, a second RRS1, a stop sequence, a second RRS2, a second nucleic acid sequence encoding the same target gene, wherein the RRS1 and RRS2 are all in the same orientation;

g) a first RRS1, a first RRS2, a stop sequence, a second RRS2, a nucleic acid encoding a target gene, a second RRS1, wherein the RRS1 and RRS2 are all in the same orientation;

h) a first RRS2, a first RRS1, a stop sequence, a second RRS1, a nucleic acid encoding a target gene, a second RRS2, wherein the RRS1 and RRS2 are all in the same orientation;

i) a first RRS1, a first RRS2, a nucleic acid encoding a target gene, a second RRS2, a second RRS1, wherein the RRS1 and RRS2 are all in the same orientation; and j) a first RRS1, a stop sequence, a second RRS1, a first RRS2, a stop sequence, a second RRS2, a nucleic acid encoding a target gene, wherein RR1 and RRS2 are all in the same orientation;

k) a first RRS1, a first RRS2, a first nucleic acid encoding a first target gene, a second RRS2, a second nucleic acid encoding a second target gene, a second RRS1, a first RRS3, a third nucleic acid encoding a third target gene, a second RRS3, a fourth nucleic acid encoding a fourth target gene, wherein the RRS1, RRS2 and RRS3 are all in the same orientation with respect to each other;

l) a first RRS1, a first RRS2, a first RRS3 in the forward orientation (RRS3for), a nucleic acid encoding a first target gene in the reverse orientation, a second RRS3 in the reverse orientation (RRS3rev), a second RRS2, a first RRS4, stop sequence, a second RRS4, a second nucleic acid sequence encoding a first target gene, a second RRS1, a first RRS5, a first RRS6, a stop sequence, a second RRS6, a third nucleic acid sequence encoding a first target gene, a second RRS5, a first RRS7 in the forward orientation (RRS7for), a forth nucleic acid sequence encoding the first target gene in the reverse orientation, a second RRS7 in the reverse orientation (RRS7rev), wherein RR1, RRS2, RRS3, RRS4, RRS5 and RRS6, are all in the same orientation with respect to each other and RRS3for and RRS3rev, and RRS7for and RRS7rev are in inverse orientation with respect to each other, m) a first RRS1, a first RRS2, a first RRS3, a first nucleic acid encoding a first target gene, a second RRS3, a second nucleic acid encoding a second target gene, a second RRS2, a first RRS4, a third nucleic acid encoding a third target gene, a second RRS4, a fourth nucleic acid encoding a fourth target gene, a second RRS1, a first RRS5, a first RRS6, a fifth nucleic acid encoding a fifth target gene, a second RRS6, a sixth nucleic acid encoding a sixth target gene, a second RRS5, a first RRS7, a seventh nucleic acid encoding a seventh target gene, a second RRS7, an eighth nucleic acid encoding an eighth target gene, wherein the RRS1, RRS2, RRS3, RRS4, RRS5, RRS6 and RRS7 are all in the same orientation with respect to each other;

n) a first RRS1, a first RRS2, a first RRS3, a stop sequence, a second RRS3, a first nucleic acid encoding a first target gene, a second RRS2, a first RRS4, a second nucleic acid encoding the first target gene, a second RRS4, a third nucleic acid encoding a second target gene, a second RRS1, a first RRS5, a first RRS6, a fourth nucleic acid encoding the first target gene, a second RRS6, a fifth nucleic acid encoding the second target gene, a second RRS5, a first RRS7 a sixth nucleic acid encoding the second target gene, a second RRS7, a seventh nucleic acid encoding the first and second target gene; wherein the RRS1, RRS2, RRS3, RRS4, RRS5, RRS6 and RRS7 are all in the same orientation with respect to each other;

o) a first RRS1, a second RRS2, a third RRS3, a stop sequence, a second RRS3, a first nucleic acid encoding a first target gene, a second RRS2, a first RRS4, a second nucleic acid encoding the first target gene and a second target gene, a second RRS4, a stop sequence, a second RRS1, a first RRS5, a first RRS6, a third nucleic acid encoding the first and the second target gene, a second RRS6, a fourth nucleic acid encoding the second target gene, a second RRS5, a first RRS7, a stop sequence, a second RRS7, a fifth nucleic acid encoding the first and second target gene, wherein the RRS1, RRS2, RRS3, RRS4, RRS5, RRS6 and RRS7 are all in the same orientation with respect to each other;

p) a first RRS1, a second RRS2, a third RRS3, a stop sequence, a second RRS3, a first nucleic acid encoding a first target gene, a second RRS2, a first RRS4, a second nucleic acid encoding the first target gene, a second RRS4, a third nucleic acid encoding a second target gene, a second RRS1, a first RRS5, a first RRS6, a stop sequence, a second RRS6, a fourth nucleic acid encoding the first and second target gene, a second RRS5, a first RRS7, a fifth nucleic acid encoding the first target gene, a second RRS7, a stop sequence; wherein the RRS1, RRS2, RRS3, RRS4, RRS5, RRS6 and RRS7 are all in the same orientation with respect to each other;

q) a first RRS1, a first RRS2, a first RRS3, a stop sequence, a second RRS3, a first nucleic acid encoding a first target gene, a second RRS2, a first RRS4, a stop sequence, a second RRS4, a second nucleic acid encoding the first target gene, a second RRS1, a first RRS5, a first RRS6, a stop sequence, a second RRS6, a third nucleic acid encoding the first target gene, a second RRS5, a first RRS7, a stop sequence, a second RRS7, a fourth nucleic acid encoding the first target gene, wherein the RRS1, RRS2, RRS3, RRS4, RRS5, RRS6 and RRS7 are all in the same orientation with respect to each other;

s) a first RRS1, a first RRS2, a stop sequence, a second RRS2, a first nucleic acid encoding a first target gene, a second RRS1, a first RRS3, a second nucleic acid encoding a second target gene, a second RRS3, a third nucleic acid encoding a third target gene, wherein the RRS1, RRS2 and RRS3 are all in the same orientation with respect to each other;

t) a half adder comprising 3 constructs, comprising:
  i. a first construct comprising in a 5' to 3' direction: a first RRS1, a second RRS2, a stop sequence, a second RRS2, a first nucleic acid encoding a first target gene, a second RRS1;
  ii. a second construct comprising in a 5' to 3' direction: a first RRS2, a second RRS1, a stop sequence, a second RRS1, a first nucleic acid encoding the first target gene, a second RRS2;
  iii. a third construct comprising in a 5' to 3' direction: a first RRS1, a stop sequence, a second RRS1, a first RRS2, a stop sequence, a second RRS2, a first nucleic acid encoding a second target gene;
  wherein the RRS1, RRS2 and RRS3 are all in the same orientation with respect to each other;

u) a half adder comprising 2 constructs, comprising:
  i. a first construct comprising in a 5' to 3' direction; a first RRS1, a first RRS3, a stop sequence, a second RRS3, a first nucleic acid encoding a first target gene, a second RRS1, a first RRS2, a second nucleic acid sequence encoding the first target gene, and a second RRS2, and
  ii. a second construct comprising in a 5' to 3' direction; a first RRS1, a stop sequence, a second RRS1, a first RRS2, a stop sequence, a second RRS2, a first nucleic acid encoding a second target gene,
  wherein the RRS1, RRS2 and RRS3 are all in the same orientation with respect to each other;

v) a first RRS1, a first RRS3, a stop sequence, a second RRS3, a first nucleic acid encoding a first target gene, a second RRS1, a first RRS2, a second nucleic acid encoding the first target gene, a second RRS2, a third nucleic acid encoding a second target gene, wherein the RRS1, RRS2 and RRS3 are all in the same orientation with respect to each other.

2. The nucleic acid logic gate of claim 1, wherein the mammalian promoter and the logic gate are flanked by a pair of nucleic acid sequences having homology to mammalian genomic DNA, for insertion of the mammalian promoter and logic cassette into the genome of a mammalian cell.

3. The nucleic acid logic cassette of claim 1, wherein the R1, R2, R3, R4, R5, R7 and R7 are each a tyrosine recombinase or a serine recombinase.

4. The nucleic acid logic cassette of claim 1, wherein the R1, R2, R3, R4, R5, R7 and R7 are each selected from the group consisting of Cre, Flp, Dre, SCre, VCre, Vika, B2, B3, KD, ΦC31, Bxb1, λ, HK022, HP1, γδ, ParA, Tn3, Gin, R4, TP901-1, TG1, PhiRv1, PhiBT1, SprA, XisF, TnpX, R, A118, spoIVCA, PhiMR11, SCCmec, TndX, XerC, XerD, XisA, Hin, Cin, mrpA, beta, PhiFC1, Fre, Clp, sTre, FimE, and HbiF.

5. A mammalian cell comprising the nucleic acid logic gate of claim 1.

6. The mammalian cell of claim 5, wherein the mammalian cell is an immune cell.

7. The mammalian cell of claim 6, wherein the immune cell is a T cell, or a B-cell, and wherein the target gene is a reporter molecule, a protein of interest, an RNA of interest, an enzyme of interest or a chimeric antigen receptor (CAR).

* * * * *